US010093678B2

(12) United States Patent
Shishido et al.

(10) Patent No.: US 10,093,678 B2
(45) Date of Patent: Oct. 9, 2018

(54) AZASPIRO DERIVATIVES AS TRPM8 ANTAGONISTS

(71) Applicant: RaQualia Pharma Inc., Aichi (JP)

(72) Inventors: Yuji Shishido, Aichi (JP); Masashi Ohmi, Aichi (JP); Kazuo Ando, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 0 days.

(21) Appl. No.: 15/125,615

(22) PCT Filed: Mar. 16, 2015

(86) PCT No.: PCT/JP2015/001454
§ 371 (c)(1),
(2) Date: Sep. 13, 2016

(87) PCT Pub. No.: WO2015/136947
PCT Pub. Date: Sep. 17, 2015

(65) Prior Publication Data
US 2017/0002016 A1    Jan. 5, 2017

Related U.S. Application Data

(60) Provisional application No. 61/953,521, filed on Mar. 14, 2014.

(51) Int. Cl.
C07D 491/056    (2006.01)
C07D 403/12     (2006.01)
(Continued)

(52) U.S. Cl.
CPC ...... *C07D 491/056* (2013.01); *A61K 31/4178* (2013.01); *A61K 31/4184* (2013.01); *A61K 31/422* (2013.01); *A61K 31/423* (2013.01); *A61K 31/427* (2013.01); *A61K 31/435* (2013.01); *A61K 31/437* (2013.01); *A61K 31/4355* (2013.01); *A61K 31/444* (2013.01); *A61K 31/4439* (2013.01); *A61K 31/4545* (2013.01); *A61K 31/4709* (2013.01); *A61K 31/4725* (2013.01); *A61K 31/497* (2013.01); *A61K 31/498* (2013.01); *A61K 31/4985* (2013.01); *A61K 31/501* (2013.01); *A61K 31/502* (2013.01); *A61K 31/506* (2013.01); *A61K 31/5025* (2013.01); *A61K 31/517* (2013.01); *A61K 31/519* (2013.01); *A61K 31/538* (2013.01); *C07D 235/02* (2013.01); *C07D 235/06* (2013.01); *C07D 263/52* (2013.01); *C07D 401/12* (2013.01); *C07D 401/14* (2013.01); *C07D 403/06* (2013.01); *C07D 403/10* (2013.01); *C07D 403/12* (2013.01); *C07D 403/14* (2013.01); *C07D 405/14* (2013.01); *C07D 409/10* (2013.01); *C07D 409/14* (2013.01); *C07D 413/06* (2013.01); *C07D 413/10* (2013.01); *C07D 413/14* (2013.01); *C07D 417/06* (2013.01); *C07D 417/10* (2013.01); *C07D 417/14* (2013.01); *C07D 471/04* (2013.01); *C07D 487/04* (2013.01); *C07D 491/048* (2013.01)

(58) Field of Classification Search
None
See application file for complete search history.

(56) References Cited

U.S. PATENT DOCUMENTS

| 5,739,336 A | 4/1998 | Weinhardt et al. |
| 8,642,660 B2 * | 2/2014 | Goldfarb ............ A61K 31/122 514/18.9 |
| 2009/0163545 A1 | 6/2009 | Goldfarb |
| 2010/0093788 A1 | 4/2010 | Player et al. |
| 2016/0008340 A1 | 1/2016 | Dezawa et al. |

FOREIGN PATENT DOCUMENTS

| WO | 2005/044978 | 5/2005 |
| WO | 2006/040103 | 4/2006 |
| WO | 2006/040136 | 4/2006 |
| WO | 2008/032191 | 3/2008 |
| WO | 2010/037081 | 4/2010 |
| WO | 2010/103381 | 9/2010 |
| WO | 2011/148962 | 12/2011 |
| WO | 2012/174342 | 12/2012 |
| WO | 2014/025651 | 2/2014 |
| WO | 2014/130582 | 8/2014 |
| WO | 2014/133170 | 9/2014 |

OTHER PUBLICATIONS

Silva, A., Mini-Reviews in Medicinal Chemistry, 2005, vol. 5, pp. 893-914.*

(Continued)

*Primary Examiner* — Heidi Reese
(74) *Attorney, Agent, or Firm* — Wenderoth, Lind & Ponack, L.L.P.

(57) ABSTRACT

The present invention relates to azaspiro derivatives of the formula (I) or a pharmaceutically acceptable salt thereof or a prodrug thereof, processes for their preparation, pharmaceutical compositions containing them and their use in the treatment of various disorders which are mediated via the TRPM8 receptor.

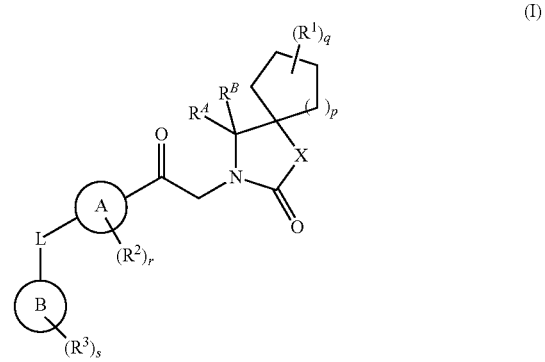

17 Claims, No Drawings

(51) Int. Cl.
| | |
|---|---|
| C07D 401/14 | (2006.01) |
| C07D 405/14 | (2006.01) |
| C07D 413/14 | (2006.01) |
| A61K 31/427 | (2006.01) |
| A61K 31/437 | (2006.01) |
| C07D 401/12 | (2006.01) |
| C07D 403/06 | (2006.01) |
| C07D 403/10 | (2006.01) |
| C07D 403/14 | (2006.01) |
| C07D 409/10 | (2006.01) |
| C07D 409/14 | (2006.01) |
| C07D 413/06 | (2006.01) |
| C07D 417/06 | (2006.01) |
| C07D 417/10 | (2006.01) |
| C07D 417/14 | (2006.01) |
| C07D 471/04 | (2006.01) |
| C07D 487/04 | (2006.01) |
| C07D 263/52 | (2006.01) |
| C07D 491/048 | (2006.01) |
| A61K 31/4178 | (2006.01) |
| A61K 31/422 | (2006.01) |
| A61K 31/435 | (2006.01) |
| C07D 235/06 | (2006.01) |
| A61K 31/4184 | (2006.01) |
| A61K 31/423 | (2006.01) |
| A61K 31/4355 | (2006.01) |
| A61K 31/4439 | (2006.01) |
| A61K 31/444 | (2006.01) |
| A61K 31/4545 | (2006.01) |
| A61K 31/4709 | (2006.01) |
| A61K 31/4725 | (2006.01) |
| A61K 31/497 | (2006.01) |
| A61K 31/498 | (2006.01) |
| A61K 31/4985 | (2006.01) |
| A61K 31/501 | (2006.01) |
| A61K 31/502 | (2006.01) |
| A61K 31/5025 | (2006.01) |
| A61K 31/506 | (2006.01) |
| A61K 31/517 | (2006.01) |
| A61K 31/519 | (2006.01) |
| A61K 31/538 | (2006.01) |
| C07D 235/02 | (2006.01) |
| C07D 413/10 | (2006.01) |

(56) References Cited

OTHER PUBLICATIONS

International Search Report dated Jun. 16, 2015 in International Application No. PCT/JP2015/001454.
Written Opinion of the International Searching Authority dated Jun. 16, 2015 in International Application No. PCT/JP2015/001454.
Written Opinion of the International No. PCT/JP2015/001454. Preliminary Examination Authority dated Apr. 19, 2016 in International Application.
International Preliminary Report on Patentability dated Jun. 27, 2016 in International Application No. PCT/JP2015/001454.
STN International, File Registry [online], Entered STN: May 1, 2012, [retrieved on May 15, 2015], e.g. Registry Nos. 1372031-46-3, 1371235-45-8, 1320872-19-2, 1320648-38-1, 1320315-93-2, 1301581-70-3, 1276337-79-1, 1259189-35-9, 1210803-22-7, 1209215-26-8, 1208713-09-0, 1197672-03-9, 1180588-51-5, 1147660-02-3, 1090567-51-3, 1087633-05-3, 1083193-07-0, 1057919-60-4, 1057755-92-6, 1057700-45-4, 1014940-67-0, 1014862-23-7, 1014367-71-5, 1014367-68-0, 1014308-64-5, 1012169-83-3, 1012169-60-6, 1012127-15-9, 1012123-18-0, 1011971-90-6, 1011971-78-0, 1011084-16-4, 1009698-68-3, 1004179-56-9, 1002949-52-1, 1002949-44-1, 1002035-76-8, 941149-81-1, 941042-07-5, 938937-97-4, 931001-07-9, 930403-55-7, 924259-30-3, 924247-27-8, 924245-50-1, 924240-13-1, 924221-64-7, 924117-57-7, 924114-47-6, 924110-77-0, 924050-21-5, 924025-57-0, 923906-39-2, 923896-72-4, 920644-55-9, 920641-75-4, 920628-57-5, 897298-70-3, 876690-52-7, 875447-88-4, 872025-23-5, 871804-45-4, 871218-66-5, 851118-27-9, 849603-78-7, 849527-78-2, 849485-24-1, 849478-16-6, 849184-07-2, 727718-78-7, 1008038-38-7, 1001511-15-4, 950004-67-8, 920909-57-5, 876541-23-0, 871218-59-6, 851898-41-4.
Caplus [online], [retrieved on May 15, 2015] : Caplus Accession Nos. 2009: 846114, 2009: 846111, 2009:846110, 2009: 846108, 2009:846104, 2009:846103, 2009:846102, 2009:846100, 2009:769551
CAS Registry Nos. 867312-77-4, 746606-14-4, 867274-68-8, 869355-15-7, 782464-74-8, 851902-35-7, 795285-06-2, 795285-18-6, 868269-97-0, 746618-58-6, 851283-38-0, 924171-23-3, 795285-20-0, 851215-21-9, 876580-41-5.
Obniska, J. et al., Synthesis, physicochemical and anticonvulsant properties of new N-4-arylpiperazin-1-yl amides of (2-aza-1,3-dioxospiro [4.5]dec-2-yl)-acetic acid, Acta Poloniae Pharmaceutica, 2005, 62(4), pp. 283-288.
Poli, Giulio et al., "Application of a FLAP-Consensus Docking Mixed Strategy for the Identification of New Fatty Acid Amide Hydrolase Inhibitors", Journal of Chemical Information and Modeling, 2015, 55(3), pp. 667-675.
McKemy, D.D., et al., "Identification of a cold receptor reveals a general role for TRP channels in thermosensation", Nature 416, 52-58, 2002.
Peier, A.D., "A TRP Channel that Senses Cold Stimuli and Menthol", Cell 108, 705-715, 2002.
Abe, J., et al., "$Ca^{2+}$-dependent PKC activation mediates menthol-induced desensitization of transient receptor potential M8", Neurosci Lett, 397(1-2), 140-144, 2006.
Premkumar, L.S., et al., "Downregulation of Transient Receptor Potential Melastatin 8 by Protein Kinase C-Medicated Dephosphorylation", J. Neurosci, 25(49), 11322-11329, 2005.
Kobayashi, K., et al., "Distinct Expression of TRPM8, TRPA1, and TRPV1 mRNAs in Rat Primary Afferent Neurons with Aδ/C-Fibers and Colocalization with Trk Receptors", J Comp Neurol, 493(4), 596-606, 2005.
Roza, C, et al., "Cold sensitivity in axotomized fibers of experimental neurons in mice", Pain, 120(1-2), 24-35, 2006.
Xing, H., et al., "Chemical and Cold Sensitivity of Two Distinct Populations of TRPM8-Expressing Somatosensory Neurons", J Neurophysiol, 95(2), 1221-30, 2006.
Jill-Desiree Bredersen et al., "Targeting TRP channels for pain relief", European Journal of Pharmacology, vol. 716, Issues 1-3, 61-76, 2013.
Ikhlas A., et al., "Human odontoblasts express functional thermosensitive TRP channels: Implications for dentin sensitivity", PAIN, vol. 152, Issue 10, 2211-2223, 2011.
Gauchan, P., et al., "Involvement of increased expression of transient receptor potential melastatin 8 in oxaliplatin-induced cold allodynia in mice", Neurosci Lett, 458, 93-95, 2009.
Sachin, S. Chaudhari, et al., "Synthesis and pharmacological evaluation of novel N-aryl-3, 4-dihydro-1'H-Spiro [chromene-2,4'-piperidine]-1'-carboxamides as TRPM8 antagonists", Bioorg. Med. Chem, 21, 6542-6553, 2013.
XP-002773864, Reg. No. 874972-85-7, entered Feb. 23, 2006.
XP-002773866, Reg. No. 1012022-14-8, entered Apr. 4, 2008.
Parks et al., "Design and Optimization of Benzimidazole-Containing Transient Receptor Potential Melastatin 8 (TRPM8) Antagonists", Journal of Medicinal Chemistry, vol. 54, No. 1: pp. 233-247 (2011).
Extended European Search Report, dated Oct. 20, 2017 in corresponding European Patent Application No. 15760744.1.
XP-002773865, Reg. No. 924110-77-0, entered Mar. 1, 2007.
XP-002773867, Reg. No. 924114-47-6, entered Mar. 1, 2007.

* cited by examiner

AZASPIRO DERIVATIVES AS TRPM8 ANTAGONISTS

TECHNICAL FIELD

This invention relates to azaspiro derivatives that act as modulators of the TRPM8 receptor. The present invention also relates to processes for the preparation of novel azaspiro derivatives and to their use in the treatment of a wide range of diseases, syndromes, and disorders, in particular for the treatment of inflammatory, pain and urological diseases or disorders.

BACKGROUND ART

Transient receptor potential (TRP) channels are one of the largest groups of ion channels, and they are divided into 6 sub-families (TRPV, TRPM, TRPA, TRPC, TRPP and TRPML). TRP channels are cation-selecive channels that are activated by a variety of physical (e.g., temperature, osmolarity, mechanical) and chemical stimuli. TRPM8 is a member of TRP channel family. The receptor was cloned in 2002 (NPL 1; NPL 2) and it was found to be sensitive to cold temperature and menthol, and therefore named as cold menthol receptor-1 (CMR-1). TRPM8 can sense temperature changes in the range of both innocuous cold (15-28° C.) and noxious cold (<15° C.) as well as by chemical agents such as menthol and icilin.

TRPM8 is located on primary nociceptive neurons including A-delta and C-fibers and is also modulated by inflammation-mediated second messenger signals (NPL 3; NPL 4). The localization of TRPM8 on both A-delta and C-fibers may provide a basis for abnormal cold sensitivity in pathologic conditions wherein these neurons are altered, resulting in pain, often of a burning nature (NPL 5; NPL 6; NPL 7, NPL 8, NPL 9). Gauchan et al. reported that the expression of TRPM8 in the primary afferents was increased in oxaliplatin-induced cold allodynia model in mice (NPL 10). Oxaliplatin, a third-generation platinum-based chemotherapy drug, induces serious sensory neurotoxicity in patients, which is aggravated by exposure to cold. Recently, Glenmark group reported that the small molecular TRPM8 antagonists produced a dose-dependent inhibition of nocifensive paw licking in oxaliplatin-induced cold allodynia in mice (NPL 11).

Cold intolerance and paradoxical burning sensations induced by chemical or thermal cooling closely parallel symptoms seen in a wide range of clinical disorders and thus provide a strong rationale for the development of TRPM8 modulators as novel antihyperalgesic or antiallodynic agents. TRPM8 is also known to be expressed in the brain, odontoblasts, lung, bladder, gastrointestinal tract, blood vessels, prostate and immune cells, thereby providing the possibility for therapeutic modulation in a wide range of maladies.

International patent application WO 2006/040136 (PTL 1) purportedly describes substituted 4-benzyloxy-phenylmethylamide derivatives as cold menthol receptor-1 (CMR-1) antagonists for the treatment of urological disorders. International patent application WO 2006/040103 (PTL 2) purportedly describes methods and pharmaceutical compositions for treatment and/or prophylaxis of respiratory diseases or disorders. Recently, International patent application WO 2014/025651 (PTL 3) from Amgen Inc. purportedly describes chroman compounds and derivatives as TRPM8 inhibitors for the treatment of migraines and neuropathic pain.

The compounds of the present invention which have TRPM8 receptor antagonist activity are structurally quite different from prior arts.

WO 2010/037081 (PTL 4) and US005739336A (PTL 5) disclose spiropiperidine derivatives. However, the chemical structures of the compounds disclosed in the both patents are quite different from the compounds of the present invention. In addition, the compounds disclosed in the both patents relate to melanocortin receptor inhibitors and selective 5HT2c receptor antagonists, respectively, which is quite different from TRPM8 receptor antagonist.

WO 2012/174342 (PTL 6) and WO 2011/148962 (PTL 7) disclose spiro[cyclohexane-oxazolidinone] derivatives. However, the chemical structures of the compounds disclosed in the both patents are quite different from the compounds of the present invention. In addition, the compounds disclosed in the both patents relate to TRPV4 antagonists and antibacterial agents, respectively, which is quite different from TRPM8 receptor antagonist. The invention in WO 2005/044978 (PTL 8) discloses spiro derivatives which relate an activated αIbβ3 (alpha1Ibbeta3) receptor antagonist, is different from the present invention in the both aspects of chemical structures and biological activities.

Therefore the azaspiro derivatives in the present invention which have TRPM8 receptor antagonist activity have never been disclosed in prior arts.

CITATION LIST

Patent Literature

{PTL 1} WO 2006/040136
{PTL 2} WO 2006/040103
{PTL 3} WO 2014/025651
{PTL 4} WO 2010/037081
{PTL 5} US005739336A
{PTL 6} WO 2012/174342
{PTL 7} WO 2011/148962
{PTL 8} WO 2005/044978

Non Patent Literature

{NPL 1} McKerny, D. D., et al., Nature 416, 52-58, 2002
{NPL 2} Peier, A. D., Cell 108, 705-715, 2002
{NPL 3} Abe, J., et al., Neurosci Lett, 397(1-2), 140-144, 2006
{NPL 4} Premkumar, L. S., et al., J. Neurosci, 25(49), 11322-11329, 2005
{NPL 5} Kobayashi, K., et al., J Comp Neurol, 493(4), 596-606, 2005
{NPL 6} Roza, C, et al., Pain, 120(1-2), 24-35, 2006
{NPL 7} Xing, H., et al., J Neurophysiol, 95(2), 1221-30, 2006
{NPL 8} European Journal of Pharmacology, Volume 716, Issues 1-3, 61-76, 2013
{NPL 9} PAIN, Volume 152, Issue 10, 2211-2223, 2011
{NPL 10} Gauchan, P., et al., Neurosci Lett, 458, 93-95, 2009
{NPL 11} Sachin, S. Chaudhari, et al., Bioorg. Med. Chem, 21, 6542-6553, 2013

SUMMARY OF INVENTION

Technical Problem

There is a need in the art for TRPM8 antagonists that can be used to treat a disease, syndrome, or condition in a mammal in which the disease, syndrome, or condition is affected by the modulation of TRPM8 receptors, such as wherein the condition or disorder is one or more of inflammatory, pain and urological diseases or disorders, including wherein the condition or disorder is one or more of inflammatory, pain and urological diseases or disorders, including chronic pain; neuropathic pain including cold allodynia and diabetic neuropathy; postoperative pain; osteoarthritis; rheumatoid arthritic pain; cancer pain; neuralgia; neuropathies; algesia; dentin hypersensitivity; nerve injury; migraine; cluster and tension headaches; ischaemia; irritable bowel syndrome; Raynaud's syndrome; neurodegeneration; fibromyalgia; stroke; itch; psychiatric disorders including anxiety and depression; inflammatory disorders including asthma, chronic obstructive pulmonary, airways disease including COPD, pulmonary hypertension; anxiety including other stress-related disorders; and urological diseases or disorders including detrusor overactivity or overactive bladder, urinary incontinence, neurogenic detrusor overactivity or detrusor hyperflexia, idiopathic detrusor overactivity or detrusor instability, benign prostatic hyperplasia, and lower urinary tract symptoms; and combinations thereof.

TRPM8 antagonists should be well absorbed from the GI tract, be metabolically stable and possess favorable pharmacokinetic properties. They should be non-toxic. Furthermore, the ideal drug candidate will exist in a physical form that is stable, non-hygroscopic and easily formulated. In particular, it has been desired that compounds would have to bind potently to the TRPM8 receptor and show functional activity as antagonists. The present invention provides novel compounds which have excellent TRPM8 antagonistic activities.

Solution to Problem

With respect to other compounds disclosed in the art, the compounds of the present invention may show less toxicity, good absorption and distribution, good solubility, less plasma protein binding, less drug-drug interaction, good metabolic stability, reduced inhibitory activity at HERG channel, and/or reduced QT prolongation.

The present invention provides:

[1] a compound of the following formula (I)

{Chem. 1}

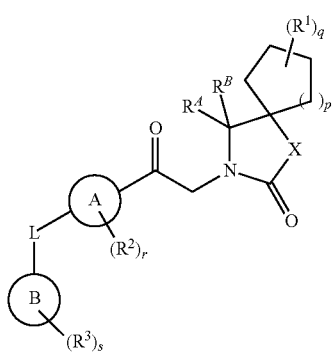

(I)

wherein
A is aryl and heteroaryl;
B is aryl and heteroaryl;
L is independently selected from the group consisting of a chemical bond, oxygen, sulfur, $-NR^4-$, $-(CR^CR^D)_t-$, $-O(CR^CR^D)_t-$, $-(CR^CR^D)_tO-$, $-N(R^4)(CR^CR^D)_t-$, $-(CR^CR^D)_tN(R^4)-$, $-N(R^4)(CR^CR^D)_tO-$, and $-O(CR^CR^D)_tN(R^4)-$ X is independently selected from the group consisting of $-CH_2-$, oxygen, sulfur and NH;

$R^A$ and $R^B$ are independently selected from the group consisting of;
(1) hydrogen, (2) halogen, (3) $(C_1-C_{10})$alkyl, (4) $(C_3-C_{10})$cycloalkyl and (5) $(C_1-C_{10})$haloalkyl; or $R^A$ and $R^B$ may form oxo group (=O); or $R^A$ and $R^B$ may form a 3 to 8 membered ring which may contain one or more heteroatoms independently selected from oxygen, sulfur and nitrogen; and said ring is optionally substituted with 1 to 6 substituents independently selected from (1) hydrogen, (2) halogen, (3) hydroxy, (4) $(C_1-C_{10})$alkyl, (5) $(C_3-C_{10})$cycloalkyl, (6) $(C_1-C_{10})$haloalkyl, (7) $(C_1-C_{10})$alkoxy and (8) $(C_1-C_{10})$haloalkoxy;

$R^C$ and $R^D$ are independently selected from the group consisting of (1) hydrogen, (2) halogen, (3) $(C_1-C_{10})$alkyl, (4) $(C_3-C_{10})$cycloalkyl and (5) $(C_1-C_{10})$haloalkyl; or $R^C$ and $R^D$ may form a 3 to 8 membered ring which may contain one or more heteroatoms independently selected from oxygen, sulfur and nitrogen; and said ring is optionally substituted with 1 to 6 substituents independently selected from (1) hydrogen, (2) halogen, (3) hydroxy, (4) $(C_1-C_{10})$alkyl, (5) $(C_3-C_{10})$cycloalky, (6) $(C_1-C_{10})$haloalkyl, (7) $(C_1-C_{10})$alkoxy and (8) $(C_1-C_{10})$haloalkoxy;

$R^1$ is independently selected from the group consisting of (1) hydrogen, (2) halogen, (3) amino, (4) cyano, (5) hydroxyl, (6) $(C_1-C_{10})$alkyl, (7) $(C_3-C_{10})$cycloalkyl, (8) $(C_1-C_{10})$haloalkyl, (9) $(C_1-C_{10})$alkoxy and (10) $(C_1-C_{10})$haloalkoxy; two $R^1$ on the same carbon or the different carbons are possible to form a 3 to 8 membered ring which may contain an atom selected from oxygen, sulfur and nitrogen; and said ring is optionally substituted with 1 to 6 substituents independently selected from (1) hydrogen, (2) halogen, (3) hydroxy, (4) $(C_1-C_{10})$alkyl, (5) $(C_3-C_{10})$cycloalkyl, (6) $(C_1-C_{10})$haloalkyl, (7) $(C_1-C_{10})$alkoxy, and (8) $(C_1-C_{10})$haloalkoxy;

$R^2$ is independently selected from the group consisting of (1) hydrogen, (2) halogen, (3) amino, (4) $-NH(C_1-C_6)$alkyl, (5) $-N[(C_1-C_6)$alkyl$]_2$ wherein the alkyl is same or different, (6) cyano, (7) hydroxyl, (8) nitro, (9) $(C_1-C_6)$alkylthio, (10) $(C_1-C_{10})$alkyl, (11) $(C_3-C_{10})$cycloalkyl, (12) $(C_1-C_{10})$alkoxy, (13) $(C_1-C_{10})$haloalkyl and (14) $(C_1-C_{10})$haloalkoxy;

$R^3$ is independently selected from the group consisting of (1) hydrogen, (2) halogen, (3) cyano, (4) nitro, (5) hydroxyl, (6) $(C_1-C_6)$alkylthio, (7) $(C_1-C_6)$alkylsulfinyl, (8) $(C_1-C_6)$alkylsulfonyl, (9) $-NR^5R^6$, (10) $-C(=O)NR^5R^6$, (11) tri$(C_1-C_6)$alkylsilyl, (12) $(C_1-C_{10})$alkyl, (13) $(C_3-C_{10})$cycloalkyl, (14) $(C_1-C_6)$alkoxy$(C_0-C_6)$alkyl, (15) $(C_3-C_{10})$cycloalkoxy, (16) $-C(=O)(C_1-C_6)$alkyl, (17) $-C(=O)O(C_1-C_6)$alkyl and (18) $-C(=O)OH$; said $(C_1-C_{10})$alkyl, $(C_3-C_{10})$cycloalkyl, $(C_1-C_6)$alkoxy$(C_0-C_6)$alkyl and $(C_3-C_{10})$cycloalkoxy are optionally substituted with 1 to 6 substituents independently selected from (1) hydrogen, (2) halogen, (3) hydroxyl, (4) cyano, (5) $(C_3-C_{10})$cycloalkyl, (6) $(C_1-C_{10})$haloalkyl, (7) $(C_1-C_{10})$alkoxy, (8) $(C_1-C_{10})$haloalkoxy and (9) $-NR^6R^5$;

wherein $R^5$ and $R^6$, together with nitrogen atom to which they are attached, may form a 3 to 10 membered ring which may contain an atom selected from oxygen, sulfur and nitrogen; and said ring is optionally substituted with 1 to 6 substituents independently selected from (1) hydrogen, (2)

halogen, (3) hydroxyl, (4) $(C_1-C_{10})$alkyl, (5) $(C_3-C_{10})$cycloalkyl, (6) $(C_1-C_{10})$haloalkyl, (7) $(C_1-C_{10})$alkoxy and (8) $(C_1-C_{10})$haloalkoxy;

$R^4$, $R^5$ and $R^6$ are independently selected from the group consisting of (1) hydrogen, (2) $(C_1-C_{10})$alkyl, (3) $(C_3-C_{10})$cycloalkyl, (4) $(C_1-C_{10})$haloalkyl, (5) hydroxyl$(C_1-C_{10})$alkyl, (6) $(C_1-C_{10})$alkoxy$(C_1-C_{10})$alkyl, (7) $H_2N$—$(C_1-C_{10})$alkyl, (8) $[(C_1-C_{10})$alkyl]NH—$(C_1-C_{10})$alkyl, (9) $[(C_1-C_{10})$alkyl]2N—$(C_1-C_{10})$alkyl, (10) $(C_1-C_{10})$alkylcarbonyl and (11) $(C_1-C_{10})$alkylsulfonyl;

p is 1, 2, 3 or 4;

q is 1, 2, 3 or 4; when q is two or more than two, $R^1$ is same or different, r is 1, 2, 3 or 4; when r is two or more than two, $R^2$ is same or different, s is 1, 2, 3, 4, 5, 6 or 7; when s is two or more than two, $R^3$ is same or different, t is 1, 2 or 3; when t is two or more than two, $R^C$ and $R^D$ are same or different, or a pharmaceutically acceptable salt thereof or a prodrug thereof;

[2] the compound described in [1] wherein

A is 6 membered aryl or 5 to 6 membered heteroaryl or a pharmaceutically acceptable salt thereof or a prodrug thereof;

[3] the compound described in [1] or [2] wherein

A is independently selected from the group consisting of benzene, pyridine, pyridazine, pyrazine, pyrimidine, triazine, thiophene, furan, pyrrole, imidazole, pyrazole, thiazole, isothiazole, oxazole, isoxazole, and triazole.

or a pharmaceutically acceptable salt thereof or a prodrug thereof;

[4] The compound as described in any one of [1] to [3] which is selected from:

3-(2-(2,5-dimethyl-1-(5-methylisoxazol-3-yl)-1H-pyrrol-3-yl)-2-oxoethyl)-8,8-difluoro-1,3-diazaspiro[4.5]decane-2,4-dione;

3-(2-(2,5-dimethyl-1-phenyl-1H-imidazol-4-yl)-2-oxoethyl)-8,8-difluoro-1,3-diazaspiro[4.5]decane-2,4-dione;

6-(4-(2-(2,4-dioxo-1,3-diazaspiro[4.5]decan-3-yl)acetyl)phenyl)picolinonitrile;

3-(2-(1-(3-chlorophenyl)-2,5-dimethyl-1H-imidazol-4-yl)-2-oxoethyl)-8,8-difluoro-1,3-diazaspiro[4.5]decane-2,4-dione;

8,8-difluoro-3-(2-(1-(3-fluorophenyl)-2,5-dimethyl-1H-imidazol-4-yl)-2-oxoethyl)-1,3-diazaspiro[4.5]decane-2,4-dione;

3-(2-(1,4-dimethyl-5-phenyl-1H-pyrazol-3-yl)-2-oxoethyl)-8,8-difluoro-1,3-diazaspiro[4.5]decane-2,4-dione;

8,8-difluoro-3-(2-(4-(6-methylpyrazin-2-yl)phenyl)-2-oxoethyl)-1,3-diazaspiro[4.5]decane-2,4-dione;

6-(4-(2-(8,8-difluoro-2,4-dioxo-1,3-diazaspiro[4.5]decan-3-yl)acetyl)phenyl)picolinonitrile;

8,8-difluoro-3-(2-(2'-(hydroxymethyl)-[1,1'-biphenyl]-4-yl)-2-oxoethyl)-1,3-diazaspiro[4.5]decane-2,4-dione;

8,8-difluoro-3-(2-(4-(3-methylpyrazin-2-yl)phenyl-2-oxoethyl)-1,3-diazaspiro[4.5]decane-2,4-dione;

3-(2-(2,5-dimethyl-1-phenyl-1H-imidazol-4-yl)-2-oxoethyl)-8,8-difluoro-1-oxa-3-azaspiro[4.5]decane-2,4-dione;

8,8-difluoro-3-(2-(4-2-(hydroxymethyl)pyridin-3-yl)phenyl)-2-oxoethyl)-1,3-diazaspiro[4.5]decane-2,4-dione;

8,8-difluoro-(2-(4-(4-(hydroxymethyl)pyridin-3-yl)phenyl)-2-oxoethyl)-1,3-diazaspiro[4.5]decane-2,4-dione;

3-(2-(2,5-dimethyl-1-(5-methylisoxazol-3-yl)-1H-pyrrol-3-yl)-2-oxoethyl)-8,8-difluoro-1-oxa-3-azaspiro[4.5]decane-2,4-dione;

8,8-difluoro(2-(5-(2-(hydroxymethyl)phenyl)-4-methylthiophen-2-yl)-2-oxoethyl)-1,3-diazaspiro[4.5]decane-2,4-dione;

3-(2-(4-(3-(hydroxymethyl)pyrazin-2-yl)phenyl)-2-oxoethyl)-1,3-diazaspiro[4.5]decane-2,4-dione;

3-(2-(1,4-dimethyl-5-phenyl-1H-pyrazol-3-yl)-2-oxoethyl)-8,8-difluoro-1-oxa-3-azaspiro[4.5]decane-2,4-dione;

8,8-difluoro-3-(2-(4-(4-methylpyridazin-3-yl)phenyl)-2-oxoethyl)-1,3-diazaspiro[4.5]decane-2,4-dione;

3-(4-(2-(8,8-difluoro-2,4-dioxo-1,3-diazaspiro[4.5]decan-3-yl)acetyl)phenyl)pyrazine-2-carbonitrile;

3-(2-(1,4-dimethyl-5-phenyl-1H-pyrrol-2-yl)-2-oxoethyl)-8,8-difluoro-1,3-diazaspiro[4.5]decane-2,4-dione;

8,8-difluoro-3-(2-(4-(3-(hydroxymethyl)pyrazin-2-yl)phenyl)-2-oxoethyl)-1,3-diazaspiro[4.5]decane-2,4-dione;

3-(2-(6-(methyl(pyridin-2-yl)amino)pyridin-3-yl)-2-oxoethyl)-1,3-diazaspiro[4.5]decane-2,4-dione;

3-(4-(2-(8,8-difluoro-2,4-dioxo-1,3-diazaspiro[4.5]decan-3-yl)acetyl)phenyl)picolinonitrile;

8,8-difluoro-3-(2-oxo-2-(4-(quinolin-8-yl)phenyl)ethyl)-1,3-diazaspiro[4.5]decane-2,4-dione;

3-(2-(4-(1H-indol-4-yl)phenyl)-2-oxoethyl)-8,8-difluoro-1,3-diazaspiro[4.5]decane-2,4-dione;

8,8-difluoro-3-(2-oxo-2-(4-(quinolin-2-yl)phenyl)ethyl-1,3-diazaspiro[4.5]decane-2,4-dione;

8,8-difluoro-3-(2-(4-(isoquinolin-8-yl)phenyl)-2-oxoethyl-1,3-diazaspiro[4.5]decane-2,4-dione;

8,8-difluoro-3-(2-(4-(isoquinolin-1-yl)phenyl)-2-oxoethyl)-1,3-diazaspiro[4.5]decane-2,4-dione;

8,8-difluoro-3-(2-(4-(furo[3,2-c]pyridin-4-yl)phenyl)-2-oxoethyl)-1,3-diazaspiro[4.5]decane-2,4-dione;

8,8-difluoro-3-(2-(6-(methyl(pyridin-2-yl)amino)pyridin-3-4)-2-oxoethyl)-1,3-diazaspiro[4.5]decane-2,4-dione;

8,8-difluoro-3-(2-(6-(methyl(phenyl)amino)pyridin-3-yl)-2-oxoethyl)-1,3-diazaspiro[4.5]decane-2,4-dione;

8,8-difluoro-3-(2-(4-(3-fluoropyridin-2-yl)phenyl)-2-oxoethyl-1,3-diazaspiro[4.5]decane-2,4-dione;

3-(4-(2-(8,8-difluoro-2,4-dioxo-1,3-diazaspiro[4.5]decan-3-yl)acetyl)phenyl)isonicotinonitrile;

8,8-difluoro-3-(2-(4-(2-methoxypyridin-3-yl)phenyl)-2-oxoethyl-1,3-diazaspiro[4.5]decane-2,4-dione;

8,8-difluoro-3-(2-(4-(3-methoxypyridin-3-yl)phenyl)-2-oxoethyl-1,3-diazaspiro[4.5]decane-2,4-dione;

8,8-difluoro-3-(2-oxo-2-(4-(2-oxoindolin-4-yl)phenyl)ethyl-1,3-diazaspiro[4.5]decane-2,4-dione;

3-(2-(4-(7H-pyrrolo[2,3-d]pyrimidin-4-yl)phenyl)-2-oxoethyl)-8,8-difluoro-1,3-diazaspiro[4.5]decane-2,4-dione;

3-(2-(4-(1H-pyrrolo[3,2-c]pyridin-4-yl)phenyl)-2-oxoethyl)-8,8-difluoro-1,3-diazaspiro[4.5]decane-2,4-dione;

3-(2-(4-(1H-pyrrolo[2,3-b]pyridin-4-yl)phenyl)-2-oxoethyl)-8,8-difluoro-1,3-diazaspiro[4.5]decane-2,4-dione;

3-(2-(4-(3-chloropyridin-2-yl)phenyl)-2-oxoethyl)-8,8-difluoro-1,3-diazaspiro[4.5]decane-2,4-dione;

8,8-difluoro-3-(2-(4-(2-methyl-1H-benzo[d]imidazol-1-yl)phenyl)-2-oxoethyl)-1,3-diazaspiro[4.5]decane-2,4-dione;

3-(2-(4-(1H-indazol-4-yl)phenyl)-2-oxoethyl)-8,8-difluoro-1,3-diazaspiro[4.5]decane-2,4-dione;

3-(2-(6-(1H-indazol-4-yl)pyridin-3-yl)-2-oxoethyl)-8,8-difluoro-1,3-diazaspiro[4.5]decane-2,4-dione;

3-(2-(4-(1H-benzo[d]imidazol-1-yl)phenyl)-2-oxoethyl)-8,8-difluoro-1,3-diazaspiro[4.5]decane-2,4-dione;

3-(5-(2-(8,8-difluoro-2,4-dioxo-1,3-diazaspiro[4.5]decan-3-yl)acetyl)-1,3-dimethyl-1H-pyrrol-2-yl)benzonitrile;

3-(2-(4-(1H-pyrrolo[2,3-c]pyridin-4-yl)phenyl)-2-oxoethyl)-8,8-difluoro-1,3-diazaspiro[4.5]decane-2,4-dione;

8,8-difluoro-3-(2-(3-fluoro-4-(quinolin-8-yl)phenyl)-2-oxoethyl)-1,3-diazaspiro[4.5]decane-2,4-dione;

3-(5-(2-(8,8-difluoro-2,4-dioxo-1,3-diazaspiro[4.5]decan-3-yl)acetyl)-1-methyl-1H-pyrrol-2-yl)benzonitrile;

3-(5-(2-(8,8-difluoro-2,4-dioxo-1,3-diazaspiro[4.5]decan-3-yl)acetyl)-3-methylthiophen-2-yl)benzonitrile;

8,8-difluoro-3-(2-(4-(2-(2-hydroxyethoxy)pyridin-3-yl)phenyl)-2-oxoethyl)-1,3-diazaspiro[4.5]decane-2,4-dione;

8,8-difluoro-3-(2-(5-(3-fluorophenyl)-1,4-dimethyl-1H-pyrrol-2-yl)-2-oxoethyl)-1,3-diazaspiro[4.5]decane-2,4-dione;

3-(2-(5-(3-chlorophenyl)-1,4-dimethyl-1H-pyrrol-2-yl)-2-oxoethyl)-8,8-difluoro-1,3-diazaspiro[4.5]decane-2,4-dione;

3-(5-(2-(8,8-difluoro-2,4-dioxo-1,3-diazaspiro[4.5]decan-3-yl)acetyl)-1,3-dimethyl-1H-pyrrol-2-yl)benzamide;

8,8-difluoro-3-(2-(5-(2-fluorophenyl)-1,4-dimethyl-1H-pyrrol-2-yl)-2-oxoethyl)-1,3-diazaspiro[4.5]decane-2,4-dione;

3-(2-(4-(1H-pyrazolo[3,4-b]pyridin-4-yl)phenyl)-2-oxoethyl)-8,8-difluoro-1,3-diazaspiro[4.5]decane-2,4-dione;

3-(2-(4-(1H-pyrazolo[4,3-c]pyridin-4-yl)phenyl)-2-oxoethyl)-8,8-difluoro-1,3-diazaspiro[4.5]decane-2,4-dione;

3-(2-(4-(1H-indazol-1-yl)phenyl)-2-oxoethyl)-8,8-difluoro-1,3-diazaspiro[4.5]decane-2,4-dione;

8,8-difluoro-3-(2-(5-(3-fluorophenyl)-1-methyl-1H-imidazol-2-yl)-2-oxoethyl)-1,3-diazaspiro[4.5]decane-2,4-dione;

8,8-difluoro-3-(2-(4-(2-methyl-3H-imidazo[4,5-b]pyridin-3-yl)phenyl)-2-oxoethyl)-1,3-diazaspiro[4.5]decane-2,4-dione;

8,8-difluoro-3-(2-oxo-2-(4-(pyridin-2-yloxy)phenyl)ethyl)-1,3-diazaspiro[4.5]decane-2,4-dione;

3-(2-(5-(3,5-difluorophenyl)-1,4-dimethyl-1H-pyrrol-2-yl)-2-oxoethyl)-8,8-difluoro-1,3-diazaspiro[4.5]decane-2,4-dione;

8,8-difluoro 3 (2-(2'-ethyl-[3,3'-bipyridin]-6-yl)-2-oxoethyl)-1,3-diazaspiro[4.5]decane-2,4-dione;

3-(2-(4-(1H-pyrazolo[3,4-d]pyrimidin-4-yl)phenyl)-2-oxoethyl)-8,8-difluoro-1,3-diazaspiro[4.5]decane-2,4-dione;

3-(2-(6-(1H-pyrrolo[2,3-c]pyridin-4-yl)pyridin-3-yl)-2-oxoethyl)-8,8-difluoro-1,3-diazaspiro[4.5]decane-2,4-dione;

8,8-difluoro-3-(2-(4-(3-(2-hydroxyethoxy)pyrazin-2-yl)phenyl)-2-oxoethyl)-1,3-diazaspiro[4.5]decane-2,4-dione;

8,8-difluoro-3-(2-oxo-2-(4-(phthalazin-1-yl)phenyl)ethyl)-1,3-diazaspiro[4.5]decane-2,4-dione;

3-(2-(4-(3H-imidazo[4,5-b]pyridin-3-yl)phenyl)-2-oxoethyl)-8,8-difluoro-1,3-diazaspiro[4.5]decane-2,4-dione;

3-(2-(2-(8,8-difluoro-2,4-dioxo-1,3-diazaspiro[4.5]decan-3-yl)acetyl)-4-methylthiazol-5-yl)benzonitrile;

3-(2-(1,4-dimethyl-5-phenyl-1H-imidazol-2-yl)-2-oxoethyl)-8,8-difluoro-1,3-diazaspiro[4.5]decane-2,4-dione;

8,8-difluoro-3-(2-(5-(3-fluorophenyl)-1,4-dimethyl-1H-imidazol-2-yl)-2-oxoethyl)-1,3-diazaspiro[4.5]decane-2,4-done;

3-(2-(2-(8,8-difluoro-2,4-dioxo-1,3-diazaspiro[4.5]decan-3-yl)acetyl)-1,4-dimethyl-1H-imidazol-5-yl)benzonitrile;

8,8-difluoro-3-(2-(5-(isoquinolin-8-yl)-1,4-dimethyl-1H-imidazol-2-yl)-2-oxoethyl)-1,3-diazaspiro[4.5]decane-2,4-dione;

8,8-difluoro-3-(2-(5-(2-(hydroxymethyl)phenyl)-1,4-dimethyl-1H-imidazol-2-yl)-2-oxoethyl)-1,3-diazaspiro[4.5]decane-2,4-dione;

8,8-difluoro-3-(2-(4-(2-(hydroxymethyl)-1H-benzo[d]imidazol-1-yl)phenyl)-2-oxoethyl)-1,3-diazaspiro[4.5]decane-2,4-dione;

8,8-difluoro-3-(2-(5-(3-fluorophenyl)-1,4-dimethyl-1H-pyrrol-3-yl)-2-oxoethyl)-1,3-diazaspiro[4.5]decane-2,4-dione;

3-(4-(2-(8,8-difluoro-2,4-dioxo-1,3-diazaspiro[4.5]decan-3-yl)acetyl)-1,3-dimethyl-1H-pyrrol-2-yl)benzonitrile;

3-(2-(5-(1H-benzo[d]imidazol-1-yl)pyrazin-2-yl)-2-oxoethyl)-4)-8,8-difluoro-1,3-diazaspiro[4.5]decane-2,4-dione;

3-(2-(4-(2,7-naphthyridin-1-yl)phenyl)-2-oxoethyl)-8,8-difluoro-1,3-diazaspiro[4.5]decane-2,4-dione;

8,8-difluoro-3-(2-oxo-2-(4-(2-oxo-2,3-dihydro-1H-benzo[d]imidazol-1-yl)phenyl)ethyl), 3-diazaspiro[4.5]decane-2,4-dione;

8,8-difluoro-3-(2-(5-(2-(hydroxymethyl)phenyl)pyrazin-2-yl)-2-oxoethyl)-1,3-diazaspiro[4.5]decane-2,4-dione;

8,8-difluoro-3(2-(5-(4-methoxypyridin-3-yl)pyrazin-2-yl)-2-oxoethyl)-1,3-diazaspiro[4.5]decane-2,4-dione;

3-(5-(2-(8,8-difluoro-2,4-dioxo-1,3-diazaspiro[4.5]decan-3-yl)acetyl)-2,4-dimethylthiophen-3-yl)benzamide;

3-(2-(5-(3,5-difluorophenyl)-1,4-dimethyl-1H-imidazol-2-yl)-2-oxoethyl)-8,8-difluoro-1,3-diazaspiro[4.5]decane-2,4-dione;

8,8-difluoro-3-(2-oxo-2-(4-(pyridazin-3-yloxy)phenyl)ethyl-1,3-diazaspiro[4.5]decane-2,4-dione;

8,8-difluoro-3-(2-oxo-2-(4-(2-oxo-1H-imidazo[4,5-b]pyridin-3(2H)-yl)phenyl)ethyl)-1,3-diazaspiro[4.5]decane-2,4-dione;

3-(2-(5-(3,5-difluorophenyl)methylthiazol-2-yl)-2-oxoethyl)-8,8-difluoro-1,3-diazaspiro[4.5]decane-2,4-dione;

4'-(2-(8,8-difluoro-2,4-dioxo-1,3-diazaspiro[4.5]decan-3-yl)acetyl)-2'-methoxy-[1,1'-biphenyl]-2-carbonitrile;

2-(4-(2-(8,8-difluoro-2,4-dioxo-1,3-diazaspiro[4.5]decan-3-yl)acetyl)phenoxy)nicotinonitrile;

3-(2-(4-((3-chloropyridin-2-yl)oxy)phenyl)-2-oxoethyl)-8,8-difluoro-1,3-diazaspiro[4.5]decane-2,4-dione;

8,8-difluoro 3-(2-(4-(3-(hydroxymethyl)pyridin-2-yl)phenyl)-2-oxoethyl)-1,3-diazaspiro[4.5]decane-2,4-dione;

3-(2-(2'-(aminomethyl)-[1,1'-biphenyl]-4-yl)-2-oxoethyl)-8,8-difluoro-1,3-diazaspiro[4.5]decane-2,4-dione;

8,8-difluoro-3-(2-oxo-2-(6-(quinolin-8-yl)pyridin-3-yl)ethyl)-1,3-diazaspiro[4.5]decane-2,4-dione;

8,8-difluoro-3-(2-(5-(2-methylpyridin-3-yl)pyrazin-2-yl)-2-oxoethyl)-1,3-diazaspiro[4.5]decane-2,4-dione;

3-(2-(4-(2,7-naphthyridin-1-yl)phenyl)-2-oxoethyl)-8,8-difluoro-1-oxa-3-azaspiro[4.5]decane 2,4-dione;

3-(4-(2-(8,8-difluoro-2,4-dioxo-1,3-diazaspiro[4.5]decan-3-yl)acetylphenyl)-2-methy-3H-imidazo[4,5-b]pyridine-5-carbonitrile;

8,8-difluoro-3-(2-oxo-2-(4-(2-oxobenzo[d]oxazol-3(2H-yl)phenyl)ethyl)-1,3-diazaspiro[4.5]decane-2,4-dione;

3-(2-(4-(2,5-dimethyl-3H-imidazo[4,5-b]pyridin-3-yl)phenyl)-2-oxoethyl)-8,8-difluoro-1,3-diazaspiro[4.5]decane-2,4-dione;

8,8-difluoro-3-(2-(5-(2-methyl-1H-benzo[d]imidazol-1-yl)pyrazin-2-yl)-2-oxoethyl)-1,3-diazaspiro[4.5]decane-2,4-dione;

8,8-difluoro-3-(2-(4-(2-methoxy-5-methyl-3H-imidazo[4,5-b]pyridin-3-yl)phenyl)-2-oxoethyl)-4)-1,3-diazaspiro[4.5]decane-2,4-dione;

8,8-difluoro-3-(2-(4-(5-methyl-2-trifluoromethyl)-3H-imidazo[4,5-b]pyridin-3-yl)phenyl)-2-oxoethyl)-1,3-diazaspiro[4.5]decane-2,4-dione;

3-(2-(4-(2-(difluoromethyl)-5-methyl-3H-imidazo[4,5-b]
pyridin-3-yl)phenyl)-2-oxoethyl)-8,8-difluoro-1,3-diaz-
aspiro[4.5]decane-2,4-dione;
8,8-difluoro-3-(2-(4-(5-methyl-2-oxo-1H-azo[4,5-b]pyri-
din-3(2H)-yl)phenyl)-2-oxoethyl)-1,3-diazaspiro[4.5]de-
cane-2,4-dione;
6-(4-(2-(8,8-difluoro-2,4-dioxo-1,3-diazaspiro[4.5]decan-3-
yl)acetyl)phenoxy)picolinonitrile;
8,8-difluoro-3-(2-(4-(5-methyl-3H-imidazo[4,5-b]pyridin-
3-yl)phenyl)-2-oxoethyl)-1,3-diazaspiro[4.5]decane-2,4-
dione;
8,8-difluoro-3-(2-(4-(3-methoxypyrazin-2-yl)phenyl)-2-
oxoethyl)-1,3-diazaspiro[4.5]decane-2,4-dione;
3-(4-(2-(8,8-difluoro-2,4-dioxo-1,3-diazaspiro[4.5]decan-3-
yl)acetyl)-3-fluorophenyl)pyrazine-2-carbonitrile;
8,8-difluoro-3-(2-(4-(imidazo[1,2-b]pyridazin-3-yl)phe-
nyl)-2-oxoethyl)-1,3-diazaspiro[4.5]decane-2,4-dione;
8,8-difluoro-3-(2-(2'-(2-hydroxyethyl)-[1,1'-biphenyl]-4-
yl)-2-oxoethyl)-1,3-diazaspiro[4.5]decane-2,4-dione;
2-(4'-(2-(8,8-difluoro-2,4-dioxo-1,3-diazaspiro[4.5]decan-
3-yl)acetyl)-[1,1'-biphenyl]-2-yl)acetonitrile;
3-(2-(4-(1H-imidazo[4,5-b]pyrazin-1-yl)phenyl)-2-oxo-
ethyl)-8,8-difluoro-1,3-diazaspiro[4.5]decane-2,4-dione;
8,8-difluoro-3-(2-(4-(4-methylpyridazin-3-yl)phenyl)-2-
oxoethyl)-1-oxa-3-azaspiro[4.5]decane-2,4-dione;
3-(4-(2-(8,8-difluoro-2,4-dioxo-1,3-diazaspiro[4.5]decan-3-
yl)acetyl)phenoxy)pyridazine-4-carbonitrile;
8,8-difluoro-3-(2-(4-(2-(hydroxymethyl)-5-methy-3H-imi-
dazo[4,5-b]pyridin-3-yl)phenyl)-2-oxoethyl)-1,3-diaz-
aspiro[4.5]decane-2,4-dione;
8,8-difluoro-3-(2-oxo-2-(4-(pyrazolo[1,5-a]pyrimidin-3-yl)
phenyl)ethyl)-1,3-diazaspiro[4.5]decane-2,4-dione;
4-(4-(2-(8,8-difluoro-2,4-dioxo-1,3-diazaspiro[4.5]decan-3-
yl)acetyl)phenyl)nicotinonitrile;
8,8-difluoro-3-(2-(2-fluoro-4-(4-methylpyridazin-3-yl)phe-
nyl)-2-oxoethyl)-1,3-diazaspiro[4.5]decane-2,4-dione;
8,8-difluoro-3-(2-(2-fluoro-4-(3-(hydroxymethyl)pyrazin-
2-yl)phenyl)-2-oxoethyl)-1,3-diazaspiro[4.5]decane-2,4-
dione; and
2-(4-(2-(8-difluoro-2,4-dioxo-1,3-diazaspiro[4.5]decan-3-
yl)acetyl)phenyl)nicotinonitrile
or a pharmaceutically acceptable salt thereof or a prodrug
thereof.
[5] a use of a compound described in any one of [1] to [4]
or a pharmaceutically acceptable salt thereof or a prodrug
thereof for the manufacture of a medicament for the treat-
ment of a condition or disorder mediated by TRPM8 recep-
tor antagonistic activity;
[6] a use as described in [5], wherein the condition or
disorder is one or more of inflammatory, pain and urological
diseases or disorders, including chronic pain; neuropathic
pain including cold allodynia and diabetic neuropathy; post-
operative pain; osteoarthritis; rheumatoid arthritic pain; can-
cer pain; neuralgia; neuropathies; algesia; dentin hypersen-
sitivity; nerve injury; migraine; cluster and tension
headaches; ischaemia; irritable bowel syndrome; Raynaud's
syndrome; neurodegeneration; fibromyalgia; stroke; itch;
psychiatric disorders including anxiety and depression;
inflammatory disorders including asthma, chronic obstruc-
tive pulmonary, airways disease including COPD, pulmo-
nary hypertension; anxiety including other stress-related
disorders; and urological diseases or disorders including
detrusor overactivity or overactive bladder, urinary inconti-
nence, neurogenic detrusor overactivity or detrusor hyper-
flexia, idiopathic detrusor overactivity or detrusor instabil-
ity, benign prostatic hyperplasia, and lower urinary tract
symptoms; and combinations thereof.

[7] a method for the treatment of a condition or disorder
mediated by TRPM8 receptor antagonistic activity in a
mammalian subject, including a human, which comprises
administering to a mammal in need of such treatment a
therapeutically effective amount of a compound described in
any one of [1] to [4] or a pharmaceutically acceptable salt
thereof or a prodrug thereof or a prodrug thereof;
[8] a method as described in [7], wherein the condition or
disorder is one or more of inflammatory, pain and urological
diseases or disorders, including chronic pain; neuropathic
pain including cold allodynia and diabetic neuropathy; post-
operative pain; osteoarthritis; rheumatoid arthritic pain; can-
cer pain; neuralgia; neuropathies; algesia; dentin hypersen-
sitivity; nerve injury; migraine; cluster and tension
headaches; ischaemia; irritable bowel syndrome; Raynaud's
syndrome; neurodegeneration; fibromyalgia; stroke; itch;
psychiatric disorders including anxiety and depression;
inflammatory disorders including asthma, chronic obstruc-
tive pulmonary, airways disease including COPD, pulmo-
nary hypertension; anxiety including other stress-related
disorders; and urological diseases or disorders including
detrusor overactivity or overactive bladder, urinary inconti-
nence, neurogenic detrusor overactivity or detrusor hyper-
flexia, idiopathic detrusor overactivity or detrusor instabil-
ity, benign prostatic hyperplasia, and lower urinary tract
symptoms; and combinations thereof.
[9] a pharmaceutical composition comprising a compound
or a pharmaceutically acceptable salt thereof or a prodrug
thereof, as described in any one of [1] to [4], and a
pharmaceutically acceptable carrier;
[10] a pharmaceutical composition as described in [9],
further comprising another pharmacologically active agent;
[11] a compound described in any one of [1] to [4] or a
pharmaceutically acceptable salt thereof or a prodrug thereof
for use in the treatment of a condition or disorder mediated
by TRPM8 receptor antagonistic activity; and
[12] a process for preparing a pharmaceutical composition,
wherein the process comprising mixing a compound
described in any one of [1] to [4] or a pharmaceutically
acceptable salt thereof or a prodrug thereof and a pharma-
ceutically acceptable carrier or excipient.

Examples of conditions or disorders mediated by TRPM8
receptor activity include, but are not limited to, TRPM8
related diseases.

Advantageous Effects of Invention

The compounds of the present invention show the
TRPM8 receptor antagonistic activity. The compounds of
the present invention may show less toxicity, good absorp-
tion, distribution, good solubility, less protein binding affin-
ity other than TRPM8 receptor, less drug-drug interaction,
and good metabolic stability.

DESCRIPTION OF EMBODIMENTS

As used herein, the term "alkyl" as a group or part of a
group e.g. alkoxy or hydroxyalkyl refers to a straight or
branched alkyl group in all isomeric forms. The term "$C_1$-$C_4$
alkyl" refers to an alkyl group, as defined above, containing
at least 1, and at most 4 carbon atoms. Examples of such
alkyl groups include methyl, ethyl, propyl, iso-propyl, n-bu-
tyl, iso-butyl, sec-butyl, or tert-butyl. Examples of such
alkoxy groups include methoxy, ethoxy, propoxy, iso-
propoxy, butoxy, iso-butoxy, sec-butoxy and tert-butoxy.

The term "cycloalkyl", as used herein, means a mono- or bicyclic ring, but not limited to, cyclopropyl, cyclobutyl, cyclopentyl, cyclohexyl, cycloheptyl, norbornyl, and adamantyl groups and the like.

Then cyclopropylmethyl and cyclopentylmethyl are as follows:

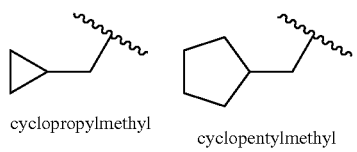

{Chem. 2} cyclopropylmethyl    cyclopentylmethyl

The term "halogen" refers to fluorine (F), chlorine (Cl), bromine (Br), or iodine (I) and the term "halo" refers to the halogen: fluoro (—F), chloro (—Cl), bromo (—Br) and iodo (—I).

The term "haloalkyl", as used herein, means an alkyl radical which is substituted by halogen atom(s) as defined above including, but not limited to, fluoromethyl, difluoromethyl, trifluoromethyl, 2-fluoroethyl, 2,2-difluoroethyl, 2,2,2-trifluoroethyl, 2,2,2-trichloroethyl, 3-fluoropropyl, 4-fluorobutyl, chloromethyl, trichloromethyl, iodomethyl and bromomethyl groups and the like.

The term "haloalkoxy", as used herein, means haloalkyl-O—, including, but not limited to, fluoromethoxy, difluoromethoxy, trifluoromethoxy, 2-fluoroethoxy, 2,2-difluoroethoxy, 2,2,2-trifluoroethoxy, 2,2,2-trichloroethoxy, 3-fluoropropoxy, 4-fluorobutoxy, chloromethoxy, trichloromethoxy, iodomethoxy and bromomethoxy groups and the like.

The term "alkoxy", as used herein, means an O-alkyl group wherein "alkyl" is defined above.

The term "heterocyclyl", as used herein, means a saturated 3- to 16-membered ring which comprises one or more heteroatoms selected from nitrogen, oxygen and sulfur. For purposes of this invention, the heterocyclyl may be a monocyclic, bicyclic or tricyclic ring system, which may include fused, bridged or spiro ring systems. Examples of such heterocyclyl groups include azetidinyl, 1,4-dioxanyl, pyrrolidinyl, piperidinyl, piperazinyl, morpholinyl, tetrahydrofuranyl, thiomorpholinyl, tetrahydrothienyl, 2-oxo-pyrrolidinyl, 2-oxo-piperidinyl, 2-oxo-imidazolidinyl, 2-oxo-oxazolidinyl, quinuclidinyl, azabicyclo[3.2.1]octyl, 2-oxa-6-azaspiro[3.4]octyl and N-oxides thereof and S-oxides thereof.

The term "aryl", as used herein, means unsaturated and partially saturated 6- to 15-membered ring which consists of carbon atoms;

Examples of such unsaturated aryl include, but are not limited to, phenyl, naphthyl, indanyl, indenyl, 1,2,3,4-tetrahydronaphthyl, and 1,2-dihydronaphthyl.

The term "heteroaryl" as used herein, means 5- to 15-membered ring, preferably 6- to 15-membered ring, in which an aromatic heteroatom containing ring is fused to a non-aromatic ring, such as heterocyclyl ring or cycloalkyl ring, and also means 5- to 15-membered ring, preferably 6- to 15-membered ring, in which an aryl ring is fused to a non-aromatic heteroatom containing ring, such as heterocyclyl ring.

Namely, the term "heteroaryl" means the following;

1) unsaturated and partially saturated 5- to 15-membered ring, preferably 6- to 15-membered ring, which consists of carbon atoms and from one to five heteroatoms selected from nitrogen, phosphorus, oxygen and sulfur.

2) unsaturated and partially saturated 5- to 15-membered ring, preferably 6- to 15-membered ring, in which a non-aromatic ring, such as heterocyclyl ring or cycloalkyl ring, is fused to a heteroaryl defined above 3) unsaturated and partially saturated 5- to 15-membered ring, preferably 6- to 15-membered ring, in which an aryl ring is fused to a heterocyclyl ring.

Examples of such heteroaryl include, but are not limited to, thiophenyl, thiazolyl, isoxazolyl, pyrazolyl, tetrazolyl, (uranyl, pyrrolyl, imidazolyl, oxazolyl, isothiazolyl, triazolyl, thiadiazolyl, pyridyl, pyrimidyl, pyridazinyl, pyrazinyl, triazinyl, benzofuranyl, benzothiophenyl, benzotriazolyl, indolyl, indazolyl, benzoimidazolyl, pyrrolopyridyl, pyrrolopyrimidinyl, pyrazolopyridyl, pyrazolopyrimidinyl, imidazopyridinyl, furopyridyl, benzoisoxazolyl, imidazopyrazinyl, imidazopyridazinyl, imidazopyrimidinyl, quinolyl, isoquinolyl, quinazolinyl, phthalazinyl, quinoxalinyl, naphthyridinyl, pyridopyrimidinyl, and N-oxides thereof and S-oxides thereof.

Examples of such heteroaryl also include the heteroaryl ring radical consisting of the following rings.

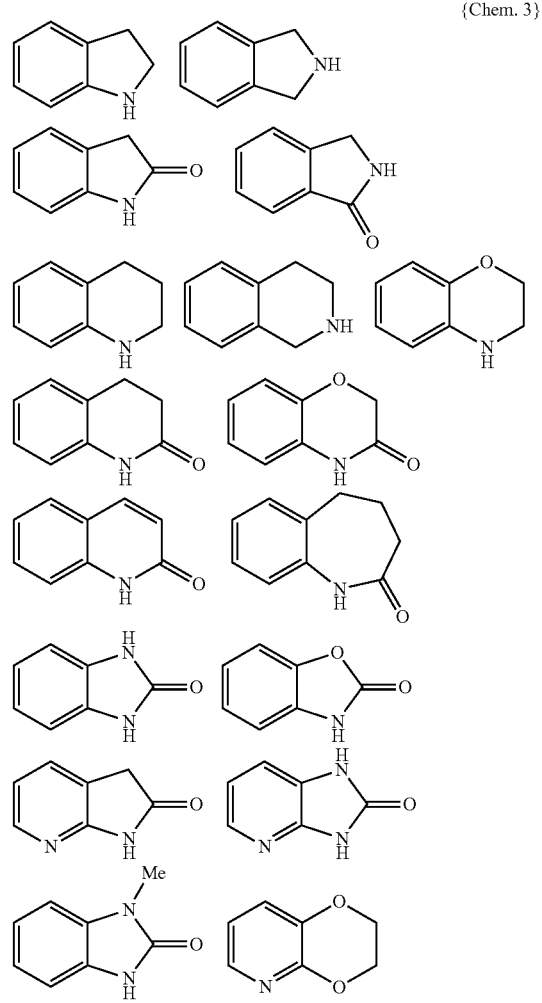

{Chem. 3}

The term "C$_0$", as used herein, means direct bond.

The substituents on the ring of the compound of the present invention may exist on the any atoms if it is chemically allowed.

The term "protecting group", as used herein, means a hydroxy or amino protecting group which is selected from typical hydroxy or amino protecting groups described in Protective Groups in Organic Synthesis Forth Edition edited by T. W. Greene et al. (John Wiley & Sons, 2006);

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

As used herein, the article "a" or "an" refers to both the singular and plural form of the object to which it refers unless indicated otherwise.

The symbol letter is written the corresponding English word in the present specification.

For example, the symbols α, β, and δ are written alpha, beta, and delta, respectively.

Included within the scope of the "compounds of the invention" are all salts, solvates, hydrates, complexes, polymorphs, prodrugs, radiolabeled derivatives, stereoisomers and optical isomers of the compounds of formula (I).

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci, 66, 1-19, 1977, such as acid addition salts formed with inorganic acids e.g. hydrochloric, hydrobromic, sulfuric, nitric or phosphoric acid; and organic acids e.g. succinic, maleic, formic, acetic, trifluoroacetic, propionic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases.

Also within the scope of the invention are so-called "prodrugs" of the compounds of formula (I). Thus certain derivatives of compounds of formula (I) which may have little or no pharmacological activity themselves, when administered into or onto the body, can be converted into compounds of formula (I) having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

Prodrugs in accordance with the invention, for example, can be produced by replacing appropriate functionalities present in the compounds of formula (I) with certain moieties known to those skilled in the art as 'pro-moieties' as described, for example, in Design of Prodrugs by H Bundgaard (Elsevier, 1985). Some examples of prodrugs in accordance with the invention include:

(i) where the compound of formula (I) contains an alcohol functionality (—OH), compounds wherein the hydroxy group is replaced with a moiety convertible in vivo into the hydroxy group. Said moiety convertible in vivo into the hydroxy group means a moiety transformable in vivo into a hydroxyl group by e.g. hydrolysis and/or by an enzyme, e.g. an esterase. Examples of said moiety include, but are not limited to, ester and ether groups which may be hydrolyzed easily in vivo. Preferred are the moieties replaced the hydrogen of hydroxy group with acyloxyalkyl, 1-(alkoxycarbonyloxy)alkyl, phthalidyl and acyloxyalkyloxycarbonyl such as pivaloyloxymethyloxycarbonyl.

(ii) where the compound of the formula (I) contains an amino group, an amide derivative prepared by reacting with a suitable acid halide or a suitable acid anhydride is exemplified as a prodrug. A particularly preferred amide derivative as a prodrug is —NHCO(CH$_2$)$_2$OCH$_3$, —NHCOCH(NH$_2$)CH$_3$ or the like.

Further examples of replacement groups in accordance with the foregoing examples and examples of other prodrug types may be found in the aforementioned references.

The compounds of formula (I), salts thereof and prodrugs thereof may be prepared in crystalline or non-crystalline form, and, if crystalline, may optionally be hydrated or solvated. This invention includes within its scope stoichiometric hydrates or solvates as well as compounds containing variable amounts of water and/or solvent.

Salts and solvates having non-pharmaceutically acceptable counter-ions or associated solvents are within the scope of the present invention, for example, for use as intermediates in the preparation of other compounds of formula (I) and their pharmaceutically acceptable salts.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of formula (I), there may be some chiral carbon atoms. In such cases, compounds of formula (I) exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$c, $^{18}$F, $^{123}$I and $^{125}$I. Compounds of the invention that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the invention can generally be prepared by carrying out the procedures disclosed in the Schemes and/or in the Examples below, then substituting a readily available isotopically labeled reagent for a non-isotopically labeled reagent.

The potencies and efficacies of the compounds of this invention for TRPM8 can be determined by reporter assay performed on the human cloned receptor as described herein. Compounds of formula (I) have demonstrated antagonistic activity at the TRPM8 receptor, using the functional assay described herein.

Compounds of formula (I) and pharmaceutically acceptable salts thereof are therefore of use in the treatment of conditions or disorders which are mediated via the TRPM8 receptor. In particular the compounds of formula (I) and pharmaceutically acceptable salts thereof are of use in the treatment of a wide range of diseases, syndromes, and disorders, in particular for the treatment of inflammatory, pain and urological diseases or disorders, such as wherein the condition or disorder is one or more of inflammatory, pain and urological diseases or disorders, including chronic pain; neuropathic pain including cold allodynia and diabetic neuropathy; postoperative pain; osteoarthritis; rheumatoid arthritic pain; cancer pain; neuralgia; neuropathies; algesia; dentin hypersensitivity; nerve injury; migraine; cluster and tension headaches; ischaemia; irritable bowel syndrome; Raynaud's syndrome; neurodegeneration; fibromyalgia; stroke; itch; psychiatric disorders including anxiety and depression; inflammatory disorders including asthma, chronic obstructive pulmonary, airways disease including COPD, pulmonary hypertension; anxiety including other stress-related disorders; and urological diseases or disorders including detrusor overactivity or overactive bladder, urinary incontinence, neurogenic detrusor overactivity or detrusor hyperflexia, idiopathic detrusor overactivity or detrusor instability, benign prostatic hyperplasia, and lower urinary tract symptoms; and combinations thereof.

Activities of the compound (I) for each diseases, syndromes, and disorders described above can be confirmed in the suitable model known to skilled in the arts. For example, activities of compounds of formula (I) for neuropathic pain have been confirmed in chronic constriction injury (CCI)-induced model, such as cold allodynia and static allodynia model.

It is to be understood that "treatment" as used herein includes prophylaxis as well as alleviation of established symptoms as described above.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administered compositions are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycolate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilising a compound of formula (I) or pharmaceutically acceptable salt thereof and a sterile vehicle. Formulations for injection may be presented in unit dosage form e.g. in ampoules or in multi-dose, utilising a compound of formula (I) or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formula (I) or pharmaceutically acceptable salts thereof may also be formulated in rectal compositions such as suppositories or retention enemas, e.g. containing conventional suppository bases such as cocoa butter or other glycerides.

The compounds of formula (I) or pharmaceutically acceptable salts may also be formulated as depot preparations. Such long acting formulations may be administered by implantation (for example subcutaneously or intramuscularly) or by intramuscular injection. Thus, for example, the compounds of formula (I) or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds formula (I) or pharmaceutically acceptable salts thereof may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose). The compounds of formula (I) and pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

A TRPM8 antagonist may be usefully combined with another pharmacologically active compound, or with two or more other pharmacologically active compounds, particularly in the treatment of inflammatory, pain and urological diseases or disorders. For example, a TRPM8 antagonist, particularly a compound of formula (I), or a pharmaceutically acceptable salt or solvate thereof, as defined above, may be administered simultaneously, sequentially or separately in combination with one or more agents selected from:

- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butabital, mephobarbital, metharbital, methohexital, pentobarbital, phenobartital, secobarbital, talbutal, thiamylal or thiopental;
- a benzodiazepine having a sedative action, e.g. chlordiazepoxide, clorazepate, diazepam, flurazepam, lorazepam, oxazepam, temazepam or triazolam;
- an H₁ antagonist having a sedative action, e.g. diphenhydramine, pyrilamine, promethazine, chlorpheniramine or chlorcyclizine;
- a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphrenadine;
- an NMDA receptor antagonist, e.g. dextromethorphan ((+)-3-methoxy-N-m ethylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex(registered trademark), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl}-3,4-dihydro-2(1H)-quinolinone;
- an alpha-adrenergic, e.g. doxazosin, tamsulosin, clonidine, guanfacine, dexmedetomidine, modafinil, or 4-amino-6,7-dimethoxy-2-(5-methanesulfonamido-1,2,3,4-tetrahydroisoquinol-2-yl)-5-(2-pyridyl)quinazoline;
- a tricyclic antidepressant, e.g. desipramine, imipramine, amitriptyline or nortriptyline;
- an anticonvulsant, e.g. carbamazepine, lamotrigine, topiramate or valproate;
- a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6,13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869, aprepitant), lanepitant, dapitant or 3-[[2-methoxy-5-(trifluoromethoxy)phenyl]methylamino]-2-phenylpiperidine (2S,3S);
- a muscarinic antagonist, e.g. oxybutynin, tolterodine, propiverine, trospium chloride, darifenacin, solifenacin, temiverine and ipratropium;
- a COX-2 selective inhibitor, e.g. celecoxib, rofecoxib, parecoxib, valdecoxib, deracoxib, etoricoxib, or lumiracoxib;
- a coal-tar analgesic, in particular paracetamol;
- a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin; iloperidone, perospirone, raclopride, zotepine, bifeprunox, asenapine, lurasidone, amisulpride, balaperidone, palindore, eplivanserin, osanetant, rimonabant, meclinertant, Miraxion(registered trademark) or sarizotan;
- a vanilloid receptor agonist (e.g. resiniferatoxin) or antagonist (e.g. capsazepine);
- a transient receptor potential cation channel subtype (V1, V2, V3, V4, M8, M2, A1) agonist or antagonist;
- a beta-adrenergic such as propranolol;
- a local anaesthetic such as mexiletine;
- a corticosteroid such as dexamethasone;
- a 5-HT receptor agonist or antagonist, particularly a 5-HT1B/1D agonist such as eletriptan, sumatriptan, naratriptan, zolmitriptan or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol(registered trademark);

a PDEV inhibitor, such as 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)pyrazino[2',1':6,1]pyrido[3,4-b]indole-1,4-dione (IC-351 or tadalafil), 2-[2-ethoxy-5-(4-ethyl-piperazin-1-yl-sulphonyl)phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (3-(aminomethyl)-bicyclo[3.2.0]hept-3-yl)acetic acid, (3S,5R)-3-(aminomethyl)-5-methylheptanoic acid, (3S,5R)-3-amino-5-methylheptanoic acid, (3S,5R)-3-amino-5-methyloctanoic acid, (2S,4S)-4-(3-chlorophenoxy)proline, (2S,4S)-4-(3-fluorobenzyl)proline, [(1R,5R,6S)-6-(aminomethyl)bicyclo[3.2.0]hept-6-yl]acetic acid, 3-((1-(aminomethyl)cyclohexyl)methyl)-4H-[1,2,4]oxadiazol-5-one, C-[1-((1H-tetrazol-5-yl)methyl)cycloheptyl]methylamine, (3S,4S)-(1-(aminomethyl)-3,4-dimethylcyclopentyl) acetic acid, (3S,5R)-3-(aminomethyl)-5-methyloctanoic acid, (3S,5R)-3-amino-5-methylnonanoic acid, (3S,5R)-3-amino-5-methyloctanoic acid, (3R,4R,5R)-3-amino-4,5-dimethylheptanoic acid, and (3R,4R,5R)-3-amino-4,5-dimethyloctanoic acid;

a cannabinoid;

a metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazapine, oxaprotiline, fezolamine, tomoxetine, mianserin, bupropion, bupropron metabolite hydroxybupropion, nom ifensine and viloxazine (Vivalan (registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl]benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl)-1,4-benzoquinone (CV-6504);

a sodium channel blocker, such as lidocaine;

a calcium channel blocker, such as ziconotide, zonisamide, mibefradil;

a 5-HT3 antagonist, such as ondansetron;

a chemotherapy drug such as oxaliplatin, 5-fluorouracil, leukovorin, paclitaxel;

a calcitonin gene related peptide (CGRP) antagonist;

a bradykinin (BK1 and BK2) antagonist;

a voltage gated sodium dependent channel blocker ($Na_{v1.3}$, $Na_{v1.7}$, $Na_{v1.8}$);

a voltage dependent calcium channel blocker (N-type, T-type);

a P2x (ion channel type ATP receptor) antagonist;

an acid-sensing ion channel (ASIC1a, ASIC3) antagonist;

an angiotensin AT2 antagonist;

a chemokine CCR2B receptor antagonist;

a cathepsin (B, S, K) inhibitor;

a sigma1 receptor agonist or antagonist;

a calcium/magnesium a goshajinkigan and the pharmaceutically acceptable salts and solvates thereof.

Such combinations offer significant advantages, including synergistic activity, in therapy.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors.

A therapeutically effective amount of a compound of formula (I) or a pharmaceutical composition thereof includes a dose range from about 0.05 mg to about 3000 mg, in particular from about 1 mg to about 1000 mg or, more particularly, from about 10 mg to about 500 mg of active ingredient in a regimen of about once a day or more than once a day, for example two, three or four times a day for an average (70 kg) human; although, it is apparent to one skilled in the art that the therapeutically effective amount for active compounds of the invention will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of the inventive compound as the active ingredient.

Advantageously, a compound of formula (I) may be administered in a single daily dose, or the total daily dosage may be administered in divided doses of two, three and four times daily.

Optimal dosages of a compound of formula (I) to be administered may be readily determined and will vary with the particular compound used, the mode of administration, the strength of the preparation, and the advancement of the disease, syndrome, condition, or disorder. In addition, factors associated with the particular subject being treated, including subject age, weight, diet and time of administration, will result in the need to adjust the dose to achieve an appropriate therapeutic level.

The above dosages are thus exemplary of the average case. There can be, of course, individual instances wherein higher or lower dosage ranges are merited, and such are within the scope of this invention.

Compounds of formula (I) may be administered in any of the foregoing compositions and dosage regimens or by means of those compositions and dosage regimens established in the art whenever use of a compound of formula (I) is required for a subject in need thereof.

As antagonists of the TRPM8 ion channel, the compounds of formula (I) are useful in methods for treating and preventing a disease, a syndrome, a condition, or a disorder in a subject, including an animal, a mammal and a human in which the disease, the syndrome, the condition, or the disorder is affected by the modulation of TRPM8 receptors. Such methods comprise, consist of, and consist essentially of administering to a subject, including an animal, a mammal, and a human in need of such treatment or prevention a therapeutically effective amount of a compound, salt, or solvate of formula (I). In particular, the compounds of formula (I) are useful for preventing or treating pain, or diseases, syndromes, conditions, or disorders causing such pain, or pulmonary or vascular dysfunction. More particularly, the compounds of formula (I) are useful for preventing or treating inflammatory pain, inflammatory hypersensitivity conditions, neuropathic pain, anxiety, depression, and cardiovascular disease aggravated by cold, including peripheral vascular disease, vascular hypertension, pulmonary hypertension, Raynaud's disease, and coronary artery disease, by administering to a subject in need thereof a therapeutically effective amount of a compound of formula (I).

Examples of inflammatory pain include pain due to a disease, condition, syndrome, disorder, or a pain state including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyrosis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, Raynaud's syndrome, cholecystitis, pancreatitis, postmastectomy pain syndrome, menstrual pain, endometriosis, sinus headache, tension headache, or arachnoiditis.

One type of inflammatory pain is inflammatory hyperalgesia, which can be further distinguished as inflammatory somatic hyperalgesia or inflammatory visceral hyperalgesia. Inflammatory somatic hyperalgesia can be characterized by the presence of an inflammatory hyperalgesic state in which a hypersensitivity to thermal, mechanical and/or chemical stimuli exists. Inflammatory visceral hyperalgesia can also be characterized by the presence of an inflammatory hyperalgesic state, in which an enhanced visceral irritability exists.

Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, Raynaud's syndrome, inflammatory bowel diseases including Crohn's Disease or ulcerative colitis.

One embodiment of the present invention is directed to a method for treating inflammatory somatic hyperalgesia in which a hypersensitivity to thermal, mechanical and/or chemical stimuli exists, comprising the step of administering to a mammal in need of such treatment a therapeutically effective amount of a compound, salt or solvate of formula (I).

A further embodiment of the present invention is directed to a method for treating inflammatory visceral hyperalgesia in which a enhanced visceral irritability exists, comprising, consisting of, and/or consisting essentially of the step of administering to a subject in need of such treatment a therapeutically effective amount of a compound, salt or solvate of formula (I).

A further embodiment of the present invention is directed to a method for treating neuropathic cold allodynia in which a hypersensitivity to a cooling stimuli exists, comprising, consisting of, and/or consisting essentially of the step of administering to a subject in need of such treatment a therapeutically effective amount of a compound, salt or solvate of formula (I).

Examples of an inflammatory hypersensitivity condition include urinary incontinence, benign prostatic hypertrophy, cough, asthma, rhinitis and nasal hypersensitivity, itch, contact dermatitis and/or dermal allergy, and chronic obstructive pulmonary disease.

Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, neuralgias (trigeminal neuralgia, glossopharyngeal neuralgia, postherpetic neuralgia and causalgia), lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paraesthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngeal neuralgia, migrainous neuralgia, idiopathic neuralgia, intercostal neuralgia, mammary neuralgia, Morton's neuralgia, nasociliary neuralgia, occipital neuralgia, red neuralgia, Sluder's neuralgia, sphenopalatine neuralgia, supraorbital neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain or neuralgia, pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

Examples of anxiety include social anxiety, post traumatic stress disorder, phobias, social phobia, special phobias, panic disorder, obsessive compulsive disorder, acute stress disorder, separation anxiety disorder, and generalized anxiety disorder.

Examples of depression include major depression, bipolar disorder, seasonal affective disorder, post natal depression, manic depression, and bipolar depression.

General Synthesis

Throughout the instant application, the following abbreviations are used with the following meanings:
AcOH: Acetic acid
aq.: aqueous
BINAP: 2,2'-Bis(diphenylphosphino)-1,1'-binaphthyl
tBuXPhos: 2-Di-tert-Butylphosphino-2',4',6'-triisopropylbiphenyl
CDI: Carbonyldiimidazole
$Cs_2CO_3$: Cesium carbonate
DBN: 1,5-diazabicyclo[4.3.0]non-5-ene
DavePhos: 2-Dicyclohexylphosphino-2'-(N,N-dimethylamino)biphenyl
DABCO: 1,4-diazabicyclo[2.2.2]octane
DBU: 1,8-Diazabicyclo[5.4.0]undec-7-ene
DCM: Dichloromethane
DEAD: Diethyl azodicarboxylate
DIPEA: Diisopropylethylamine
DMF: N,N-Dimethylformamide
DMA: N,N-Dimethylacetamide
DME: 1,2-Dimethoxyethane
DMSO: Dimethyl sulfoxide
Dess-Martin Periodinane: 1,1,1-Tris(acetyloxy)-1,1-dihydro-1,2-benziodoxol-3-(1H)-one
ESI: Electrospray Ionization
Et: Ethyl
EtOAc: Ethyl acetate
EtOH: Ethanol
eq.: equivalent
HPLC: High-Performance Liquid Chromatography
INT: Intermediate
IPE: Isopropyl ether
$K_2CO_3$: Potassium carbonate
$K_3PO_4$: Potassium phosphate
KO t-Bu: Potassium tert-butoxide
LC: Liquid Chromatography
LDA: Lithium diisopropylamide
LG: Leaving Group
tR: Retention Time
Me: Methyl
MeCN: Acetonitrile
MeOH: Methanol
min: minute
$NaHCO_3$: Sodium Bicarbonate
$Na_2SO_4$: Sodium Sulfate
$Na_2S_2O_3$: Sodium thiosulfate
NaO t-Bu: Sodium tert-butoxide
MHz: Megahertz
mp: melting point
MS: Mass Spectrometry
NMP: N-methyl-2-pyrrolidone
NMR: Nuclear Magnetic Resonance
Oxone (Registered Trademark): Potassium peroxymonosulfate
PG: Protecting Group
$Pd_2(dba)_3$: Tris(dibenzylideneacetone)dipalladium(0)
$Pd(OAc)_2$: Palladium (II) acetate
$PdCl_2(dppf)$ $CH_2Cl_2$: [1, 1'-Bis(diphenylphosphino)ferrocene]dichloropalladium (II), Dichloromethane Adduct
$PdCl_2(Amphos)_2$: Bis(di-tert-butyl(4-dimethylaminophenyl)phosphine)dichloropalladium(II)
PEPPSI(Trademark)-IPr: [1,3-Bis(2,6-Diisopropylphenyl)imidazol-2-ylidene](3-chloropyridyl)palladium(II) dichloride
$Pd(PPh_3)_4$: Tetrakis(triphenylphosphine)palladium (0)
$POCl_3$: Phosphorus(V) oxychloride
quant.: quantitative
rt: room temperature
sat.: saturated
TFA: Triethylamine
TFA: Trifluoroacetic Acid
THF: Tetrahydrofuran
THP: 2-Tetrahydropyranyl
p-TsOH: p-Toluenesulfonic acid
XPhos: 2-Dicyclohexylphosphino-2',4',6'-triisopropylbiphenyl
Xantphos: 4,5-Bis(diphenylphosphino)-9,9-dimethylxanthene The term of "base" is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, triethylamine, diisopropylethylamine, DBU, DBN, DABCO, pyridine, lutidine, colidine, sodium carbonate, sodium hydrogencarbonate, sodium hydroxide, potassium carbonate, potassium hydrogencarbonate, potassium hydroxide, potassium phosphate, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as DCM, chloroform, carbon tetrachloride, and dichloroethane; ethers, such as diethyl ether, diisopropyl ether, THF, and dioxane; aromatic hydrocarbons, such as benzene, toluene and nitrobenzene; amides, such as, DMF, DMA, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMA, DMSO, THF, diethylether, diisopropylether, dimethoxyethane, acetonitrile, DCM, dichloroethane and chloroform are preferred.

EXAMPLES

The invention is illustrated in the following non-limiting examples in which, unless stated otherwise: all reagents are commercially available, all operations are carried out at room or ambient temperature, that is, in the range of about 18 to 25° C.; evaporation of solvent is carried out using a rotary evaporator under reduced pressure with a bath temperature of up to about 60° C.; reactions are monitored by thin layer chromatography (TLC) and reaction times are given for illustration only; the structure and purity of all isolated compounds are assured by at least one of the following techniques: TLC (Merck silica gel 60 $F_{254}$ precoated TLC plates or Merck $NH_2$ $F_{254}$ precoated HPTLC plates), mass spectrometry or nuclear magnetic resonance (NMR). Microwave reaction is conducted by Intiator (registered trademark) Sixty (Biotage). Yields are given for illustrative purposes only. The column chromatography systems are conducted by Yamazen flash chromatography and Biotage (SP1, Isolera one). Flash column chromatography is carried out using Merck silica gel 60 (230-400 mesh ASTM), Fuji Silysia Chromatorex (registered trademark) DM2035 (Amino Type, 30-50 micrometer), Biotage silica (32-63 mm, KP-Sil), Biotage amino bounded silica (45-75 mm, KP-NH), Wakogel (registered trademark)C-300HGT, Hi-Flash (registered trademark) column (YAMAZEN, silica gel, 40 micro meters, 60 angstrom), Hi-Flash (registered trademark) column (YAMAZEN, amino, 40 micro meters, 60 angstrom). LC-MS analysis for intermediates and Examples are carried out by Waters 2695 Alliance HPLC with ZQ 2000 mass spectrometer and 2996 PDA detector.

Analytical conditions (method-A, method-B, method-C, method-D, method-E and method-F) are as follows.

Conditions for Method-A, Method-B, and Method-C:

| Column | Waters XTerra C18 2.1 × 30 mm, 3.5 micrometer |
|---|---|
| Column temperature | 45° C. |
| Flow rate | 0.5 mL/min |
| PDA detection | 210-400 nm scan (Extracted wave length: 254 nm) |
| MS detection | ESI positive & negative mode |
| Mobile phases | A: MeCN (HPLC grade) |
|  | B: 0.5% aqueous $HCO_2H$ |
|  | C: 0.2% aqueous $NH_3$ |
|  | D: $H_2O$ (Milli-Q water) |

| Time (min) | A(%) | B(%) | C(%) | D(%) |
|---|---|---|---|---|
| Method-A ||||| 
| 0 | 4 | 4.8 | 4.8 | 86.4 |
| 2 | 96 | 0.2 | 0.2 | 3.6 |
| Method-B |||||
| 0 | 4 | 0 | 4.8 | 91.2 |
| 2 | 96 | 0 | 0.2 | 3.8 |
| Method-C |||||
| 0 | 32 | 3.4 | 3.4 | 61.2 |
| 2 | 96 | 0.2 | 0.2 | 3.6 | run time: 4 min

Conditions for Method-D and Method-E:

| Column | Waters SunFire C18 4.8 × 50 mm, 5 micrometer |
|---|---|
| Column temperature: | 45° C. |
| Flow rate: | 0.8 mL/min |
| PDA detection: | 210-400 nm scan (Extracted wave length: 215 nm) |
| MS detection: | ESI positive & negative mode |
| Mobile phases | A: MeCN (HPLC grade) |
|  | B: 0.5% aqueous $HCO_2H$ |
|  | C: 0.2% aqueous $NH_3$ |
|  | D: $H_2O$ (Milli-Q water) |

| Time (min) | A(%) | B(%) | C(%) | D(%) |
|---|---|---|---|---|
| Method-D |||||
| 0 | 5 | 2.5 | 2.5 | 90 |
| 0.5 | 5 | 2.5 | 2.5 | 90 |
| 3.5 | 95 | 2.5 | 2.5 | 0 |
| 4 | 95 | 2.5 | 2.5 | 0 |
| Method-E |||||
| 0 | 5 | 0 | 5 | 90 |
| 0.5 | 5 | 0 | 5 | 90 |
| 3.5 | 95 | 0 | 5 | 0 |
| 4 | 95 | 0 | 5 | 0 | run time: 4.5 min

The purification of compounds using HPLC (preparative LC-MS) is performed by the following apparatus and conditions.

Apparatus; Waters MS-trigger AutoPurification(trademark) system

Column; Waters XTerra C18, 19×50 mm, 5 micrometer particle

Condition A: Methanol or acetonitrile/0.01% (v/v) ammonia aqueous solution

Condition B: Methanol or acetonitrile/0.05% (v/v) formic acid aqueous solution

Low-resolution mass spectral data (ESI) are obtained by the following apparatus and conditions: Apparatus; Waters Alliance HPLC system on ZQ or ZMD mass spectrometer and UV detector. LC/MS/MS data are determined at the triple quadrupole mass spectrometry (AB SCIEX API4000) with HPLC (Agilent 1100 series) and autosampler (AMR CTC-PAL). NMR data are determined at 270 MHz (JEOL JNM-LA 270 spectrometer), 300 MHz (JEOL JNM-LA300) or 600 MHz (Bruker Avance 600) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings; M (mol(s) per liter), L (liter(s)), mL (milliliter(s)), g (gram(s)), mg (milligram(s)), mol (moles), mmol (millimoles).

Each prepared compound is generally named by Chem-BioDraw (Ultra, version 12.0, CambridgeSoft).

Conditions for Determining HPLC Retention Time:
Method: QC1
Apparatus: Waters ACQUITY Ultra Performance LC with TUV Detector and ZQ mass spectrometer
Column: Waters ACQUITY C18, 2.1×100 mm, 1.7 micrometer particle size
Column Temperature: 60° C.
Flow rate: 0.7 mL/min
Run time: 3 min
UV detection: 210 nm
MS detection: ESI positive/negative mode
Mobile phases:
A1: 10 mM Ammonium acetate
B1: acetonitrile
Gradient program: (QC_neutral_full_3 min)

| Time (min) | A1(%) | B1(%) |
|---|---|---|
| 0 | 95 | 5 |
| 0.1 | 95 | 5 |
| 1.8 | 5 | 95 |
| 2.3 | 95 | 5 |

Method: QC2
Apparatus: Waters 2795 Alliance HPLC with ZQ2000 mass spectrometer and 2996 PDA Detector
Column: XBridge C18, 2.1×50 mm, 3.5 micrometer particle size
Column Temperature: 45° C.
Flow rate: 1.2 mL/min
Run time: 4.5 min
UV detection: 210-400 nm scan
MS detection: ESI positive/negative mode
Mobile phases:
A: Water
B: MeCN
C: 1% aqueous $HCO_2H$ solution
D: 1% aqueous $NH_3$ solution
Gradient program:

| Time (min) | A (%) | B (%) | C (%) | D (%) |
|---|---|---|---|---|
| 0 | 85 | 10 | 2.5 | 2.5 |
| 0.2 | 85 | 10 | 2.5 | 2.5 |
| 3.2 | 0 | 95 | 2.5 | 2.5 |
| 3.7 | 0 | 95 | 2.5 | 2.5 |
| 3.71 | 85 | 10 | 2.5 | 2.5 |
| 4.5 | 85 | 10 | 2.5 | 2.5 |

All of the azaspiro derivatives of the formula (I) can be prepared by the procedures described in the general methods presented below or by the specific methods described in the Example synthesis part and Intermediate synthesis part, or by routine modifications thereof. The present invention also encompasses any one or more of these processes for preparing the azaspiro derivatives of formula (I), in addition to any novel intermediates used therein.

In the following general methods, descriptors are as previously defined for the azaspiro derivatives of the formula (I) unless otherwise stated.

Scheme-1: Synthesis of compound of formula (I) via compound of formula (III)

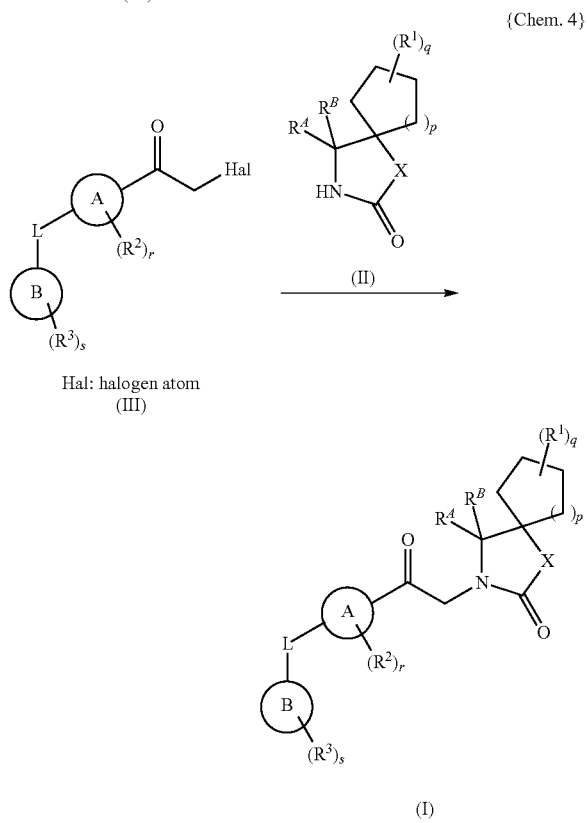

{Chem. 4}

Hal: halogen atom

In this scheme-1, an azaspiro compound of the general formula (I) can be prepared by the N-alkylation reaction of an azaspiro compound of formula (II) with the alpha-haloketone compound of formula (III) in the presence of a base in an inert solvent. A preferred base is selected from, for example, but not limited to: an alkali or alkaline earth metal hydroxide, alkoxide, carbonate, halide or hydride, such as sodium hydroxide, potassium hydroxide, sodium methoxide, sodium ethoxide, potassium tert-butoxide, cesium carbonate, sodium carbonate, potassium carbonate, potassium phosphate, potassium fluoride, sodium hydride or potassium hydride; or an amine such as TEA, tributylamine, diisopropylethylamine, 2,6-lutidine, pyridine or 4-dimethylaminopyridine. Examples of suitable inert aqueous or non-aqueous organic solvents include: ethers, such as THF or 1,4-dioxane; acetone; N,N-Dimethylformamide; DMSO; halogenated hydrocarbons, such as DCM, 1,2-dichloroethane or chloroform; and pyridine; or mixtures thereof. The reaction can be carried out at a temperature in the range of from −80° C. to 200° C., preferably in the range of from −10° C. to 150° C. Reaction times are, in general, from 10 minutes to 4 days, preferably from 10 minutes to 24 h. A microwave oven may optionally be used to increase reaction rates.

Scheme-2: Synthesis of compound of formula (I) via compound of formula (III)

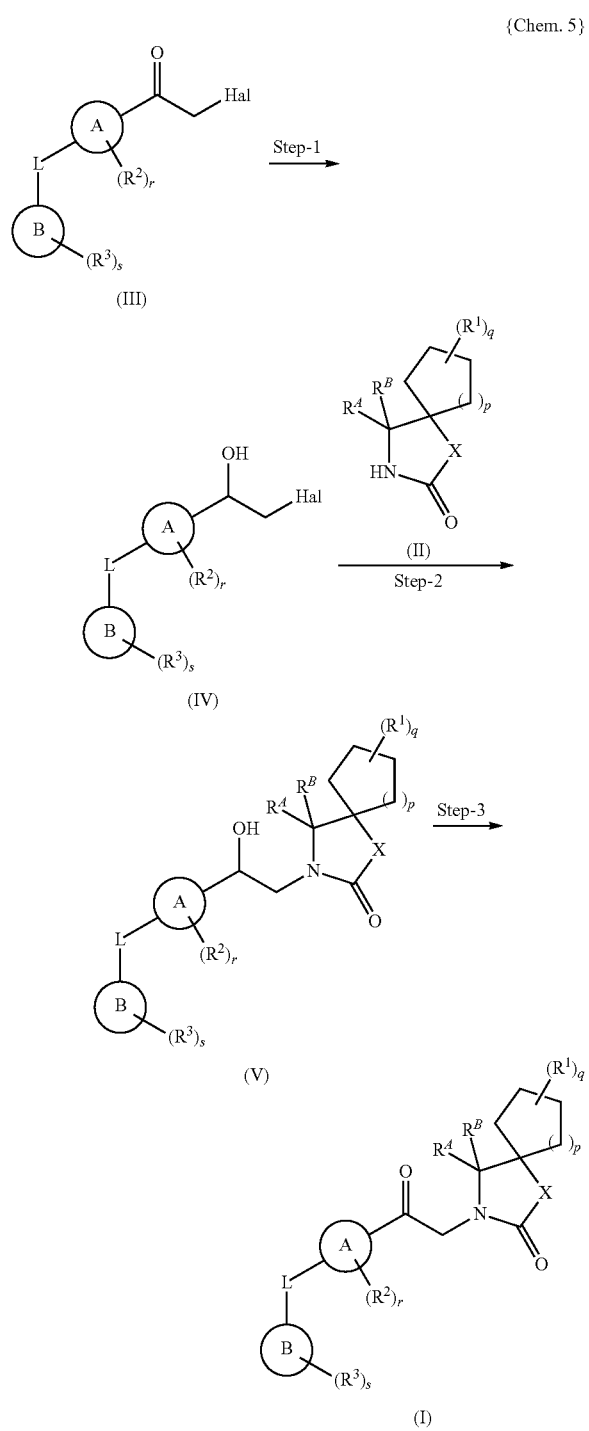

Scheme-3: Synthesis of compound of formula (I-a) via compound of formula (VI)

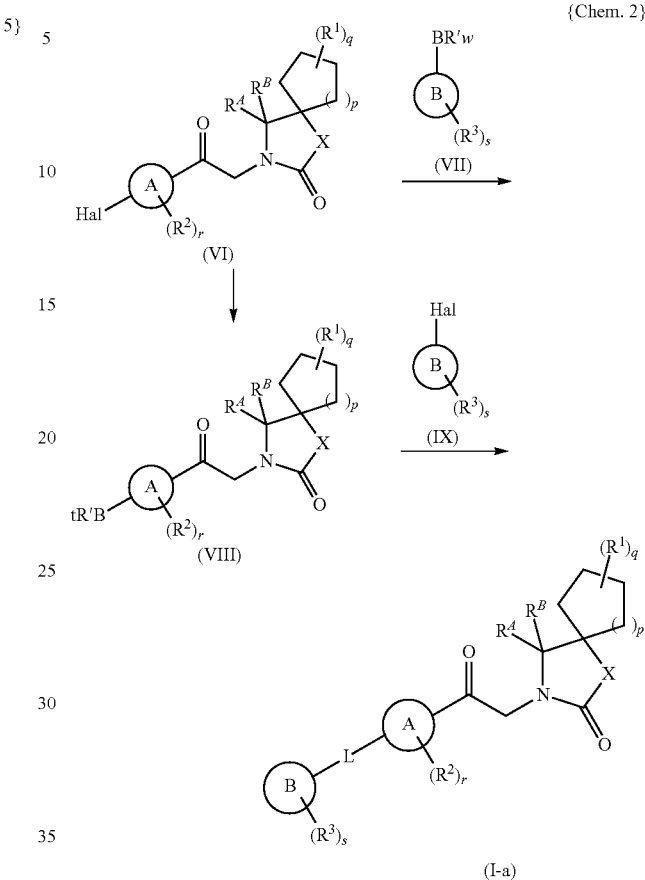

In scheme-2, a compound of the general formula (IV) can be prepared from a compound (III) using a suitable reduction reagent (for example, sodium borohydride) in an inert solvent (for example, methanol). Then, a compound of the general formula (V) can be prepared from a compound (IV) according to the N-alkylation described in the generally synthetic method in scheme-1. Finally, a compound of the general formula (I) can be prepared from a compound (V) using a suitable oxidation reagent (for example, Dess-Martin reagent) in an inert solvent (for example, dichloromethane).

In scheme-3, a compound of the general formula (I-a) can be prepared by the cross coupling reaction of a halide compound of formula (VI) with a boronic (or boronic ester) compound of formula (VII) in organic solvent or water-organic co-solvent mixture under coupling conditions in the presence of a suitable transition metal catalyst and in the presence or absence of a base. In a representation of $BR'_w$, R' means OH, O-low alkyl or fluorine, and w is 2 or 3, B is boron atom. As the concrete representation of substituent, $B(OH)_2$, $B(O\text{-lower alkyl})_2$, $B(\text{lower alkyl})_2$, potassium trifluoroborate $(BF_3^-)(BF_3K)$ are described, but when $B(O\text{-lower alkyl})_2$ may form the cyclic ring between the lower alkyl groups. Furthermore, a compound of the general formula (I-a) can also be prepared by the same cross coupling reaction from a halide compound of formula (IX) with a boronic (or boronic ester) compound of formula (VIII) converted from the halide compound of formula (VI). The boronic (or boronic ester) compounds of formula (VII) and (VIII) are utilized as the isolated reagents or the reagents generated in in situ for the cross coupling reaction. Examples of suitable transition metal catalysts include: tetrakis(triphenylphosphine)palladium(0), bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper (II) acetate, copper(II) bromide, copper(II) chloride, copper(II) iodide, copper(II) oxide, copper(II) trifluoromethanesulfonate, palladium(II) acetate, palladium(II) chloride, bis(acetonitrile)dichloropalladium(II), bis(dibenzylideneacetone)palladium(0), tris(dibenzylideneacetone) dipalladium(0) and [1,1-bis(diphenylphosphino)ferrocene]

palladium(II) dichloride. Preferred catalysts are tetrakis(triphenylphosphine)palladium(0), bis(triphenylphosphine)palladium(II) chloride, palladium(II) acetate, palladium(II) chloride, bis(acetonitrile)dichloropalladium(0), bis(dibenzylideneacetone)palladium(0), tris(dibenzylideneacetone)dipalladium(0) and [1,1-bis(diphenylphosphino)ferrocene]palladium(II) dichloride.

Examples of suitable organic solvent for the anhydrous solvent and the water-organic co-solvent mixture include: THF; 1,4-dioxane; DME; DMF; acetonitrile; alcohols, such as methanol or ethanol; halogenated hydrocarbons, such as DCM, 1,2-dichloroethane, chloroform or carbon tetrachloride; and diethylether. This reaction can be carried out in the presence or absence of a base such as potassium hydroxide, sodium hydroxide, lithium hydroxide, sodium bicarbonate, sodium carbonate, potassium carbonate and potassium phosphate. This reaction can be carried out in the presence of a suitable additive agent. Examples of such additive agents include: triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl, triphenylarsine, tetrabutylammonium chloride, tetrabutylammonium fluoride, lithium acetate, lithium chloride, triethylamine, potassium or sodium methoxide, sodium hydroxide, cesium carbonate, tripotassium phosphate, sodium carbonate, sodium bicarbonate, and/or sodium iodide. The reaction can be carried out at a temperature of from 0° C. to 200° C., more preferably from 20° C. to 150° C. Reaction times are, in general, from 5 minutes to 96 h, more preferably from 30 minutes to 24 h. In an alternative case, the reaction can be carried out in a microwave system in the presence of a base in an inert solvent. The reaction can be carried out at a temperature in the range of from 100° C. to 200° C., preferably in the range of from 120° C. to 150° C. Reaction times are, in general, from 10 minutes to 3 h, preferably from 15 minutes to 1 h. Other than a Suzuki-Miyaura cross coupling shown above, Stille cross coupling reaction using trialkyltin instead of $BR'_w$ substituent, and Negishi coupling reaction using zinc-halogen, wherein as a halogen, chlorine, bromine, iodide are cited, instead of $BR'_w$ substituent can be used.

Scheme-4: Synthesis of compound of formula (III) via compound of formula (X) and (XI)

{Chem. 6}

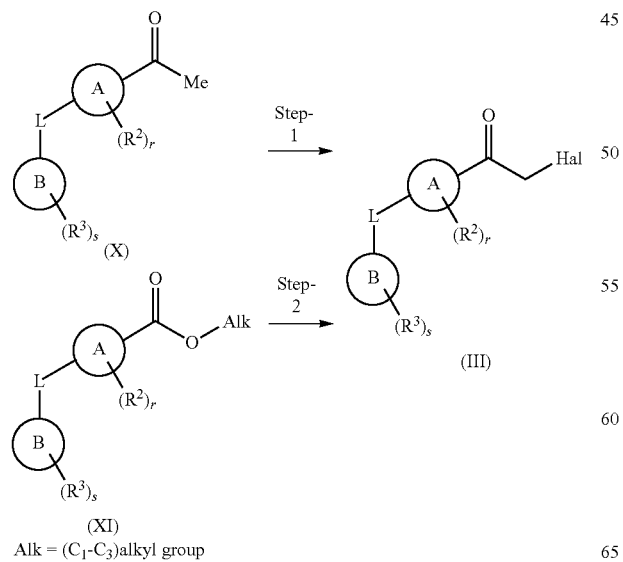

Alk = $(C_1-C_3)$alkyl group

In the step-1 of scheme-4, a alpha-haloketone compound of the general formula (III) can be prepared by the alpha-halogenation reaction (Hal=Cl, Br, I) of compound (X) using an appropriate halogenation reagent. As an appropriate halogenation reagent, for example, bromine, chlorine, iodide, sulfuryl chloride, hydrogen bromine, N-bromosuccinimide (NBS), copper (II) bromide 5,5-dibromo-2,2-dimethyl-4,6-dioxo-1,3-dioxane, trimethylphenylammonium tribromide, benzyltrimethylammonium tribromide, and benzyltrimethylammonium dichloroiodate are cited. As an appropriate organic solvent, for example, acetic acid, 25% hydrogen bromide-acetic acid solution, 48% hydrogen bromide solution, carbon disulfide, diethyl ether, tetrahydrofuran, N,N-dimethylformamide (DMF), halogenated hydrocarbon such as dichloromethane, 1,2-dichloroethane, chloroform, carbon tetrachloride can be used. The reaction period is about 5 minutes to 96 h, and is generally about 30 minutes to 24 h. The reaction temperature is about 0° C. to 250° C., and is generally about 30° C. to 150° C. Further, in the step-2 of scheme-4, alpha-haloketone compound of the general formula (III) can also be prepared from an ester compound (XI) according to the procedure described in *Tetrahedron Letters*, 38, 3175, 1997. Typically, compound of formula (III) is prepared by the reaction with an ester compound (XI) under the condition of iodochloromethane and lithium diisopropylamide (LDA) in tetrahydrofuran (THF) at −78° C.

Scheme-5: Synthesis of compound of formula (XIII) via compound of formula (XII)

{Chem. 7}

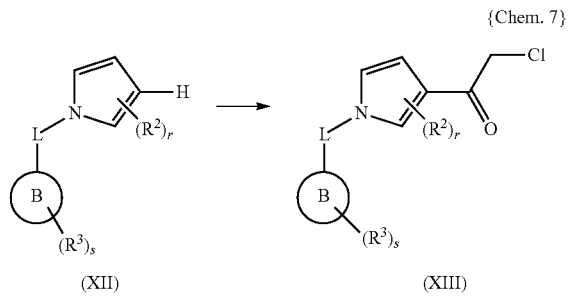

In scheme-5, an alpha-haloketone compound of the general formula (XIII) can be prepared by the Friedel-Crafts reaction of a pyrrole compound (XII) using chloroacetyl chloride and appropriate Lewis acid (for example, aluminum chloride) in an inert solvent (for example, dichloromethane).

Scheme-6: Synthesis of compound of formula (XV) via compound of formula (XIV)

{Chem. 8}

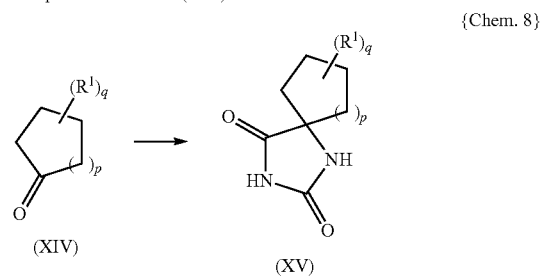

In scheme-6, a compound of the general formula (XV)(the general formula (II): $R^A$ and $R^B$ are oxo, X is NH) can be prepared from compounds of the general formula (XIV) by the methodology (Bucherer-Bergs reaction) described in the literature (for example, *Chem. Rev.*, 46 (3), pp 403-470, 1950). Typically, compound of formula (XV) is prepared by the reaction of a ketone compound of formula (XIV) under the condition of potassium cyanide (or trimethylsilyl cyanide) and ammonium carbonate in ethanol/water (1:1 v/v) at 70° C. for 20 h.

Scheme-7: Synthesis of compound of formula (XVII) via compound of formula (XIV)

{Chem. 9}

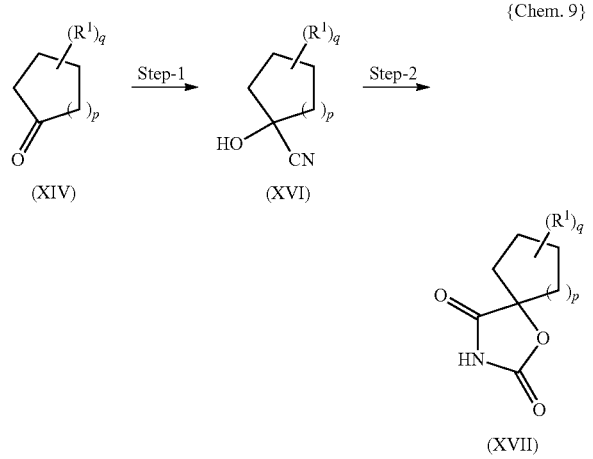

In Scheme-7, a compound of formula (XVII) (the general formula (II): $R^A$ and $R^B$ are oxo, and X is O) can be prepared from a cyanohydrin compound of the general formula (XVI). The compound of formula (XVI) can be prepared from a ketone compound of the general formula (XIV) by the condition of trimethylsilyl cyanide and the catalytic zinc (II) iodide, followed by deprotection of O-trimethylsilyl moiety under the acidic condition in the step-1. Further, a compound of formula (XVI) can be converted to a 2,4-oxazolidinedione derivative of formula (XVII) according to the procedure described in *Synthesis*, p 697 (1991). Typically, a compound of formula (XVII) is prepared by the reaction of a compound of formula (XVI) with chlorosulfonyl isocyanate, followed by acid hydrolysis in the step-2.

Scheme-8: Synthesis of compound of formula (XX) via compound of formula (XVIII)

{Chem. 10}

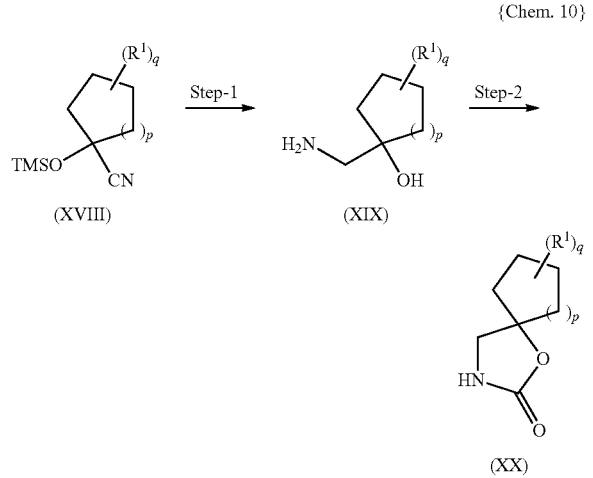

In Scheme-8, a compound of the general formula (XX) (the general formula (II): $R^A$ and $R^B$ are hydrogen, and X is O) can be prepared from a compound of the general formula (XVIII) (an intermediate compound of formula (XVI)). A compound of the general formula (XIX) can be prepared under the condition of reduction reaction by using the reduction reagent, such as borane-dimethylsulfide complex, in this step-1. Further, a compound of the general formula (XIX) can be converted to an oxazolidin-2-one derivative of formula (XX) by the reaction with the 1,1'-carbonyldiimidazole (CDI) in this step-2.

Scheme-9: Synthesis of compound of formula (XXIV) via compound of formula (XIV)

{Chem. 11}

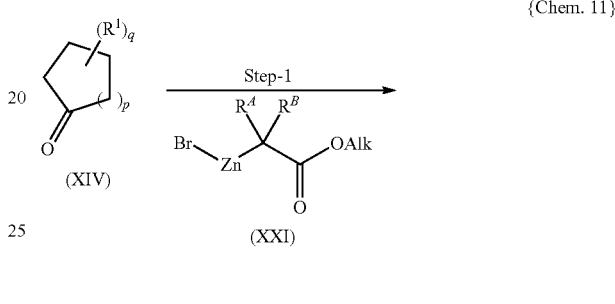

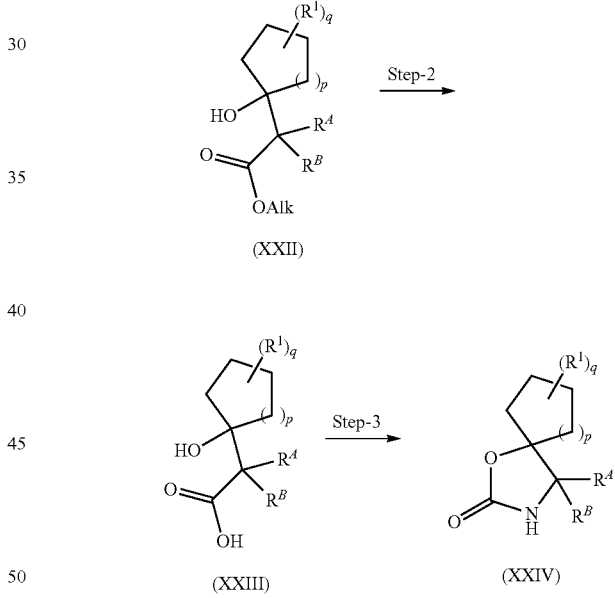

In Scheme-9, a compound of the general formula (XXIV) (the general formula (II): $R^A$ is alkyl; $R^B$ is hydrogen or alkyl, and X is O) can be prepared from a compound of the general formula (XIV). A compound of the general formula (XXIII) can be prepared by the Reformatsky reaction of the activated reagent (XXI) prepared from zinc metal and alpha-bromoacetic acid ester derivatives with a compound of the general formula (XIV) in this step-1, followed by the alkali hydrolysis of a compound of the general formula (XXII). Further, a compound of the general formula (XXIII) can be converted to an oxazolidin-2-one derivative of formula (XXIV) by the reaction with the diphenylphosphoryl azide (DPPA) in this step-3.

Scheme-10: Synthesis of compound of formula (XXVIII) via compound of formula (XXV) and (XXVII)

{Chem. 12}

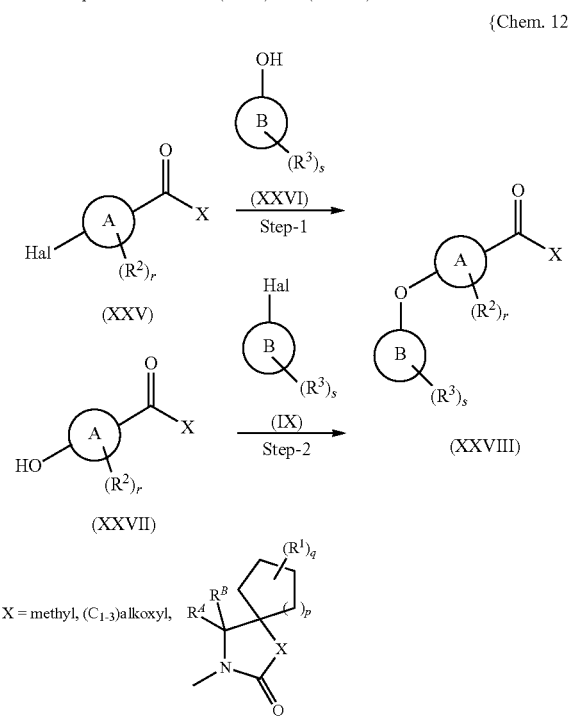

In scheme-10, a compound of the general formula (XXVIII) can be prepared by the reaction of a halide compound of formula (XXV) with compound of formula (XXVI)(step-1). Alternatively the compound of the general formula (XXVIII) can be also prepared by the reaction of a phenol compound of formula (XXVII) with compound of formula (IX)(step-2) by using the selected procedure from palladium coupling reaction, nucleophilic substitution reaction and ullmann reaction. The coupling reaction can be carried out by the combination a suitable palladium catalyst, ligand and base in organic solvent or water-organic co-solvent mixture. Examples of suitable transition metal catalysts include: palladium(II) acetate, tris(dibenzylideneacetone)dipalladium(0) and [1,3-Bis(2,6-Diisopropylphenyl) imidazol-2-ylidene] (3-chloropyridyl)palladium(II) dichloride. Examples of suitable organic solvent for the anhydrous solvent and the water-organic co-solvent mixture include: THF; DME; 1,4-dioxane; DMF; acetonitrile and alcohols, such as methanol, ethanol and tert-butyl alcohol. Examples of suitable base include: sodium bicarbonate, sodium carbonate, potassium carbonate, cesium carbonate, potassium phosphate, sodium tert-butoxide and potassium tert-butoxide. This reaction can be carried out in the presence of a suitable ligand agent. Examples of such ligand agents include: 2,2'-Bis(diphenylphosphino)-1,1'-binaphthyl (BINAP), 2-Dicyclohexylphosphino-2'-(N,N-dimethylamino)biphenyl(DavePhos), 4,5-Bis(diphenylphosphino)-9,9-dimethylxanthene(Xantphos) and 2-Dicyclohexylphosphino-2',4',6'-triisopropylbiphenyl (XPhos). The nucleophilic substitution reaction can be carried out in organic solvent or water-organic co-solvent mixture under coupling conditions in the presence of a base. Examples of suitable organic solvent include N,N-dimethylformamide, dimethylsulfoxide and N-methyl-2-pyrrolidinone. Examples of suitable base include sodium carbonate, potassium carbonate, cesium carbonate, potassium phosphate, sodium hydride, sodium tert-butoxide and potassium tert-butoxide. Furthermore, the Ullmann reaction can be carried out under the coupling conditions by using a suitable copper reagent, ligand and base in organic solvent. As an appropriate copper reagent, for example, copper (I) iodide, copper (I) bromide, and copper (I) chloride can be used. As an appropriate ligand and base, for example, ligand such as N,N-dimethylglycine, L-proline, N,N'-dimethylethylenediamine and trans-N,N'-dimethylcyclohexane-1,2-diamine and base such as sodium carbonate, potassium carbonate and cesium carbonate. Examples of suitable organic solvent include THF, 1,4-dioxane, N,N-dimethylformamide, dimethylsulfoxide and N-methyl-2-pyrrolidinone. These reaction can be carried out at a temperature of from 20° C. to 200° C., more preferably from 100° C. to 160° C. Reaction times are, in general, from 5 minutes to 96 h, more preferably from 30 minutes to 24 h. In an alternative case, the reaction can be carried out in a microwave system in the presence of a base in an inert solvent. The reaction can be carried out at a temperature in the range of from 100° C. to 200° C., preferably in the range of from 120° C. to 150° C. Reaction times are, in general, from 10 minutes to 3 h, preferably from 15 minutes to 1 h.

Scheme-11: Synthesis of compound of formula (XXXII) via compound of formula (XXV)

{Chem. 13}

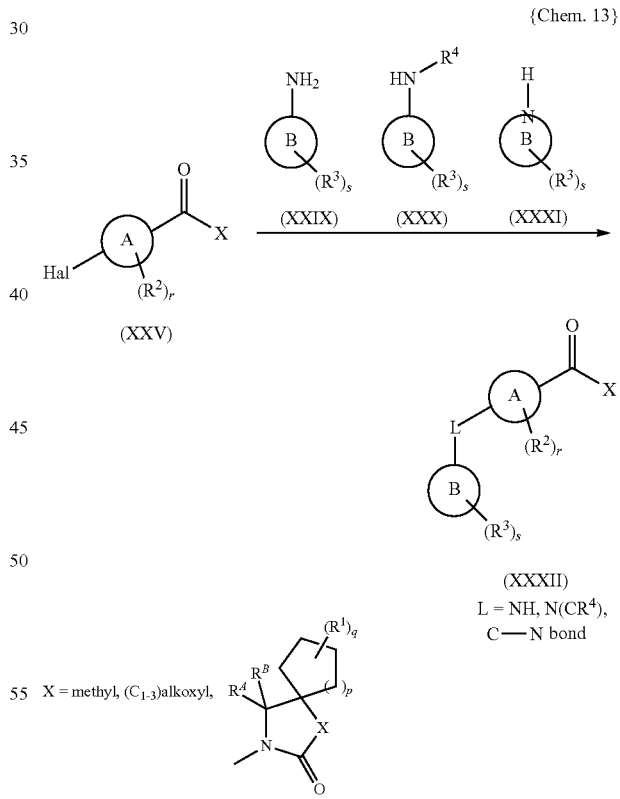

In scheme-11, a compound of the general formula (XXXII) can be prepared by the reaction of a halide compound of formula (XXV) with compound of formula (XXIX), (XXX) or (XXXI) by using the selected procedure from palladium coupling reaction, nucleophilic substitution reaction or the Ullmann reaction according to the general synthetic method in scheme-10.

Preparation of Intermediate

Intermediate-1-1-A (INT-1-1-A): 8,8-difluoro-1,3-diazaspiro[4.5]decane-2,4-dione {Chem. 14}

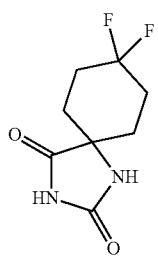

A mixture of 4,4-difluorocyclohexane (3.00 g, 22.37 mmol), potassium cyanide (2.91 g, 44.7 mmol) and ammonium carbonate (8.60 g, 89.0 mmol) in ethanol/water (1:1 v/v, 90 mL) is heated at 70° C. for 20 h. After cooling to rt, the organic solvent (ethanol) is evaporated in vacuo until half volume. The residue is diluted with cold water (250 mL) and stirred for 60 min. The precipitated solid is filtered and dried in vacuum pump at 40° C. (inner temp) using phosphorus pentoxide to give the titled compound (3.75 g, slightly gray solid).

$^1$H-NMR (270 MHz, DMSO-$d_6$): delta 10.77 (br.s, 1H), 8.53 (s, 1H), 2.20-1.65 (m, 8H).

The following hydantoin derivative (INT-1-2-A) is prepared according to the procedure (INT-1-1-A) from the known or synthesized ketone derivatives in Table 1.

TABLE 1

| Ketones | Hydantoins | Yield and Analytical data |
|---|---|---|
| INT-1-2 | INT-1-2-A | 4.7% yield (white solid) $^1$H-NMR (300 MHz, DMSO-$d_6$): delta 10.50 (br.s, 1H), 8.37 (s, 1H), 2.50-2.30 (m, 2H), 2.05-1.35 (m, 12H). |

Intermediate-1-3-A (INT-1-3-A): 8,8-difluoro-1-oxa-3-azaspiro[4.5]decane-2,4-dione {Chem. 15}

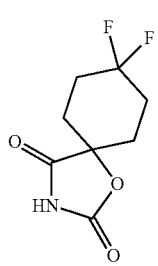

The titled compound is prepared according to the procedure described in *Synthesis*, p 697 (1991) from 4,4-difluoro-1-hydroxycyclohexanecarbonitrile (495 mg, 3.07 mmol) and chlorosulfonyl isocyanate (281 microL, 3.23 mmol) and triethylamine (450 microL, 3.23 mmol) in anhydrous benzene (10 mL) to give the product (600 mg, 95% yield) as a slightly yellow solid.

$^1$H-NMR (270 MHz, DMSO-$d_6$): delta 12.01 (br.s, 1H), 2.25-1.85 (m, 8H).

Intermediate-1-4-A (INT-1-4-A): 8,8-difluoro-1-oxa-3-azaspiro[4.5]decan-2-one {Chem. 16}

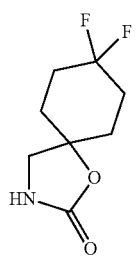

A mixture of 1-(aminomethyl)-4,4-difluorocyclohexanol hydrochloride (5.15 g, 25.5 mmol), CDI (12.42 g, 77 mmol) and triethylamine (7.68 mL, 51.1 mmol) in THF (100 mL) is heated at 75° C. for 20 h. To this is added 2 M NaOH aq. solution (6 eq.) and the mixture is stirred at rt for 5 h. The mixture is extracted with DCM (×3) and the combined organic extracts are evaporated in vacuo to give a yellow oil. The crude product is dissolved in DCM (300 mL) and washed with 2 M HCl aq. solution (×1) then saturated NaHCO$_3$ solution, brine, dried over sodium sulfate, filtered and concentrated in vacuo to give the crude product (a slightly yellow solid), which is purified by column chromatography (Biotage) on silica gel (100 g) eluting with 65-100% ethyl acetate in hexane to give the titled compound (3.34 g, 68% yield) as a white solid.

$^1$H-NMR (270 MHz, CDCl$_3$): delta 5.79 (br.s, 1H), 3.38 (s, 2H), 2.35-1.75 (m, 8H).

Intermediate-1-5-A (INT-1-5-A): 8,8-difluoro-2-azaspiro[4.5]decane-1,3-dione {Chem. 17}

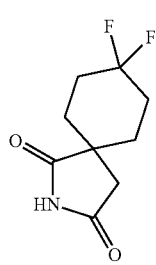

<Step-1>: Intermediate-1-5-1 (INT-1-5-1): ethyl 2-cyano-2-(4,4-difluorocyclohexylidene) acetate

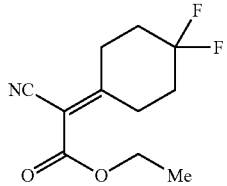
{Chem. 18}

A mixture of 4,4-difluorocyclohexanone (1.00 g, 7.46 mmol), ethyl 2-cyanoacetate (1.10 g, 9.69 mmol), molecular sieves 4 angstrom (1.00 g) and Et$_3$N (2.08 mL, 14.91 mmol) in DCM (10 mL) is stirred at rt for 1 day. The mixture is filtered and concentrated. The residual oil is used for next step without further purification. MS (ESI) m/z: 228.3 (M–H)$^-$.

<Step-2>: Intermediate-1-5-2 (INT-1-5-2): 1-(cyanomethyl)-4,4-difluorocyclohexanecarbonitrile

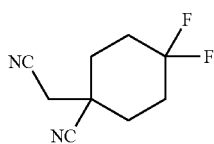
{Chem. 19}

A mixture of INT-1-5-1 (7.46 mmol, crude mixture from 4,4-difluorocyclohexanone) and potassium cyanide (1.46 g, 22.38 mmol) in EtOH (20 mL)-H$_2$O (4 mL) is stirred at 75° C. for 1 day. After the removal of solvent, the residual oil is diluted with sat. NaHCO$_3$ solution and extracted with EtOAc. The combined organic solution is dried over Na$_2$SO$_4$, filtered and concentrated. The residual oil is purified by column chromatography on silica gel eluting with 0-20% ethyl acetate in hexane to give the titled compound (1.01 g, 74% yield in 2 steps) as an off-white solid.
$^1$H-NMR (300 MHz, CDCl$_3$): delta 2.75 (s, 2H), 2.32-2.05 (m, 6H), 2.92-2.77 (m, 2H).

<Step-3>: Intermediate-1-5-A (INT-1-5-A): 8,8-difluoro-2-azaspiro[4.5]decane-1,3-dione

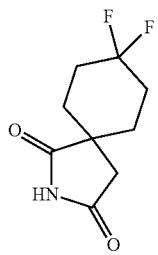
{Chem. 20}

A mixture of INT-1-5-2 (200 mg, 1.09 mmol) in H$_2$SO$_4$ (0.3 mL) and AcOH (1.5 mL) is stirred at 125° C. for 1 h. The mixture is poured into ice water. Then, the mixture is neutralized with 2 M NaOH aq. solution and extracted with DCM. The combined organic solution is dried over Na$_2$SO$_4$, filtered and concentrated. The residual oil is purified by column chromatography on silica gel eluting with 0-50% ethyl acetate in hexane to give the the titled compound (80 mg, 36% yield) as an off-white solid.
$^1$H-NMR (300 MHz, CDCl$_3$): delta 8.08 (br s, 1H), 2.63 (s, 2H), 2.41-2.06 (m, 4H), 1.96-1.69 (m, 4H).
MS (ESI) m/z: 202.2 (M–H)$^-$.

Intermediate-1-6-A (INT-1-6-A): 8,8-difluoro-4-methyl-1-oxa-3-azaspiro[4.5]decan-2-one

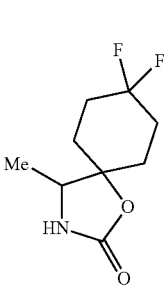
{Chem. 21}

<Step-1>: Intermediate-1-6-1 (INT-1-6-1): ethyl 2-(4,4-difluoro-1-hydroxycyclohexyl)propanoate

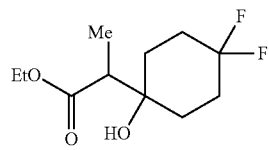
{Chem. 22}

A mixture of 4,4-difluorocyclohexanone (1.00 g, 7.46 mmol), ethyl 2-bromopropanoate (1.35 g, 7.46 mmol), zinc powder (561 mg, 8.57 mmol) in dioxane (20 mL) is stirred at 100° C. for 1 day. The mixture is filtered by using Celite pad. After the removal of solvent, the residual oil is purified by column chromatography on silica gel eluting with 0-30% ethyl acetate in hexane to give the titled compound (1.50 g, 85% yield) as a pale yellow oil.
$^1$H-NMR (270 MHz, CDCl$_3$): delta 4.19 (q, J=7.3 Hz, 2H,), 3.33 (d, J=2.0 Hz, 1H), 2.75-1.82 (m, 6H), 1.73-1.59 (m, 2H), 1.54-1.36 (m, 1H), 1.28 (t, J=7.3 Hz, 3H), 1.23 (d, J=7.3 Hz, 3H).

<Step-2>: Intermediate-1-6-2 (INT-1-6-2): 2-(4,4-difluoro-1-hydroxycyclohexyl)propanoic acid

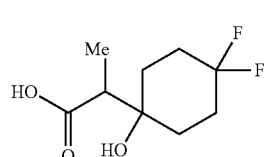
{Chem. 23}

A mixture of INT-1-6-1 (1.50 g, 6.35 mmol), 2 M NaOH aq. solution (5 mL, 10 mmol) in THF (10 mL) is stirred at 60° C. for 5 h. The mixture is acidified with 2 M HCl aq. solution and extracted with DCM. The combined organic solution is dried over Na$_2$SO$_4$, filtered and concentrated to give the titled compound (1.43 g) as a crude oil.

MS (ESI) m/Z: 207.1 (M−H)$^−$.

<Step-3>: Intermediate-1-6-A (INT-1-6-A): 8,8-difluoro-4-methyl-1-oxa-3-azaspiro[4.5]decan-2-one A mixture of INT-1-6-2 (1.43 g, crude mixture), diphenyl phosphorazidate (2.27 g, 8.24 mmol), TEA (1.44 mL, 10.3 mmol) in toluene (30 mL) is stirred at 100° C. for 2 h. The mixture is quenched with 2 M NaOH aq. solution and extracted with EtOAc. The organic layer is washed with water and brine, dried over Na$_2$SO$_4$, filtered and concentrated in vacuo. The residual oil is purified by column chromatography on silica gel eluting with 0-70% ethyl acetate in hexane to give the titled compound (507 mg, 39% yield in 2 steps) as a pale yellow solid.

$^1$H-NMR (270 MHz, CDCl$_3$): delta 5.61 (br s, 1H), 3.66 (q, J=6.6 Hz, 1H), 2.38-1.95 (m, 6H), 1.88-1.59 (m, 2H), 1.20 (d, J=6.6 Hz, 3H).

MS (ESI) m/z: 206.1 (M+H)$^+$.

Intermediate-1-7-A (INT-1-7-A): 8,8-difluoro-4,4-dimethyl-1-oxa-3-azaspiro[4.5]decan-2-one

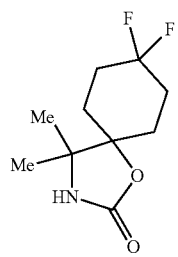

{Chem. 24}

<Step-1>: Intermediate-1-7-1 (INT-1-7-1): ethyl 2-(4,4-difluoro-1-hydroxycyclohexyl)-2-methylpropanoate

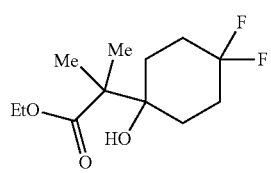

{Chem. 25}

A mixture of 4,4-difluorocyclohexanone (1.00 g, 7.46 mmol), ethyl 2-bromo-2-methylpropanoate (1.45 g, 7.46 mmol), zinc powder (561 mg, 8.57 mmol) in dioxane (20 mL) is stirred at 85° C. for 2 days. The mixture is filtered by using Celite pad. After the removal of solvent, the residual oil is purified by column chromatography on silica gel eluting with 0-30% ethyl acetate in hexane to give the titled compound (1.14 g, 61% yield) as a pale yellow oil.

MS (ESI) m/z: 249.1 (M−H)$^−$.

<Step-2>: Intermediate-1-7-2 (INT-1-7-2): 2-(4,4-difluoro-1-hydroxycyclohexyl)-2-methylpropanoic acid

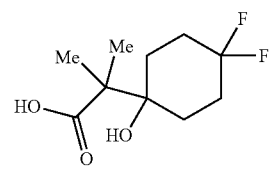

{Chem. 26}

A mixture of INT-1-7-1 (1.14 g, 4.55 mmol), 4 M NaOH aq. (5 mL, 20 mmol) in THF (5 mL) is stirred at 90° C. for 2 days. After the removal of undesired material by IPE, the aqueous layer is acidified with 2 M HCl aq. solution and extracted with DCM. The combined organic solution is dried over Na$_2$SO$_4$, filtered and concentrated in vacuo to give the titled compound (0.77 g, 76% yield) as a crude solid.

MS (ESI) m/z: 221.1 (M−H)$^−$.

<Step-3>: Intermediate-1-7-A (INT-1-7-A): 8,8-difluoro-4,4-dimethyl-1-oxa-3-azaspiro[4.5]decan-2-one A mixture of INT-1-7-2 (770 mg, 3.46 mmol), diphenyl phosphorazidate (1.14 g, 4.16 mmol), TEA (0.724 mL, 5.20 mmol) in toluene (15 mL) is stirred at 85° C. for 1 day. The mixture is quenched with 2 M NaOH aq. solution and extracted with EtOAc. The organic layer is washed with water and brine, dried over Na$_2$SO$_4$, filtered and concentrated in vacuo. The residual oil is purified by column chromatography on silica gel eluting with 0-70% ethyl acetate in hexane to give the titled compound (567 mg, 75% yield) as a pale yellow solid.

$^1$H-NMR (270 MHz, CDCl$_3$): delta 5.80 (br s, 1H), 2.33-2.02 (m, 6H), 1.80-1.60 (m, 2H), 1.27 (s, 3H), 1.27 (s, 3H).

MS (ESI) m/z: 220.2 (M+H)$^+$.

Intermediate-1-8-A (INT-1-8-A): 8,8-difluoro-4-isopropyl-1-oxa-3-azaspiro[4.5]decan-2-one

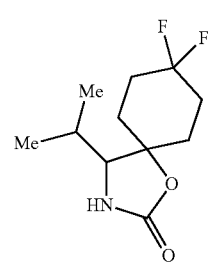

{Chem. 27}

\<Step-1\>: Intermediate-1-8-1 (INT-1-8-1): ethyl 2-(4,4-difluoro-1-hydroxycyclohexyl)-3-methylbutanoate

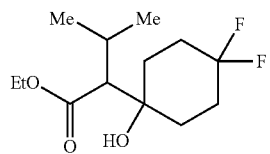
{Chem.28}

A mixture of 4,4-difluorocyclohexanone (1.00 g, 7.46 mmol), ethyl 2-bromo-3-methylbutanoate (1.56 g, 7.46 mmol), zinc powder (561 mg, 8.57 mmol) in dioxane (20 mL) is stirred at 85° C. for 2 days. After the removal of solvent, the filtrate is concentrated in vacuo. The residual oil is purified by column chromatography on silica gel eluting with 0-30% ethyl acetate in hexane to give the titled compound (1.46 g, 74% yield) as a pale yellow oil.

\<Step-2\>: Intermediate-1-8-2 (INT-1-8-2): 2-(4,4-difluoro-1-hydroxycyclohexyl)-3-methylbutanoic acid

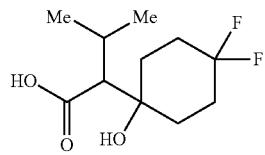
{Chem. 29}

A mixture of INT-1-8-1 (1.25 g, 4.73 mmol), 6 M NaOH aq. solution (5 mL, 30 mmol) in EtOH (5 mL) is stirred at 80° C. for 1 day. After the removal of undesired material by IPE, the aqueous layer is acidified with 2 M HCl aq. solution and extracted with DCM. The combined organic solution is dried over $Na_2SO_4$, filtered and concentrated in vacuo to give the titled compound (0.88 g, 68% yield) as a crude solid.

MS (ESI) m/z: 235.1 (M−H)⁻.

\<Step-3\>: Intermediate-1-8-A (INT-1-8-A): 8,8-difluoro-4-isopropyl-1-oxa-3-azaspiro[4.5]decan-2-one A mixture of INT-1-8-2 (880 mg, 3.72 mmol), diphenyl phosphorazidate (1.23 g, 4.47 mmol), TEA (0.779 mL, 5.59 mmol) in toluene (15 mL) is stirred at 85° C. for 1 day. The mixture is quenched with 2 M NaOH aq. solution and extracted with EtOAc. The organic layer is washed with water and brine, dried over $Na_2SO_4$, filtered and concentrated in vacuo. The residual oil is purified by column chromatography on silica gel eluting with 0-70% ethyl acetate in hexane to give the titled compound (476 mg, 55% yield) as a pale yellow solid.

¹H-NMR (270 MHz, $CDCl_3$): delta 6.37 (br s, 1H), 3.21 (d, J=7.9 Hz, 1H), 2.35-2.18 (m, 1H), 2.18-1.98 (m, 5H), 1.98-1.73 (m, 3H), 1.00 (d, J=6.6 Hz, 3H), 0.92 (d, J=6.6 Hz, 3H).

MS (ESI) m/z: 234.2 (M+H)⁺.

Intermediate-2-1-A (INT-2-1-A): 5-(2,5-dimethyl-1H-pyrrol-1-yl)-3-methylisoxazole

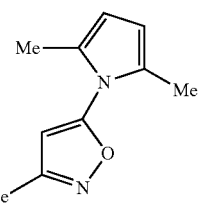
{Chem. 30}

The mixture of 3-methylisoxazol-5-amine (1.50 g, 15.29 mmol), hexane-2,5-dione (1.75 g, 15.29 mmol) and p-TsOH monohydrate (291 mg, 1.53 mmol) in ethanol (25 mL) is heated at 80° C. for 15 h. After the removal of solvent, the residue is quenched with sat. sodium bicarbonate solution. The aqueous layer is extracted with ethyl acetate (2 times) and the combined solution is washed with brine, dried over sodium sulfate, filtered and concentrated in vacuo to give the crude product. The crude product is purified by column chromatography (Biotage) on silica gel (100 g) eluting with 5-10% ethyl acetate in hexane to give the titled compound (2.13 g, 79% yield) as a dark red solid.

¹H-NMR (300 MHz, $CDCl_3$): delta 5.92 (s, 1H), 5.90 (s, 2H), 2.37 (s, 3H), 2.19 (s, 6H).

The following pyrrole derivatives (INT-2-2-A and INT-2-6-A) are prepared according to the procedure of intermediate 2-1-A from the known or synthesized aniline derivatives in Table 2.

TABLE 2

| Anilines | Products | Yield and Analytical data |
|---|---|---|
| INT-2-2 | INT-2-2-A | 90% yield (a pale yellow solid)<br>¹H-NMR (270 MHz, $CDCl_3$): delta 7.69-7.63 (m, 2H), 7.54 (d, J = 7.9 Hz, 1H), 7.40-7.34 (m, 1H), 6.00 (s, 2H), 2.15 (s, 6H).<br>MS (ESI) m/z: 213.3 (M + H)⁺. |

TABLE 2-continued

| Anilines | Products | Yield and Analytical data |
|---|---|---|
| INT-2-3 | INT-2-3-A | 54% yield (slightly yellow solid)<br>$^1$H-NMR (300 MHz, CDCl$_3$): delta 8.49 (s, 1H), 8.34 (s, 1H), 7.38 (s, 1H), 5.93 (s, 2H), 2.42 (s, 3H), 2.04 (s, 6H)<br>MS (ESI) m/z 187.33 (M + H)$^+$. |
| INT-2-4 | INT-2-4-A | 72% yield (yellow oil)<br>$^1$H-NMR (300 MHz, CDCl$_3$): delta 8.45 (s, 1H), 8.38 (s, 1H), 5.94 (s, 2H), 2.62 (s, 3H), 2.16 (s, 6H)<br>MS (ESI) m/z: 188.24 (M + H)$^+$. |
| INT-2-5 | INT-2-5-A | 12% yield (yellow oil)<br>$^1$H-NMR (270 MHz, CDCl$_3$): delta 8.33-8.23 (m, 1H), 8.11 (d, J = 7.9 Hz, 1H), 7.89 (d, J = 7.9 Hz 1H), 7.83-7.70 (m, 1H), 7.65-7.55 (m, 1H), 7.40-7.32 (m, 1H), 5.95 (s, 2H), 2.21 (s, 6H)<br>MS (ESI) m/z: 223.3 (M + H)$^+$. |
| INT-2-6 | INT-2-6-A | 95% yield (colorless amorphous solid)<br>$^1$H-NMR (300 MHz, CDCl$_3$): delta 5.92 (s, 2H), 4.39 (s, 3H), 2.26 (s, 6H).<br>MS (ESI) m/z: 178.3 (M + H)$^+$. |

Intermediate-3-1-A (INT-3-1-A): Ethyl 2,5-dimethyl-1-phenyl-1H-imidazole-4-carboxylate {Chem. 31}

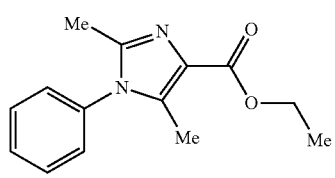

The titled compound is prepared according to the procedure described in WO 2011/005052 from aniline (3.73 g, 40.1 mmol) and ethyl 2-acetamido-3-oxobutanoate (2.50 g, 13.4 mmol). The purification is carried out by column chromatography on silica gel eluting with hexane-EtOAc (1:3 v/v) to give the product (4.06 g, 62% yield) as a slightly brown solid.

$^1$H-NMR (270 MHz, CDCl$_3$): delta 7.60-7.50 (m, 3H), 7.24-7.15 (m, 2H), 4.41 (q, J=7.3 Hz, 2H), 2.32 (s, 3H), 2.23 (s, 3H), 1.42 (t, J=7.3 Hz, 3H).

MS (ESI) m/z: 245.2 (M+H)$^+$.

The following imidazole derivatives (INT-3-2-A to INT-3-4-A) are prepared according to the procedure of intermediate 3-1-A from the known or synthesized aniline derivatives and ethyl 2-acetamido-3-oxobutanoate in Table 3.

TABLE 3

| Anilines | Products | Yield and Analytical data |
|---|---|---|
| INT-3-2 (3-chloroaniline) | INT-3-2-A | 51% yield (pale yellow solid)<br>¹H-NMR (270 MHz, DMSO-d$_6$): delta 7.52-7.49 (m, 2H), 7.22 (br, 1H), 7.12-7.08 (m. 1H), 4.40 (q, J = 7.2 Hz, 2H), 2.33 (s, 3H), 2.24 (s, 3H), 1.42 (t, J = 7.2 Hz, 3H). |
| INT-3-3 (3-methylaniline) | INT-3-3-A | 72% yield (a pale yellow solid)<br>¹H-NMR (270 MHz, DMSO-d$_6$): delta 7.48 (t, J = 6.6 Hz, 1H), 7.37 (d, J = 6.6 Hz, 1H), 7.28-7.17 (m, 2H), 4.22 (q, J = 6.6 Hz, 2H), 2.39 (s, 3H), 2.21 (s, 3H), 2.09 (s, 3H), 1.27 (t, J = 6.6 Hz, 3H).<br>MS (ESI) m/z: 259.3 (M + H)⁺. |
| INT-3-4 (3-fluoroaniline) | INT-3-4-A | 56% yield (colorless amorphous solid)<br>¹H-NMR (270 MHz, CDCl$_3$): delta 7.58-7.50 (m, 1H), 7.29-7.25 (m, 1H), 7.03-6.93 (m, 2H), 4.40 (q, J = 72. Hz, 2H), 2.33 (s, 3H), 2.24 (s, 3H), 1.42 (t, J = 7.2 Hz, 3H).<br>MS (ESI) m/z: 263.3 (M + H)⁺. |

Intermediate-3-5-A (INT-3-5-A): Ethyl 1,4-dimethyl-5-(pyridin-3-yl)-1H-pyrazole-3-carboxylate {Chem. 32}

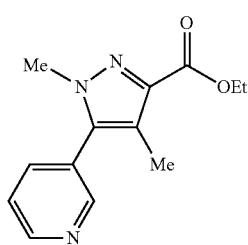

A mixture of ethyl 1,4-dimethyl-5-(((trifluoromethyl)sulfonyl)oxy)-1H-pyrazole-3-carboxylate (500 mg, 1.58 mmol), pyridin-3-yl boronic acid (214 mg, 1.74 mmol), Pd(PPh$_3$)$_4$ (183 mg, 0.158 mmol) and 2M Na$_2$CO$_3$ aq. solution (3.2 mL, 6.32 mmol) in DME (5 mL) is irradiated with microwave at 120° C. for 30 min. After cooling, the reaction mixture is filtered through Celite pad and the filter cake is washed with EtOAc. The filtrate and washings are washed with water, brine, dried over sodium sulfate, filtered and concentrated in vacuo. The residue is purified by column chromatography (Biotage) on silica gel (25 g) eluting with 10-100% ethyl acetate in hexane to give the titled compound (136 mg, 35% yield) as a brown amorphous solid.

1H-NMR (270 MHz, CDCl$_3$): delta 9.07 (dd, J=4.6, 1.3 Hz, 1H), 8.06 (d, J=8.5 Hz, 2H), 7.84 (dd, J=9.2, 4.6 Hz, 1H), 7.59-7.55 (m, 1H), 7.36 (d, J=8.5 Hz, 2H), 2.60 (s, 3H). MS (ESI) m/z: 246.3 (M+H)⁺.

Intermediate-4-1-A (INT-4-1-A): 2-chloro-1-(2,5-dimethyl-1-(3-methylisoxazol-5-yl)-1H-pyrrol-3-yl)ethanone {Chem. 33}

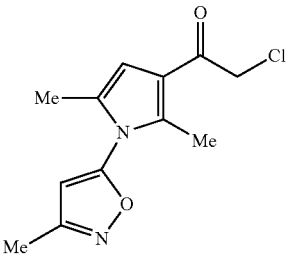

To a stirred solution of 5-(2,5-dimethyl-1H-pyrrol-1-yl)-3-methylisoxazole (2120 mg, 12.03 mmol)(INT-2-1-A) in DCM (40 mL) is added 2-chloroacetyl chloride (1.15 mL, 14.44 mmol) via a syringe with ice-cooling. To this added the crushed aluminum chloride (3210 mg, 24.06 mmol) in one portion at the same temperature and the mixture is stirred at rt for 1.5 h. After quenching with ice water followed by the adjustment to pH>8 with sat. sodium bicarbonate solution, the mixture is filtered through a pad of celite and the filter cake is washed with DCM. The organic layer is separated and the aqueous layer is extracted with DCM (2 times). The combined organic solution is washed with brine, dried over sodium sulfate, filtered and concentrated in vacuo to give the crude product, which is purified by column chromatography (Biotage) on silica gel (100 g) eluting with 10-40% ethyl acetate in hexane to give the desired product. Finally, the product is recrystallized from ethyl acetate-hexane to give the title compound (983 mg, 32% yield) as a pale tan solid.

$^1$H-NMR (270 MHz, CDCl$_3$): delta 6.31 (s, 1H), 6.10 (s, 1H), 4.45 (s, 2H), 2.46 (s, 3H), 2.41 (s, 3H), 2.15 (s, 3H).

MS (ESI) m/z: 253.17 (M+H)$^+$.

The following alpha-chloroacetyl derivatives (INT-4-2-A to INT-4-12-A) are prepared according to the procedure of intermediate 4-1-A from the known or synthesized pyrrole derivatives in Table 4.

TABLE 4

| Pyrroles | Products | Yield and Analytical data |
| --- | --- | --- |
| INT-2-2-A | INT-4-2-A | 47% yield (a pale yellow amorphous solid)<br>$^1$H-NMR (270 MHz, CDCl3): delta 7.75-7.66 (m, 2H), 7.50-7.39 (m, 2H), 6.42 (s, 1H), 4.51 (s, 2H), 2.45 (s, 3H), 2.12 (s, 3H).<br>MS (ESI) m/z: 289.2 (M + H)$^+$. |
| INT-4-3 | INT-4-3-A | 56% yield (yellow amorphous solid)<br>$^1$H-NMR (270 MHz, CDCl3): delta 9.40 (s, 1H), 8.47 (s, 1H), 8.20-8.10 (m, 1H), 7.80-6.98 (m, 2H), 7.24-7.18 (m, 1H), 6.45 (s, 1H), 4.55 (s, 2H), 2.24 (s, 3H), 1.90 (s, 3H).<br>MS (ESI) m/z: 299.3 (M + H)$^+$. |
| INT-2-3-A | INT-4-4-A | 78% yield (white solid)<br>$^1$H-NMR (300 MHz, CDCl3): delta 8.58 (br.s, 1H), 8.31 (br.s, 1H), 7.37 (br.s, 1H), 6.34 (s, 1H), 4.49 (s, 2H), 2.46 (s, 3H), 2.34 (s, 3H), 2.00 (s, 3H).<br>MS (ESI) m/z: 263.23 (M + H)$^+$. |
| INT-4-5 | INT-4-5-A | 39% yield<br>$^1$H-NMR (270 MHz, CDCl3): delta 7.47 (s, 1H), 4.49 (s, 2H), 2.24 (s, 3H). |

TABLE 4-continued

| Pyrroles | Products | Yield and Analytical data |
|---|---|---|
| INT-4-6 | INT-4-6-A | 42% yield<br>¹H-NMR (270 MHz, CDCl₃): delta 6.69 (s, 1H), 4.47 (s, 2H), 2.52 (s, 3H), 2.50 (s, 3H). |
| INT-4-7 | INT-4-7-A | 63% yield (a plae yellow amorphous solid)<br>¹H-NMR (270 MHz, DMSO-d₆): delta 8.15 (td, J = 8.1, 1.3 Hz, 1H), 7.73 (d, J = 7.3 Hz, 1H), 7.62 (d, J = 6.6 Hz, 1H), 6.49 (s, 1H), 4.79 (s, 2H), 2.32 (s, 3H), 2.04 (s, 3H).<br>MS (ESI) m/z: 283.2 (M + H)⁺. |
| INT-4-8 | INT-4-8-A | 40% yield (pale yellow solid)<br>¹H-NMR (300 MHz, CDCl3): delta 6.31 (s, 1H), 6.07 (s, 1H), 4.47 (s, 2H), 2.55 (s, 3H), 2.48 (s, 3H), 2.15 (s, 3H).<br>MS (ESI) m/z: 253.1 (M + H)⁺. |
| INT-2-4-A | INT-4-9-A | 72% yield (brown amorphous solid)<br>¹H-NMR (270 MHz, CDCl₃): delta 8.58 (s, 1H), 8.40 (s, 1H), 6.34 (s, 1H), 4.49 (s, 2H), 2.66 (s, 3H), 2.42 (s, 3H), 2.09 (s, 3H).<br>MS (ESI) m/z: 264.3 (M + H)⁺. |
| INT-2-5-A | INT-4-10-A | 70% yield (yellow oil)<br>¹H-NMR (270 MHz, CDCl₃): delta 8.38 (d, J = 8.6 Hz, 1H), 8.13 (d, J = 8.6 Hz, 1H), 7.95 (d, J = 8.6 Hz, 1H), 7.88-7.79 (m, 1H), 7.73-7.63 (m, 1H), 7.34 (d, J = 7.9 Hz, 1H), 6.36 (s, 1H), 4.52 (s, 2H), 2.46 (s, 3H), 2.13 (s, 3H).<br>MS (ESI) m/z: 299.3 (M + H)⁺. |

TABLE 4-continued

| Pyrroles | Products | Yield and Analytical data |
|---|---|---|
| 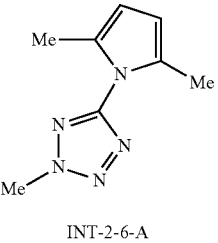 [SMILES: Cc1ccc(C)n1-c1nnn(C)n1]<br>INT-2-6-A | 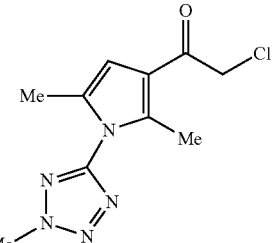<br>INT-4-11-A | 53% yield (white solid)<br>$^1$H-NMR (270 MHz, CDCl$_3$): delta 6.33 (s, 1H), 4.48 (s, 2H), 4.46 (s, 3H), 2.51 (s, 3H), 2.18 (s, 3H).<br>MS (ESI) m/z: 254.2 (M + H)$^+$. |
| 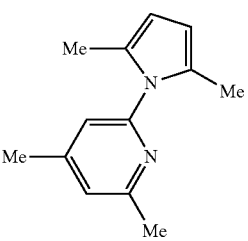<br>INT-4-12 | 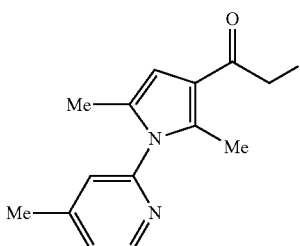<br>INT-4-12-A | 77% yield (pale purple solid)<br>$^1$H-NMR (300 MHz, CDCl$_3$): delta 7.10 (s, 1H), 6.85 (s, 1H), 6.27 (s, 1H), 4.49 (s, 2H), 2.56 (s, 3H), 2.42 (s, 3H), 2.38 (s, 3H), 2.05 (s, 3H).<br>MS (ESI) m/z: 277.23 (M + H)$^+$. |

Intermediate-5-1-A (INT-5-1-A): 2-chloro-1-(2,5-dimethyl-1-phenyl-1H-imidazol-4-yl)ethanone {Chem. 34}

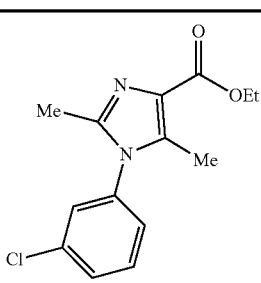

To a solution of ethyl 2, 5-dimethyl-1-phenyl-1H-imidazole-4-carboxylate (INT-3-1-A)(600 mg, 2.46 mmol) and chloroiodomethane (1300 mg, 7.37 mmol) in anhydrous THF (20 mL) is added LDA (1.09 M in THF solution; 6.76 mL, 7.34 mmol) at −80° C. and the resulting mixture is stirred at same temperature for 1.5 h. The mixture is quenched with sat. NH$_4$Cl solution (20 mL) and extracted with DCM (×3). The combined organic layers are washed with brine, dried over sodium sulfate, filtered and concentrated in vacuo to give the crude product, which is purified by column chromatography on silica gel (45 g) eluting with 30-40% EtOAc in hexane to give the titled compound (385 mg, 63% yield) as a slightly yellow solid.

$^1$H-NMR (270 MHz, CDCl$_3$): delta 7.62-7.52 (m, 3H), 7.24-7.17 (m, 2H), 4.88 (s, 2H), 2.35 (s, 3H), 2.21 (s, 3H).
MS (ESI) m/z: 249.2 (M+H)$^+$.

The following alpha-chloromethyl ketone derivatives (INT-5-2-A to INT-5-19-A) are prepared according to the procedure of intermediate 5-1-A from the known or synthesized ester derivatives in Table 5.

TABLE 5

| Esters | Products | Yield and Analytical data |
|---|---|---|
| 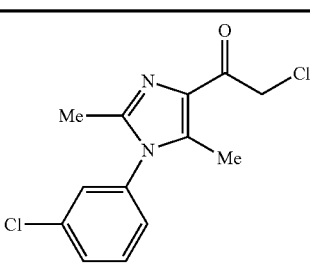<br>INT-3-2-A | INT-5-2-A | 56% yield<br>$^1$H-NMR (270 MHz, CDCl$_3$): delta 7.57-7.48 (m, 2H), 7.32-7.21 (m, 1H), 7.11 (ddd, 1H, J = 6.6, 2.0, 2.0 Hz), 4.87 (s, 2H), 2.36 (s, 3H), 2.23 (s, 3H). |

TABLE 5-continued

| Esters | Products | Yield and Analytical data |
|---|---|---|
| 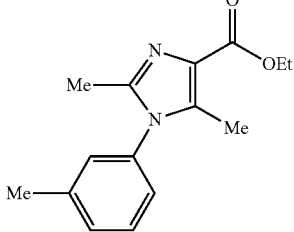<br>INT-3-3-A | 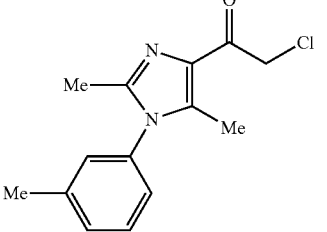<br>INT-5-3-A | 31% yield (a brown amorphous solid)<br>$^1$H-NMR (270 MHz, CDCl3): delta 7.44 (t, J = 6.6 Hz, 1H), 7.34 (d, J = 6.6 Hz, 1H), 6.99 (s, 2H), 4.88 (s, 2H), 2.44 (s, 3H), 2.34 (s, 3H), 2.21 (s, 3H).<br>MS (ESI) m/z: 263.2 (M + H)$^+$. |
| 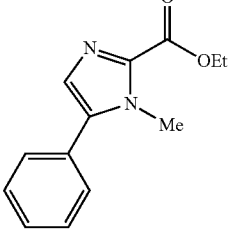<br>INT-5-4 | 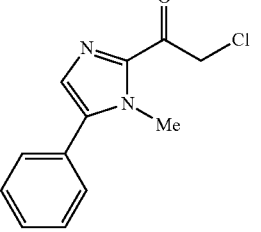<br>INT-5-4-A | 45% yield (slightly yellow solid)<br>$^1$H-NMR (270 MHz, CDCl$_3$): delta 7.56-7.36 (m, 5H), 4.98 (s, 2H), 3.98 (s, 3H).<br>MS (ESI) m/z: 235.26 (M + H)$^+$. |
| 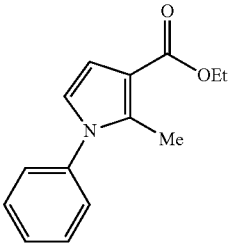<br>INT-5-5 | 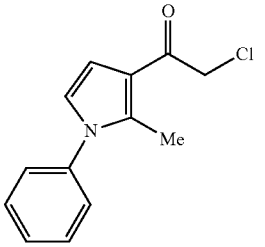<br>INT-5-5-A | 48% yield (a brown amorphous solid)<br>$^1$H-NMR (270 MHz, CDCl3): delta 7.52-7.44 (m, 4H), 7.29 (d, J = 1.3 Hz, 1H), 6.71 (d, J = 2.6 Hz, 1H), 6.61 (d, J = 3.3 Hz, 1H), 4.53 (s, 2H), 2.48 (s, 3H).<br>MS (ESI) m/z: 234.2 (M + H)$^+$. |
| 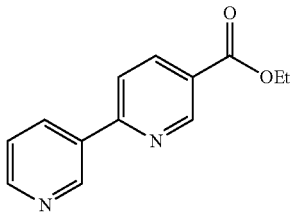<br>INT-5-6 | 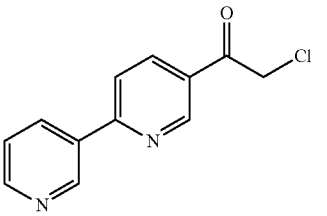<br>INT-5-6-A | 32% yield (brown solid)<br>$^1$H-NMR (300 MHz, CDCl3): delta 9.33-9.25 (m, 2H), 8.73 (dd, J = 5.1, 1.5 Hz, 1H), 8.48-8.35 (m, 2H), 7.93 (d, J = 8.8 Hz, 1H), 7.47 (dd, J = 8.8, 5.1 Hz, 1H), 4.72 (s, 2H).<br>MS (ESI) m/z: 233.1 (M + H)$^+$. |
| 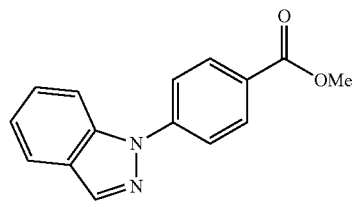<br>INT-5-7 | 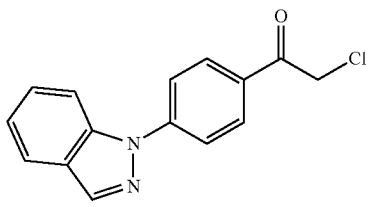<br>INT-5-7-A | 41% yield (slightly dark yellow solid)<br>$^1$H-NMR (270 MHz, CDCl$_3$): delta 8.27 (s, 1H), 8.20-8.12 (m, 2H), 8.00-7.80 (m, 4H), 7.56-7.47 (m, 1H), 7.35-7.25 (m, 1H), 4.75 (s, 2H).<br>MS (ESI) m/z: 271.18 (M + H)$^+$. |

TABLE 5-continued

| Esters | Products | Yield and Analytical data |
| --- | --- | --- |
| INT-5-8 | INT-5-8-A | 75% yield<br>¹H-NMR (270 MHz, CDCl$_3$): delta 6.78 (s, 1H), 6.69 (s, 1H), 4.45 (s, 2H), 3.89 (s, 3H), 2.08 (s, 3H). |
| INT-5-9 | INT-5-9-A | 39% yield<br>¹H-NMR (270 MHz, CDCl$_3$): delta 7.22 (d, J = 2.0 Hz, 1H), 6.40 (br.s, 1H), 4.39 (s, 2H), 3.64 (s, 3H), 2.29 (s, 3H). |
| INT-5-10 | INT-5-10-A | 45% yield<br>MS (ESI) m/z: 262 (M + H)⁺. |
| INT-5-11 | INT-5-11-A | 80% yield<br>¹H-NMR (270 MHz, CDCl$_3$): delta 7.63-7.57 (m, 2H), 7.44-7.38 (m, 2H), 7.33-7.29 (m, 2H), 7.12-7.04 (m, 1H), 4.74 (s, 2H), 3.91 (s, 3H).<br>MS (ESI) m/z: 277 (M − H)⁻. |
| INT-5-12 | INT-5-12-A | 47% yield<br>¹H-NMR (270 MHz, CDCl$_3$): delta 7.74 (d, J = 7.9 Hz, 1H), 7.68-7.75 (m, 3H), 7.49-7.42 (m, 2H), 7.37 (d, J = 7.3 Hz, 1H), 4.73 (s, 2H), 3.89 (s, 3H).<br>MS (ESI) m/z: 286 (M + H)⁺, 284 (M − H)⁻. |
| INT-5-13 | INT-5-13-A | 49% yield (pale brown oil)<br>MS (ESI) m/z: 248.1 (M + H)⁺. |

TABLE 5-continued

| Esters | Products | Yield and Analytical data |
|---|---|---|
| INT-5-14 | INT-5-14-A | 39% yield (slightly yellow solid)<br>$^1$H-NMR (270 MHz, CDCl$_3$): delta 7.56-7.42 (m, 3H), 7.34-7.25 (m, 2H), 4.87 (s, 2H), 3.80 (s, 3H), 2.23 (s, 3H).<br>MS (ESI) m/z: 249.2 (M + H)$^+$. |
| INT-3-4-A | INT-5-15-A | 52% yield (brown solid)<br>$^1$H-NMR (270 MHz, CDCl$_3$): delta 7.60-7.52 (m, 1H), 7.31-7.26 (m, 1H), 7.04-6.94 (m, 2H), 4.87 (s, 2H), 2.36 (s, 3H), 2.23 (s, 3H).<br>MS (ESI) m/z: 267.2 (M + H)$^+$. |
| INT-3-5-A | INT-5-16-A | quant. (brown amorphous solid)<br>$^1$H-NMR (270 MHz, CDCl$_3$): delta 8.75-8.73 (m, 1H), 8.61-8.60 (m, 1H), 7.70-7.64 (m, 1H), 7.49-7.46 (m, 1H), 4.86 (s, 2H), 3.84 (s, 3H), 2.26 (s, 3H).<br>MS (ESI) m/z: 250.2 (M + H)$^+$. |
| INT-5-17 | INT-5-17-A | 53% yield (slightly yellow solid)<br>$^1$H-NMR (270 MHz, CDCl$_3$): delta 8.19-8.13 (m, 1H), 7.96 (d, J = 8.6 Hz, 2H), 7.66-7.54 (m, 3H), 6.95-6.81 (m, 2H), 5.46 (s, 2H), 4.71 (s, 2H).<br>MS (ESI) m/z: 262.0 (M + H)$^+$. |
| INT-5-18 | INT-5-18-A | 37% yield (brown oil)<br>$^1$H-NMR (270 MHz, CDCl$_3$): delta 8.53 (d, J = 4.6 Hz, 2H), 8.01 (d, J = 8.6 Hz, 2H), 7.78 (d, J = 8.6 Hz, 2H), 7.05 (t, J = 4.6 Hz, 1H), 4.73 (s, 2H).<br>MS (ESI) m/z: 265.0 (M + H)$^+$. |

TABLE 5-continued

| Esters | Products | Yield and Analytical data |
|---|---|---|
| 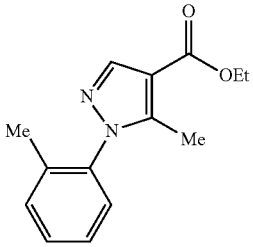<br>INT-5-19-A | <br>INT-5-19-A | 67% yield (pale yellow oil)<br>$^1$H-NMR (270 MHz, CDCl$_3$): delta 8.07 (s, 1H), 7.48-7.17 (m, 4H), 4.52 (s, 2H), 2.40 (s, 3H), 2.04 (s, 3H).<br>MS (ESI) m/z: 249.2 (M + H)$^+$. |

Halogenation Via Ketone Derivatives
(Method-A): Chlorination Using Benzyltrimethylammonium Dichloroiodate Intermediate-6-1-A (INT-6-1-A: 1-(5-bromo-1-methyl-1H-pyrrol-2-yl)-2-chloroethanone {Chem. 35}

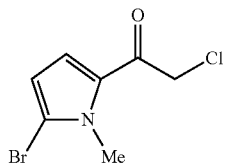

To a stirred solution of 1-(5-bromo-1-methyl-1H-pyrrol-2-yl)ethanone (480 mg, 2.38 mmol) in THF (8 mL) is added benzyltrimethylammonium dichloroiodate (1.24 g, 3.56 mmol) in one portion at rt. The mixture is heated at 70° C. for 2 h (yellow to dark brown suspension). After cooling, the mixture is diluted with ethyl acetate and washed with 2 M HCl aq. solution, sat. sodium thiosulfide solution and brine, dried over sodium sulfate, filtered and concentrated in vacuo to give the crude product. The crude product is purified by column chromatography on silica gel eluting with 10-50% EtOAc in hexane to give the titled compound (498 mg, 89% yield).

(Method-B) Bromination Using Copper (II) Bromide

Intermediate-6-3-A (INT-6-3-A): 2-bromo-1-(1,4-dimethyl-5-phenyl-1H-pyrrol-2-yl)ethanone {Chem. 36}

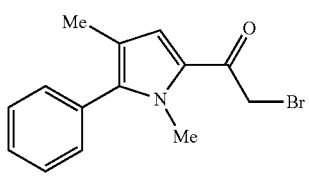

A mixture of copper (II) bromide (1.05 g, 4.69 mmol) and 1-(1,4-dimethyl-5-phenyl-1H-pyrrol-2-yl)ethanone (500 mg, 2.34 mmol) in ethyl acetate (10 mL) is heated under reflux for 4 h. After cooling to room temperature, the mixture is filtered through a pad of silica gel and the filter cake is washed with ethyl acetate. The combined organic fractions are evaporated to afford the titled compound (41 mg, 6% yield).

(Method-C) Bromination Using Bromine in 25% HBr-Acetic Acid Solution

Intermediate-6-4-A (INT-6-4-A): 2-bromo-1-(5-bromo-1,4-dimethyl-1H-imidazol-2-yl)ethanone hydrobromide {Chem. 37}

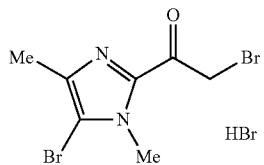

A mixture of 1-(5-bromo-1,4-dimethyl-1H-imidazol-2-yl)ethanone (260 mg, 1.20 mmol) and bromine (201 mg, 1.26 mmol) in 25% HBr in AcOH (5 mL) is stirred at 60° C. for 2 h. The mixture is concentrated. The residual solid is triturated with IPE to give the titled compound (451 mg, quantitive yield).

The following alpha-halomethyl ketone derivatives (INT-6-1-A to INT-6-15-A) are prepared according to the procedure of methods (A-C) from the known or synthesized methyl ketone derivatives in Table 6.

TABLE 6

| ketones | alpha-haloketones | Yield and Analytical data |
|---|---|---|
| 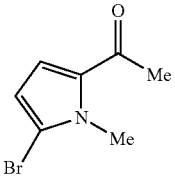<br>INT-6-1 | 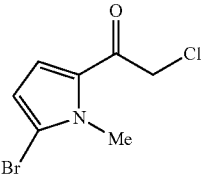<br>INT-6-1-A | 89% yield (method A)<br>¹H-NMR (270 MHz, CDCl$_3$): delta 7.00 (d, J = 4.6 Hz, 1H), 6.29 (d, J = 4.6 Hz, 1H), 4.46 (s, 2H), 3.97 (s, 3H). |
| 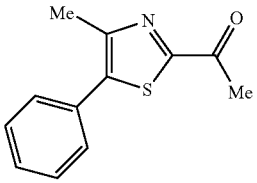<br>INT-6-2 | 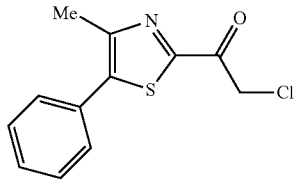<br>INT-6-2-A | 67% yield (method A)<br>¹H-NMR (270 MHz, CDCl$_3$): delta 7.50-7.42 (m, 5H), 4.97 (s, 2H), 2.57 (s, 3H). |
| 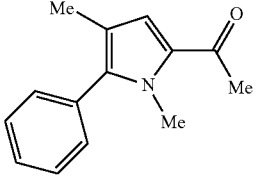<br>INT-6-3 | 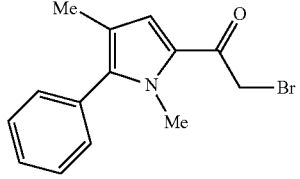<br>INT-6-3-A | 6% yield (method B)<br>¹H-NMR (270 MHz, CDCl$_3$): delta 7.46-7.28 (m, 6H), 4.22 (s, 2H), 3.52 (s, 3H), 2.23 (s, 3H). |
| 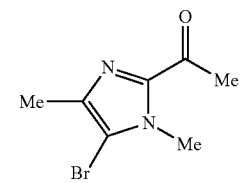<br>INT-6-4 | 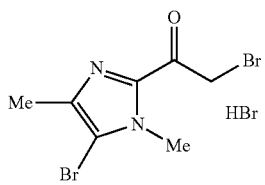<br>INT-6-4-A | 100% yield (pale yellow solid)(method C)<br>¹H-NMR (270 MHz, DMSO-d$_6$): delta 4.77 (s, 2H), 3.89 (s, 3H), 2.19 (s, 3H).<br>MS (ESI) m/z: 296.9 (M + H)⁺. |
| 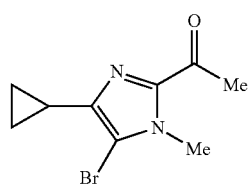<br>INT-6-5 | 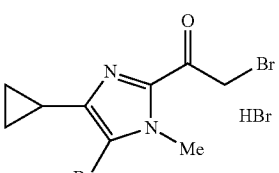<br>INT-6-5-A | 100% yield (a pale yellow solid)(method C)<br>MS (ESI) m/z: 322.9 (M + H)⁺. |
| 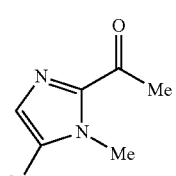<br>INT-6-6 | 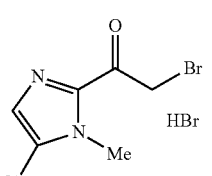<br>INT-6-6-A | 87% yield (pale yellow solid)(method C)<br>MS (ESI) m/z: 239.1 (M + H)⁺. |

TABLE 6-continued

| ketones | alpha-haloketones | Yield and Analytical data |
|---|---|---|
| 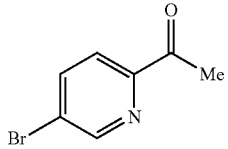<br>INT-6-7 | 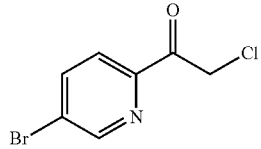<br>INT-6-7-A | 100% yield (off-white solid)(method A)<br>$^1$H-NMR (270 MHz, CDCl3): delta 8.73 (d, J = 2.0 Hz, 1H), 8.02 (d, J = 2.0 Hz, 1H), 7.99 (s, 1H), 5.06 (s, 2H).<br>MS (ESI) m/z: 234.1 (M + H)$^+$. |
| 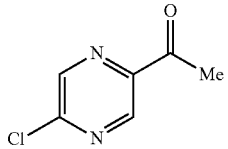<br>INT-6-8 | 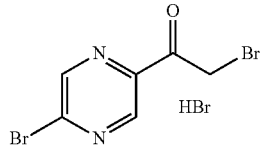<br>INT-6-8-A | 100% yield (brown solid)(method C)<br>MS (ESI) m/z: 280.9 (M + H)$^+$. |
| 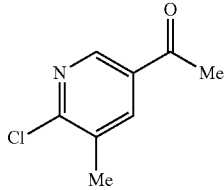<br>INT-6-9 | 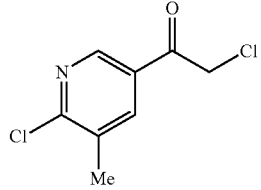<br>INT-6-9-A | 88% yield (pale yellow solid)(method A)<br>$^1$H-NMR (270 MHz, CDCl$_3$): delta 8.78 (d, J = 2.0 Hz, 1H), 8.11 (d, J = 2.0 Hz, 1H), 4.64 (s, 2H), 2.47 (s, 3H).<br>MS (ESI) m/z: 204.1 (M + H)$^+$. |
| 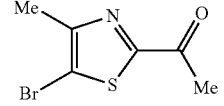<br>INT-6-10 | 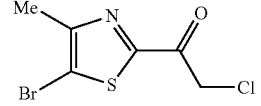<br>INT-6-10-A | 75% yield (method A)<br>$^1$H-NMR (270 MHz, CDCl$_3$): delta 4.89 (s, 2HH), 2.48 (s, 3H). |
| 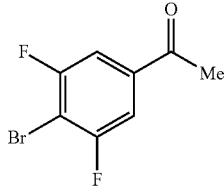<br>INT-6-11 | 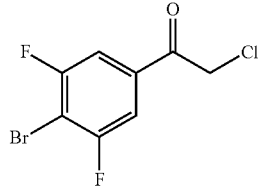<br>INT-6-11-A | 89% yield (method A)<br>$^1$H-NMR (270 MHz, CDCl$_3$): delta 7.58-7.52 (m, 2H), 4.62 (s, 2H). |
| 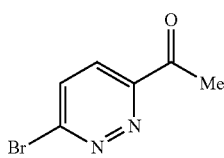<br>INT-6-12 | 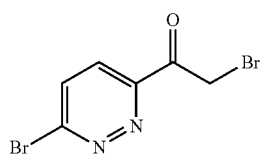<br>INT-6-12-A | 80% yield (off-white solid)(method C)<br>$^1$H-NMR (270 MHz, CDCl$_3$): delta 8.04 (d, J = 8.6 Hz, 1H), 7.88 (d, J = 8.6 Hz, 1H), 4.92 (s, 2H).<br>MS (ESI) m/z: 281.0 (M + H)$^+$. |
| 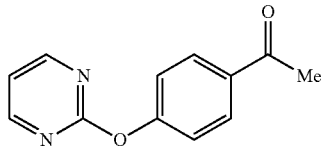<br>INT-6-13 | 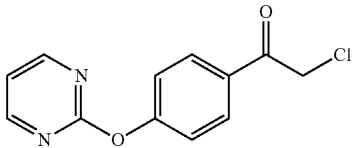<br>INT-6-13-A | 60% yield (white solid)(method A)<br>$^1$H-NMR (270 MHz, DMSO-d$_6$): delta 8.69 (d, J = 4.6 Hz, 2H), 8.07 (d, J = 8.5 Hz, 2H), 7.41-7.32 (m, 3H), 5.24 (s, 2H).<br>MS (ESI) m/z: 249.1 (M + H)$^+$. |

TABLE 6-continued

| ketones | alpha-haloketones | Yield and Analytical data |
|---|---|---|
| 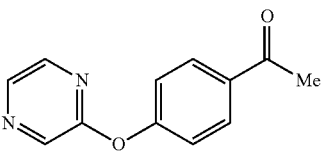<br>INT-6-14 | <br>INT-6-14-A | 69% yield (white solid)(method A)<br>$^1$H-NMR (270 MHz, DMSO-d$_6$): delta 8.65 (d, J = 1.3 Hz, 1H), 8.46 (d, J = 2.6 Hz, 1H), 8.26 (dd, J = 2.6, 1.3 Hz, 1H), 8.07 (d, J = 8.5 Hz, 2H), 7.39 (d, J = 8.5 Hz, 2H), 5.23 (s, 2H).<br>MS (ESI) m/z: 249.1 (M + H)$^+$. |
| 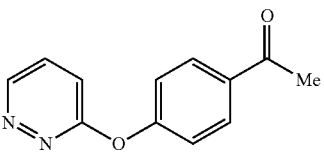<br>INT-6-15 | <br>INT-6-15-A | 47% yield (pale yellow solid)(method A)<br>$^1$H-NMR (270 MHz, DMSO-d$_6$): delta 9.08 (dd, J = 4.6, 1.3 Hz, 1H), 8.08 (d, J = 8.5 Hz, 2H), 7.84 (dd, J = 8.5, 4.6 Hz, 1H), 7.61-7.57 (m, 1H), 7.39 (d, J = 8.5 Hz, 2H), 5.24 (s, 2H).<br>MS (ESI) m/z: 249.1 (M + H)$^+$. |

Intermediate-6-2 (INT-6-2): 1-(4-methyl-5-phenylthiazol-2-yl)ethanone

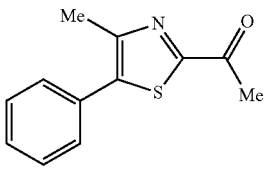

{Chem. 38}

Potassium carbonate (1.47 g, 10.62 mmol), palladium acetate (2 mmol %)(32 mg, 0.142 mmol), tricyclohexylphosphine tetrafluoroborate (4 mol %)(104 mg, 0.283 mmol), and pivalic acid (30 mol %)(217 mg, 2.13 mmol) are weighed to air and placed in a screw-cap vial equipped with a magnetic stir bar. The vial is purged with argon, and DMA (24 mL) is added. The 1-(4-methylthiazol-2-yl)ethanone (1.00 g, 7.08 mmol) and bromobenzene (1.11 g, 7.08 mmol) are added. The reaction mixture is then vigorously stirred at 100° C. for 16 h. The solution is then cooled to rt, diluted with EtOAc, washed with H$_2$O, dried over MgSO$_4$, filtered, and evaporated under reduced pressure. The crude product is purified by column chromatography on silica gel eluting with 10-50% ethyl acetate in hexane to afford the corresponding product. This product is washed with ethyl acetate-hexane mixture to give the titled compound (586 mg, 38% yield).

$^1$H-NMR (270 MHz, CDCl$_3$): delta 7.48-7.40 (m, 5H), 2.71 (s, 3H), 2.57 (s, 3H).

Intermediate-6-3 (INT-6-3): 1-(1,4-dimethyl-5-phenyl-1H-pyrrol-2-yl)ethanone

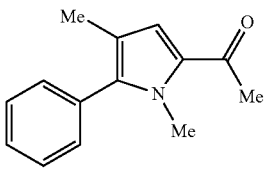

{Chem. 39}

N,N-dimethyl acetoamide (0.714 mL, 7.71 mmol) is cooled at 0-5° C. and to this is added phosphoryl trichloride (0.699 mL, 7.71 mmol) slowly in a dropwise manner. The resulting mixture is then stirred at room temperature for 20 minutes. The reaction mixture is then diluted with 1, 2-dichloroethane (30 mL) and cooled to 0° C. To the cooled reaction mixture is then added a solution of 1, 3-dimethyl-1H-pyrrole (1.20 g, 7.01 mmol) in 1, 2-dichloroethane (30 mL) dropwise. The reaction mixture is then heated to reflux for 30 minutes. The mixture so obtained is allowed to cool to room temperature and is diluted with sodium acetate trihydrate aq. solution (10 g in 25 mL water). The mixture is further heated to reflux for 30 minutes and two layers are separated. The aqueous layer is extracted with dichloromethane (3×50 mL). The combined organic layer is washed with water (1×50 mL) and dried over anhydrous Na$_2$SO$_4$. The solvent from the reaction mixture is evaporated under reduced pressure to obtain a crude product. This crude product is purified by column chromatography on silica gel eluting with 0-30% ethyl acetate in hexane to obtain the titled compound (1.23 g, 83% yield).

$^1$H-NMR (270 MHz, CDCl$_3$): delta 7.51-7.37 (m, 3H), 7.30-7.26 (m, 2H), 6.88 (s, 1H), 3.75 (s, 3H), 2.45 (s, 3H), 2.02 (s, 3H).

Intermediate-6-4 (INT-6-4): 1-(5-bromo-1,4-dimethyl-1H-imidazol-2-yl)ethanone

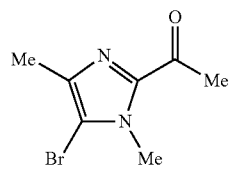

{Chem. 40}

<Step-1>: Intermediate-6-4-1 (INT-6-4-1): 1-(4-bromo-1-methyl-1H-imidazol-2-yl)ethanone

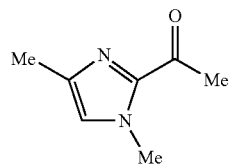

{Chem. 41}

To a solution of 1-(1-methyl-1H-imidazol-2-yl)ethanone (3.67 g, 29.6 mmol) in MeCN (50 mL) is added N-bromosuccinimide (5.52 g, 31.0 mmol). The mixture is stirred at 60° C. for 1 day. After the removal of solvent, the residual solid is purified by column chromatography on silica gel eluting with 0-50% ethyl acetate in hexane to give the titled compound (3.83 g, 64% yield) as a brown solid.

¹H-NMR (270 MHz, CDCl₃): delta 7.00 (s, 1H), 3.98 (s, 3H), 2.63 (s, 3H).

MS (ESI) m/z: 205.1 (M+H)⁺.

<Step-2>: Intermediate-6-4-2 (INT-6-4-2): 1-(1,4-dimethyl-1H-imidazol-2-yl)ethanone

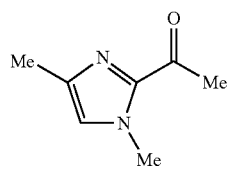

{Chem. 42}

A mixture of 1-(4-bromo-1-methyl-1H-imidazol-2-yl)ethanone (INT-6-4-1) (500 mg, 2.46 mmol), trimethylboroxine (1.55 g, 12.3 mmol), bis(di-tert-butyl(4-dimethylaminophenyl)phosphine)dichloropalladium(II) (101 mg, 0.12 mmol) in 1,4-dioxane (10 mL)-sat. NaHCO₃ solution (10 mL) is stirred at 80° C. for 1 day. The mixture is diluted with water and extracted with EtOAc. The combined organic solution is dried over Na₂SO₄, filtered and concentrated. The residual oil is purified by column chromatography on silica gel eluting with 0-30% ethyl acetate in hexane to give the titled compound (140 mg, 41% yield) as a yellow oil.

¹H-NMR (270 MHz, CDCl₃): delta 6.77 (s, 1H), 3.93 (s, 3H), 2.63 (s, 3H), 2.26 (s, 3H).

MS (ESI) m/z: 139.2 (M+H)⁺.

<Step-3>: Intermediate-6-4 (INT-6-4): 1-(5-bromo-1,4-dimethyl-1H-imidazol-2-yl)ethanone

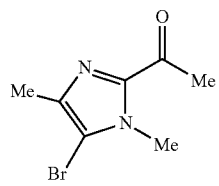

{Chem. 43}

To a solution of 1-(1,4-dimethyl-1H-imidazol-2-yl)ethanone (INT-6-4-2)(220 mg, 1.59 mmol) in MeCN (5 mL) is added N-bromosuccinimide (312 mg, 1.75 mmol). The mixture is stirred at 60° C. for 1 h. After the removal of solvent in vacuo, the residual solid is purified by column chromatography on silica gel eluting with 0-25% ethyl acetate in hexane to give the titled compound (270 mg, 78% yield) as a pale yellow oil.

¹H-NMR (270 MHz, CDCl₃): delta 3.96 (s, 3H), 2.62 (s, 3H), 2.26 (s, 3H).

MS (ESI) m/z: 219.1 (M+H)⁺.

Intermediate-6-5 (INT-6-5): 1-(5-bromo-4-cyclopropyl-1-methyl-1H-imidazol-2-yl)ethanone

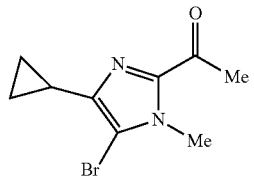

{Chem. 44}

<Step-1>: Intermediate-6-5-1 (INT-6-5-1): 1-(4-cyclopropyl-1-methyl-1H-imidazol-2-yl)ethanone

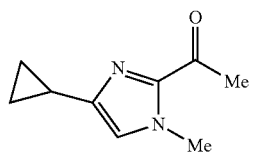

{Chem. 45}

A mixture of 1-(4-bromo-1-methyl-1H-imidazol-2-yl)ethanone (INT-6-4-1) (500 mg, 2.46 mmol), cyclopropylboronic acid (635 mg, 7.39 mmol), bis(di-tert-butyl(4-dimethylaminophenyl)phosphine)dichloropalladium(II) (101 mg, 0.12 mmol) in dioxane (10 mL)-sat. NaHCO₃ solution (10 mL) is refluxed for 2 days. The mixture is diluted with H₂O and extracted with EtOAc (×2). The combined organic solution is dried over Na₂SO₄, filtered and concentrated. The residual oil is purified by column chromatography on silica gel eluting with 0-50% ethyl acetate in hexane to give the titled compound (103 mg, 26% yield) as a yellow oil.

¹H-NMR (600 MHz, CDCl₃): delta 6.70 (s, 1H), 3.91 (s, 3H), 2.61 (s, 3H), 1.88-1.82 (m, 1H), 0.91-0.86 (m, 2H), 0.73-0.69 (m, 2H).

MS (ESI) m/z: 165.2 (M+H)⁺.

<Step-2>: Intermediate-6-5 (INT-6-5):1-(5-bromo-4-cyclopropyl-1-methyl-1H-imidazol-2-yl)ethanone

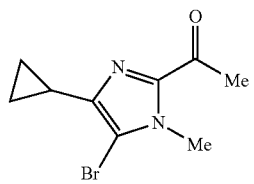

{Chem. 46}

To a solution of 1-(4-cyclopropyl-1-methyl-1H-imidazol-2-yl)ethanone (INT-6-5-1)(103 mg, 0.63 mmol) in MeCN (5 mL) is added N-bromosuccinimide (128 mg, 0.72 mmol). The mixture is stirred at 60° C. for 30 min. After the removal of solvent in vacuo, the residual solid is purified by column chromatography on silica gel eluting with 0-25% ethyl acetate in hexane to give the titled compound (96 mg, 63% yield) as a pale yellow oil.

¹H-NMR (270 MHz, CDCl₃): delta 3.94 (s, 3H), 2.57 (s, 3H), 1.92-1.80 (m, 1H), 0.95-0.88 (m, 4H).
MS (ESI) m/z: 243.1 (M+H)⁺.

Intermediate-6-6 (INT-6-6): 1-(5-chloro-1-methyl-1H-imidazol-2-yl)ethanone

{Chem. 47}

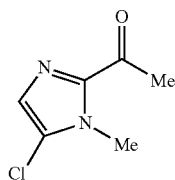

To a solution of 5-chloro-1-methyl-1H-imidazole (500 mg, 4.29 mmol) and acetyl chloride (0.31 mL, 4.29 mmol) in DCM (30 mL) is added DIPEA (1.50 mL, 8.58 mmol) at 0° C. The mixture is stirred at rt for 1 day. The mixture is quenched with 2 M NaOH aq. solution and extracted with DCM. The combined organic solution is dried over Na₂SO₄, filtered and concentrated. The residual oil is purified by column chromatography on silica gel eluting with 0-30% ethyl acetate in hexane to give the titled compound (172 mg, 25% yield) as an off-white solid.

¹H-NMR (270 MHz, CDCl₃): delta 7.11 (s, 1H), 3.95 (s, 3H), 2.63 (s, 3H).
MS (ESI) m/z: 159.2 (M+H)⁺.

Intermediate-6-15 (INT-6-15): 1-(4-(pyridazin-3-yloxy)phenyl)ethanone

{Chem. 48}

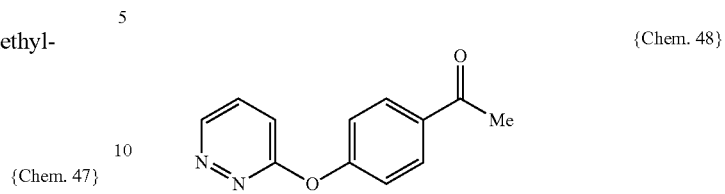

A mixture of 1-(4-hydroxyphenyl)ethanone (283 mg, 2.08 mmol), 3-chloropyridazine (238 mg, 2.08 mmol) and potassium carbonate (574 mg, 4.16 mmol) in DMF (5 mL) is irradiated in a microwave reactor (Biotage Initiator) for 60 min. at 140° C. After cooling, the reaction mixture is filtered through Celite pad and the filter cake is washed with EtOAc. The filtrate and washings are washed with water and brine, dried over sodium sulfate, filtered and concentrated in vacuo. The residue is purified by column chromatography (Biotage) on silica gel (25 g) eluting with 10-80% ethyl acetate in DCM to give the the titled compound (58 mg, 13% yield) as a white solid.

¹H-NMR (270 MHz, DMSO-d₆): delta 9.07 (dd, J=4.6, 1.3 Hz, 1H), 8.06 (d, J=8.5 Hz, 2H), 7.84 (dd, J=9.2, 4.6 Hz, 1H), 7.59-7.55 (m, 1H), 7.36 (d, J=8.5 Hz, 2H), 2.60 (s, 3H).
MS (ESI) m/z: 215.1 (M+H)⁺.

The following alpha-bromomethyl ketone derivatives (INT-6-16-A to INT-6-31-A) are prepared according to the procedure of intermediate 6-4-A (Method C) or intermediate 6-1-A (Method A) from the known or synthesized methyl ketone derivatives in Table 7.

TABLE 7

| Ketones | alpha-haloketones | Yield and Analytical data |
|---|---|---|
| INT-6-16 | INT-6-16-A | quant. (HBr salt)(orange solid)(method C)<br>¹H-NMR (270 MHz, CD₃OD): delta 9.85 (s, 1H), 8.38 (d, J = 9.2 Hz, 2H), 8.00-7.96 (m, 3H), 7.76-7.73 (m, 3H), 4.76 (s, 2H).<br>MS (ESI) m/z: 317.2 (M + H)⁺. |
| INT-6-17 | INT-6-17-A | 95% yield (HBr salt)(orange solid)(method C)<br>¹H-NMR (270 MHz, CD₃OD): delta 8.39 (d, J = 8.6 Hz, 2H), 7.86 (d, J = 8.6 Hz, 2H), 7.68-7.58 (m, 4H), 4.78 (s, 2H), 2.79 (s, 3H)<br>MS (ESI) m/z: 331.1 (M + H)⁺. |

TABLE 7-continued

| Ketones | alpha-haloketones | Yield and Analytical data |
|---|---|---|
| 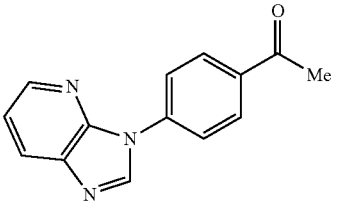<br>INT-6-18 | 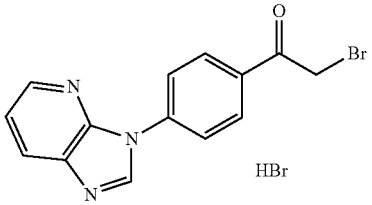<br>INT-6-18-A | 96% yield (HBr salt)<br>(pale yellow solid)(method C)<br>$^1$H-NMR (270 MHz, DMSO-d$_6$): delta 9.35 (s, 1H), 8.55 (dd, J = 4.6, 1.3 Hz, 1H), 8.30 (dd, J = 7.9, 1.3 Hz, 1H), 8.25 (s, 4H), 7.51 (dd, J = 8.5, 4.6 Hz, 1H), 5.01 (s, 2H)<br>MS (ESI) m/z: 316.1 (M + H)$^+$. |
| 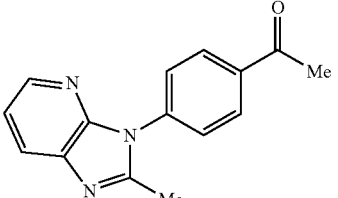<br>INT-6-19 | 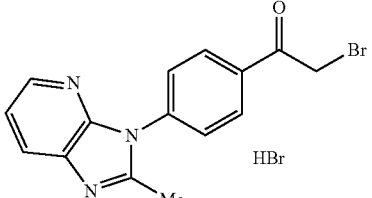<br>INT-6-19-A | 97% yield (HBr salt)(yellow solid)(method C)<br>$^1$H-NMR (270 MHz, DMSO-d$_6$): delta 8.51 (d, J = 3.3 Hz, 1H), 8.37 (d, J = 7.9 Hz, 1H), 8.30 (d, J = 8.5 Hz, 2H), 7.89 (d, J = 8.5 Hz, 2H), 7.65-7.59 (m, 1H), 5.07 (s, 2H), 2.72 (s, 3H).<br>MS (ESI) m/z: 331.9 (M + H)$^+$. |
| 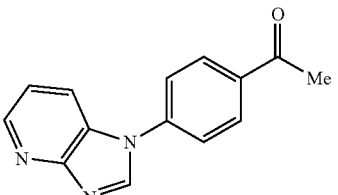<br>INT-6-20 | 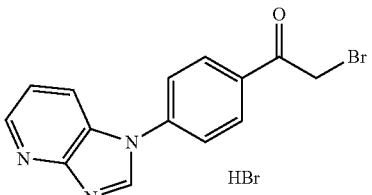<br>INT-6-20-A | 82% yield (HBr salt)(pale yellow solid)(method C)<br>$^1$H-NMR (270 MHz, DMSO-d$_6$): delta 9.17 (s, 1H), 8.63 (d, J = 5.3 Hz, 1H), 8.37 (d, J = 7.9 Hz, 1H), 8.27 (d, J = 8.5 Hz, 2H), 7.97 (d, J = 8.5 Hz, 2H), 7.56-7.51 (m, 1H), 5.03 (s, 2H) |
| 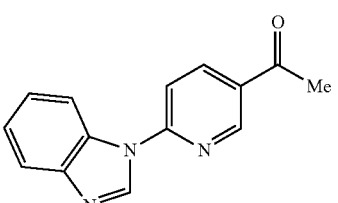<br>INT-6-21 | 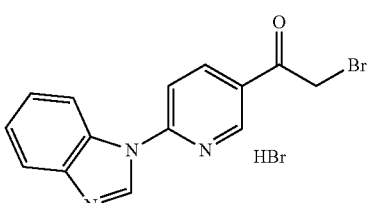<br>INT-6-21-A | quant. (HBr salt)(pale pink solid)(method C)<br>$^1$H-NMR (270 MHz, DMSO-d$_6$): delta 9.57 (s, 1H), 9.25 (d, J = 2.0 Hz, 1H), 8.63 (dd, J = 8.5, 2.0 Hz, 1H), 8.49 (d, J = 7.2 Hz, 1H), 8.21 (d, J = 8.5 Hz, 1H), 7.86 (d, J = 7.2 Hz, 1H), 7.57-7.46 (m, 2H), 5.07 (s, 2H).<br>MS (ESI) m/z: 318.0 (M + H)$^+$. |
| 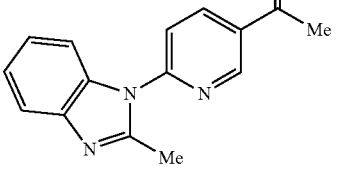<br>INT-6-22 | 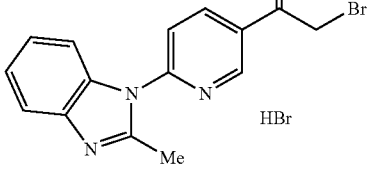<br>INT-6-22A | quant. (HBr salt)(yellow solid)(method C)<br>$^1$H-NMR (270 MHz, DMSO-d$_6$): delta 9.35 (d, J = 2.0 Hz, 1H), 8.75 (dd, J = 8.5, 2.0 Hz, 1H), 8.08 (d, J = 8.5 Hz, 1H), 7.91-7.87 (m, 1H), 7.75-7.72 (m, 1H), 7.59-7.53 (m, 2H), 5.12 (s, 2H), 2.84 (s, 3H).<br>MS (ESI) m/z: 331.9 (M + H)$^+$. |

TABLE 7-continued

| Ketones | alpha-haloketones | Yield and Analytical data |
|---|---|---|
| 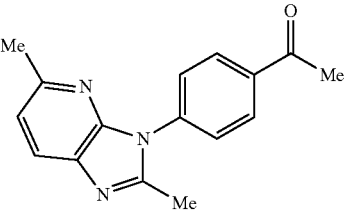<br>INT-6-23 | 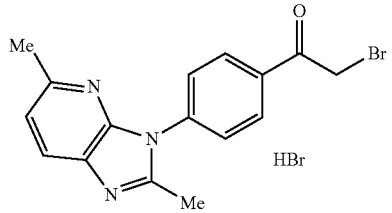<br>INT-6-23-A | quant. (HBr salt)(tan solid)(method C)<br>$^1$H-NMR (270 MHz, DMSO-d$_6$): delta 8.36-8.26 (m, 3H), 7.90 (d, J = 8.6 Hz, 2H), 7.55 (d, J = 8.6 Hz, 1H), 5.08 (s, 2H), 2.72 (s, 3H), 2.57 (s, 3H).<br>MS (ESI) m/z: 344.0 (M + H)$^+$. |
| 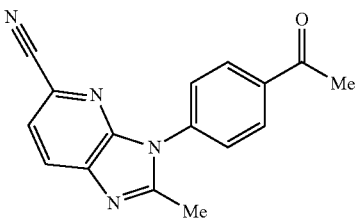<br>INT-6-24 | 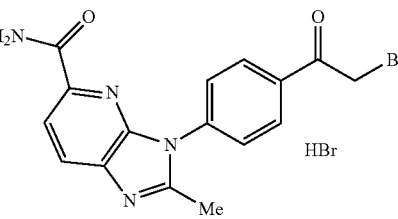<br>INT-6-24-A | quant. (HBr salt)(slightly yellow solid)(method C)<br>MS (ESI) m/z: 373.1 (M + H)$^+$. |
| 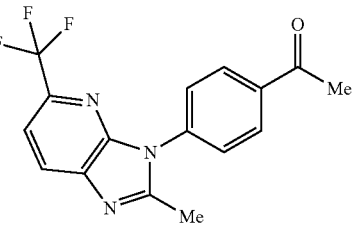<br>INT-6-25 | 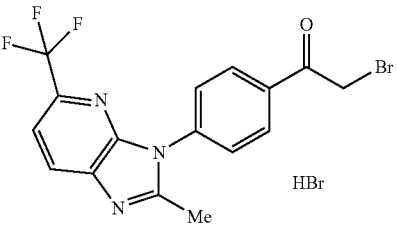<br>INT-6-25-A | quant. (HBr salt)<br>(brown amorphous solid)(method C)<br>MS (ESI) m/z: 398.0 (M + H)$^+$. |
| 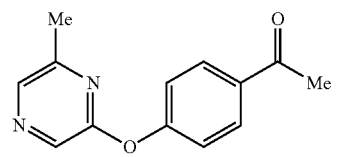<br>INT-6-26 | 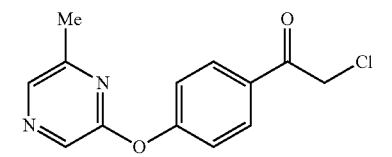<br>INT-6-26-A | 29% yield (white solid)(method A)<br>$^1$H-NMR (270 MHz, DMSO-d$_6$): delta 8.41 (s, 1H), 8.36 (s, 1H), 8.06 (d, J = 8.6 Hz, 2H), 7.36 (d, J = 8.6 Hz, 2H), 5.23 (s, 2H), 2.36 (s, 3H).<br>MS (ESI) m/z: 263.0 (M + H)$^+$. |
| 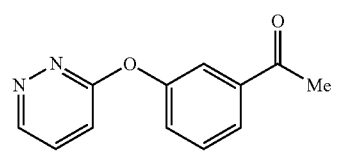<br>INT-6-27 | 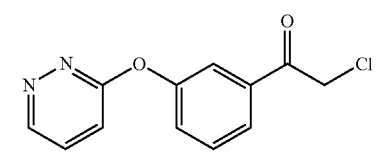<br>INT-6-27-A | 35% yield (orange solid)(method A)<br>$^1$H-NMR (270 MHz, DMSO-d$_6$): delta 9.04 (d, J = 4.6 Hz, 1H), 7.90 (d, J = 7.3 Hz, 1H), 7.84-7.79 (m, 2H), 7.69-7.53 (m, 3H), 5.24 (s, 2H).<br>MS (ESI) m/z: 215.1 (M + H)$^+$. |
| 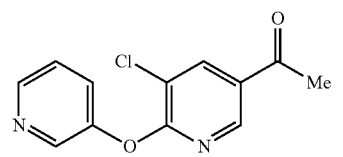<br>INT-6-28 | 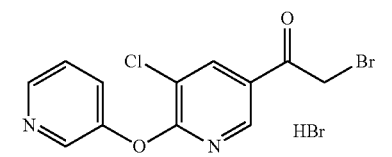<br>INT-6-28-A | 85% yield (HBr salt)(pale yellow solid)<br>(method C)<br>MS (ESI) m/z: 329.0 (M + H)$^+$. |

TABLE 7-continued

| Ketones | alpha-haloketones | Yield and Analytical data |
|---|---|---|
| INT-6-29 | INT-6-29-A | 87% yield (HBr salt)(pale yellow solid) (method C)<br>MS (ESI) m/z: 327.0 (M + H)+. |
| INT-6-30 | INT-6-30-A | 8% yield (orange solid)(method A)<br>1H-NMR (270 MHz, DMSO-d6): delta 9.12 (d, J = 5.3 Hz, 1H), 8.13 (d, J = 8.3 Hz, 2H), 7.81 (d, J = 8.3 Hz, 2H), 7.69 (d, J = 5.3 Hz, 1H), 5.30 (s, 2H), 2.34 (s, 3H).<br>MS (ESI) m/z: 247.2 (M + H)+. |
| INT-6-31 | INT-6-31-A | 90% yield (white solid)(method C)<br>1H-NMR (270 MHz, DMSO-d6): delta 7.99 (s, 1H), 7.68-7.60 (m, 2H), 7.56-7.48 (m, 3H), 4.32 (s, 2H), 3.98 (s, 3H).<br>MS (ESI) m/z: 279.2 (M + H)+. |

Synthesis of Ketone Derivatives

Intermediate-6-19 (INT-6-19): 1-(4-(2-methyl-3H-imidazo[4,5-b]pyridin-3-yl)phenyl)ethanone {Chem. 49}

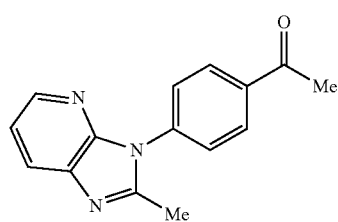

<Step-1>: Intermediate-6-19-1 (INT-6-19-1): 1-(4-((2-nitrophenyl)amino)phenyl)ethanone {Chem. 50}

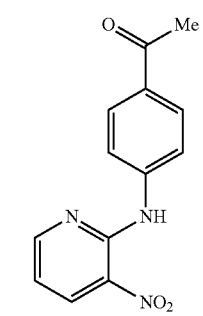

A mixture of 2-chloro-3-nitropyridine (951 mg, 6.00 mmol), 1-(4-aminophenyl)ethanone (811 mg, 6.00 mmol), sodium iodide (90 mg, 0.60 mmol), racemic-BINAP (224 mg, 0.36 mmol), palladium acetate (81 mg, 0.36 mmol) and potassium carbonate (1659 mg, 12.0 mmol) in toluene (30 mL) is heated at 100° C. for 20 h. After cooling to rt, the mixture is diluted with EtOAc and water and filtered through a pad of celite. The filter cake is washed with EtOAc and the filtrate and washings are washed with brine, dried over sodium sulfate, filtered and concentrated in vacuo to give the crude product, which is purified by column chromatography (Biotage) on silica gel (100 g) eluting with 3-5% ethyl acetate in DCM to give the titled compound (1273 mg, 82% yield) as a reddish yellow solid.

$^1$H-NMR (270 MHz, CDCl$_3$): delta 10.36 (br.s, 1H), 8.62-8.54 (m, 2H), 8.05-7.96 (m, 2H), 7.88-7.80 (m, 2H), 7.00-6.92 (m, 1H), 2.61 (s, 3H).

MS (ESI) m/z: 258.1 (M+H)$^+$.

<Step-2>: Intermediate-6-19-2 (INT-6-19-2): 1-(4-((2-aminophenyl)amino)phenyl)ethanone

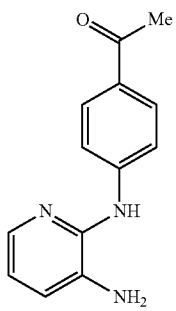

{Chem. 51}

A mixture of INT-6-19-1 (2.6 g, 10.11 mmol), Iron (3.39 g, 60.6 mmol) and solid ammonium chloride (1.62 g, 30.3 mmol) in EtOH/water (4/1 v/v)(50 mL) is heated at reflux for 2.5 h. After cooling to rt, the reaction mixture is filtered through a pad of Celite, and the filtrate is concentrated. The residue is partitioned between EtOAc and 2 M NaOH aq. solution. The organic layer is washed with brine, dried over sodium sulfate, filtered and concentrated in vacuo to give the titled compound (2.22 g, 97% yield) as a brown solid.

$^1$H-NMR (270 MHz, DMSO-d$_6$): delta 8.28 (s, 1H), 7.85 (d, J=8.5 Hz, 2H), 7.69 (d, J=8.5 Hz, 2H), 7.57 (dd, J=4.6, 1.3 Hz, 1H), 6.98 (dd, J=7.9, 1.3 Hz, 1H), 6.75 (dd, J=7.9, 4.6 Hz, 1H), 5.20 (s, 2H), 2.46 (s, 3H).

MS (ESI) m/z: 228.1 (M+H)$^+$.

<Step-3>: Intermediate-6-19-3 (INT-6-19-3): N-(2-((4-acetylphenyl)amino)phenyl)acetamide

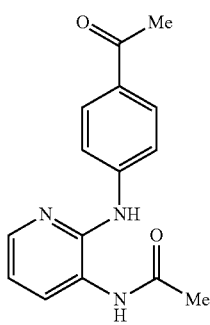

{Chem. 52}

A mixture of INT-6-19-2 (2.22 g, 9.77 mmol), acetic anhydride (1.05 g, 10.26 mmol) and triethylamine (2.97 g, 29.3 mmol) in DCM (40 mL) is stirred at rt for 4 h. The mixture is concentrated in vacuo to give the titled compound, which is used for the next step without the further purification.

$^1$H-NMR (270 MHz, DMSO-d$_6$): delta 9.56 (s, 1H), 8.62 (s, 1H), 8.08 (d, J=3.3 Hz, 1H), 7.89 (d, J=9.2 Hz, 2H), 7.76-7.71 (m, 3H), 6.95 (dd, J=7.3, 4.6 Hz, 1H), 2.50 (s, 3H), 2.12 (s, 3H).

MS (ESI) m/z: 270.1 (M+H)$^+$.

<Step-4>: Intermediate-6-19 (INT-6-19): 1-(4-(2-methyl-3H-imidazo[4,5-b]pyridin-3-yl)phenyl)ethanone To a solution of INT-6-19-3 (2.63 g, 9.77 mmol) in acetic acid (40 mL) is stirred at 100° C. for 15 h. After cooling, the reaction mixture is concentrated in vacuo. The residual oil is diluted with EtOAc and the mixture is basified to pH>10 with sat. NaHCO$_3$ solution. The extracted organic layers are washed with brine, dried over sodium sulfate, filtered and concentrated in vacuo. The residual solid is purified by column chromatography (Biotage) on silica gel (100 g) eluting with 10-100% ethyl acetate in DCM to give the titled compound (2.32 g, 95% yield) as a light brown solid.

$^1$H-NMR (270 MHz, DMSO-d$_6$): delta 8.25 (dd, J=5.3, 1.3 Hz, 1H), 8.18 (d, J=8.5 Hz, 2H), 8.06 (dd, J=7.9, 1.3 Hz, 1H), 7.77 (d, J=8.5 Hz, 2H), 7.32 (dd, J=7.9, 5.3 Hz, 1H), 2.68 (s, 3H), 2.53 (s, 3H).

MS (ESI) m/z: 252.1 (M+H)$^+$.

Intermediate-6-18 (INT-6-18): 1-(4-(3H-imidazo[4,5-b]pyridin-3-yl)phenyl)ethanone

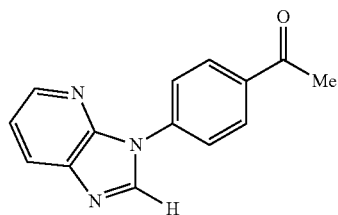

{Chem. 53}

A mixture of INT-6-19-2 (1.49 g, 6.56 mmol) and triethoxymethane (30 mL, 180 mmol) is heated at reflux for 15 h. After cooling, the reaction mixture is diluted with EtOAc and water. The organic layer is separated and the aqueous layer is extracted with EtOAc. The combined organic solution is washed with brine, dried over sodium sulfate, filtered and concentrated in vacuo. The residual oil is purified by column chromatography (Biotage) on silica gel (50 g) eluting with 10-80% ethyl acetate in DCM to give the titled compound (1.32 g, 85% yield) as a pale brown solid.

$^1$H-NMR (270 MHz, DMSO-d$_6$): delta 9.07 (s, 1H), 8.49 (dd, J=4.6, 1.3 Hz, 1H), 8.27-8.17 (m, 5H), 7.44 (dd, J=7.9, 4.6 Hz, 1H), 2.66 (s, 3H).

MS (ESI) m/z: 238.1 (M+H)$^+$.

Intermediate-6-20 (INT-6-20): 1-(4-(1H-imidazo[4,5-b]pyridin-1-yl)phenyl)ethanone

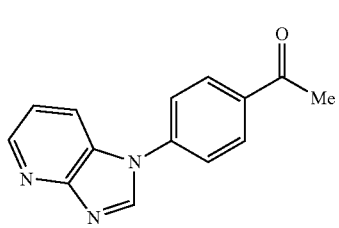
{Chem. 54}

To a mixture of 60% sodium hydride (170 mg, 4.34 mmol) in DMF (15 mL) is added 1H-imidazo[4,5-b]pyridine (310 mg, 2.61 mmol) at 0° C. After addition, to the mixture is added 1-(4-fluorophenyl)ethanone (300 mg, 2.17 mmol) at 0° C. and The mixture is stirred at 60° C. overnight. After cooling, the reaction mixture is quenched with water and extracted with EtOAc. The combined organic layers are washed with brine, dried over sodium sulfate filtered and concentrated in vacuo. The residue is purified by column chromatography (Biotage) on silica gel (25 g) eluting with 20% MeOH in DCM to give the titled compound (100 mg, 19% yield) as a yellow solid.

$^1$H-NMR (270 MHz, DMSO-$d_6$): delta 8.99 (s, 1H), 8.55 (d, J=4.6 Hz, 1H), 8.22-8.19 (m, 3H), 7.92 (d, J=8.6 Hz, 2H), 7.41 (dd, J=7.9, 4.6 Hz), 2.67 (s, 3H).

MS (ESI) m/z: 238.3 (M+H)$^+$.

Intermediate-6-21 (INT-6-21): 1-(6-(1H-benzo[d]imidazol-1-yl)pyridin-3-yl)ethanone

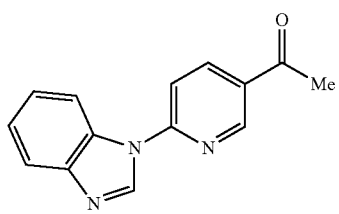
{Chem. 55}

A mixture of 1-(6-chloropyridin-3-yl)ethanone (593 mg, 3.81 mmol), 1H-benzo[d]imidazole (150 mg, 1.27 mmol) and $K_2CO_3$ (702 mg, 5.08 mmol) in DMSO (10 mL) is irradiated in a microwave reactor (Biotage Initiator) for 30 min. at 180° C. After cooling, the reaction mixture is quenched with water and extracted with EtOAc. The combined organic layers are washed with brine, dried over sodium sulfate, filtered and concentrated in vacuo. The residue is purified by column chromatography (Biotage) on silica gel (25 g) eluting with 10-100% ethyl acetate in DCM to give the titled compound (217 mg, 72% yield) as a yellow solid.

$^1$H-NMR (270 MHz, DMSO-$d_6$): delta 9.19 (s, 1H), 9.12 (s, 1H), 8.51 (dd, J=8.5, 1.3 Hz, 1H), 8.45 (d, J=7.9 Hz, 1H), 8.13 (d, J=8.5 Hz, 1H), 7.80 (d, J=7.9 Hz, 1H), 7.46-7.35 (m, 2H), 2.68 (s, 3H).

MS (ESI) m/z: 238.1 (M+H)$^+$.

Intermediate-6-22 (INT-6-22): 1-(6-(2-methyl-1H-benzo[d]imidazol-1-yl)pyridin-3-yl)ethanone

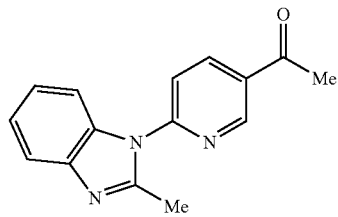
{Chem. 56}

The titled compound is prepared according to the procedure of INT-6-21 from the 1-(6-chloropyridin-3-yl)ethanone (200 mg, 1.29 mmol) and 2-methyl-1H-benzo[d]imidazole (57 mg, 0.428 mmol) to give the product (43 mg, 40% yield) as a yellow solid.

$^1$H-NMR (270 MHz, DMSO-$d_6$): delta 9.25 (d, J=2.0 Hz, 1H), 8.59-8.56 (m, 1H), 7.91 (d, J=8.5 Hz, 1H), 7.68-7.65 (m, 1H), 7.55-7.52 (m, 1H), 7.29-7.25 (m, 2H), 2.72 (s, 3H), 2.65 (s, 3H).

MS (ESI) m/z: 252.0 (M+H)$^+$.

Intermediate-6-23 (INT-6-23): 1-(4-(2,5-dimethyl-3H-imidazo[4,5-b]pyridin-3-yl)phenyl)ethanone

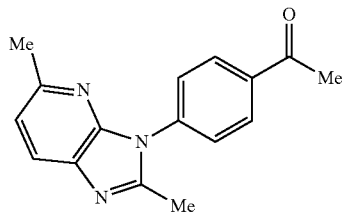
{Chem. 57}

<Step-1>: Intermediate-6-23-1 (INT-6-23-1): 1-(4-((6-methyl-3-nitropyridin-2-yl)amino)phenyl)ethanone

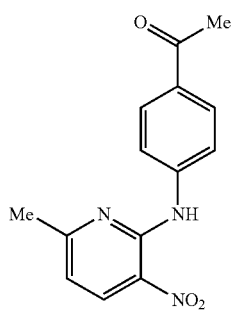
{Chem. 58}

The titled compound is prepared according to the procedure of INT-6-19-1 from 2-chloro-6-methyl-3-nitropyridine (951 mg, 5.51 mmol), 1-(4-aminophenyl)ethanone (745 mg, 5.51 mmol), sodium iodide (83 mg, 0.551 mmol), racemic-BINAP (206 mg, 0.331 mmol), palladium acetate (74 mg, 0.331 mmol) and potassium carbonate (1659 mg, 12.0 mmol) in toluene (30 mL) to give the product (1290 mg, 86% yield) as a reddish yellow solid.

$^1$H-NMR (270 MHz, CDCl$_3$): delta 10.46 (br. s, 1H), 8.45 (d, J=7.9 Hz, 1H), 8.05-7.95 (m, 2H), 7.93-7.85 (m, 2H), 6.79 (d, J=7.9 Hz, 1H), 2.61 (s, 3H), 2.59 (s, 3H).

MS (ESI) m/z: 272.1 (M+H)$^+$.

<Step-2>: Intermediate-6-23-2 (INT-6-23-2): 1-(4-((3-amino-6-methylpyridin-2-yl)amino)phenyl)ethanone

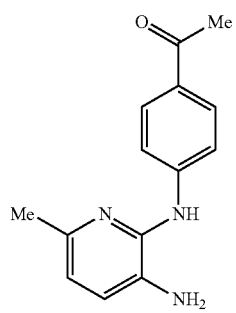

{Chem. 59}

The titled compound is prepared according to the procedure of INT-6-19-2 from INT-6-23-1 (400 mg, 1.47 mmol), ammonium chloride (237 mg, 4.42 mmol) and iron powder (494 mg, 8.85 mmol) in EtOH (12 mL)-water (3 mL) to give the product (369 mg, quant.) as a dark yellow amorphous solid.

$^1$H-NMR (270 MHz, CDCl$_3$): delta 7.90 (d, J=8.6 Hz, 2H), 7.32 (d, J=8.6 Hz, 2H), 7.01 (d, J=7.9 Hz, 1H), 6.73 (d, J=7.9 Hz, 1H), 6.65 (br.s, 1H), 3.33 (br.s, 2H), 2.55 (s, 3H), 2.43 (s, 3H).

MS (ESI) m/z: 242.2 (M+H)$^+$.

<Step-3>: Intermediate-6-23 (INT-6-23): 1-(4-(2,5-dimethyl-3H-imidazo[4,5-b]pyridin-3-yl)phenyl)ethanone The titled compound is prepared according to the procedure of INT-6-19-3 and INT-6-19 from INT-6-23-2 (350 mg, 1.45 mmol) to give the product (179 mg, 47% yield in two steps) as a dark yellow solid.

$^1$H-NMR (270 MHz, CDCl$_3$): delta 8.22-8.14 (m, 2H), 7.93 (d, J=7.9 Hz, 1H), 7.77-7.69 (m, 2H), 7.17 (d, J=7.9 Hz, 1H), 2.68 (s, 3H), 2.48 (s, 6H).

MS (ESI) m/z: 266.2 (M+H)$^+$.

Intermediate-6-24 (INT-6-24): 3-(4-acetylphenyl)-2-methyl-3H-imidazo[4,5-b]pyridine-5-carbonitrile

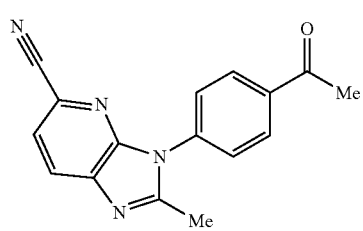

{Chem. 60}

<Step-1>: Intermediate-6-24-1 (INT-6-24-1): 1-(4-((6-chloro-3-nitropyridin-2-yl)amino)phenyl)ethanone

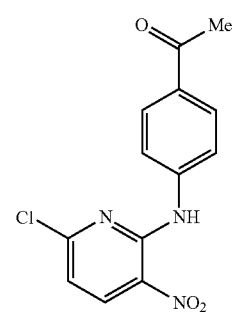

{Chem. 61}

A mixture of 2, 6-dichloro-3-nitropyridine (1500 mg, 7.77 mmol), 1-(4-aminophenyl)ethanone (525 mg, 3.89 mmol) and potassium carbonate (1343 mg, 9.72 mmol) in 1,4-dioxane (16 mL) is irradiated with microwave at 170° C. for 60 min. After the usual workup, the crude product is purified by column chromatography on silica gel (100 g) with DCM only to give the titled compound (817 mg, 72% yield) as a yellow solid.

$^1$H-NMR (270 MHz, CDCl$_3$): delta 10.45 (br.s, 1H), 8.51 (d, J=8.6 Hz, 1H), 8.08-7.97 (m, 2H), 7.87-7.75 (m, 2H), 6.92 (d, J=8.6 Hz, 1H), 2.61 (s, 3H).

<Step-2>: Intermediate-6-24-2 (INT-6-24-2): 1-(4-((3-amino-6-chloropyridin-2-yl)amino)phenyl)ethanone

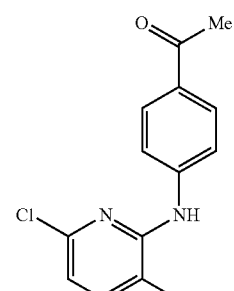

{Chem. 62}

The titled compound is prepared according to the procedure of INT-6-19-2 from INT-6-24-1 (1640 mg, 5.62 mmol), ammonium chloride (902 mg, 16.87 mmol) and iron (1884 mg, 33.7 mmol) in ethanol (60 mL)-water (15 mL) to give the product (1100 mg, 72% yield) as a green solid.

$^1$H-NMR (270 MHz, DMSO-d$_6$): delta 8.45 (br.s, 1H), 7.90 (d, J=8.6 Hz, 2H), 7.69 (d, J=8.6 Hz, 2H), 7.01 (d, J=7.9 Hz, 1H), 6.78 (d, J=7.9 Hz, 1H), 5.35 (s, 2H), 2.50 (s, 3H).

MS (ESI) m/z: 262.2 (M+H)$^+$.

<Step-3>: Intermediate-6-24-3 (INT-6-24-3): 1-(4-(5-chloro-2-methyl-3H-imidazo[4,5-b]pyridin-3-yl)phenyl)ethanone

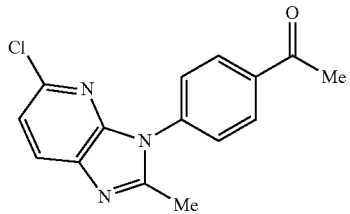

{Chem. 63}

The titled compound is prepared according to the procedure of INT-6-19-3 (use of acetyl chloride instead of acetic anhydride) and INT-6-19 (irradiation at 170° C. for 1 h in microwave system) from INT-6-24-2 (1100 mg, 4.20 mmol) to give the product (1111 mg, 93% yield in two steps) as a slightly tan solid.

$^1$H-NMR (270 MHz, CDCl$_3$): delta 8.24-8.13 (m, 2H), 7.96 (d, J=7.9 Hz, 1H), 7.60-7.50 (m, 2H), 7.27 (d, J=7.9 Hz, 1H), 2.69 (s, 3H), 2.58 (s, 3H).

MS (ESI) m/z: 286.2 (M+H)$^+$.

<Step-4>: Intermediate-6-24 (INT-6-24): 3-(4-acetylphenyl)-2-methyl-3H-imidazo[4,5-b]pyridine-5-carbonitrile A mixture of INT-6-24-3 (555 mg, 1.94 mmol), zinc cyanide (456 mg, 3.88 mmol) and Pd(PPh$_3$)$_4$ (449 mg, 0.388 mmol) in DMF (16 mL) is irradiated with microwave at 140° C. for 30 min. After the usual workup, the product is purified by column chromatography on silica gel (100 g) eluting with 45-50% ethyl acetate in DCM to give the titled compound (820 mg, 76% yield) as a slightly yellow solid.

$^1$H-NMR (270 MHz, DMSO-d$_6$): delta 8.29 (d, J=7.9 Hz, 1H), 8.22 (d, J=8.6 Hz, 2H), 7.95 (d, J=7.9 Hz, 1H), 7.80 (d, J=8.6 Hz, 2H), 2.69 (s, 3H), 2.58 (s, 3H).

MS (ESI) m/z: 277.3 (M+H)$^+$.

Intermediate-6-25 (INT-6-25): 1-(4-(2-methyl-5-(trifluoromethyl)-3H-imidazo[4,5-b]pyridin-3-yl)phenyl)ethanone

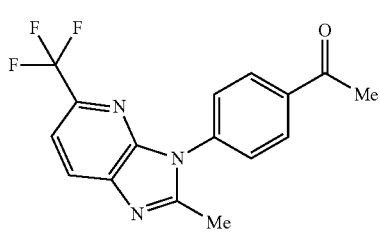

{Chem. 64}

<Step-1>: Intermediate-6-25-1 (INT-6-25-1): 1-(4-((3-nitro-6-(trifluoromethyl)pyridin-2-yl)amino)phenyl)ethanone

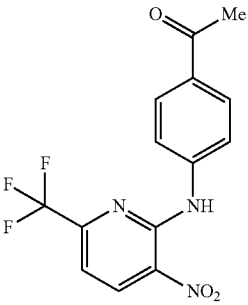

{Chem. 65}

The titled compound is prepared according to the procedure of INT-6-19-1 from 2-chloro-3-nitro-6-(trifluoromethyl)pyridine (827 mg, 3.47 mmol), 1-(4-aminophenyl)ethanone (469 mg, 3.47 mmol), sodium iodide (52 mg, 0.347 mmol), racemic-BINAP (130 mg, 0.208 mmol), palladium acetate (46.7 mg, 0.208 mmol) and potassium carbonate (959 mg, 6.94 mmol) in toluene (30 mL) to give the product (1072 mg, 95% yield) as a ocher solid.

$^1$H-NMR (270 MHz, DMSO-d$_6$): delta 10.37 (br.s, 1H), 8.74 (d, J=8.6 Hz, 1H), 8.08-7.98 (m, 2H), 7.90-7.82 (m, 2H), 7.28 (dd, J=8.6, 2.0 Hz, 1H), 2.62 (s, 3H).

<Step-2>: Intermediate-6-25-2 (INT-6-25-2): 1-(4-((3-amino-6-(trifluoromethyl)pyridin-2-yl)amino)phenyl)ethanone

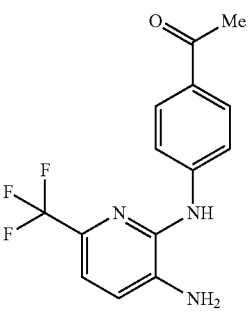

{Chem. 66}

The titled compound is prepared according to the procedure of INT-6-19-2 from INT-6-25-1 (1060 mg, 3.26 mmol), ammonium chloride (523 mg, 9.78 mmol) and iron (1092 mg, 19.55 mmol) in ethanol (40 mL)-water (10 mL) to give the product (962 mg, quant.) as a dark red solid.

MS (ESI) m/z: 296.2 (M+H)$^+$.

<Step-3>: Intermediate-6-25-A (INT-6-25-A): 1-(4-(2-methyl-5-(trifluoromethyl)-3H-imidazo[4,5-b]pyridin-3-yl)phenyl)ethanone The titled compound is prepared according to the procedure of INT-6-19-3 (use of acetyl chloride instead of acetic anhydride) and INT-6-19 (irradiation at 170° C. for 1 h in microwave system) from INT-6-25-2 (~3.26 mmol) to give the product (699 mg, 67% yield in two steps) as a slightly brown solid.

¹H-NMR (270 MHz, CDCl₃): delta 8.24-8.16 (m 2H), 8.13 (d, J=8.6 Hz, 1H), 7.70-7.64 (m, 1H), 7.62-7.55 (m, 2H), 2.70 (s, 3H), 2.65 (s, 3H).
MS (ESI) m/z: 320.1 (M+H)⁺.

Intermediate-6-26 (INT-6-26): 1-(4-((6-methyl-pyrazin-2-yl)oxy)phenyl)ethanone

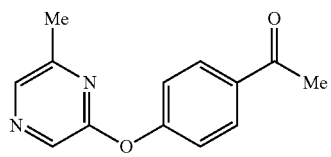

{Chem. 67}

The titled compound is prepared according to the procedure of INT-6-15 from 1-(4-hydroxyphenyl)ethanone (200 mg, 1.47 mmol), 2-chloro-6-methylpyrazine (264 mg, 2.06 mmol) and potassium carbonate (406 mg, 2.94 mmol) to give the product (190 mg, 57%, chemical purity of 40%) as a pale yellow solid.
¹H-NMR (270 MHz, CDCl₃): delta 8.39 (s, 1H), 8.35 (s, 3H), 8.04 (d, J=8.6 Hz, 2H), 7.32 (d, J=8.6 Hz, 2H), 2.59 (s, 3H), 2.36 (s, 3H).
MS (ESI) m/z: 229.13 (M+H)⁺.

Intermediate-6-27 (INT-6-27): 1-(3-(pyridazin-3-yloxy)phenyl)ethanone

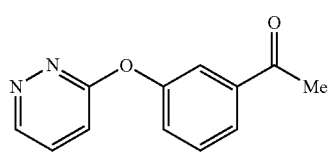

{Chem. 68}

A mixture of 1-(3-hydroxyphenyl)ethanone (466 mg, 3.42 mmol), 3-chloropyridazine (784 mg, 6.85 mmol), tBuXPhos (495 mg, 1.17 mmol), Pd₂(dba)₃ (313 mg, 0.342 mmol) and K₃PO₄ (2180 mg, 10.27 mmol) in 1,4-dioxane (15 mL) is irradiated with microwave at 160° C. for 90 min. The mixture is filtered through a pad of celite, and the filter cake is washed with EtOAc (50 mL). The filtrate and washings are washed brine, dried over Na₂SO₄, filtered and concentrated in vacuo. The residue is purified by column chromatography on silica gel (25 g) eluting with 5-60% ethyl acetate in DCM to give the titled compound (513 mg, 70% yield) as a pale brown solid.
¹H-NMR (270 MHz, DMSO-d₆): delta 9.04 (d, J=4.6 Hz, 1H), 7.89 (d, J=6.6 Hz, 1H), 7.84-7.76 (m, 2H), 7.63 (t, J=7.9 Hz, 1H), 7.56-7.51 (m, 2H), 2.61 (s, 3H).

Intermediate-6-28 (INT-6-28): 1-(5-chloro-6-(pyridin-3-yloxy)pyridin-3-yl)ethanone

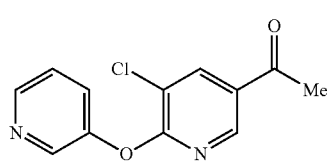

{Chem. 69}

A mixture of 1-(5,6-dichloropyridin-3-yl)ethanone (100 mg, 0.526 mmol), pyridin-3-ol (60 mg, 0.631 mmol), cesium carbonate (343 mg, 1.052 mmol) in DMSO (0.5 mL) is stirred at rt for 2 h. The mixture is diluted water and extracted with DCM. After the removal of solvent in vacuo, the residual oil is purified by column chromatography on silica gel eluting with 0-100% ethyl acetate in hexane to give the titled compound (120 mg, 92% yield) as a pale yellow solid.
¹H-NMR (270 MHz, CDCl₃): delta 8.58-8.54 (m, 3H), 8.35 (d, J=2.0 Hz, 1H), 7.61-7.53 (m, 1H), 7.41 (dd, J=8.6, 4.6 Hz, 1H), 2.58 (s, 3H).
MS (ESI) m/z: 249.2 (M+H)⁺.

Intermediate-6-29 (INT-6-29): 1-(3-chloro-4'-methyl-[2,3'-bipyridin]-5-yl)ethanone

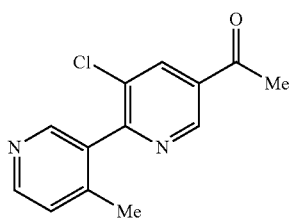

{Chem. 70}

A mixture of 1-(5,6-dichloropyridin-3-yl)ethanone (75 mg, 0.395 mmol), (4-methylpyridin-3-yl)boronic acid (81 mg, 0.592 mmol), saturated NaHCO₃ solution (0.6 mL), and PdCl₂(dppf) CH₂Cl₂ (32 mg, 0.039 mmol) in 1,4-dioxane (0.6 mL) is irradiated with microwave at 120° C. for 20 min. The mixture is diluted water and extracted with DCM-MeOH. The combined organic solution is dried over Na₂SO₄, filtered and concentrated in vacuo. The residual oil is purified by column chromatography on amino silica gel eluting with 0-100% ethyl acetate in hexane to give the titled compound (64 mg, 66% yield) as a pale yellow solid.
MS (ESI) m/z: 247.2 (M+H)⁺.

Intermediate-6-30 (INT-6-30): 1-(4-(4-methyl-pyridazin-3-yl)phenyl)ethanone

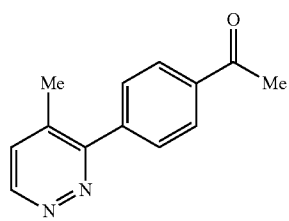

{Chem. 71}

A mixture of (4-acetylphenyl)boronic acid (561 mg, 3.42 mmol), 3-chloro-4-methylpyridazine (440 mg, 3.42 mmol) and PdCl₂(dppf) CH₂Cl₂ (279 mg, 0.342 mol) in 1,4-dioxane (5 mL) and sat. NaHCO₃ solution (5 mL) is stirred at 80° C. for 3 h. The mixture is quenched with water and extracted with EtOAc. The organic phase is washed with brine, dried over Na₂SO₄, filtered and concentrated in vacuo to give a black solid. The crude product is purified by column chromatography on silica gel (50 g) eluting with 0-80% EtOAc in DCM to give the titled compound (265 mg, 36% yield) as a pale brown solid.

$^1$H-NMR (270 MHz, DMSO-d$_6$): delta 9.12 (d, J=5.3 Hz, 1H), 8.11 (d, J=8.6 Hz, 2H), 7.78 (d, J=8.6 Hz, 2H), 7.69 (d, J=5.3 Hz, 1H), 2.66 (s, 3H), 2.34 (s, 3H).

MS (ESI) m/z: 213.3 (M+H)$^+$.

Intermediate-7-1-A (INT-7-1-A): 3-(2-(4-bromophenyl)-2-oxoethyl)-8,8-difluoro-1,3-diazaspiro[4.5]decane-2,4-dione {Chem. 72}

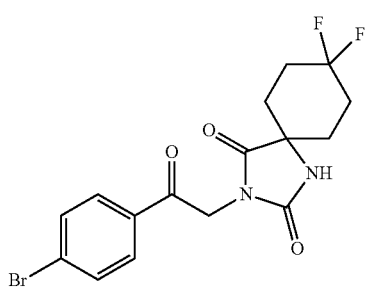

To a stirred solution of 8,8-difluoro-1,3-diazaspiro[4.5]decane-2,4-dione (INT-1-1-A)(10.2 g, 49.9 mmol) and anhydrous potassium carbonate (20.59 g, 149.0 mmol) in anhydrous DMF (110 mL) under nitrogen atmosphere is added 2,4'-dibromoacetophenone (13.84 g, 49.9 mmol) in a drop wise manner over a period of 10 min. After 2 h at 80° C., the mixture is poured into crushed ice and extracted with DCM (2×100 mL). The combined organic layers are dried over anhydrous Na$_2$SO$_4$, filtered, and evaporated in vacuo to afford the crude product, which is purified by column chromatography on silica gel eluting with 10-20% EtOAc in DCM to afford the product including a little bit of impure compound. Finally, this compound is triturated with tert-butyl methyl ether to afford the titled compound (17.0 g, 79% yield) as an off white solid.

$^1$H-NMR (270 MHz, DMSO-d$_6$): delta 9.03 (s, 1H), 7.98 (d, J=8.6 Hz, 2H), 7.81 (d, J=8.6 Hz, 2H), 4.97 (s, 2H), 2.25-1.75 (m, 8H).

MS (ESI) m/z: 399.0 (M−H)$^−$.

The following hydantoin derivatives (INT-7-2-A to INT-7-20-A) are prepared according to the procedure of intermediate 7-1-A from the known or synthesized alpha-haloacetyl derivatives and azaspiro derivatives in Table 8.

TABLE 8

| Halides | Products | Yield and Analytical data |
|---|---|---|
| ![INT-7-2 structure: 4-bromo-3-methylphenyl chloroacetyl] INT-7-2 | ![INT-7-2-A structure] INT-7-2-A | 53% yield<br>$^1$H-NMR (270 MHz, CDCl$_3$): delta 7.81 (s, 1H), 7.69-7.58 (m, 2H), 5.98 (br.s, 1H), 4.86 (s, 2H), 2.46 (s, 3H), 2.00-1.60 (m, 8H), 1.50-1.30 (m, 2H). |
| ![INT-7-2 structure] INT-7-2 | ![INT-7-2-B structure] INT-7-2-B | 79% yield<br>$^1$H-NMR (270 MHz, CDCl$_3$): delta 7.81 (s, 1H), 7.69-7.59 (m, 2H), 6.42 (br.s, 1H), 4.87 (s, 2H), 2.47 (s, 3H), 2.5-2.18 (m, 4H), 2.10-1.88 (m, 4H). |

TABLE 8-continued

| Halides | Products | Yield and Analytical data |
| --- | --- | --- |
| 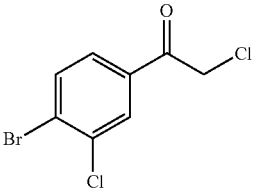<br>INT-7-3 | 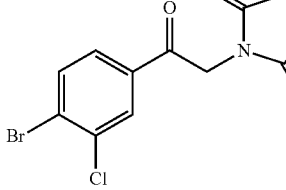<br>INT-7-3-A | 58% yield<br>$^1$H-NMR (270 MHz, CDCl$_3$): delta 8.03 (d, J = 2.0 Hz, 1H), 7.80 (d, J = 8.3 Hz, 1H), 7.68 (dd, J = 8.3, 2.0 Hz, 1H), 6.42 (br.s, 1H), 4.86 (s, 2H), 2.5-2.18 (m, 4H), 2.10-1.88 (m, 4H). |
| 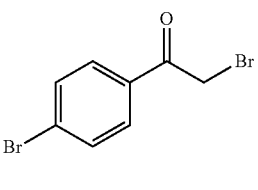<br>INT-7-4 | <br>INT-7-4-A | 66% yield (brown solid)<br>$^1$H-NMR (300 MHz, DMSO-d$_6$): delta 8.87 (br s, 1H), 7.96 (d, J = 8.1 Hz, 2H), 7.78 (d, J = 8.1 Hz, 2H), 4.91 (s, 2H), 1.78-1.46 (m, 9H), 1.38-1.20 (m, 1H).<br>MS (ESI) m/z: 367.0 (M + H)$^+$. |
| 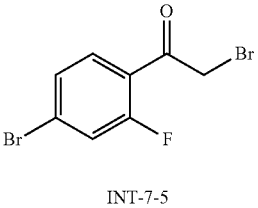 [SMILES: O=C(CBr)c1ccc(Br)cc1F]<br>INT-7-5 | 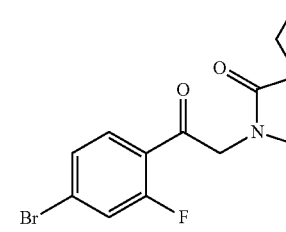<br>INT-7-5-A | 22% yield (pale yellow oil)<br>$^1$H-NMR (300 MHz, CDCl3): delta 7.85 (t, J = 8.1 Hz, 1H), 7.46-7.38 (m, 2H), 6.12 (br s, 1H), 4.82 (d, J = 3.7 Hz, 2H), 2.02-1.66 (m, 8H), 1.52-1.32 (m, 2H).<br>MS (ESI) m/z: 384.9 (M + H)$^+$. |
| 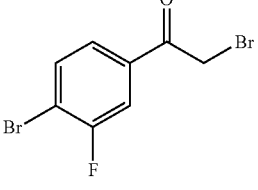<br>INT-7-6 | <br>INT-7-6-A | 57% yield (white solid)<br>$^1$H-NMR (270 MHz, DMSO-d$_6$): delta 9.04 (s, 1H), 8.05-7.95 (m, 2H), 7.83 (d, J = 7.3 Hz, 1H), 5.00 (s, 2H), 2.18-1.85 (m, 8H).<br>MS (ESI) m/z: 417.1 (M − H)$^-$. |

TABLE 8-continued
| Halides | Products | Yield and Analytical data |
|---|---|---|
| 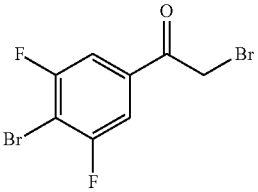<br>INT-6-11-A | 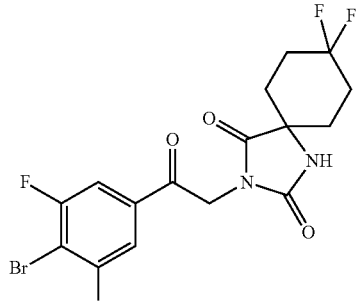<br>INT-7-7-A | 29% yield<br>¹H-NMR (270 MHz, CDCl₃): delta 7.53 (d, J = 5.9 Hz, 2H), 4.85 (s, 2H), 2.55-1.82 (m, 8H). |
| 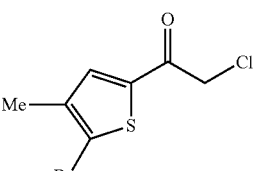<br>INT-4-5-A | 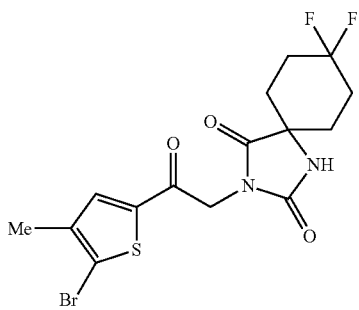<br>INT-7-8-A | 27% yield<br>¹H-NMR (270 MHz, CDCl₃): delta 7.48 (s, 1H), 4.76 (s, 2H), 2.25 (s, 3H), 2.50-1.90 (m, 8H) a signal due to NH is not observed. |
| 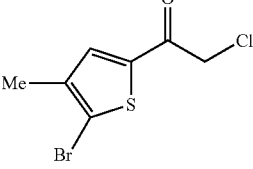<br>INT-4-5-A | 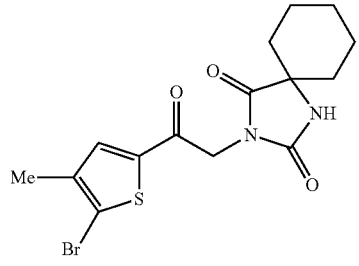<br>INT-7-8-B | 33% yield<br>¹H-NMR (270 MHz, CDCl₃): delta 7.46 (s, 1H), 5.80 (br.s, 1H), 4.75 (s, 2H), 2.24 (s, 3H), 2.00-1.70 (m, 8H), 1.40-1.20 (m, 2H). |
| 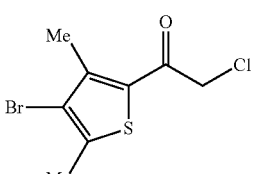<br>INT-7-9 | 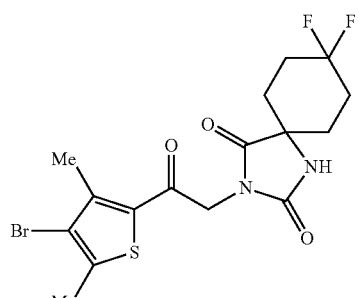<br>INT-7-9-A | 82% yield<br>¹H-NMR (270 MHz, CDCl₃): delta 6.44 (br.s, 1H), 4.68 (s, 2H), 2.56 (s, 3H), 2.50 (s, 3H), 2.50-1.80 (m, 8H). |

TABLE 8-continued

| Halides | Products | Yield and Analytical data |
|---|---|---|
| 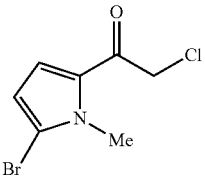<br>INT-6-1-A | 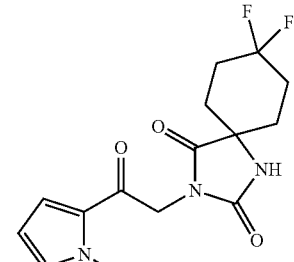<br>INT-7-10-A | 60% yield<br>$^1$H-NMR (270 MHz, CDCl$_3$): delta 7.05 (d, J = 4.3 Hz, 1H), 6.81 (br.s, 1H), 6.30 (d, J = 4.3 Hz, 1H), 4.71 (s, 2H), 3.93 (s, 3H), 2.50-1.90 (m, 8H). |
| 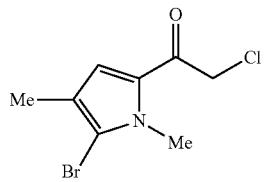<br>INT-7-11 | 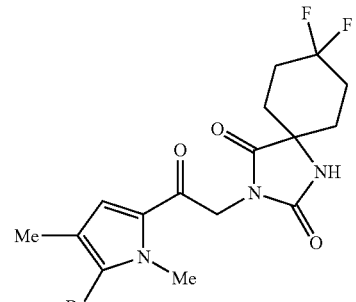<br>INT-7-11-A | 97% yield<br>$^1$H-NMR (270 MHz, CDCl$_3$): delta 6.92 (s, 1H), 4.89 (s, 2H), 3.91 (s, 3H), 2.08 (s, 3H), 2.50-1.80 (m, 8H), a signal due to NH is not observed. |
| 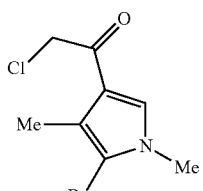<br>INT-7-12 | 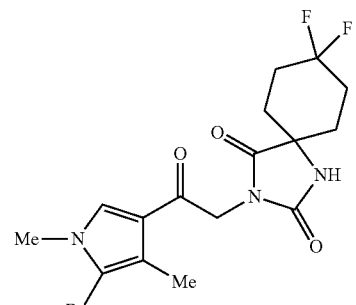<br>INT-7-12-A | 83% yield<br>$^1$H-NMR (270 MHz, CDCl$_3$): delta 7.42 (s, 1H), 4.62 (s, 2H), 3.65 (s, 3H), 2.45-2.3 (m, 4H), 2.23 (s, 3H), 2.18-1.85 (m, 4H). |
| 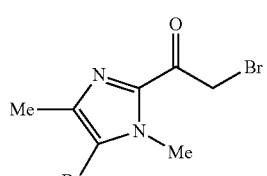<br>INT-6-4-A | 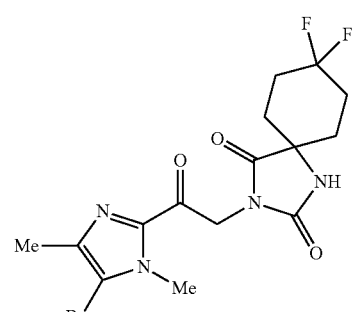<br>INT-7-13-A | 72% yield (pale yellow solid)<br>$^1$H-NMR (270 MHz, CDCl$_3$): delta 7.13 (br s, 1H), 5.01 (s, 2H), 3.94 (s, 3H), 2.45-2.17 (m, 4H), 2.27 (s, 3H), 2.10-1.87 (m, 4H).<br>MS (ESI) m/z: 420.9 (M + H)$^+$. |

TABLE 8-continued

| Halides | Products | Yield and Analytical data |
|---|---|---|
| 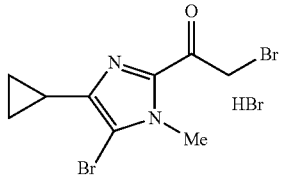<br>INT-6-5-A | 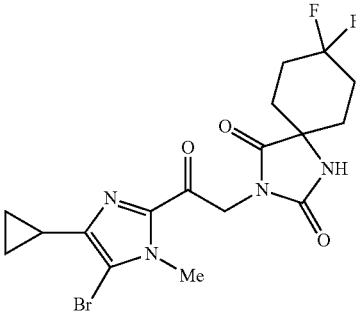<br>INT-7-15-A | 35% yield (pale yellow solid)<br>$^1$H-NMR (270 MHz, CDCl$_3$): delta 6.43 (br s, 1H), 4.97 (s, 2H), 3.92 (s, 3H), 2.49-2.15 (m, 4H), 2.08-1.80 (m, 5H), 0.98-0.86 (m, 4H).<br>MS (ESI) m/z: 446.9 (M + H)$^+$. |
| 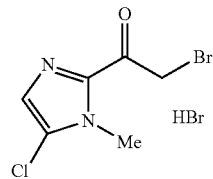<br>INT-6-6-A | 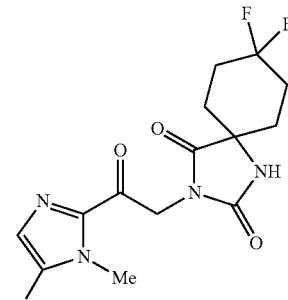<br>INT-7-15-A | 100% yield (pale yellow solid)<br>$^1$H-NMR (270 MHz, CDCl$_3$): delta 8.59 (br s, 1H), 7.15 (s, 1H), 5.00 (s, 2H), 3.94 (s, 3H), 2.32-1.73 (m, 8H).<br>MS (ESI) m/z: 361.1 (M + H)$^+$. |
| 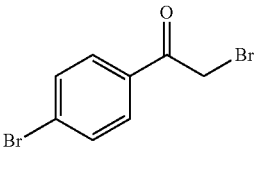<br>INT-7-4 | 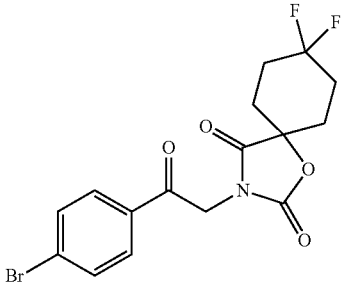<br>INT-7-16-A | 71% yield (yellow solid)<br>$^1$H-NMR (270 MHz, CDCl$_3$): delta 7.82 (d, J = 8.6 Hz, 2H), 7.68 (d, J = 8.6 Hz, 2H), 4.92 (s, 2H), 2.41-2.00 (m, 8H).<br>MS (ESI) m/z: 401.8 (M − H)$^-$. |
| 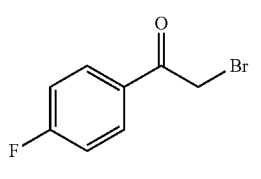<br>INT-7-17 | 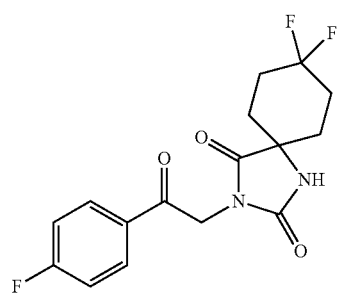<br>INT-7-17-A | 72% yield (white solid)<br>$^1$H-NMR (270 MHz, DMSO-d$_6$): delta 9.02 (br.s, 1H), 8.20-8.10 (m, 2H), 7.48-7.36 (m, 2H), 4.97 (s, 2H), 2.28-1.74 (m, 8H).<br>MS (ESI) m/z: 341.1 (M + H)$^+$. |

TABLE 8-continued

| Halides | Products | Yield and Analytical data |
|---|---|---|
| INT-7-18 | INT-7-18-A | 92% yield (yellow solid)<br>$^1$H-NMR (270 MHz, DMSO-d$_6$): delta 9.01 (br.s, 1H), 7.89-7.80 (m, 2H), 7.63 (dd, J = 8.6, 2.0 Hz, 1H), 4.79 (d, J = 2.6 Hz, 2H), 2.27-1.72 (8H, m).<br>MS (ESI) m/z: 421.0 (M + H)$^+$. |
| INT-7-19 | INT-7-19-A | 49% yield (yellow solid)<br>$^1$H-NMR (270 MHz, CDCl$_3$): delta 7.89 (d, J = 2.0 Hz, 1H), 7.62 (dd, J = 8.6, 2.0 Hz, 1H), 7.55-7.45 (m, 2H), 6.43 (br.s, 1H), 4.93 (s, 2H), 2.50-2.15 (m, 4H), 2.08-1.80 (m, 4H).<br>MS (ESI) m/z: 440.9 (M − H)$^-$. |
| INT-7-6 | INT-7-20-A | 57% yield (off-white solid)<br>$^1$H-NMR (270 MHz, DMSO-d$_6$): delta 9.03 (br.s, 1H), 8.05-7.91 (m, 2H), 7.86-7.77 (m, 1H), 4.99 (s, 2H), 2.30-1.70 (m, 8H).<br>MS (ESI) m/z: 417.2 (M − H)$^-$. |

Intermediate-7-9 (INT-7-9):1-(4-bromo-3,5-dimethylthiophen-2-yl)-2-chloroethanone {Chem. 73}

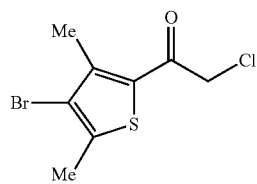

A stirred suspension of aluminum trichloride (1.09 g, 8.16 mmol) in chloroform (10 mL) at room temperature is treated sequentially with 2-chloro-1-(3,5-dimethylthiophen-2-yl)ethanone (INT-4-6-A)(700 mg, 3.71 mmol) and bromine (623 mg, 3.90 mmol), stirred for 17 h, poured into iced water and diluted with DCM. The organic phase is separated and the aqueous phase is extracted with DCM. The combined organic layers are washed with water and brine, dried over sodium sulfate and concentrated. The crude product is purified by column chromatography on silica gel eluting with 0-30% EtOAc in hexane to give the titled compound (890 mg, 90% yield)

$^1$H-NMR (270 MHz, CDCl$_3$): delta 4.48 (s, 2H), 2.58 (s, 3H), 2.48 (s, 3H).

Intermediate-7-11 (INT-7-11): 1-(5-bromo-1,4-dimethyl-1H-pyrrol-2-yl)-2-chloroethanone

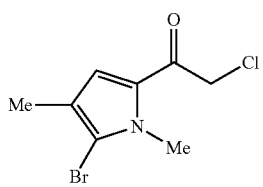

{Chem. 74}

N-bromosuccinimide (674 mg, 3.79 mmol) is added portion wise to a solution of INT-5-8-A (500 mg, 2.91 mmol) in THF (50 mL) at −10° C. The mixture is stirred at the same temperature for 2 h. After the removal of solvent under reduced pressure, the residue is dissolved in DCM (100 mL) and the organic phase is washed with water (3×50 mL) and brine, dried over $Na_2SO_4$, filtered and concentrated in vacuo. The residue is purified by column chromatography on silica gel eluting with 10-50% EtOAc in hexane to give the titled compound (597 mg, 82% yield).

$^1$H-NMR (270 MHz, $CDCl_3$): delta 6.88 (s, 1H), 4.42 (s, 2H), 3.95 (s, 3H), 2.07 (s, 3H).

Intermediate-7-12 (INT-7-12): 1-(5-bromo-1,4-dimethyl-1H-pyrrol-3-yl)-2-chloroethanone

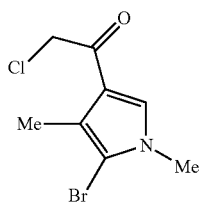

{Chem. 75}

The titled compound is prepared according to the procedure of intermediate-7-11 (INT-7-11) from the INT-5-9-A (193 mg, 1.13 mmol) and N-bromosuccinimide (200 mg, 1.13 mmol) at −78° C. to the ambient temperature to give the product (229 mg, 81% yield).

$^1$H-NMR (270 MHz, $CDCl_3$): delta 7.38 (s, 1H), 4.36 (s, 2H), 3.64 (s, 3H), 2.27 (s, 3H).

Intermediate-8-1-A (INT-8-1-A): 3-(2-(6-chloropyridin-3-yl)-2-oxoethyl)-8,8-difluoro-1,3-diazaspiro[4.5]decane-2,4-dione

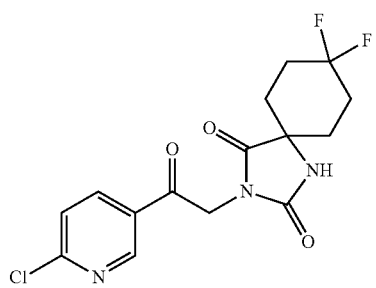

{Chem. 76}

The titled compound is prepared according to the procedure described in N-alkylation reaction of intermediate-7-1-A from 8,8-difluoro-1,3-diazaspiro[4.5]decane-2,4-dione (INT-1-1-A)(1.62 g, 5.22 mmol), 2-chloro-1-(6-chloropyridin-3-yl)ethanone (991 mg, 5.22 mmol) and $K_2CO_3$ (2.16 g, 15.6 mmol) in DMF (15 mL). The purification is carried out by column chromatography on silica gel eluting with 10-80% EtOAc in DCM to give the product (850 mg, 40% yield) as a pale yellow solid $^1$H-NMR (270 MHz, DMSO-$d_6$): delta 9.08 (d, J=2.6 Hz, 1H), 9.04 (s, 1H), 8.41 (dd, J=8.6, 2.6 Hz, 1H), 7.76 (d, J=8.6 Hz, 1H), 5.05 (s, 2H), 2.25-1.65 (m, 8H).

MS (ESI) m/z: 358.2 (M+H)$^+$.

The following hydantoin derivatives (INT-8-2-A to INT-8-5-A) are prepared according to the procedure of intermediate 8-1-A from the known or synthesized alpha-haloacetyl derivatives and hydantoin derivatives in Table 9.

TABLE 9

| Halides | Products | Yield and Analytical data |
|---|---|---|
| INT-6-7-A | INT-8-2-A | 17% yield (a brown solid)<br>1H-NMR (270 MHz, CDCl3): delta 8.77 (d, J = 2.0 Hz, 1H), 8.01 (dd, J = 8.6, 2.0 Hz, 1H), 7.91 (d, J = 8.6 Hz, 1H), 5.15 (s, 2H), 2.50-2.16 (m, 4H), 2.10-1.88 (m, 4H), a signal due to NH is not observed.<br>MS (ESI) m/z: 404.0 (M + H)$^+$. |

TABLE 9-continued

| Halides | Products | Yield and Analytical data |
|---|---|---|
| INT-8-3 | INT-8-3-A | 64% yield (orange solid)<br>$^1$H-NMR (270 MHz, CDCl3): delta 8.97 (d, J = 2.0 Hz, 1H), 8.20 (dd, J = 8.6, 2.0 Hz, 1H), 8.57 (d, J = 8.6 Hz, 1H), 6.55 (br.s, 1H), 4.89 (s, 2H), 2.00-1.60 (m, 8H), 1.53-1.33 (m, 2H).<br>MS (ESI) m/z: 322.3 (M + H)$^+$. |
| INT-6-9-A | INT-8-4-A | 57% yield (a pale brown solid)<br>$^1$H-NMR (270 MHz, DMSO-d$_6$): delta 8.79 (d, J = 2.6 Hz, 1H), 8.08 (d, J = 2.0 Hz, 1H), 6.29 (s, 1H), 4.87 (s, 2H), 2.46 (s, 3H), 1.97-1.65 (m, 10H).<br>MS (ESI) m/z: 336.1 (M + H)$^+$. |
| INT-6-12-A | INT-8-5-A | 15% yield (pale yellow solid)<br>$^1$H-NMR (270 MHz, CDCl$_3$): delta 7.97 (d, J = 8.6 Hz, 1H), 7.88 (d, J = 8.6 Hz, 1H), 5.29 (s, 2H), 2.50-2.14 (m, 2H), 2.14-1.90 (m, 4H).<br>MS (ESI) m/z: 405.1 (M + H)$^+$. |

Intermediate-9-1-A (INT-9-1-A): 3-(2-(5-bromopyrazin-2-yl)-2-oxoethyl)-8,8-difluoro-1,3-diazaspiro[4.5]decane-2,4-dione {Chem. 77}

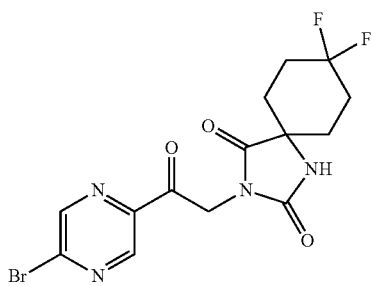

<Step-1>: Intermediate-9-1-1 (INT-9-1-1): 2-bromo-1-(5-bromopyrazin-2-yl)ethanol {Chem. 78}

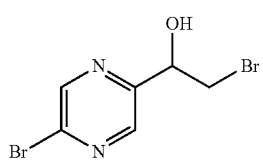

To a solution of 2-bromo-1-(5-bromopyrazin-2-yl)ethanone hydrobromide (INT-6-8-A)(crude solid, 3.35 mmol) in MeOH (15 mL) is added sodium borohydride (317 mg, 8.38 mmol) at 0° C. The mixture is stirred at rt for 1 h. The mixture is quenched with water and extracted with DCM. The combined organic solution is dried over Na$_2$SO$_4$, filtered and concentrated to give the titled compound as a yellow crude oil (740 mg, 78% yield).

MS (ESI) m/z: 282.9 (M+H)$^+$.

<Step-2>: Intermediate-9-1-2 (INT-9-1-2): 3-(2-(5-bromopyrazin-2-yl)-2-hydroxyethyl)-8,8-difluoro-1,3-diazaspiro[4.5]decane-2,4-dione

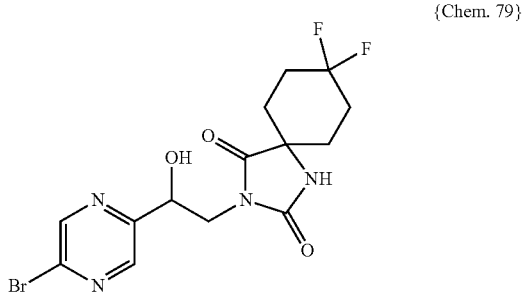

{Chem. 79}

A mixture of 8,8-difluoro-1,3-diazaspiro[4.5]decane-2,4-dione (INT-1-1-A)(536 mg, 2.62 mmol), 2-bromo-1-(5-bromopyrazin-2-yl)ethanol (INT-9-1-1)(740 mg, 2.62 mmol) and Cs₂CO₃ (1.28 g, 3.94 mmol) in DMSO (5 mL) is stirred at 60° C. for 1 h. The mixture is diluted with H₂O and extracted with DCM. The combined organic solution is dried over Na₂SO₄, filtered and concentrated in vacuo. The residual oil is purified by column chromatography (Biotage) on silica gel eluting with 0-70% ethyl acetate in hexane to give titled compound (490 mg, 46% yield) as a pale yellow solid.

$^1$H-NMR (270 MHz, DMSO-d$_6$): delta 8.82 (s, 1H), 8.77 (s, 1H), 8.71 (s, 1H), 6.19 (d, J=5.3 Hz, 1H), 4.87 (td, J=6.6, 5.3 Hz, 1H), 3.64 (ABqd, J=13.8, 6.6 Hz, 2H), 2.20-1.65 (m, 8H).

MS (ESI) m/z: 406.8 (M+H)$^+$.

<Step-3>: Intermediate-9-1-A (INT-9-1-A): 3-(2-(5-bromopyrazin-2-yl)-2-oxoethyl)-8,8-difluoro-1,3-diazaspiro[4.5]decane-2,4-dione

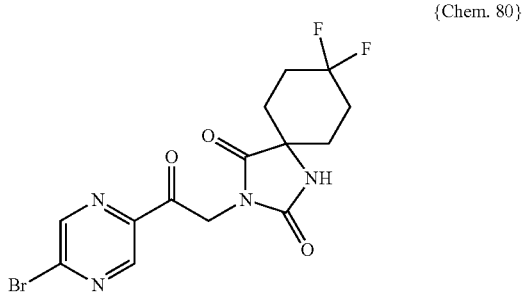 [SMILES: O=C(CN1C(=O)NC2(CCC(F)(F)CC2)C1=O)c1ccc(Cl)nc1]

{Chem. 80}

A mixture of INT-9-1-2 (560 mg, 1.38 mmol), potassium 2-iodo-5-methylbenzenesulfonate (23 mg, 0.069 mmol), OXONE (Registered Trademark), (552 mg, 0.898 mmol) in MeCN (10 mL) is stirred at 60° C. for 1 day. The mixture is quenched with 5% Na₂S₂O₃ aq. solution-sat. NaHCO₃ solution (1:1 v/v) and extracted with DCM. The combined organic solution is dried over Na₂SO₄, filtered and concentrated. The residual solid is purified by column chromatography (Biotage) on silica gel eluting with 0-50% ethyl acetate in hexane to give the titled compound (397 mg, 71% yield) as an off-white solid.

$^1$H-NMR (270 MHz, DMSO-d$_6$): delta 9.09 (d, J=1.3 Hz, 1H), 9.08 (s, 1H), 8.96 (s, 1H), 5.00 (s, 2H), 2.25-1.78 (m, 8H).

MS (ESI) m/z: 404.9 (M+H)$^+$.

Intermediate-9-2-A (INT-9-2-A): 3-(2-(5-bromo-4-methylthiazol-2-yl)-2-oxoethyl)-8,8-difluoro-1,3-diazaspiro[4.5]decane-2,4-dione

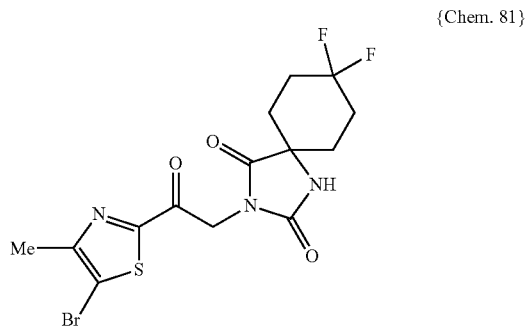 [SMILES: Cc1nc(C(=O)CN2C(=O)NC3(CCC(F)(F)CC3)C2=O)sc1Br]

{Chem. 81}

<Step-1>: Intermediate-9-2-1 (INT-9-2-1): 1-(5-bromo-4-methylthiazol-2-yl)-2-chloroethanol

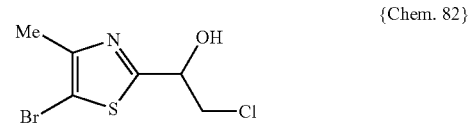 [SMILES: Cc1nc(C(O)CCl)sc1Br]

{Chem. 82}

The titled compound is prepared according to the procedure of INT-9-1-1 from the INT-6-10-A (1.0 g, 3.93 mmol) to give the product (796 mg, 79% yield).

MS (ESI) m/z: 258.0 (M+H)$^+$.

<Step-2>: Intermediate-9-2-2 (INT-9-2-2): 3-(2-(5-bromo-4-methylthiazol-2-yl)-2-hydroxyethyl)-8,8-difluoro-1,3-diazaspiro[4.5]decane-2,4-dione

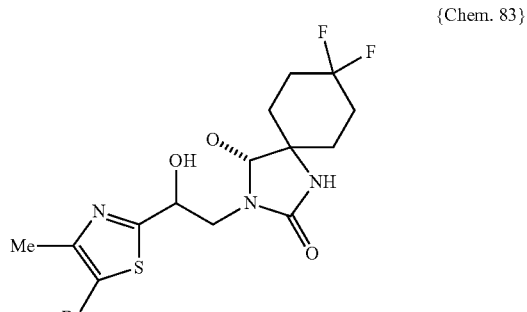

{Chem. 83}

The titled compound is prepared according to the procedure of INT-9-1-2 from the INT-9-2-1 (796 mg, 3.90 mmol) to give the product (968 mg, 59% yield).

$^1$H-NMR (270 MHz, DMSO-d$_6$): delta 8.84 (br.s, 1H), 6.75 (d, J=5.3 Hz, 1H), 4.95 (td, J=7.2, 5.3 Hz, 1H), 3.58 (dd, J=7.2, 1.3 Hz, 2H), 2.24 (s, 3H), 2.25-1.3 (m, 8H).

<Step-3> Intermediate-9-2-A (INT-9-2-A): 3-(2-(5-bromo-4-methylthiazol-2-yl)-2-oxoethyl)-8,8-difluoro-1,3-diazaspiro[4.5]decane-2,4-dione {Chem. 84}

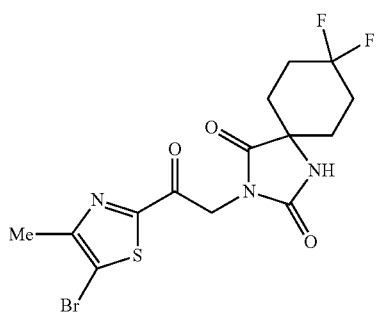

To a suspension of INT-9-2-2 (600 mg, 1.41 mmol) in DCM (5 mL) is added 1,1,1-Triacetoxy-1,1-dihydro-1,2-benziodoxol-3(1H)-one (Dess-Martin reagent)(1.02 g, 2.40 mmol) at rt. The mixture is stirred at rt for 1 h. The mixture is quenched with 5% $Na_2S_2O_3$ aq. solution, then sat. $NaHCO_3$ solution. The resulting mixture is extracted with DCM and the combined organic solution is dried over $Na_2SO_4$, filtered and concentrated. The residual solid is recrystallized with ethyl acetate (6 mL) to give the titled compound (230 mg, 38.5% yield) as a white solid. The mother liquid is concentrated and the resulting solid is purified by column chromatography on silica gel eluting with 20-80% EtOAC in hexane to give $2^{nd}$ crop of the titled compound (279 mg, 46.7% yield) as a white solid.

$^1$H-NMR (270 MHz, $CDCl_3$): delta 6.36 (br.s, 1H), 5.02 (s, 2H), 2.50 (s, 3H), 2.50-2.15 (m, 4H), 2.10-1.90 (m, 4H).

The following alcohol derivatives (INT-10-1-A to INT-10-6-A) are prepared according to the procedure of intermediate 9-1-1 from the synthesized alpha-haloacetyl derivatives in Table 10.

TABLE 10

| Halides | Products | Yield and Analytical data |
|---|---|---|
| INT-6-18-A | INT-10-1-A | (crude: yellow oil)<br>MS (ESI) m/z: 318.2 (M + H)$^+$. |
| INT-6-19-A | INT-10-2-A | (crude: yellow amorphous solid)<br>MS (ESI) m/z: 252.2 (M + H)$^+$.<br>(identified as the epoxide derivative) |
| INT-6-17-A | INT-10-3-A | (crude: yellow amorphous solid)<br>MS (ESI) m/z: 332.9 (M + H)$^+$.<br>A mixture of product and epoxide derivative (2:1) |
| INT-6-16-A | INT-10-4-A | 95% yield (crude: yellow oil)<br>MS (ESI) m/z: 319.0 (M + H)$^+$.<br>1H-NMR (270 MHz, CDCl3): 8.11 (s, 1H), 7.93-7.84 (m, 1H), 7.63 (d, J = 8.6 Hz, 2H), 7.60-7.49 (m, 1H), 7.55 (d, J = 8.6 Hz, 2H), 7.38-7.32 (m, 2H), 5.10-5.03 (m, 1H), 3.73 (dd, J = 10.6, 3.3 Hz, 1H), 3.61 (dd, J = 10.6, 9.1 Hz, 1H), 2.90-2.82 (m, 1H).<br>MS (ESI) m/z: 319.0 (M + H)$^+$. |

TABLE 10-continued

| Halides | Products | Yield and Analytical data |
|---|---|---|
| 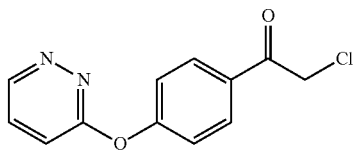 INT-6-15-A | 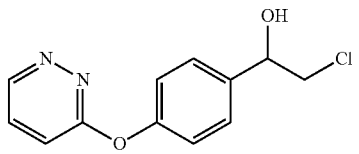 INT-10-5-A | (crude: brown amorphous solid) MS (ESI) m/z: 251.1 (M + H)+. |
| 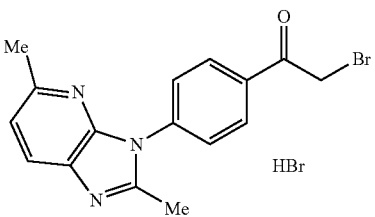 INT-6-23-A | 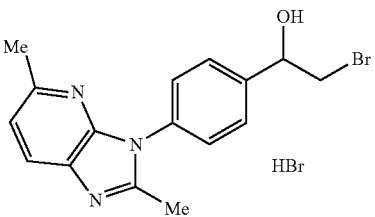 INT-10-6-A | (crude: colorless amorphous solid) MS (ESI) m/z: 346.0 (M + H)+. |

The following alcohol derivatives (INT-11-1-A to INT-11-6-A) are prepared according to the procedure of intermediate 9-1-2 from the synthesized 2-haloethanol derivatives and INT-1-4-A in Table 11.

TABLE 11

| Halides | Products | Yield and Analytical data |
|---|---|---|
| 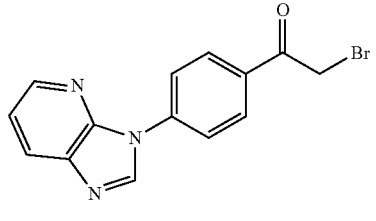 INT-10-1-A | 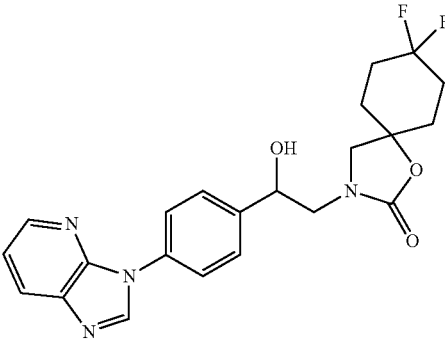 INT-11-1-A | 37% yield (in 2 steps)(pale yellow amorphous solid) $^1$H-NMR (270 MHz, DMSO-$d_6$): delta 8.92 (s, 1H), 8.44 (dd, J = 4.6, 1.3 Hz, 1H), 8.22 (dd, J = 7.9, 1.3 Hz, 1H), 7.95 (d, J = 7.9 Hz, 2H), 7.59 (d, J = 7.9 Hz, 2H), 7.40 (dd, J = 7.9, 4.6 Hz, 1H), 5.78 (d, J = 4.6 Hz, 1H), 4.91-4.83 (m, 1H), 3.51 (d, J = 9.2 Hz, 1H), 3.35 (s, 2H), 3.17 (d, J = 5.3 Hz, 1H), 2.00-1.80 (m, 8H). MS (ESI) m/z: 429.1 (M + H)+. |
| 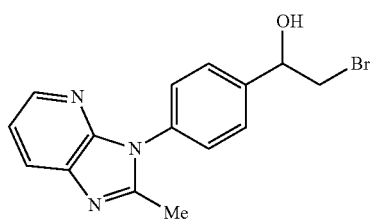 INT-10-2-A | 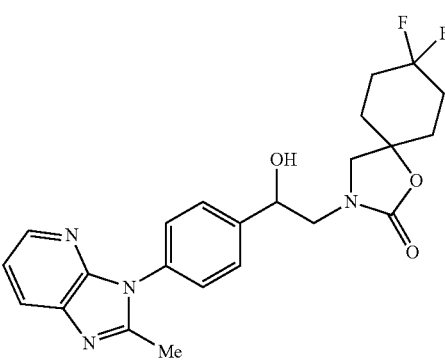 INT-11-2-A | 18% yield (in 2 steps) (pale yellow amorphous solid) MS (ESI) m/z: 443.1 (M + H)+. |

TABLE 11-continued

| Halides | Products | Yield and Analytical data |
|---|---|---|
| 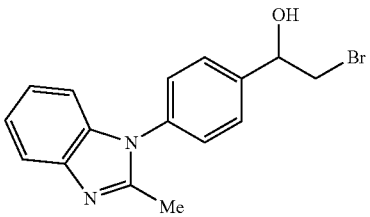<br>INT-10-3-A | 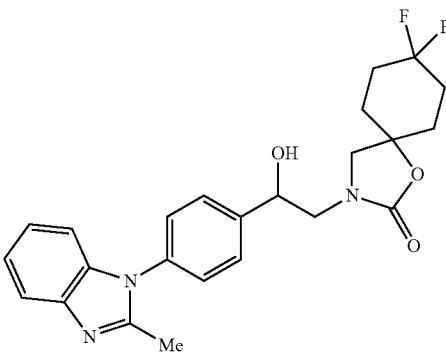<br>INT-11-3-A | 40% yield (in 2 steps)(a colorless amorphous solid)<br>$^1$H-NMR (270 MHz, DMSO-$d_6$): delta 7.62 (d, J = 7.9 Hz, 3H), 7.53 (d, J = 7.9 Hz, 2H), 7.23-7.17 (m, 2H), 7.09-7.06 (m, 1H), 5.8 (d, J = 3.9 Hz, 1H), 4.95-4.89 (m, 1H), 3.17 (d, J = 5.3 Hz, 1H), 2.54 (s, 2H), 2.42 (s, 3H), 2.00-1.85 (m, 8H).<br>MS (ESI) m/z: 442.1 (M + H)$^+$. |
| 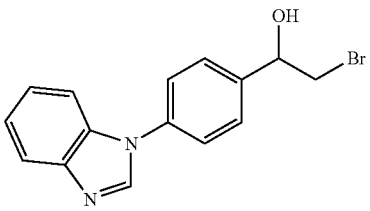<br>INT-10-4-A | 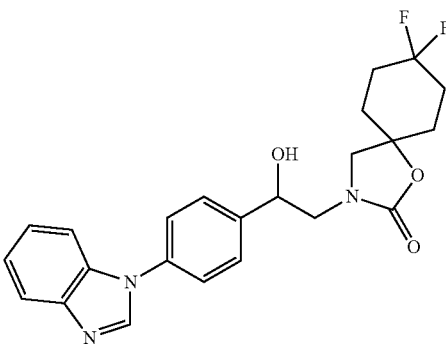<br>INT-11-4-A | 74% yield (in 2 steps)(yellow gum)<br>MS (ESI) m/z: 428.2 (M + H)$^+$.<br>$^1$H-NMR (270 MHz, CDCl$_3$): delta 7.97 (s, 1H), 7.88-7.80 (m, 1H), 7.62 (d, J = 8.6 Hz, 2H), 7.60-7.45 (m, 1H), 7.50 (d, J = 8.6 Hz, 2H), 7.40-7.30 (m, 2H), 5.13 (dd, J = 8.6, 3.3 Hz, 1H), 3.63-3.37 (m, 2H), 3.49 (s, 2H), 2.32-1.70 (m, 8H). |
| 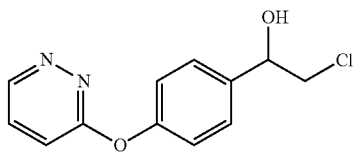<br>INT-10-5-A | 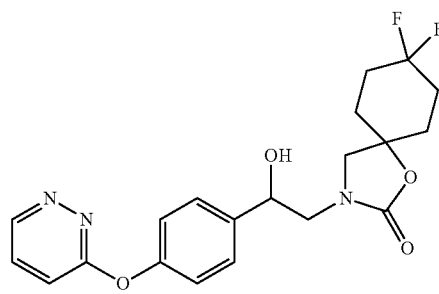<br>INT-11-5-A | 57% yield (in 2 steps)<br>(pale yellow amorphous solid)<br>MS (ESI) m/z: 406.0 (M + H)$^+$. |
| 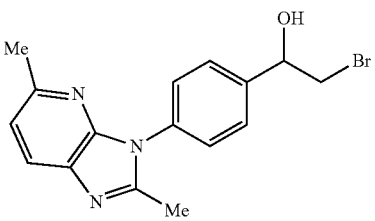<br>INT-10-6-A | 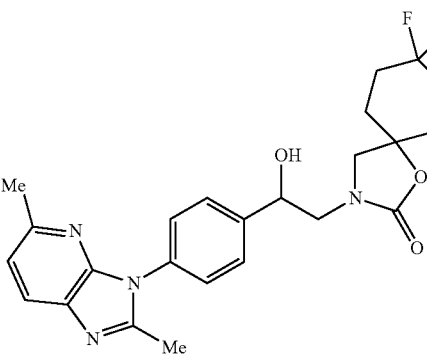<br>INT-11-6-A | Crude 51 mg (in 2 steps)<br>MS (ESI) m/z: 457.0 (M + H)$^+$. |

Intermediate 12-1-A (INT-12-1-A): 8,8-difluoro-3-(2-oxo-2-(4-(4,4,5,5-tetramethyl-1,3,2-dioxaborolan-2-yl)phenyl)ethyl)-1,3-diazaspiro[4.5]decane-2,4-dione

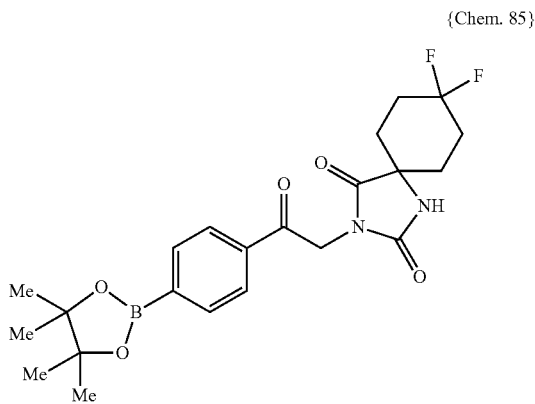 [SMILES: CC1(C)OB(c2ccc(C(=O)CN3C(=O)NC4(CCC(F)(F)CC4)C3=O)cc2)OC1(C)C]

{Chem. 85}

A mixture of 3-(2-(4-bromophenyl)-2-oxoethyl)-8,8-difluoro-1,3-diazaspiro[4.5]decane-2,4-dione (INT-7-1-A) (2.00 g, 4.99 mmol), bis(pinacolato)diboron (1.46 g, 5.73 mmol), potassium acetate (1.22 g, 12.5 mmol) and PdCl$_2$(dppf) CH$_2$Cl$_2$ (204 mg, 0.249 mmol) in 1,4-dioxane (20 mL) is stirred at 80° C. for 3 h. After cooling to rt, the reaction mixture is filtered through a pad of celite and the filter pad is washed with 1,4-dioxane. The filtrate and washings are concentrated in vacuo to give the residual oil, which is triturated with DCM/hexane to give the titled compound (2.03 g, 91% yield) as a pale yellow solid.

$^1$H-NMR (270 MHz, DMSO-d$_6$): delta 9.02 (s, 1H), 8.04 (d, J=7.9 Hz, 2H), 7.84 (d, J=7.9 Hz, 2H), 4.97 (s, 2H), 2.25-1.75 (m, 8H), 1.32 (s, 12H).

MS (ESI) m/z: 449.2 (M+H)$^+$.

Intermediate-12-2-A (INT-12-2-A): 8,8-difluoro-3-(2-oxo-2-(4-(4,4,5,5-tetramethyl-1,3,2-dioxaborolan-2-yl)phenyl)ethyl)-1-oxa-3-azaspiro[4.5]decan-2-one

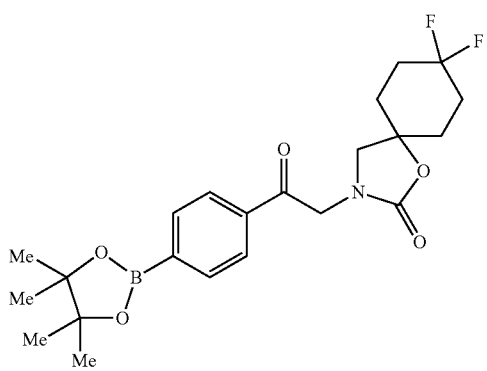

{Chem. 86}

<Step-1>: Intermediate-12-2-1 (INT-12-2-1): 3-(2-(4-bromophenyl)-2-hydroxyethyl)-8,8-difluoro-1-oxa-3-azaspiro[4.5]decan-2-one

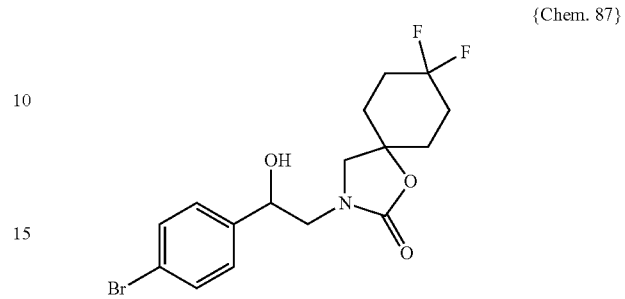

{Chem. 87}

A mixture of INT-1-4-A (500 mg, 2.62 mmol), cesium carbonate (1.70 g, 5.23 mmol) and 2-(4-bromophenyl)oxirane (599 mg, 3.01 mmol) in DMSO (5 mL) is stirred at 75° C. for 5 h. The mixture is diluted with water and extracted with EtOAc-hexane (2:1). The combined organic solution is washed with brine, dried over Na$_2$SO$_4$, filtered and concentrated. The purification is carried out by column chromatography on silica gel eluting with a gradient of 0-70% EtOAc in hexane to give the titled compound (972 mg, 95% yield) as an off-white solid.

$^1$H-NMR (270 MHz, CDCl$_3$): delta 7.51 (d, J=7.9 Hz, 2H), 7.27 (d, J=7.9 Hz, 2H), 5.03-4.92 (m, 1H), 3.59-3.23 (m, 4H), 2.90 (br.s, 1H), 2.31-1.95 (m, 6H), 1.83-1.68 (m, 2H).

MS (ESI) m/z: 390.1 (M+H)$^+$.

<Step-2>: Intermediate-12-2-2 (INT-12-2-2): 3-(2-(4-bromophenyl)-2-oxoethyl)-8,8-difluoro-1-oxa-3-azaspiro[4.5]decan-2-one

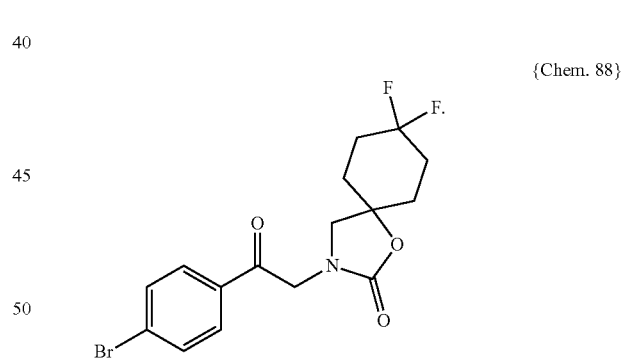

{Chem. 88}

To a solution of INT-12-2-1 (390 mg, 0.999 mmol) in DCM (20 mL) is added Dess-Martin periodinane (721 mg, 1.699 mmol) at rt. The mixture is stirred at rt for 1 h. The mixture is quenched with 5% Na$_2$S$_2$O$_3$ aq. solution, followed by sat. NaHCO$_3$ solution and extracted with EtOAc. The organic layer is dried over Na$_2$SO$_4$, filtered and concentrated. The purification is carried out by column chromatography on silica gel eluting with a gradient of 0-50% EtOAc in hexane to give the titled compound (315 mg, 81% yield) as an off-white solid.

$^1$H-NMR (270 MHz, CDCl$_3$): delta 7.80 (d, J=8.6 Hz, 2H), 7.64 (d, J=8.6 Hz, 2H), 4.67 (s, 2H), 3.47 (s, 2H), 2.38-2.00 (m, 6H), 2.00-1.80 (m, 2H).

MS (ESI) m/z: 390.1 (M+H)$^+$.

<Step-3>: Intermediate-12-2-A (INT-12-2-A): 8,8-difluoro-3-(2-oxo-2-(4-(4,4,5,5-tetramethyl-1,3,2-dioxaborolan-2-yl)phenyl)ethyl)-1-oxa-3-azaspiro[4.5]decan-2-one A mixture of INT-12-2-2 (200 mg, 0.515 mmol), bis(pinacolato)diboron (150 mg, 0.592 mmol), PdCl$_2$(dppf) CH$_2$Cl$_2$ (21 mg, 0.026 mmol) and potassium acetate (126 mg, 1.288 mmol) in 1,4-dioxane (3 mL) is stirred at 80° C. for 3 h. The reaction mixture (3 mL in dioxane) is used for the next Suzuki-Miyaura cross coupling reaction.

Intermediate 12-3-A (INT-12-3-A): 3-(2-(4-(5,5-dimethyl-1,3,2-dioxaborinan-2-yl)phenyl)-2-oxoethyl)-1,3-diazaspiro[4.5]decane-2,4-dione {Chem. 89}

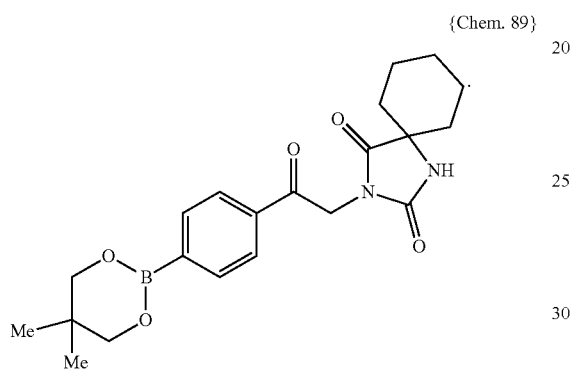

A mixture of INT-7-4-A (1.15 g, 3.15 mmol), PdCl$_2$(dppf) CH$_2$Cl$_2$ (203 mg, 0.252 mmol), potassium acetate (1.24 g, 12.6 mmol), and 5,5,5',5'-tetramethyl-2,2'-bi(1,3,2-dioxaborinane) (854 mg, 3.78 mmol) in DMSO (10 mL) is stirred at 80° C. for 1.5 h. The mixture is diluted with water and extracted with EtOAc-hexane (2:1). The combined organic solution is dried over Na$_2$SO$_4$, filtered and concentrated. The purification is carried out by column chromatography on silica gel eluting with a gradient of 0-70% EtOAc in hexane to give the titled compound (475 mg, 38% yield) as a pale yellow solid.

Intermediate-12-4-A (INT-12-4-A): 3-(2-oxo-2-(4-(4,4,5,5-tetramethyl-1,3,2-dioxaborolan-2-yl)phenyl)ethyl)-1,3-diazaspiro[4.5]decane-2,4-dione {Chem. 90}

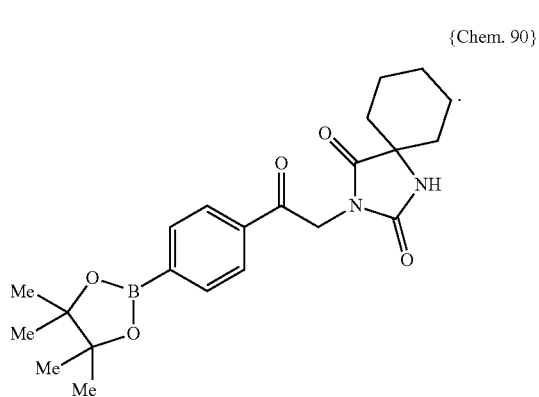 [SMILES: CC1(C)OB(c2ccc(C(=O)CN3C(=O)NC4(CCCCC4)C3=O)cc2)OC1(C)C]

A mixture of INT-7-4-A (120 mg, 0.329 mmol), PdCl$_2$(dppf) CH$_2$Cl$_2$ (21 mg, 0.026 mmol), potassium acetate (97 mg, 0.986 mmol) and bis(pinacolato)diboron (100 mg, 0.394 mmol) in DMSO (1 mL) is stirred at 80° C. for 4 h. After completion of the reaction, the reaction mixture is used for the next Suzuki-Miyaura cross coupling reaction without the further purification.

Intermediate-12-5-A (INT-12-5-A): 8,8-difluoro-3-(2-(3-fluoro-4-(4,4,5,5-tetramethyl-1,3,2-dioxaborolan-2-yl)phenyl)-2-oxoethyl)-1,3-diazaspiro[4.5]decane-2,4-dione {Chem. 91}

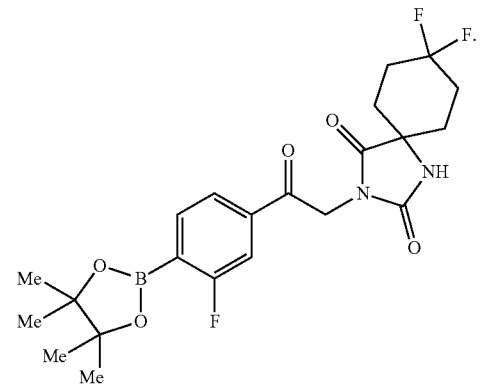

A mixture of INT-7-6-A (50 mg, 0.119 mmol), bis(pinacolato)diboron (36 mg, 0.143 mmol), PdCl$_2$(dppf) CH$_2$Cl$_2$ (8 mg, 0.0095 mmol) and potassium acetate (35 mg, 0.358 mmol) in 1, 4-dioxane (2 mL) is stirred at 80° C. for 3 h. After cooling, the reaction mixture is used for the next step without the further purification.

MS (ESI) m/z: 383.2 (M–H)$^-$ (as the boronic acid derivatives).

Intermediate-12-6-A (INT-12-6-A): 8,8-difluoro-3-(2-(2-fluoro-4-(4,4,5,5-tetramethyl-1,3,2-dioxaborolan-2-yl)phenyl)-2-oxoethyl)-1,3-diazaspiro[4.5]decane-2,4-dione {Chem. 92}

A mixture of INT-7-18-A (120 mg, 0.286 mmol), bis(pinacolato)diboron (84 mg, 0.329 mmol), PdCl$_2$(dppf) CH$_2$Cl$_2$ (19 mg, 0.023 mmol) and potassium acetate (84 mg, 0.859 mmol) in DMF (0.9 mL) is stirred at 80° C. for 1.5 h. After cooling, the reaction mixture is used for the next step without the further purification.

Intermediate-12-7-A (INT-12-7-A): 8,8-difluoro-3-(2-oxo-2-(4-(4,4,5,5-tetramethyl-1,3,2-dioxaborolan-2-yl)phenyl)ethyl)-1-oxa-3-azaspiro[4.5]decane-2,4-dione {Chem. 93}

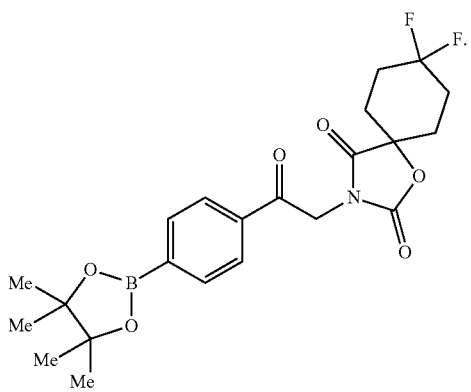

A mixture of INT-7-16-A (303 mg, 0.753 mmol), bis(pinacolato)diboron (230 mg, 0.904 mmol), PdCl$_2$(dppf) CH$_2$Cl$_2$ (49 mg, 0.060 mmol) and potassium acetate (222 mg, 2.26 mmol) in 1,4-dioxane (3 mL) is stirred at 80° C. for 1.5 h. After cooling, the reaction mixture is concentrated in vacuo. The residual oil is purified by column chromatography on silica gel eluting with 0-30% ethyl acetate in hexane to give the titled compound (332 mg, 98%) as a yellow solid.

MS (ESI) m/z: 448.1 (M−H)⁻.

Intermediate-13-1-A (INT-13-1-A): 3-(2-(4-bromophenyl)-2-oxoethyl)-1-oxa-3-azaspiro[4.5]decan-2-one {Chem. 94}

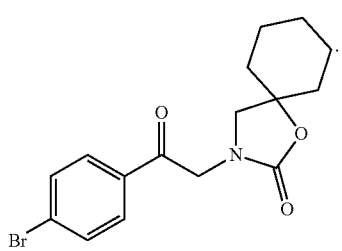

<Step-1>: Intermediate-13-1-1 (INT-13-1-1): 3-(2-(4-bromophenyl)-2-hydroxyethyl)-1-oxa-3-azaspiro[4.5]decan-2-one {Chem. 95}

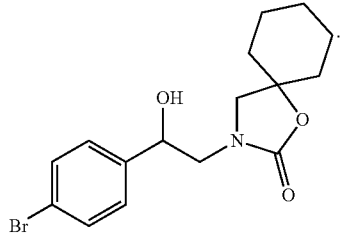

A mixture of 1-oxa-3-azaspiro[4.5]decan-2-one (200 mg, 1.29 mmol), cesium carbonate (840 mg, 2.58 mmol) and 2-(4-bromophenyl)oxirane (385 mg, 1.93 mmol) in DMSO (2 mL) is stirred at 75° C. for 3 h. The mixture is diluted with water and extracted with EtOAc-hexane (2:1). The combined organic solution is washed with brine, dried over Na$_2$SO$_4$, filtered and concentrated. The purification is carried out by column chromatography on silica gel eluting with a gradient of 0-80% EtOAc in hexane to give the titled compound (441 mg, 97% yield) as an off-white solid.

$^1$H-NMR (270 MHz, CDCl$_3$): delta 7.50 (d, J=7.9 Hz, 2H), 7.28 (d, J=7.9 Hz, 2H), 4.97 (dt, J=7.9, 3.3 Hz, 1H), 3.52 (dd, J=15.2, 3.3 Hz, 1H), 3.39 (dd, J=15.2, 7.9 Hz, 1H), 3.19 (s, 2H), 3.20-3.14 (m, 1H), 1.85-1.63 (m, 4H), 1.60-1.32 (m, 6H).

MS (ESI) m/z: 356.0 (M+H)⁺.

<Step-2>: Intermediate-13-1-A (INT-13-1-A): 3-(2-(4-bromophenyl)-2-oxoethyl)-1-oxa-3-azaspiro[4.5]decan-2-one To a solution of INT-13-1-1 (116 mg, 0.327 mmol) in DCM (5 mL) is added Dess-Martin periodinane (278 mg, 0.655 mmol) at rt. The mixture is stirred at rt for 3 h. The mixture is quenched with 5% Na$_2$S$_2$O$_3$ aq. solution, followed by saturated NaHCO$_3$ solution and extracted with EtOAc. The combined organic layer is dried over Na$_2$SO$_4$, filtered and concentrated. The purification is carried out by column chromatography on silica gel eluting with a gradient of 0-50% EtOAc in hexane to give the titled compound (106 mg, 92% yield) as an off-white solid.

$^1$H-NMR (270 MHz, CDCl$_3$): delta 7.81 (d, J=8.5 Hz, 2H), 7.64 (d, J=8.5 Hz, 2H), 4.65 (s, 2H), 3.39 (s, 2H), 2.00-1.32 (m, 10H).

MS (ESI) m/z: 354.0 (M+H)⁺.

Intermediate-13-2-A (INT-13-2-A): 3-(2(4-bromophenyl)-2-oxoethyl)-8,8-difluoro-4-methyl-1-oxa-3-azaspiro[4.5]decan-2-one {Chem. 96}

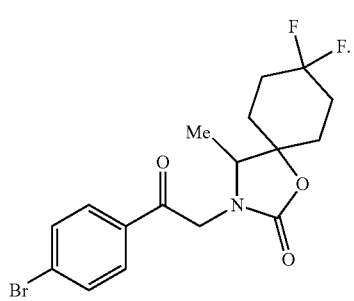

Step-1: Intermediate-13-2-1 (INT-13-2-1): 3-(2 (4-bromophenyl)-2-hydroxyethyl)-8,8-difluoro-4-methyl-1-oxa-3-azaspiro[4.5]decan-2-one

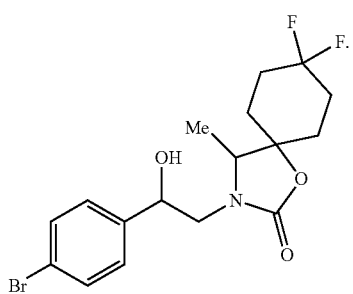

{Chem. 97}

A mixture of INT-1-6-A (150 mg, 0.731 mmol), 2-(4-bromophenyl)oxirane (145 mg, 0.731 mmol) and cesium carbonate (476 mg, 1.462 mmol) in DMSO (5 mL) is stirred at 75° C. for 5 h. The mixture is diluted with water and extracted with EtOAc-hexane (2:1). The organic layer is washed with brine, dried over $Na_2SO_4$, filtered and concentrated in vacuo. The purification is carried out by column chromatography on silica gel eluting with a gradient of 0-70% EtOAc in hexane to give the the titled compound (245 mg, 83% yield, mixture of diastereomers) as an off-white solid.
MS (ESI) m/z: 387.9 (M+H—OH)$^+$.

Step-2: Intermediate-13-2-A (INT-13-2-A): 3-(2 (4-bromophenyl)-2-oxoethyl)-8,8-difluoro-4-methyl-1-oxa-3-azaspiro[4.5]decan-2-one To a solution of INT-13-2-1 (245 mg, 0.606 mmol) in DCM (10 mL) is added Dess-Martin periodinane (450 mg, 1.061 mmol) at rt. The mixture is stirred at rt for 1 h. The mixture is quenched with 5% $Na_2S_2O_3$ aq. solution, followed by sat. $NaHCO_3$ solution and extracted with DCM. The combined organic layer is dried over $Na_2SO_4$, filtered and concentrated in vacuo. The purification is carried out by column chromatography on silica gel eluting with a gradient of 0-50% EtOAc in hexane to give the titled compound (217 mg, 89% yield) as an off-white solid.
$^1$H-NMR (270 MHz, CDCl$_3$): delta 7.82 (d, J=8.6 Hz, 2H), 7.65 (d, J=8.6 Hz, 2H), 4.92 (d, J=18.5 Hz, 1H), 4.33 (d, J=18.5 Hz, 1H), 3.82 (q, J=6.6 Hz, 1H), 2.40-1.98 (m, 6H), 1.93-1.66 (m, 2H), 1.15 (d, J=6.6 Hz, 3H).
MS (ESI) m/z: 403.8 (M+H)$^+$.

Intermediate-13-3-A (INT-13-3-A): 3-(2-(4-bromophenyl)-2-oxoethyl)-8,8-difluoro-4,4-dimethyl-1-oxa-3-azaspiro[4.5]decan-2-one

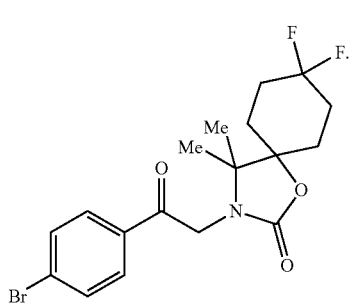

{Chem. 98}

Step-1: Intermediate-13-3-1 (INT-13-3-1): 3-(2-(4-bromophenyl)-2-hydroxyethyl)-8,8-difluoro-4,4-dimethyl-1-oxa-3-azaspiro[4.5]decan-2-one

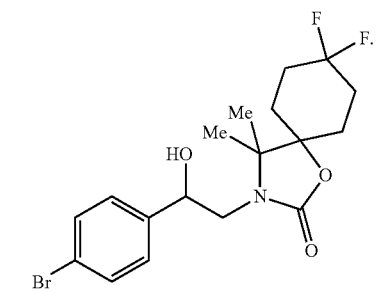

{Chem. 99}

A mixture of INT-1-7-A (175 mg, 0.798 mmol), 2-(4-bromophenyl)oxirane (159 mg, 0.798 mmol) and cesium carbonate (520 mg, 1.597 mmol) in DMSO (2 mL) is stirred at 85° C. for 1 day. The mixture is diluted with water and extracted with EtOAc-hexane (2:1). The combined organic solution is washed with brine, dried over $Na_2SO_4$, filtered and concentrated in vacuo to give the titled compound as a crude oil.
MS (ESI) m/z: 419.8 (M+H)$^+$.

Step-2: Intermediate-13-3-A (INT-13-3-A): 3-(2-(4-bromophenyl)-2-oxoethyl)-8,8-difluoro-4,4-dimethyl-1-oxa-3-azaspiro[4.5]decan-2-one To a solution of INT-13-3-1 (crude) in DCM (10 mL) is added Dess-Martin periodinane (592 mg, 1.397 mmol) at rt. The mixture is stirred at rt for 1 h. The mixture is quenched with 5% $Na_2S_2O_3$ aq. solution, followed by saturated $NaHCO_3$ solution and extracted with DCM. The combined organic solution is dried over $Na_2SO_4$, filtered and concentrated in vacuo. The purification is carried out by column chromatography on silica gel eluting with a gradient of 0-40% EtOAc in hexane to give the titled compound (265 mg, 80% yield in 2 steps) as a pale yellow solid.
$^1$H-NMR (270 MHz, CDCl$_3$): delta 7.83 (d, J=8.6 Hz, 2H), 7.65 (d, J=8.6 Hz, 2H), 4.52 (s, 2H), 2.39-2.02 (m, 6H), 1.85-1.64 (m, 2H), 1.17 (s, 6H).
MS (ESI) m/z: 417.8 (M+H)$^+$.

Intermediate-13-4-A (INT-13-4-A): 3-(2-(4-bromophenyl)-2-oxoethyl)-8,8-difluoro-4-isopropyl-1-oxa-3-azaspiro[4.5]decan-2-one

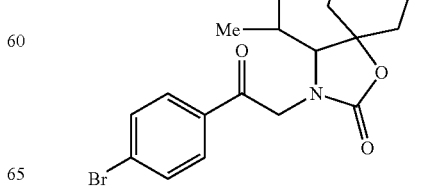

{Chem. 100}

\<Step-1\>: Intermediate-13-4-1 (INT-13-4-1): 3-(2-(4-bromophenyl)-2-hydroxyethyl)-8,8-difluoro-4-isopropyl-1-oxa-3-azaspiro[4.5]decan-2-one {Chem. 101}

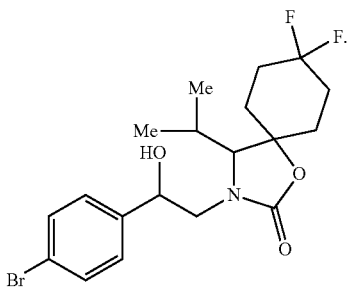

A mixture of INT-1-8-A (186 mg, 0.798 mmol), 2-(4-bromophenyl)oxirane (159 mg, 0.798 mmol) and cesium carbonate (520 mg, 1.597 mmol) in DMSO (2 mL) is stirred at 85° C. for 1 day. The mixture is diluted with water and extracted with EtOAc-hexane (2:1). The combined organic solution is washed with brine, dried over $Na_2SO_4$, filtered and concentrated in vacuo to give the titled compound as a crude oil.

MS (ESI) m/z: 433.8 (M+H)$^+$.

\<Step-2\>: Intermediate-13-4-A (INT-13-4-A): 3-(2-(4-bromophenyl)-2-oxoethyl)-8,8-difluoro-4-isopropyl-1,3-diazaspiro[4.5]decan-2-one To a solution of INT-13-4-1 (crude) in DCM (10 mL) is added Dess-Martin periodinane (592 mg, 1.397 mmol) at rt. The mixture is stirred at rt for 1 h. The mixture is quenched with 5% $Na_2S_2O_3$ aq. solution, followed by sat. $NaHCO_3$ solution and extracted with DCM. The combined organic solution is dried over $Na_2SO_4$, filtered and concentrated in vacuo. The purification is carried out by column chromatography on silica gel eluting with a gradient of 0-40% EtOAc in hexane to give the titled compound (268 mg, 78% yield in 2 steps) as a pale yellow solid.

$^1$H-NMR (270 MHz, CDCl$_3$): delta 7.81 (d, J=8.6 Hz, 2H), 7.65 (d, J=8.6 Hz, 2H), 5.22 (d, J=18.5 Hz, 1H), 4.40 (d, J=18.5 Hz, 1H), 3.60 (d, J=2.0 Hz, 1H), 2.62-2.49 (m, 1H), 2.41-1.72 (m, 8H), 1.04 (d, J=6.6 Hz, 6H).

MS (ESI) m/z: 431.8 (M+H)$^+$.

Intermediate-14-1-A (INT-14-1-A): 8,8-difluoro-3-(2-(4-hydroxyphenyl)-2-oxoethyl)-1,3-diazaspiro[4.5]decane-2,4-dione {Chem. 102}

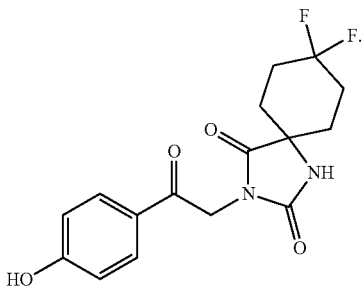

To a stirred solution of 2-bromo-1-(4-((tert-butyldiphenylsilyl)oxy)phenyl)ethanone (1295 mg, 2.86 mmol) in DMF (30 mL) is added INT-1-1-A (612 mg, 3.00 mmol) and potassium carbonate (987 mg, 7.14 mmol). The mixture is heated at 85° C. for 3.5 h. After cooling to rt., the mixture is quenched with 1 M HCl aq. solution and extracted with ethyl acetate-toluene (8:1). The combined organic solution is washed with water, brine, dried over sodium sulfate, filtered and concentrated in vacuo to give the crude product (pale yellow oil). The crude product is purified by column chromatography on silica gel (100 g) with 30-70% ethyl acetate in hexane to give the titled compound (789 mg, 82% yield) as a white solid.

$^1$H-NMR (270 MHz, DMSO-d$_6$): delta 10.58 (br.s, 1H), 8.98 (s, 1H), 7.92 (d, J=8.6 Hz, 2H), 6.89 (d, J=8.6 Hz, 2H), 4.84 (s, 2H), 2.25-1.70 (m, 8H).

MS (ESI) m/z: 339.06 (M+H)$^+$.

Intermediate-15-1-A (INT-15-1-A): 3-(2-(4-((3-aminopyridin-2-yl)amino)phenyl)-2-oxoethyl)-8,8-difluoro-1,3-diazaspiro[4.5]decane-2,4-dione {Chem. 103}

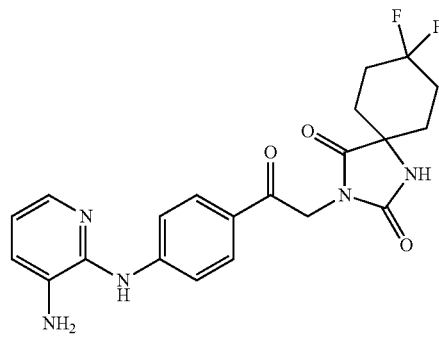

\<Step-1\>: Intermediate-15-1-1 (INT-15-1-1): 2-bromo-1-(4-((3-nitropyridin-2-yl)amino)phenyl)ethanone {Chem. 104}

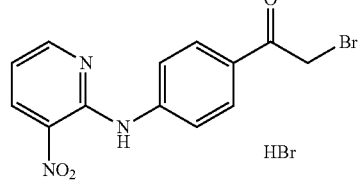

A mixture of 1-(4-((3-nitropyridin-2-yl)amino)phenyl)ethanone (INT-6-19-1)(1.0 g, 3.89 mmol) and bromine (0.621 g, 3.89 mmol) in 25% HBr—AcOH (20 mL) is stirred at rt for 1.5 h. The reaction mixture is concentrated by nitrogen flow. The residue is triturated with a mixture of IPE and MeOH (2/1 v/v) to give the titled compound monohydrobromide (1.56 g, quant.) as a yellow solid.

$^1$H-NMR (270 MHz, DMSO-d$_6$): delta 10.1 (s, 1H), 8.63-8.59 (m, 2H), 8.01 (d, J=8.5 Hz, 2H), 7.90 (d, J=8.5 Hz, 2H), 7.14 (dd, J=7.9, 4.6 Hz, 1H), 4.89 (s, 2H).

MS (ESI) m/z: 337.9 (M+H)$^+$.

\<Step-2\>: Intermediate-15-1-2 (INT-15-1-2): 8,8-difluoro-3-(2-(4-((3-nitropyridin-2-yl)amino)phenyl)-2-oxoethyl)-1,3-diazaspiro[4.5]decane-2,4-dione {Chem. 105}

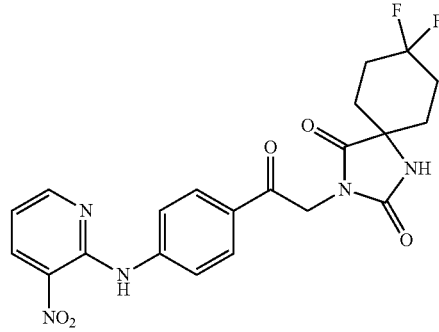

A mixture of INT-1-1-A (104 mg, 0.507 mmol), INT-15-1-1 (235 mg, 0.563 mmol) and potassium carbonate (234 mg, 1.69 mmol) in DMF (5 mL) is stirred under microwave irradiation at 120° C. for 20 min. After cooling, the reaction mixture is quenched with water and extracted with EtOAc. The combined organic layers are washed with brine, dried over sodium sulfate, filtered and concentrated in vacuo. The residue is purified by column chromatography (Biotage) on silica gel (10 g) eluting with 10-80% ethyl acetate in DCM to give the titled compound (0.138 g, 53% yield) as a pale yellow solid.

$^1$H-NMR (270 MHz, DMSO-$d_6$): delta 10.2 (s, 1H), 9.02 (s, 1H), 8.62-8.57 (m, 2H), 8.05 (d, J=8.5 Hz, 2H), 7.94 (d, J=8.5 Hz, 2H), 7.15 (dd, J=7.9, 4.6 Hz, 1H), 4.94 (s, 2H), 2.18-1.81 (m, 8H).

MS (ESI) m/z: 460.0 (M+H)$^+$.

<Step-3>: Intermediate-15-1-A (INT-15-1-A): 3-(2-(4-((3-aminopyridin-2-yl)amino)phenyl)-2-oxo-ethyl)-8,8-difluoro-1,3-diazaspiro[4.5]decane-2,4-dione A mixture of INT-15-1-2 (138 mg, 0.300 mmol), Iron (101 mg, 1.80 mmol) and solid ammonium chloride (48 mg, 0.901 mmol) in EtOH/water (4/1 v/v)(10 mL) is heated at reflux for 2.5 h. After coiling to rt, the reaction mixture is filtered through a pad of celite and the filtrate and washings are concentrated in vacuo. The residue is partitioned between EtOAc and 2 M NaOH aq. solution. The separated organic layer is washed with brine, dried over sodium sulfate, filtered and concentrated in vacuo to give the titled compound (75 mg, 58% yield) as a brown solid.

$^1$H-NMR (270 MHz, DMSO-$d_6$): delta 8.98 (s, 1H), 8.41 (s, 1H), 7.92 (d, J=9.2 Hz, 2H), 7.72 (d, J=9.2 Hz, 2H), 7.59 (dd, J=4.6, 1.3 Hz, 1H), 7.02-6.98 (m, 1H), 6.78 (dd, J=7.9, 4.6 Hz, 1H), 5.22 (s, 2H), 4.84 (s, 2H), 2.17-1.85 (m, 8H).

MS (ESI) m/z: 430.1 (M+H)$^+$.

Intermediate-15-2-A (INT-15-2-A): 3-(2-(4-((3-amino-6-methylpyridin-2-yl)amino)phenyl)-2-oxo-ethyl)-8,8-difluoro-1,3-diazaspiro[4.5]decane-2,4-dione {Chem. 106}

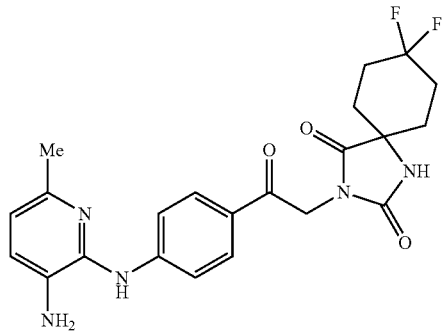

<Step-1>: Intermediate-15-2-1 (INT-15-2-1): 2-bromo-1-(4-((6-methyl-3-nitropyridin-2-yl)amino)phenyl)ethanone hydrobromide {Chem. 107}

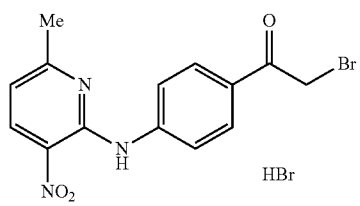

The titled compound is prepared according to the procedure of INT-15-1-1 from INT-6-23-1 (740 mg, 2.73 mmol), bromine (126 microL, 2.46 mmol) in 25% HBr—AcOH (20 mL) to give the product (1232 mg, quant., chemical purity of mono-bromo product: 90%) as a yellow solid. This is used for the next step without the further purification.

$^1$H-NMR (270 MHz, DMSO-$d_6$): delta 10.23 (br.s, 1H), 8.53-8.45 (m, 1H), 8.06-7.92 (m, 4H), 7.04-6.96 (m, 1H), 4.90 (s, 2H), 2.52 (s, 3H).

MS (ESI) m/z: 350.1 (M+H)$^+$.

<Step-2>: Intermediate-15-2-2 (INT-15-2-2): 8,8-difluoro-3-(2-(4-((6-methyl-3-nitropyridin-2-yl)amino)phenyl)-2-oxoethyl)-1,3-diazaspiro[4.5]decane-2,4-dione {Chem. 108}

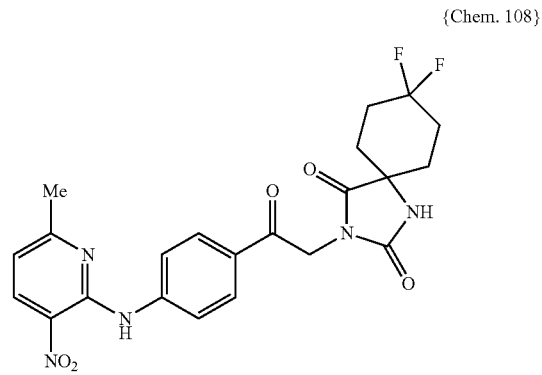 [SMILES: Cc1ccc([N+](=O)[O-])c(Nc2ccc(C(=O)CN3C(=O)NC4(CCC(F)(F)CC4)C3=O)cc2)n1]

The titled compound is prepared according to the procedure of INT-15-1-2 from INT-15-2-1 (700 mg, 1.62 mmol), INT-1-1-A (298 mg, 1.46 mmol) and potassium carbonate (786 mg, 5.68 mmol) in DMF (15 mL) to give the product (314 mg, 41% yield) as a yellow solid.

$^1$H-NMR (270 MHz, DMSO-$d_6$): delta 10.25 (br.s, 1H), 9.02 (br.s, 1H), 8.53-8.46 (m, 1H), 8.10-7.95 (m, 4H), 7.05-6.97 (m, 1H), 4.94 (s, 2H), 2.53 (s, 3H), 2.27-1.75 (m, 8H).

MS (ESI) m/z: 474.0 (M+H)$^+$.

<Step-3>: Intermediate-15-2-A (INT-15-2-A): 3-(2-(4-((3-amino-6-methylpyridin-2-yl)amino)phenyl)-2-oxoethyl)-8,8-difluoro-1,3-diazaspiro[4.5]decane-2,4-dione The titled compound is prepared according to the procedure of INT-15-1-A (step-3) from INT-15-2-2 (310 mg, 0.655 mmol), ammonium chloride (105 mg, 1.96 mmol) and iron (219 mg, 3.93 mmol) in ethanol-water (4:1)(20 mL) to give the product (281 mg, 97% yield) as a dark yellow solid.

$^1$H-NMR (270 MHz, DMSO-$d_6$): delta 8.98 (br.s, 1H), 8.37 (br.s, 1H), 7.92 (d, J=8.6 Hz, 2H), 7.74 (d, J=8.6 Hz, 2H), 6.93 (d, J=7.9 Hz, 1H), 6.63 (d, J=7.9 Hz, 1H), 4.98 (br.s, 2H), 4.84 (br.s, 2H), 2.29 (s, 3H), 2.26-1.75 (m, 8H).

MS (ESI) m/z: 444.0 (M+H)$^+$.

Intermediate-16-1-A (INT-16-1-A): 4'-(2-(8,8-difluoro-2,4-dioxo-1,3-diazaspiro[4.5]decan-3-yl)acetyl)-[1,1'-biphenyl]-2-carboxylic acid

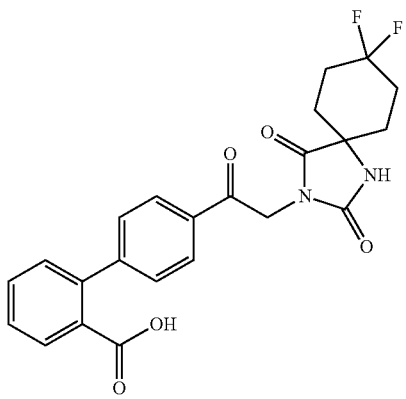

{Chem. 109}

<Step-1>: Intermediate-16-1-1 (INT-16-1-1): tert-butyl 4'-(2-(8,8-difluoro-2,4-dioxo-1,3-diazaspiro[4.5]decan-3-yl)acetyl)-[1,1'-biphenyl]-2-carboxylate

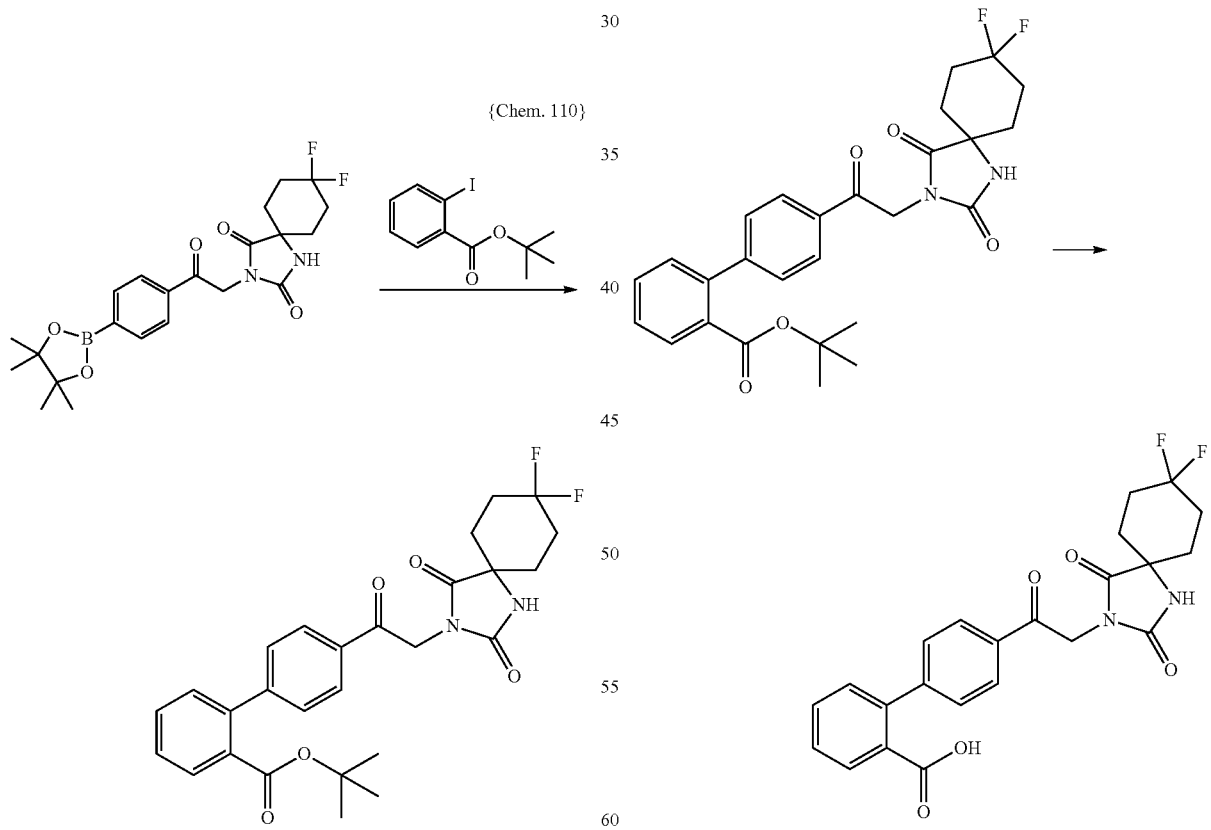

A mixture of 8,8-difluoro-3-(2-oxo-2-(4-(4,4,5,5-tetramethyl-1,3,2-dioxaborolan-2-yl)phenyl)ethyl)-1,3-diazaspiro[4.5]decane-2,4-dione (INT-12-1-A) (300 mg, 0.67 mmol), tert-butyl 2-iodobenzoate (244 mg, 0.80 mmol), potassium phosphate (284 mg, 1.34 mmol) and $PdCl_2$(dppf) $CH_2Cl_2$ (109 mg, 0.134 mmol) in DMF (8 mL) is stirred at 100° C. for 2 h. After cooling to rt, the reaction mixture is diluted with EtOAc, and washed with water. The organic layer is dried over sodium sulfate, filtered and concentrated in vacuo. The residue is purified by column chromatography (Biotage) on silica gel (25 g) eluting with 50% ethyl acetate in hexane to give the titled compound (245 mg, 73% yield) as a white solid.

$^1$H-NMR (270 MHz, $CDCl_3$): delta 8.00 (d, J=7.9 Hz, 2H), 7.86 (d, J=7.9 Hz, 1H), 7.53-7.46 (m, 4H), 7.30 (d, J=7.3 Hz, 1H), 6.56 (s, 1H), 4.97 (s, 2H), 2.48-2.21 (m, 4H), 2.12-1.90 (m, 4H), 1.29 (s, 9H).

MS (ESI) m/z: 497.2 (M−H)⁻.

<Step-2>: Intermediate-16-1-A (INT-16-1-A): 4'-(2-(8,8-difluoro-2,4-dioxo-1,3-diazaspiro[4.5]decan-3-yl)acetyl)-[1,1'-biphenyl]-2-carboxylic acid {Chem. 111}

A mixture of INT-16-1-1 (245 mg, 0.491 mmol), TFA (2 mL) and DCM (4 mL) is stirred at rt for 1 h. The solvent is concentrated in vacuo to give the titled compound (217 mg, >99% yield) as a white solid.

MS (ESI) m/z: 441.2 (M−H)⁻.

Intermediate-16-2-A (INT-16-2-A): 4-(4-(2-(8,8-difluoro-2,4-dioxo-1,3-diazaspiro[4.5]decan-3-yl)acetyl)phenyl)-1H-indole-2-carboxylic acid {Chem. 112}

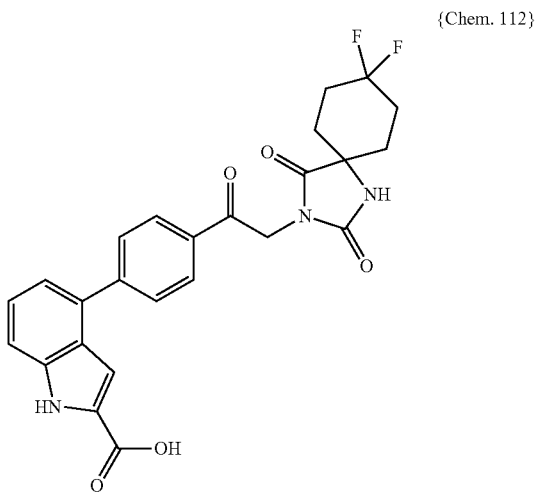 [SMILES: O=C(CN1C(=O)NC2(CCC(F)(F)CC2)C1=O)c1ccc(-c2cccc3[nH]c(C(=O)O)cc23)cc1]

A mixture of INT-12-1-A (150 mg, 0.335 mmol), 4-bromo-1H-indole-2-carboxylic acid (80 mg, 0.335 mmol), saturated NaHCO$_3$ solution (0.6 mL) and PdCl$_2$(dppf) CH$_2$Cl$_2$ (27 mg, 0.033 mmol) in 1,4-dioxane (0.6 mL) is irradiated in a microwave system at 120° C. for 20 min. The mixture is acidified with 2 M HCl aq. solution and extracted with DCM. The organic layer is dried over Na$_2$SO$_4$, filtered and concentrated in vacuo. The residual oil is purified by PE-AX to give the titled compound (100 mg, 62%) as a brown solid.

MS (ESI) m/z: 480.3 (M−H)⁻.

Intermediate-17-1-A (INT-17-1-A): 3-(2-(4-(2-(chloromethyl)-5-methyl-3H-imidazo[4,5-b]pyridin-3-yl)phenyl)-2-oxoethyl)-8,8-difluoro-1,3-diazaspiro[4.5]decane-2,4-dione {Chem. 113}

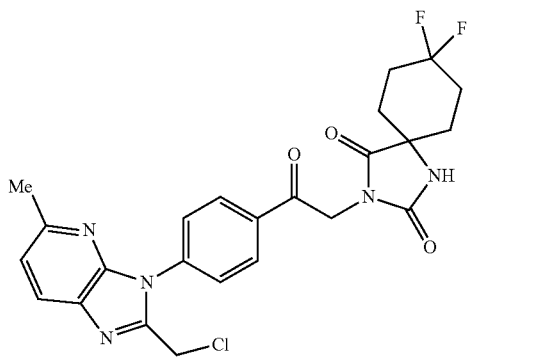

To a stirred solution of INT-15-2-A (70 mg, 0.158 mmol) and triethylamine (88 microL, 0.631 mmol) in THF (2.5 mL) is added a solution of chloroacetyl chloride (23 mg, 0.205 mmol) in THF (0.5 mL) via a syringe at rt. After stirring at rt for 2 h, the starting material is disappeared on TLC. After the removal of solvent, the crude product is dissolved in AcOH (3 mL) and heated at 100° C. for 2 h. After the removal of solvent, the residue is dissolved in DCM and washed with sat. NaHCO$_3$ solution (pH>10) and brine. The organic solution is dried over sodium sulfate, filtered and concentrated in vacuo to give the crude product, which is purified by column chromatography on silica gel (12 g) eluting with 40-100% ethyl acetate in DCM to give the titled compound (53.1 mg, 67% yield) as a slightly orange amorphous solid.

$^1$H-NMR (270 MHz, DMSO-d$_6$): delta 9.05 (br.s, 1H), 8.30 (d, J=8.6 Hz, 2H), 8.09 (d, J=7.9 Hz, 1H), 7.85 (d, J=8.6 Hz, 2H), 7.29 (d, J=7.9 Hz, 1H), 5.09 (br.s, 2H), 4.96 (br.s, 2H), 2.52 (s, 3H), 2.28-1.78 (m, 8H).

MS (ESI) m/z: 502.2 (M+H)⁺.

Intermediate-17-2-A (INT-17-2-A): (3-(4-(2-(8,8-difluoro-2,4-dioxo-1,3-diazaspiro[4.5]decan-3-yl)acetyl)phenyl)-3H-imidazo[4,5-b]pyridin-2-yl)methyl acetate {Chem. 114}

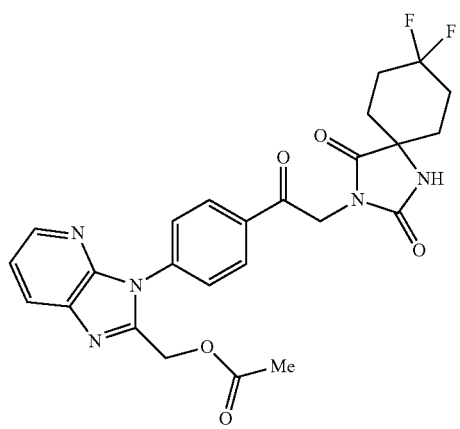

The titled compound is prepared according to the procedure of INT-17-1 from the INT-15-1-A (50 mg, 0.116 mmol) and acetoxyacetyl chloride (25.4 mg, 0.186 mmol) to give the product (55 mg, 92% yield) as a yellow amorphous solid.

MS (ESI) m/z: 512.0 (M+H)⁺.

Intermediate-17-3-A (INT-17-3-A): (3-(4-(2-(8,8-difluoro-2,4-dioxo-1,3-diazaspiro[4.5]decan-3-yl)acetyl)phenyl)-5-methyl-3H-imidazo[4,5-b]pyridin-2-yl)methyl acetate {Chem. 115}

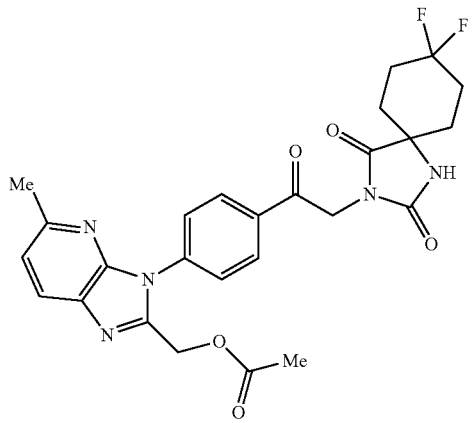

The titled compound is prepared according to the procedure of INT-17-1 from the INT-15-2-A (70 mg, 0.158 mmol) and acetoxyacetyl chloride (43.1 mg, 0.316 mmol) to give the product (75.9 mg, 91% yield) as a slightly orange amorphous solid.

MS (ESI) m/z: 526.3 (M+H)⁺.

EXAMPLES

Example-1-1: 3-(2-(2,5-dimethyl-1-(5-methylisoxazol-3-yl)-1H-pyrrol-3-yl)-2-oxoethyl)-8,8-difluoro-1,3-diazaspiro[4.5]decane-2,4-dione {Chem. 116}

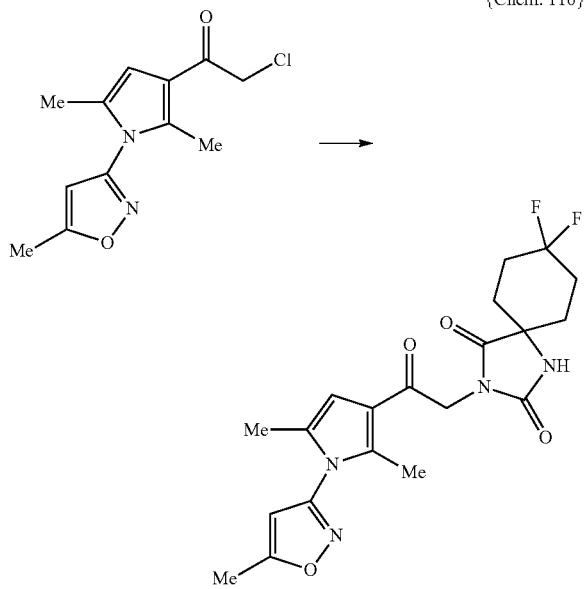

A mixture of 2-chloro-1-(2,5-dimethyl-1-(5-methylisoxazol-3-yl)-1H-pyrrol-3-yl)ethanone (INT-4-8-A)(200 mg, 0.791 mmol), 8,8-difluoro-1,3-diazaspiro[4.5]decane-2,4-dione (INT-1-1-A)(170 mg, 0.831 mmol) and anhydrous $K_2CO_3$ (273 mg, 1.98 mmol) in DMF (8 mL) is irradiated in a microwave reactor (Biotage Initiator, Trademark) for 15 minutes at 160° C. The mixture is diluted with 10% toluene in EtOAc and water. The organic layer is separated and the aqueous layer is extracted with 10% toluene in EtOAc (2 times). The combined organic extracts are washed with water (2 times), then brine, dried over $Na_2SO_4$, filtered and concentrated in vacuo to give the crude product, which is purified by column chromatography on silica gel eluting with 50-65% EtOAc in hexane to give the titled compound (257 mg, 77% yield) as a yellow amorphous solid.

$^1$H-NMR (270 MHz, DMSO-$d_6$): delta 8.95 (s, 1H), 6.70 (s, 1H), 6.65 (s, 1H), 4.59 (s, 2H), 2.52 (s, 3H), 2.36 (s, 3H), 2.12 (s, 3H), 2.25-1.70 (m, 8H).

MS (ESI) m/z: 421.3 (M+H)$^+$.

The following Examples (1-2 to 1-15) are prepared according to the procedure of Example-1 from the intermediate-4-8-A (INT-4-8-A) or known alpha-haloketone derivatives and the known or synthesized azaspiro derivatives in Table 12. The further purification is carried out by preparative LC-MS system in the usual manner. The retention time and observed MS by HPLC-QC method are summarized in Table 12.

TABLE 12

| Examples | alpha-haloketones | azaspiro derivatives | observed MS | tR/method |
|---|---|---|---|---|
| Example-1-2 | INT-4-8-A | INT-1-3-A | 420.2 | 1.76 min. (QC1) |
| Example-1-3 | INT-4-8-A | | 386.1 | 1.82 min. (QC1) |

TABLE 12-continued
| Examples | alpha-haloketones | azaspiro derivatives | observed MS | tR/method |
|---|---|---|---|---|
| Example-1-4 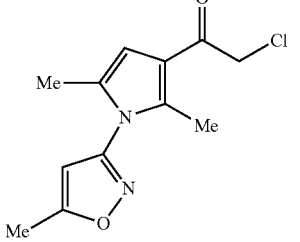 | INT-4-8-A 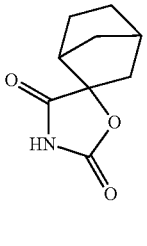 [SMILES: O=C1NC(=O)C2(CC3CCC2C3)O1] | 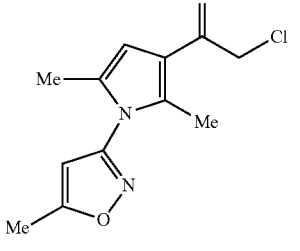 | 397.3 | 1.64 min. (QC1) |
| Example-1-5 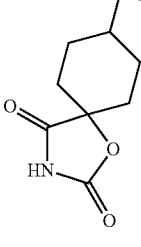 | INT-4-8-A 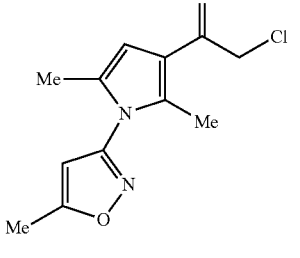 | 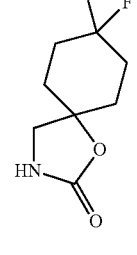 | 453.2 | 1.68 min. (QC1) |
| Example-1-6 | INT-4-8-A | INT-1-4-A | 406.3 | 2.27 min (QC2) |

TABLE 12-continued
| Examples | alpha-haloketones | azaspiro derivatives | observed MS | tR/method |
|---|---|---|---|---|
| Example-1-7 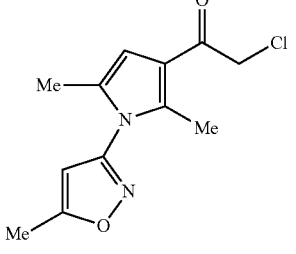 | 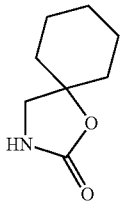 INT-4-8-A | 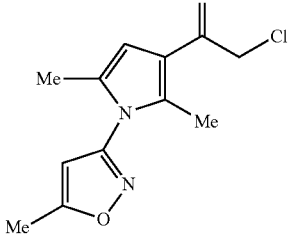 | 372.2 | 1.73 min. (QC1) |
| Example-1-8 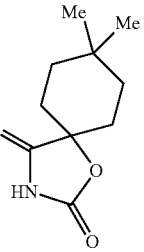 | 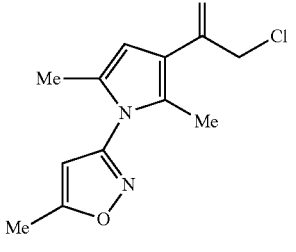 INT-4-8-A | 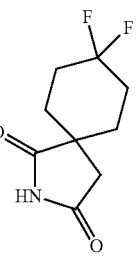 | 413.3 | 1.75 min. (QC1) |
| Example 1-9 | INT-4-8-A | INT-1-5-A | 418.5 | 1.70 min. (QC1) |

TABLE 12-continued
| Examples | alpha-haloketones | azaspiro derivatives | observed MS | tR/method |
|---|---|---|---|---|
| Example 1-10 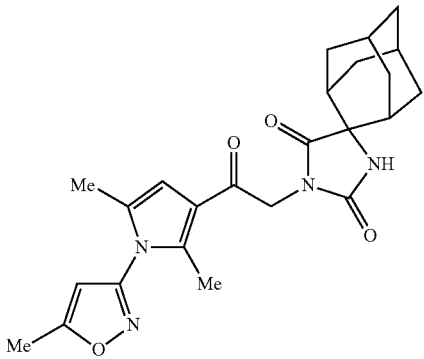 |  INT-4-8-A | 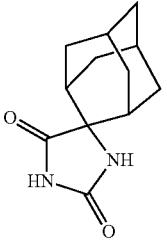 [SMILES: O=C1NC(=O)C2(N1)C1CC3CC(C1)CC2C3] | 437.2 | 1.84 min. (QC1) |
| Example 1-11 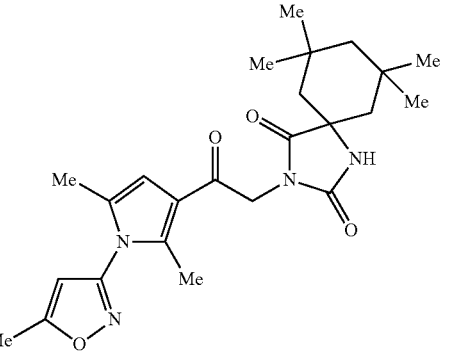 | 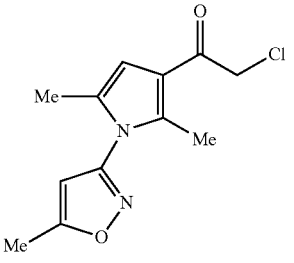 INT-4-8-A | 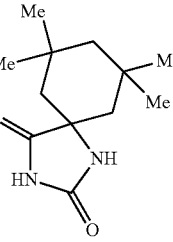 | 441.3 | 1.91 min. (QC1) |
| Example 1-12 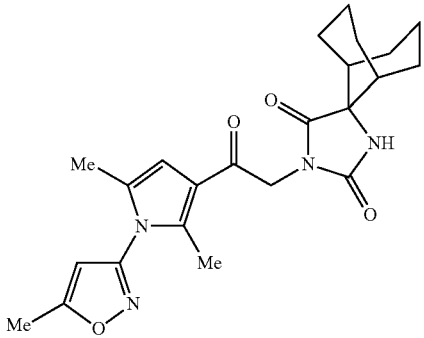 | 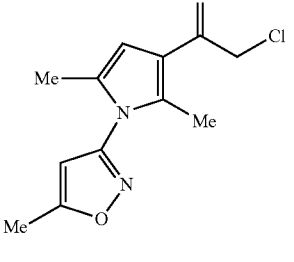 INT-4-8-A | 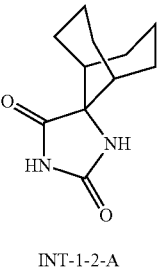 [SMILES: O=C1NC(=O)C2(N1)C1CCCC2CCC1] INT-1-2-A | 425.2 | 1.81 min. (QC1) |

TABLE 12-continued

| Examples | alpha-haloketones | azaspiro derivatives | observed MS | tR/method |
|---|---|---|---|---|
| Example 1-13 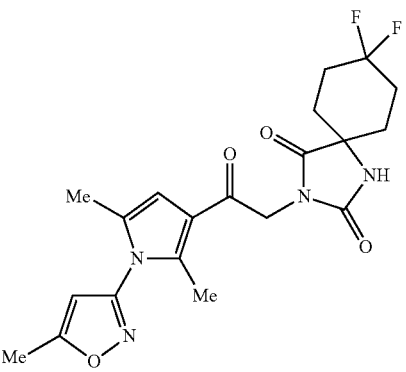 | 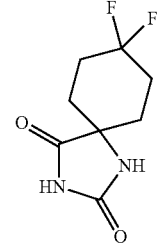 | 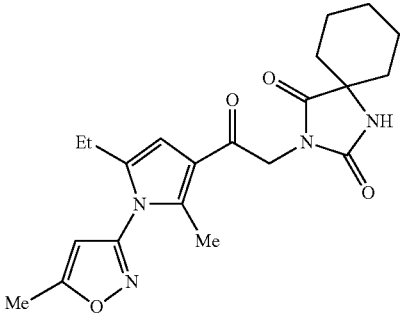 INT-1-A | 435.2 | 1.67 min. (QC1) |
| Example 1-14 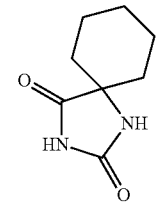 [SMILES: O=C1NC(=O)C2(CCCCC2)N1] | 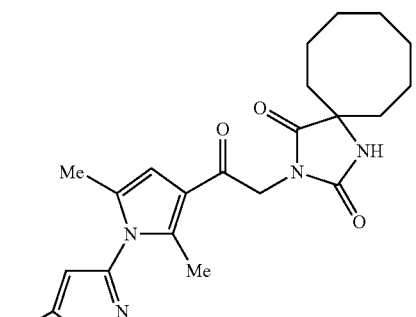 | 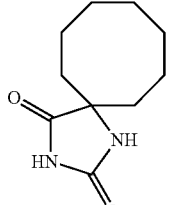 | 399.3 | 1.67 min. (QC1) |
| Example 1-15 | | INT-4-8-A | 413.4 | 1.73 min. (QC1) |

The following examples (2-1 to 2-18) are prepared according to the procedure of Example-1 from the known or synthesized alpha-haloketone derivatives and azaspiro derivatives in Table 13. The further purification is carried out by preparative LC-MS system in the usual manner. The retention time and observed MS by HPLC-QC method are summarized in Table 13.

TABLE 13

| Examples | alpha-haloketones | azaspiro derivatives | observed MS | tR/method |
| --- | --- | --- | --- | --- |
| Example-2-1 | INT-5-1-A | | 382.1 | 1.78 min. (QC1) |
| Example-2-2 | INT-5-1-A | INT-1-1-A | 417.2 | 1.55 min. (QC1) |
| Example-2-3 | INT-5-1-A | INT-1-3-A | 418.1 | 1.72 min. (QC1) |

TABLE 13-continued

| Examples | alpha-haloketones | azaspiro derivatives | observed MS | tR/method |
|---|---|---|---|---|
| Example-2-4 | INT-5-1-A | | 381.2 | 1.53 min. (QC1) |
| Example-2-5 | INT-5-1-A | | 393.5 | 1.60 min. (QC1) |
| Example-2-6 | INT-5-1-A | | 368.3 | 1.67 min. (QC1) |
| Example-2-7 | INT-5-1-A | INT-1-4-A | 404.1 | 2.19 min. (QC2) |

TABLE 13-continued
| Examples | alpha-haloketones | azaspiro derivatives | observed MS | tR/method |
|---|---|---|---|---|
| Example-2-8 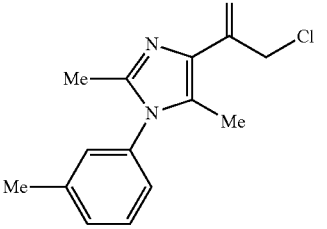 | INT-5-3-A 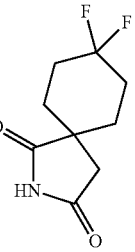 | INT-1-5-A 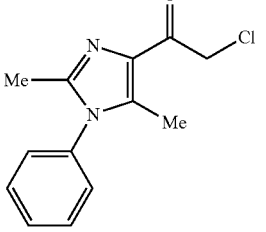 | 430.2 | 1.74 min. (QC1) |
| Example-2-9 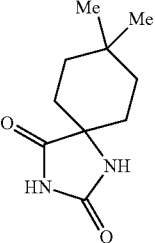 [SMILES: CC1(C)CCC2(CC1)NC(=O)NC2=O] | INT-5-1-A 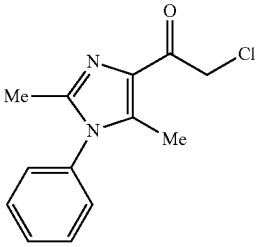 | 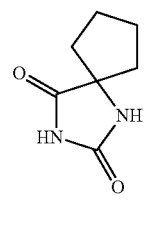 [SMILES: O=C1NC(=O)C2(CCCC2)N1] | 407.3 | 1.69 min. (QC1) |
| Example-2-10 | INT-5-1-A | | 365.5 | 1.45 min. (QC1) |

TABLE 13-continued
| Examples | alpha-haloketones | azaspiro derivatives | observed MS | tR/method |
|---|---|---|---|---|
| Example-2-11 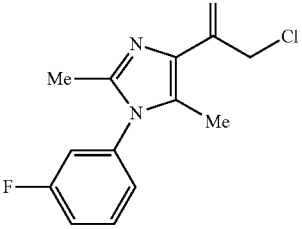 | 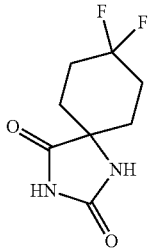 INT-5-15-A | 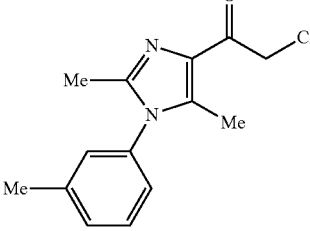 INT-1-1-A | 433.3 | 1.56 min. (QC1) |
| Example-2-12 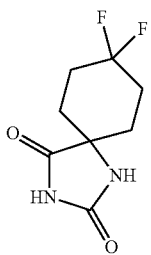 | 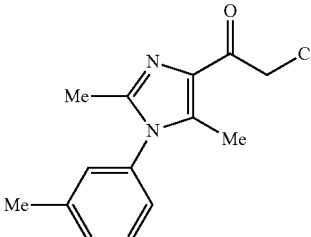 INT-5-3-A | 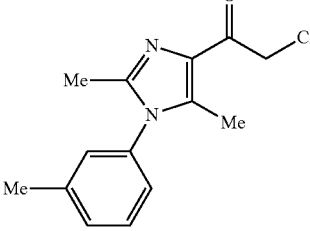 INT-1-1-A | 429.2 | 2.19 min. (QC2) |
| Example-2-13 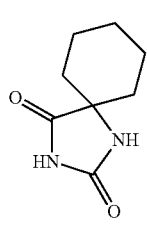 [SMILES: O=C1NC(=O)C2(CCCCC2)N1] | 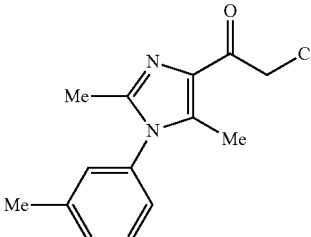 INT-5-3-A | 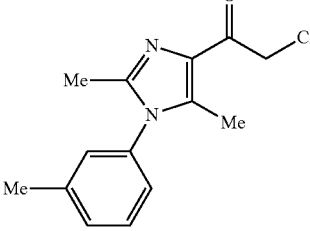 | 393.2 | 2.14 min. (QC2) |

TABLE 13-continued
| Examples | alpha-haloketones | azaspiro derivatives | observed MS | tR/method |
|---|---|---|---|---|
| Example-2-14 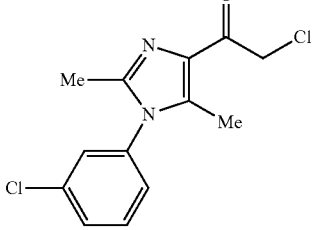 | 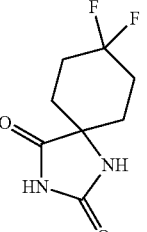 INT-5-2-A | 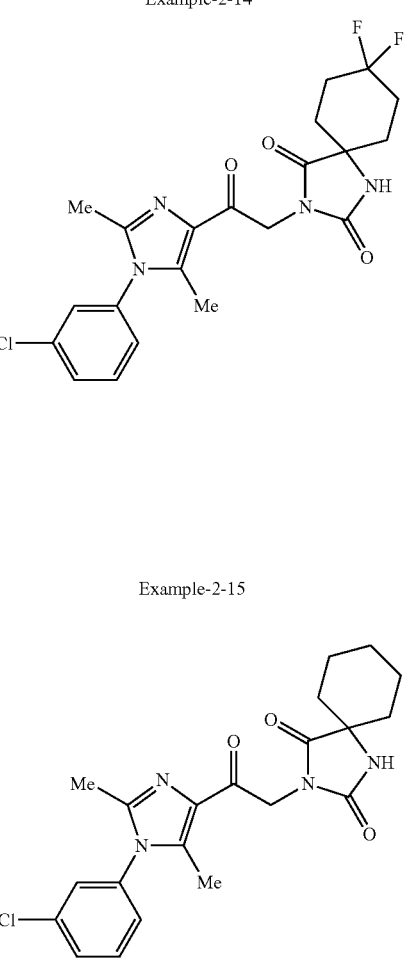 INT-1-1-A | 449.3 | 1.64 min. (QC1) |
| Example-2-15 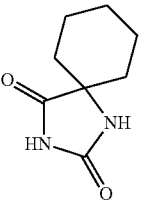 | 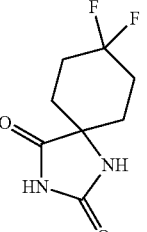 INT-5-2-A | 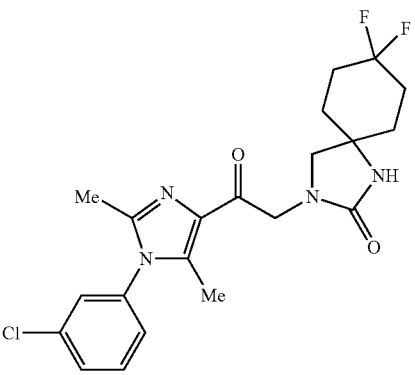 | 413.3 | 1.63 min. (QC1) |
| Example-2-16 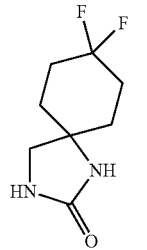 | 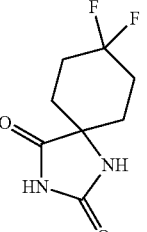 INT-5-2-A | 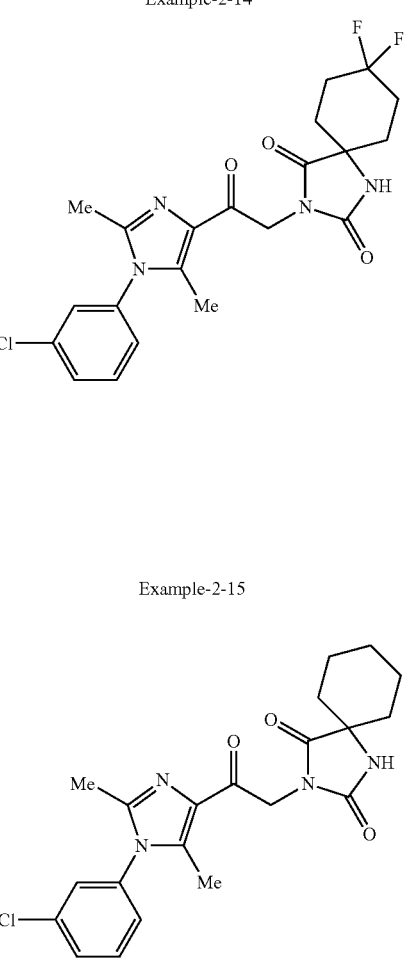 INT-1-4-A | 436.3 | 1.69 min. (QC1) |

TABLE 13-continued

| Examples | alpha-haloketones | azaspiro derivatives | observed MS | tR/method |
|---|---|---|---|---|
| Example-2-17 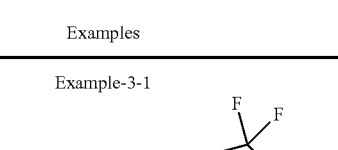 | INT-5-3-A | INT-1-4-A | 418.1 | 2.34 min. (QC2) |
| Example-2-18 | INT-5-15-A | INT-1-4-A | 420.3 | 1.61 min. (QC1) |

The following examples (3-1 to 3-27) are prepared according to the procedure of Example-1 from the known or synthesized alpha-haloketone derivatives and azaspiro derivatives in Table 14. The further purification is carried out by preparative LC-MS system in the usual manner. The retention time and observed MS by HPLC-QC method are summarized in Table 14.

TABLE 14

| Examples | alpha-haloketones | azaspiro derivatives | observed MS | tR/method |
|---|---|---|---|---|
| Example-3-1 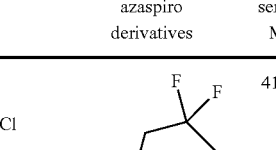 | INT-4-1-A | INT-1-1-A | 419.2 | 1.57 min. (QC1) |

TABLE 14-continued

| Examples | alpha-haloketones | azaspiro derivatives | observed MS | tR/method |
|---|---|---|---|---|
| Example-3-2 | INT-4-9-A | INT-1-1-A | 430.2 | 1.96 min. (QC2) |
| Example-3-3 | INT-4-9-A | | 396.2 | 1.50 min. (QC1) |
| Example-3-4 | | INT-1-1-A | 414.2 | 2.34 min. (QC2) |

TABLE 14-continued

| Examples | alpha-haloketones | azaspiro derivatives | observed MS | tR/method |
|---|---|---|---|---|
| Example-3-5 | | INT-1-1-A | 430.2 | 1.83 min. (QC1) |
| Example-3-6 | | | 394.3 | 1.83 min. (QC1) |
| Example-3-7 | | INT-1-1-A | 448.5 | 1.82 min. (QC1) |
| Example-3-8 | | | 438.2 | 1.71 min. (QC1) |

TABLE 14-continued
| Examples | alpha-haloketones | azaspiro derivatives | observed MS | tR/method |
|---|---|---|---|---|
| Example-3-9 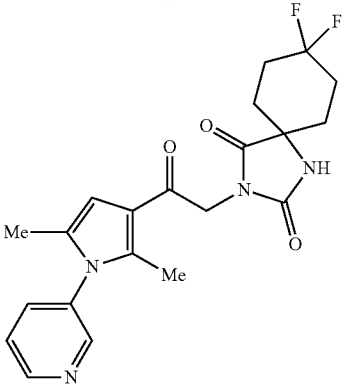 [SMILES: Cc1cc(C(=O)CN2C(=O)NC3(CCC(F)(F)CC3)C2=O)c(C)n1-c1cccnc1] | 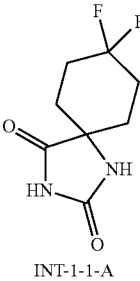 | 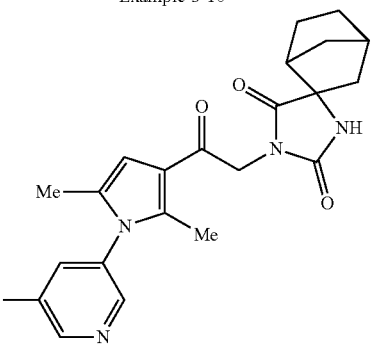 INT-1-1-A | 415.2 | 1.88 min (QC2) |
| Example-3-10 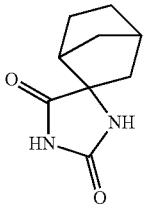 [SMILES: O=C1NC(=O)C2(CC3CCC2C3)N1] | 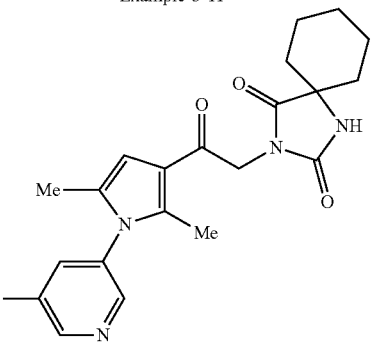 INT-4-4-A | 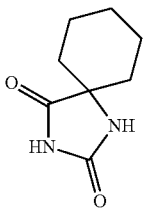 [SMILES: O=C1NC(=O)C2(CCCCC2)N1] | 407.3 | 1.57 min. (QC1) |
| Example-3-11 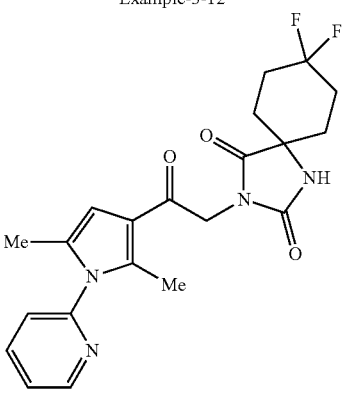 | 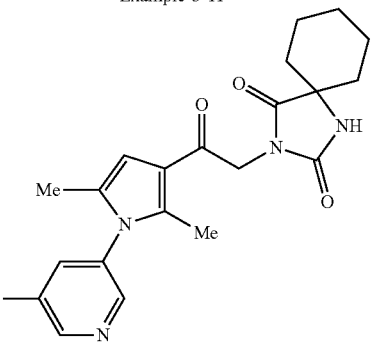 INT-4-4-A | 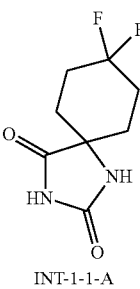 | 395.3 | 1.51 min. (QC1) |
| Example-3-12 | | | 415.2 | 1.96 min (QC2) |

TABLE 14-continued
| Examples | alpha-haloketones | azaspiro derivatives | observed MS | tR/ method |
|---|---|---|---|---|
| Example-3-13 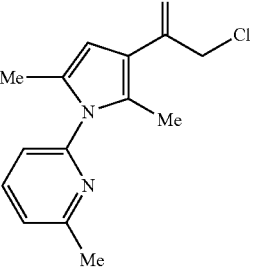 | 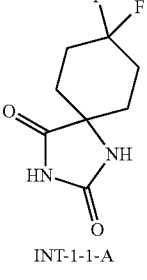 | 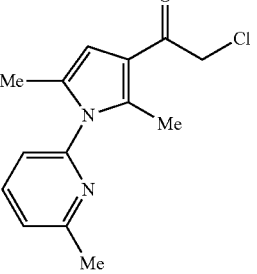 INT-1-1-A | 431.2 | 1.59 min. (QC1) |
| Example-3-14 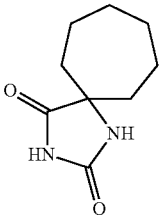 [SMILES: O=C1NC(=O)C2(CCCCCC2)N1] | 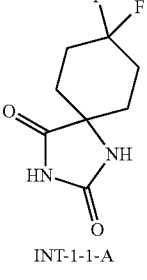 | 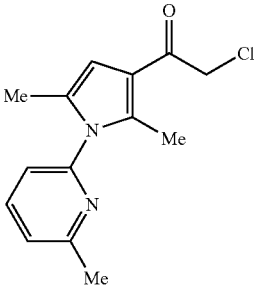 [SMILES: Cc1cccc(-n2c(C)cc(C(=O)CCl)c2C)n1] | 409.3 | 1.66 min. (QC1) |
| Example-3-15 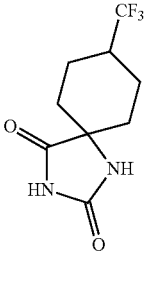 [SMILES: O=C1NC(=O)C2(CCC(C(F)(F)F)CC2)N1] | 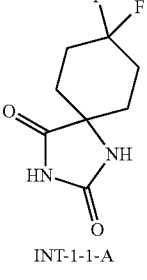 | | 463.2 | 1.67 min. (QC1) |

TABLE 14-continued
| Examples | alpha-haloketones | azaspiro derivatives | observed MS | tR/method |
|---|---|---|---|---|
| Example-3-16 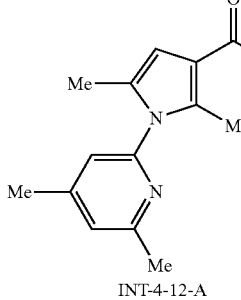 | 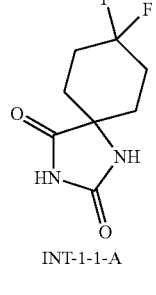 INT-4-12-A | 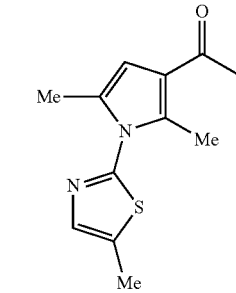 INT-1-1-A | 445.3 | 1.67 min. (QC1) |
| Example-3-17 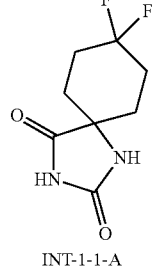 | 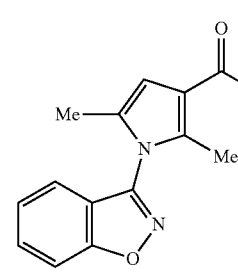 | 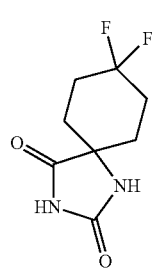 [SMILES: O=C1NC(=O)C2(CCC(F)(F)CC2)N1] INT-1-1-A | 435.5 | 1.64 min. (QC1) |
| Example-3-18 | INT-4-2-A | INT-1-1-A | 455.3 | 1.74 min. (QC1) |

TABLE 14-continued
| Examples | alpha-haloketones | azaspiro derivatives | observed MS | tR/ method |
|---|---|---|---|---|
| Example-3-19 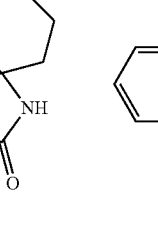 | 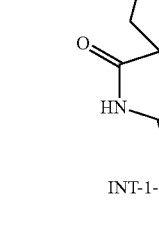 INT-4-3-A |  INT-1-1-A | 465.3 | 1.62 min. (QC1) |
| Example-3-20 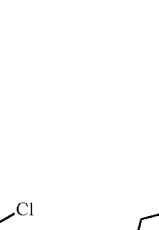 | 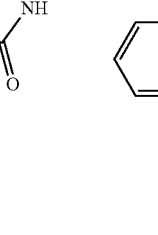 INT-4-10-A | INT-1-1-A | 465.3 | 1.73 min. (QC1) |
| Example-3-21  | INT-4-11-A | INT-1-1-A | 420.3 | 1.49 min. (QC1) |

TABLE 14-continued

| Examples | alpha-haloketones | azaspiro derivatives | observed MS | tR/method |
|---|---|---|---|---|
| Example-3-22 | | INT-1-4-A | 418.1 | 2.24 min. (QC2) |
| Example-3-23 | | | 381.3 | 1.97 min. (QC1) |
| Example-3-24 | INT-4-4-A | | 382.3 | 1.66 min. (QC1) |

TABLE 14-continued
| Examples | alpha-haloketones | azaspiro derivatives | observed MS | tR/ method |
|---|---|---|---|---|
| Example-3-25 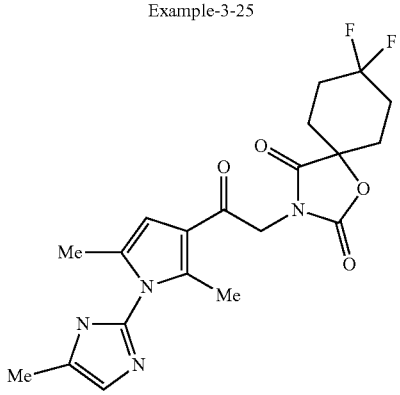 | 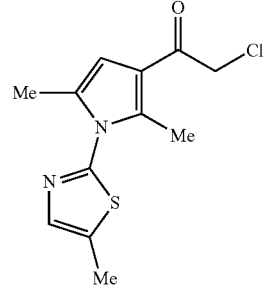 [SMILES: Cc1cnc(-n2c(C)cc(C(=O)CCl)c2C)s1] | 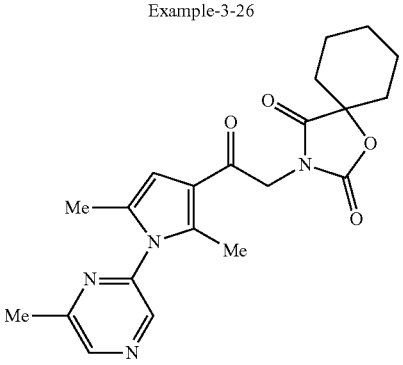 INT-1-4-A | 424.3 | 1.70 min. (QC1) |
| Example-3-26 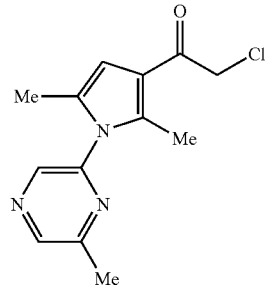 [SMILES: Cc1cncc(-n2c(C)cc(C(=O)CCl)c2C)n1] | 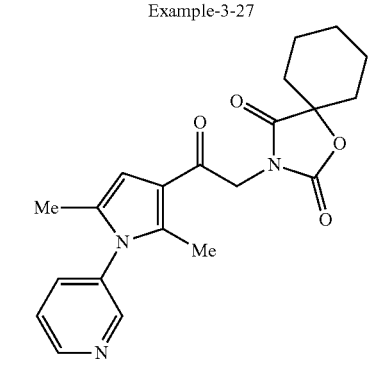 INT-4-9-A | 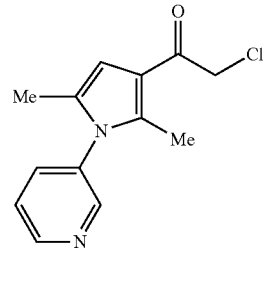 [SMILES: Cc1cc(C(=O)CCl)c(C)n1-c1cccnc1] | 381.2 | 2.13 min (QC2) |
| Example-3-27 | | | 368.3 | 1.58 min. (QC1) |

Example 3-28: 3-(2-(1-(6-(cyclopropylmethoxy)pyridin-2-yl)-2,5-dimethyl-1H-pyrrol-3-yl)-2-oxoethyl)-1,3-diazaspiro[4.5]decane-2,4-dione

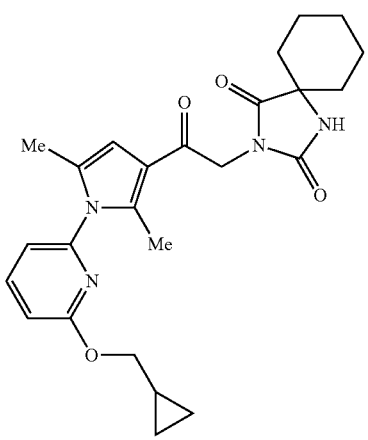

{Chem. 117}

<Step-1>: Intermediate-3-28-1 (INT-3-28-1): 3-(2-(1-(6-chloropyridin-2-yl)-2,5-dimethyl-1H-pyrrol-3-yl)-2-oxoethyl)-1,3-diazaspiro[4.5]decane-2,4-dione

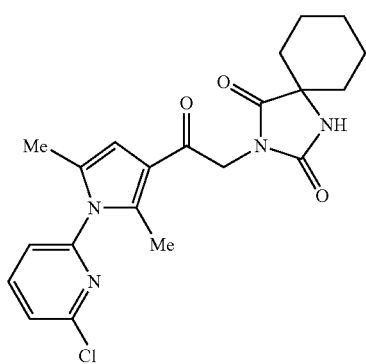

{Chem. 118}

The titled compound is prepared according to the procedure of example-1 from INT-4-7-A (1.00 g, 3.53 mmol), 1,3-diazaspiro[4.5]decane-2,4-dione (624 mg, 3.71 mmol) and potassium carbonate (1.22 g, 8.83 mmol) in DMF (20 mL) in a microwave irradiation system at 160° C. for 10 min. The residue is purified by column chromatography (Biotage) on silica gel (100 g) eluting with 10-80% ethyl acetate in DCM to give the compound (1.33 g, 91% yield) as a pale yellow amorphous solid.

$^1$H-NMR (270 MHz, DMSO-d$_6$): delta 8.79 (s, 1H), 8.15 (t, J=7.2 Hz, 1H), 7.73 (d, J=6.6 Hz 1H), 7.62 (d, J=7.2 Hz, 1H), 6.61 (s, 1H), 4.56 (s, 2H), 2.29 (s, 3H), 2.06 (s, 3H), 1.72-1.57 (m, 8H).

MS (ESI) m/z: 415.2 (M+H)$^+$.

<Step-2>: Example 3-28: 3-(2-(1-(6-(cyclopropylmethoxy)pyridin-2-yl)-2,5-dimethyl-1H-pyrrol-3-yl)-2-oxoethyl)-1,3-diazaspiro[4.5]decane-2,4-dione To a solution of 60% sodium hydride (14 mg, 0.362 mmol) in DMA (2 mL) is added cyclopropylmethanol (10 mg, 0.133 mmol) at 0° C. After the completion of addition, to this mixture is added INT-3-28-1 (50 mg, 0.121 mmol) at 0° C. and stirred at rt for 5 h. The reaction mixture is quenched sat. NH$_4$Cl solution (pH=5-6) and extracted with EtOAc. The combined organic layer is dried over sodium sulfate, filtered and concentrated in vacuo. The residue is purified by column chromatography (Biotage) on silica gel (10 g) eluting with 10-80% ethyl acetate in Hexane to give the titled compound (9 mg, 16% yield) as a pale brown amorphous. The further purification is carried out by preparative LC-MS system in the usual manner.

Observed MS: 451.2 tR/method: 1.86 min./(QC1)

Example 3-29: 3-(2-(1-(6-(3-hydroxypiperidin-1-yl)pyridin-2-yl)-2,5-dimethyl-1H-pyrrol-3-yl)-2-oxoethyl)-1,3-diazaspiro[4.5]decane-2,4-dione

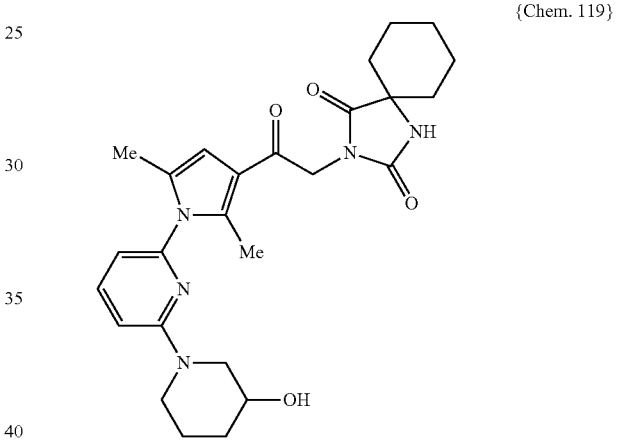

{Chem. 119}

To a solution of INT-3-28-1 (20 mg, 0.048 mmol) in DMSO (1 mL) is added piperidin-3-ol (8 mg, 0.096 mmol) and cesium carbonate (79 mg, 0.241 mmol). The mixture is stirred at 80° C. for 15 h. The reaction mixture is filtered through a pad of celite and washed with EtOAc. The filtrate and washings are washed with water, brine, dried over sodium sulfate, filtered and concentrated in vacuo. The residue is purified by column chromatography (Biotage) on silica gel (10 g) eluting with 10-100% ethyl acetate in hexane to give the titled compound (8 mg, 35% yield) as a pale yellow amorphous solid. The further purification is carried out by preparative LC-MS system in the usual manner.

Observed MS: 480.2 tR/method: 1.58 min./(QC1)

The following examples (4-1 to 4-12) are prepared according to the procedure of Example-1 from the known or synthesized alpha-haloketone derivatives and azaspiro derivatives in Table 15. The further purification is carried out by preparative LC-MS system in the usual manner. The retention time and observed MS by HPLC-QC method are summarized in Table 15.

TABLE 15
| Examples | alpha-haloketones | azaspiro derivetives | observed MS | tR/method |
|---|---|---|---|---|
| Example-4-1 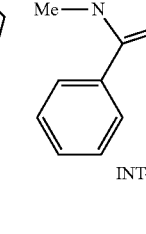 | INT-5-14-A | INT-1-1-A | 415.2 | 1.73 min. (QC1) |
| Example-4-2 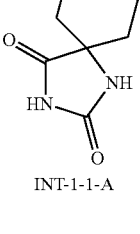 | INT-5-14-A | | 379.3 | 1.72 min. (QC1) |
| Example-4-3 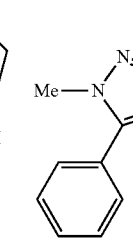 | INT-6-3-A | INT-1-1-A | 414.3 | 2.28 min. (QC2) |
| Example-4-4 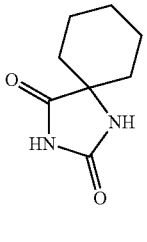 [SMILES: O=C1NC(=O)C2(CCCCC2)N1] | INT-5-4-A | INT-1-1-A | 401.4 | 1.61 min. (QC1) |

TABLE 15-continued

| Examples | alpha-haloketones | azaspiro derivatives | observed MS | tR/method |
|---|---|---|---|---|
| Example-4-5 | INT-6-2-A | INT-1-1-A | 418.3 | 1.81 min. (QC1) |
| Example-4-6 | INT-5-5-A | INT-1-1-A | 400.5 | 1.67 min. (QC1) |
| Example-4-7 | INT-5-16-A | INT-1-1-A | 416.3 | 1.42 min. (QC1) |
| Example-4-8 | INT-5-16-A | | 380.4 | 1.40 min. (QC1) |

TABLE 15-continued

| Examples | alpha-haloketones | azaspiro derivetives | observed MS | tR/method |
| --- | --- | --- | --- | --- |
| Example-4-9 | INT-5-5-A | INT-1-4-A | 389.3 | 1.73 min. (QC1) |
| Example-4-10 | INT-5-14-A | INT-1-3-A | 416.3 | 1.90 min. (QC1) |
| Example-4-11 | INT-6-31-A | INT-1-1-A | 403.1 | 1.46 min. (QC1) |

TABLE 15-continued

| Examples | alpha-haloketones | azaspiro derivetives | observed MS | tR/method |
|---|---|---|---|---|
| Example-4-12 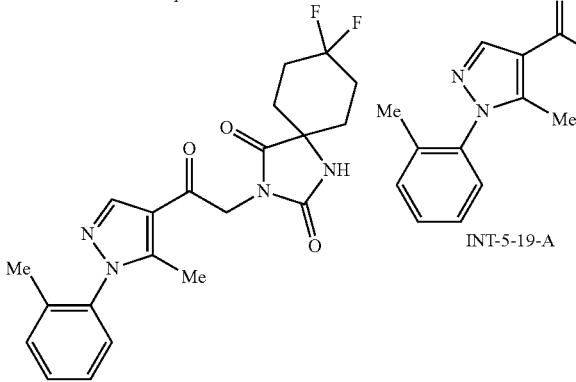 | 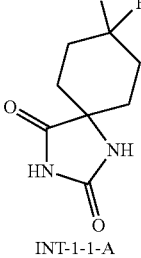 INT-5-19-A | 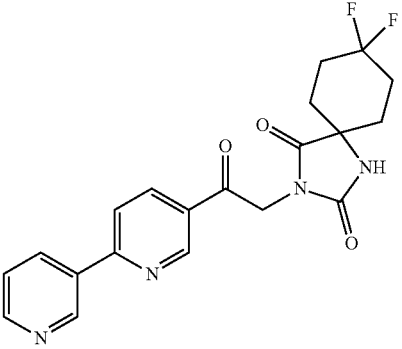 [SMILES: O=C(CN1C(=O)NC2(CCC(F)(F)CC2)C1=O)c1ccc(-c2cccnc2)nc1] INT-1-1-A | 417.1 | 1.59 min. (QC1) |

The following examples (5-1 to 5-5) are prepared according to the procedure of Example-1 from the known or synthesized alpha-haloketone derivatives and hydantoin derivatives in Table 16. The further purification is carried out by preparative LC-MS system in the usual manner. The retention time and observed MS by HPLC-QC method are summarized in Table 16.

TABLE 16

| Examples | alpha-haloketones | azaspiro derivetives | observed MS | tR/method |
|---|---|---|---|---|
| Example-5-1 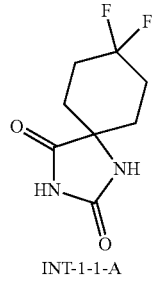 | 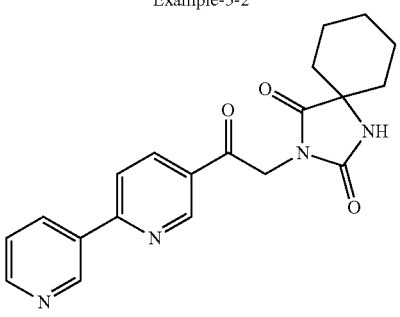 INT-5-6-A | 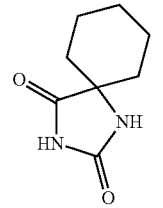 [SMILES: O=C1NC(=O)C2(CCCCC2)N1] INT-1-1-A | 399.4 | 1.34 min. (QC1) |
| Example-5-2 | | | 365.3 | 1.34 min. (QC1) |

TABLE 16-continued

| Examples | alpha-haloketones | azaspiro derivatives | observed MS | tR/method |
|---|---|---|---|---|
| Example-5-3 | INT-5-10-A | INT-1-1-A | 428.4 | 1.48 min. (QC1) |
| Example-5-4 | INT-5-11-A | INT-1-1-A | 445.5 | 1.80 min. (QC1) |
| Example-5-5 | INT-5-12-A | INT-1-1-A | 452.2 | 1.66 min. (QC1) |

The following examples (5-6 to 5-14) are prepared according to the procedure of Example-1 from the known or synthesized alpha-haloketone derivatives and hydantoin derivatives in Table 17. The further purification is carried out by preparative LC-MS system in the usual manner. The retention time and observed MS by HPLC-QC method are summarized in Table 17.

TABLE 17
| Examples | alpha-haloketones | azaspiro derivetives | observed MS | tR/method |
|---|---|---|---|---|
| Example-5-6 | 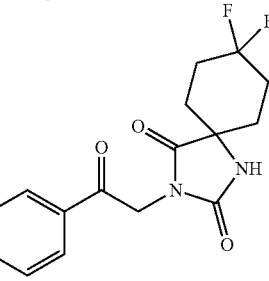 INT-5-7-A | 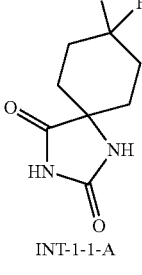 INT-1-1-A | 437.3 | 1.73 min. (QC1) |
| Example-5-7 | 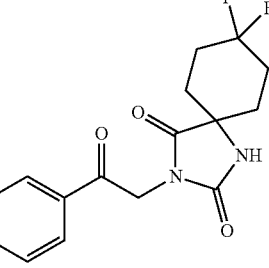 INT-6-16-A | 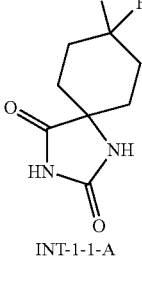 INT-1-1-A | 437.3 | 1.51 min. (QC1) |
| Example-5-8 | 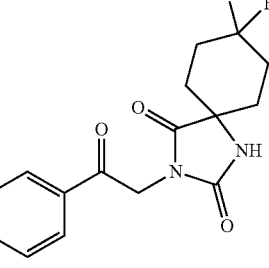 INT-6-17-A | 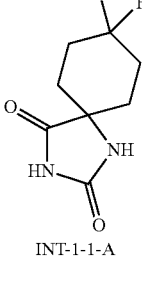 INT-1-1-A | 451.3 | 1.51 min. (QC1) |
| Example-5-9 | 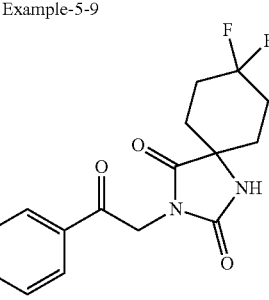 INT-6-18-A | 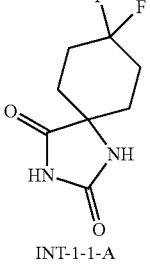 INT-1-1-A | 438.3 | 1.42 min. (QC1) |

TABLE 17-continued

| Examples | alpha-haloketones | azaspiro derivetives | observed MS | tR/ method |
|---|---|---|---|---|
| Example-5-10 | INT-6-19-A | INT-1-1-A | 452.3 | 1.38 min. (QC1) |
| Example-5-11 | INT-6-20-A | INT-1-1-A | 438.3 | 1.32 min. (QC1) |
| Example-5-12 | INT-6-21-A | INT-1-1-A | 438.4 | 1.49 min. (QC1) |
| Example-5-13 | INT-6-17-A | | 429.5 | 1.59 min. (QC1) |

TABLE 17-continued

| Examples | alpha-haloketones | azaspiro derivetives | observed MS | tR/ method |
|---|---|---|---|---|
| Example-5-14 | INT-6-22-A | INT-1-1-A | 452.3 | 1.45 min. (QC1) |

Example-5-15: 8,8-difluoro-3-(2-(4-(2-(hydroxymethyl)-1H-benzo[d]imidazol-1-yl)phenyl)-2-oxoethyl)-1,3-diazaspiro[4.5]decane-2,4-dione {Chem. 120}

<Step-1>: Intermediate-5-15-1 (INT-5-15-1): N-(2-((4-acetylphenyl)amino)phenyl)-2-(benzyloxy)acetamide {Chem. 121}

A mixture of 1-(4-((2-aminophenyl)amino)phenyl)ethanone (170 mg, 0.751 mmol), 2-(benzyloxy)acetyl chloride (170 mg, 0.902 mmol) and triethylamine (228 mg, 2.25 mmol) in DCM (5 mL) is stirred at rt for 1 h. After the removal of solvent, the residue is purified by column chromatography (Biotage) on silica gel (25 g) eluting with 5-80% ethyl acetate in DCM to give the titled compound (0.289 g, quant.) as a yellow amorphous solid.

$^1$H-NMR (270 MHz, DMSO-d$_6$): delta 8.71 (s, 1H), 7.89-7.74 (m, 3H), 7.36-7.17 (m, 8H), 6.74-6.70 (m, 2H), 6.27 (s, 1H), 4.50 (s, 2H), 4.09 (s, 2H), 2.51 (s, 3H).

MS (ESI) m/z: 375.1 (M+H)$^+$.

<Step-2>: Intermediate-5-15-2 (INT-5-15-2): 1-(4-(2-((benzyloxy)methyl)-1H-benzo[d]imidazol-1-yl)phenyl)ethanone {Chem. 122}

To a solution of INT-5-15-1 (289 mg, 0.772 mmol) in acetic acid (5 mL) is heated at 60° C. for 15 h. The reaction mixture is concentrated in vacuo to the crude product, which is purified by column chromatography (Biotage) on silica gel (25 g) eluting with 10-100% ethyl acetate in DCM to give the titled compound (246 mg, 92% yield) as a yellow amorphous solid.

$^1$H-NMR (270 MHz, DMSO-d$_6$): delta 8.18 (d, J=8.5 Hz, 2H), 7.80-7.75 (m, 3H), 7.34-7.25 (m, 6H), 7.14-7.11 (m, 2H), 4.72 (s, 2H), 4.45 (s, 2H), 2.68 (s, 3H), 2.46 (s, 3H).

MS (ESI) m/z: 357.1 (M+H)$^+$.

<Step-3>: Intermediate-5-15-3 (INT-5-15-3): (1-(4-(2-bromoacetyl)phenyl)-1H-benzo[d]imidazol-2-yl)methyl acetate hydrobromide {Chem. 123}

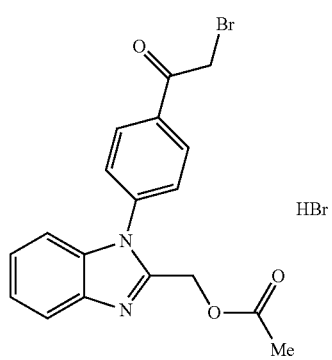

A mixture of INT-5-15-2 (246 mg, 0.690 mmol) and bromine (110 mg, 0.690 mmol) in 25% HBr—AcOH (5 mL) is stirred at rt for 1.5 h. The reaction mixture is concentrated by nitrogen flow. The residue is triturated with a mixture of IPE and MeOH (2/1 v/v) to give a mixture of the titled compound (352 mg, chemical purity of 80%) as a dark yellow amorphous solid.

MS (ESI) m/z: 270.1 (M+H)$^+$.

<Step-4>: Example-5-15: 8,8-difluoro-3-(2-(4-(2-(hydroxymethyl)-1H-benzo[d]imidazol-1-yl)phenyl)-2-oxoethyl)-1,3-diazaspiro[4.5]decane-2,4-dione A mixture of INT-1-1-A (154 mg, 0.752 mmol), INT-5-15-3 (352 mg, 2.26 mmol) and potassium carbonate (312 mg, 2.26 mmol) in DMF (5 mL) is heated at 80° C. for 3 h. After cooling, to the reaction mixture is added water and the mixture is stirred for 10 min. After the extraction with EtOAc, the combined organic layer is washed brine, dried over sodium sulfate, filtered and concentrated in vacuo. The residue is purified by column chromatography (Biotage) on silica gel (25 g) eluting with 10-80% ethyl acetate in DCM to give the titled compound (209 mg, 59% yield) as a pale yellow solid.

$^1$H-NMR (270 MHz, DMSO-d$_6$): delta 9.06 (s, 1H), 8.30 (d, J=8.5 Hz, 2H), 7.84 (d, J=8.5 Hz, 2H), 7.32-7.28 (m, 4H), 5.61 (t, J=5.9 Hz, 1H), 5.07 (s, 2H), 4.65 (d, J=5.9 Hz, 2H), 2.19-1.76 (m, 8H).

MS (ESI) m/z: 469.1 (M+H)$^+$.

Example-5-16: 3-(2-(4-(2-(aminomethyl)-1H-benzo[d]imidazol-1-yl)phenyl)-2-oxoethyl)-8,8-difluoro-1,3-diazaspiro[4.5]decane-2,4-dione {Chem. 124}

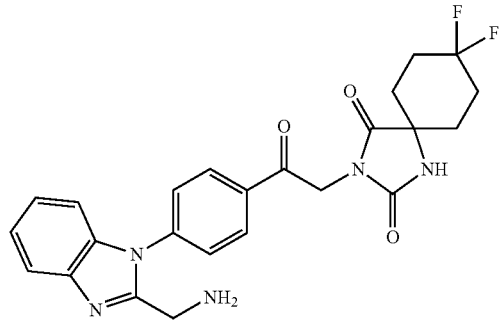

<Step-1>: Intermediate-5-16-1 (INT-5-16-1): 3-(2-(4-(2-(azidomethyl)-1H-benzo[d]imidazol-1-yl)phenyl)-2-oxoethyl)-8,8-difluoro-1,3-diazaspiro[4.5]decane-2,4-dione {Chem. 125}

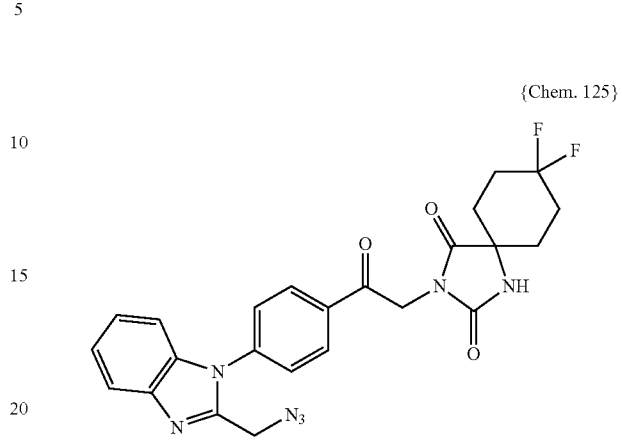

To a solution of example-5-15 (50 mg, 0.107 mmol) in THF (2 mL) is added diphenyl phosphorazidate (DPPA)(41 mg, 0.149 mmol) at 0° C. After 5 min, DBU (19 mg, 0.128 mmol) is added to this and the reaction mixture is stirred for 2 h at 0° C. After 5 h at rt, the reaction mixture is quenched with water and extracted with EtOAc. The combined organic layers are dried over sodium sulfate, filtered and concentrated in vacuo. The residue is purified by column chromatography (Biotage) on silica gel (10 g) eluting with 10-80% ethyl acetate in DCM to give the titled compound (32 mg, 61% yield) as a colorless amorphous solid.

MS (ESI) m/z: 493.9 (M+H)$^+$.

<Step-2>: Example-5-16: 3-(2-(4-(2-(aminomethyl)-1H-benzo[d]imidazol-1-yl)phenyl)-2-oxoethyl)-8,8-difluoro-1,3-diazaspiro[4.5]decane-2,4-dione To a solution of INT-5-16-1 (32 mg, 0.065 mmol) in THF (1 mL) is added triphenylphosphine (24 mg, 0.091 mmol) and water (0.17 mL). The mixture is stirred at rt for 3 h. Then, it is treated with 25% ammonium hydroxide aq. solution (0.17 mL) and stirred at rt for an additional 1 h. The reaction mixture is quenched with water and extracted with EtOAc. The combined layers are dried over sodium sulfate, filtered and concentrated in vacuo. The residue is loaded onto an SCX cartridge (Biotage, ISOLUTE SCX-2; 1 g/6 mL×2) conditioned with 1 mL of MeOH, rinsed with 5 mL of MeOH and eluted with 5 mL of 1M NH$_3$/MeOH. Volatiles are removed by nitrogen flow to give the titled compound (23 mg, 76% yield) as a colorless amorphous. The further purification is carried out by preparative LC-MS system in the usual manner.

Observed MS: 466.5 tR/method: 1.37 min./(QC1)

The following examples (5-17 to 5-42) are prepared according to the procedure of Example-1 from the known or synthesized alpha-haloketone derivatives and azaspiro derivatives in Table 18. The further purification is carried out by preparative LC-MS system in the usual manner. The retention time and observed MS by HPLC-QC method are summarized in Table 18.

TABLE 18

| Examples | alpha-haloketones | azaspiro derivetives | observed MS | tR/method |
|---|---|---|---|---|
| Example-5-17 | | INT-1-1-A | 414.2 | 1.57 min. (QC1) |
| Example-5-18 | | | 378.3 | 1.56 min. (QC1) |
| Example-5-19 | | | 379.2 | 1.78 min. (QC1) |
| Example-5-20 | INT-6-13-A | INT-1-1-A | 415.5 | 1.39 min. (QC1) |
| Example-5-21 | INT-6-14-A | INT-1-1-A | 415.5 | 1.46 min. (QC1) |
| Example-5-22 | INT-6-15-A | INT-1-1-A | 415.2 | 1.35 min. (QC1) |

TABLE 18-continued

| Examples | alpha-haloketones | azaspiro derivetives | observed MS | tR/method |
|---|---|---|---|---|
| Example-5-23 | INT-5-13-A | INT-1-1-A | 416.2 | 1.64 min. (QC1) |
| Example-5-24 | INT-5-13-A | | 380.2 | 1.64 min. (QC1) |
| Example-5-25 | INT-6-29-A | INT-1-1-A | 449.6 | 1.44 min. (QC1) |
| Example-5-26 | INT-6-30-A | | 393.7 | 1.40 min. (QC1) |
| Example-5-27 | INT-6-23-A | INT-1-1-A | 468.2 | 1.44 min. (QC1) |

TABLE 18-continued
| Examples | alpha-haloketones | azaspiro derivetives | observed MS | tR/ method |
|---|---|---|---|---|
| Example-5-28 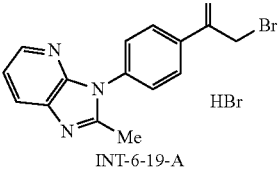 | 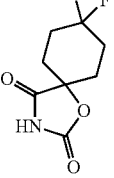 INT-6-19-A | 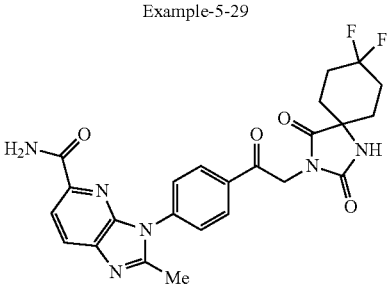 INT-1-3-A | 455.4 | 1.54 min. (QC1) |
| Example-5-29 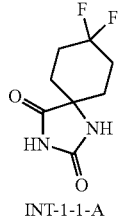 | 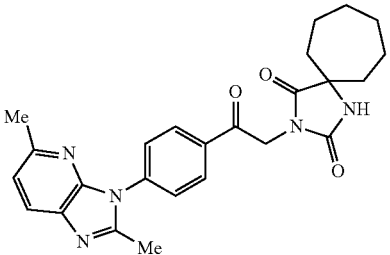 [SMILES: Cc1ccc2nc(C)n(-c3ccc(C(=O)CN4C(=O)NC5(CCCCCC5)C4=O)cc3)c2n1] INT-6-24-A | 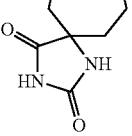 INT-1-1-A | 497.2 | 1.69 min. (QC2) |
| Example-5-30 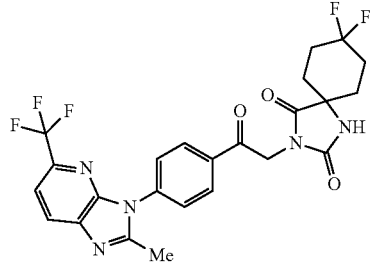 [SMILES: Cc1nc2ccc(C(F)(F)F)nc2n1-c1ccc(C(=O)CN2C(=O)NC3(CCC(F)(F)CC3)C2=O)cc1] | 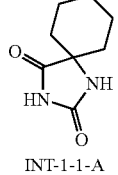 INT-6-23-A | 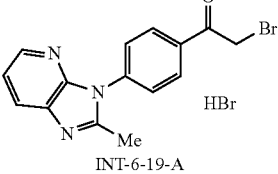 | 460.4 | 1.60 min. (QC1) |
| Example-5-31 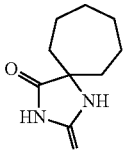 | INT-6-25-A | INT-1-1-A | 522.5 | 1.58 min. (QC1) |
| Example-5-32 | INT-6-19-A | | 432.6 | 1.43 min. (QC1) |

TABLE 18-continued

| Examples | alpha-haloketones | azaspiro derivetives | observed MS | tR/ method |
|---|---|---|---|---|
| Example-5-33 | INT-6-19-A | | 418.7 | 1.34 min. (QC1) |
| Example-5-34 | INT-6-19-A | | 404.6 | 1.26 min. (QC1) |
| Example-5-35 | INT-6-26-A | INT-1-1-A | 431.3 | 1.52 min. (QC1) |
| Example-5-36 | INT-6-27-A | INT-1-1-A | 417.3 | 1.36 min. (QC1) |
| Example-5-37 | INT-6-28-A | INT-1-1-A | 451.5 | 1.51 min. (QC1) |

TABLE 18-continued

| Examples | alpha-haloketones | azaspiro derivetives | observed MS | tR/method |
|---|---|---|---|---|
| Example-5-38 | INT-5-17-A | INT-1-1-A | 430.3 | 1.65 min. (QC1) |
| Example-5-39 | INT-5-18-A | INT-1-1-A | 433.1 | 2.03 min. (QC2) |
| Example-5-40 | INT-6-15-A | | 381.6 | 1.33 min. (QC1) |
| Example-5-41 | INT-6-15-A | | 395.6 | 1.41 min. (QC1) |
| Example-5-42 | INT-6-15-A | | 367.6 | 1.24 min. (QC1) |

General Procedure (Condition-A)

{Chem. 126}

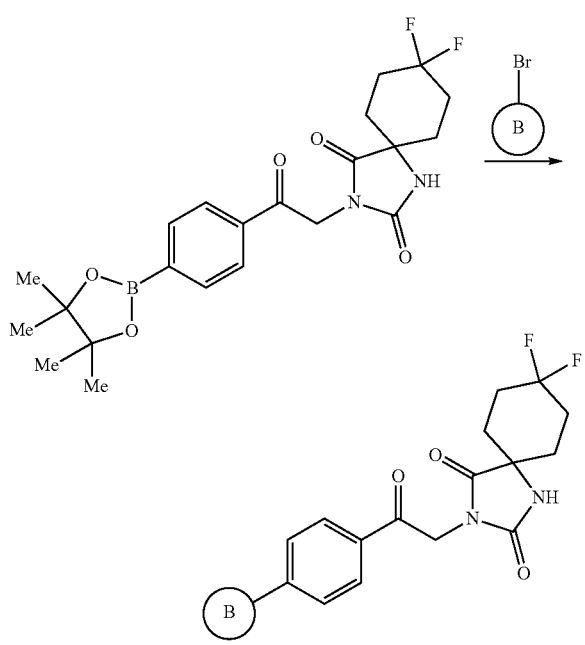

To a solution of INT-12-1-A (0.067 mmol) in 1,4-dioxane (1 mL) is added halide derivative (0.067 mmol), saturated NaHCO$_3$ solution (0.5 mL) and PdCl$_2$(dppf) CH$_2$Cl$_2$ (10% mol). The mixture is stirred at 100° C. for 3~15 h in oil bath or irradiated in a microwave system (MW)(Biotage, initiator) under the conditions of Table 19. To the reaction mixture is added water and ethyl acetate and the mixture is filtered through a pad of celite. The separated organic solution is washed with brine, dried over Na$_2$SO$_4$ and concentrated in vacuo. Purification of neutral compound: short filtration using amine silica gel or the purification by column chromatography.

Purification of basic compound: The residue is loaded onto an SCX cartridge (Varian Bond Elute, 1 g/6 mL) conditioned with 1 mL of MeOH, rinsed with 5 mL of MeOH and eluted with 5 mL of 1M NH$_3$/MeOH. Volatiles are removed by nitrogen flow to give the crude title compound. If necessary, the purification by column chromatography is carried out before the purification using SCX.

The further purification is carried out by preparative LC-MS system in the usual manner. The retention time and observed MS by HPLC-QC method are noted in Table 20.

Other than the above condition A, the following conditions (B-F) are also summarized in Table 19.

TABLE 19

| Condition | Pd catalyst | Base | Solved | Temperature/Times |
|---|---|---|---|---|
| A | PdCl$_2$(dppf)·CH$_2$Cl$_2$ | NaHCO$_3$ | 1,4-dioxane-water | 80-150° C./3-15 h (oil bath) 100-150° C./20-60 min (MW) |
| B | PdCl$_2$(dppf)·CH$_2$Cl$_2$ | K$_3$PO$_4$ | DMF | 80-150° C./3-15 h (oil bath) 100-150° C./20-60 min (MW) |
| C | Pd(Amphos)$_2$Cl$_2$ | NaHCO$_3$ | 1,4-dioxane-water | 80-150° C./3-15 h (oil bath) 100-150° C./20-60 min (MW) |
| D | Pd(PPh$_3$)$_4$ | NaHCO$_3$ | 1,4-dioxane-water | 100-120° C./20-60 min (MW) |
| E | PdCl$_2$(dppf)·CH$_2$Cl$_2$ | CsOAc | 1,4-dioxane | 170° C./20 min (MW) |
| F | PdCl$_2$(dppf)·CH$_2$Cl$_2$ | CuI | DMF | 120° C./20 min (MW) |

The following examples (6-1 to 6-53) are prepared according to the condition A to F in Table 19 from the synthesized aryl boronic acid derivative (INT-12-1-A) and the known or synthesized halide derivatives in Table 20. The further purification is carried out by preparative LC-MS system in the usual manner. The retention time and observed MS by HPLC-QC method are summarized in Table 20.

TABLE 20

| Examples | Bronic acid derivative | halides | conditions | observed MS | tR/method |
|---|---|---|---|---|---|
| Example-6-1 | (structure) | (structure) | A | 438.3 | 1.39 min. (QC1) |

TABLE 20-continued

| Examples | Bronic acid derivative | halides | conditions | observed MS | tR/method |
|---|---|---|---|---|---|
| | INT-12-1-A | | | | |
| Example-6-2 | INT-12-1-A | 4-chloroquinazoline | A | 449.3 | 1.53 min. (QC1) |
| Example-6-3 | INT-12-1-A | 3-chloropyrazine-2-carbonitrile | A | 424.2 | 1.93 min. (QC2) |
| Example-6-4 | INT-12-1-A | 4-bromo-1H-pyrazolo[3,4-c]pyridine | A | 438.3 | 1.33 min. (QC1) |
| Example-6-5 | INT-12-1-A | 4-bromo-1H-pyrrolo[2,3-c]pyridine | A | 437.3 | 1.38 min. (QC1) |

TABLE 20-continued
| Examples | Bronic acid derivative | halides | conditions | observed MS | tR/method |
|---|---|---|---|---|---|
| Example-6-6 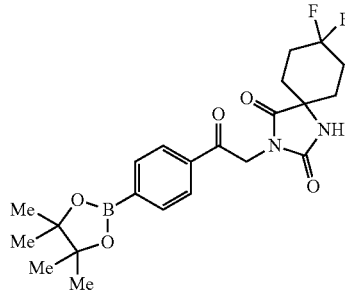 | 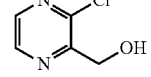  INT-12-1-A | 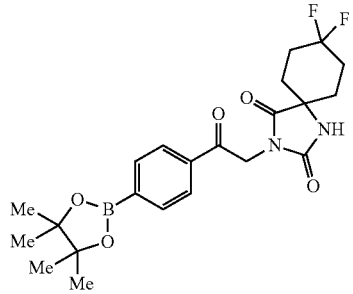 [SMILES: CC1(C)OB(c2ccc(C(=O)CN3C(=O)NC4(CCC(F)(F)CC4)C3=O)cc2)OC1(C)C] | A | 429.3 | 1.59 min. (QC2) |
| Example-6-7  | 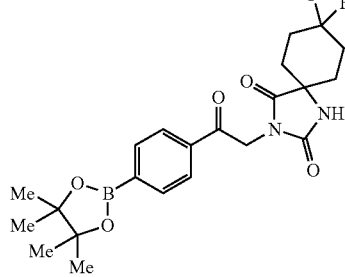  INT-12-1-A | 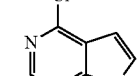 | A | 427.2 | 1.50 min. (QC1) |
| Example-6-8 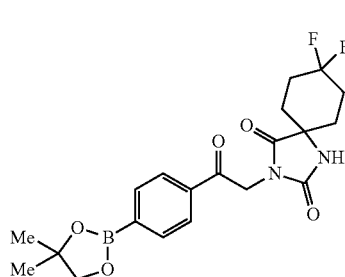 | 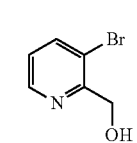  INT-12-1-A | (4-chloro-7H-pyrrolo[2,3-d]pyrimidine) | A | 438.3 | 1.36 min. (QC1) |
| Example-6-9 | INT-12-1-A | (3-bromo-2-(hydroxymethyl)pyridine) | A | 428.3 | 1.36 min. (QC1) |

TABLE 20-continued
| Examples | Bronic acid derivative | halides | conditions | observed MS | tR/ method |
|---|---|---|---|---|---|
| Example-6-10 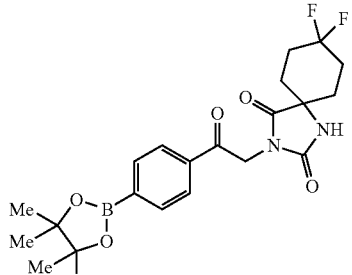 |   INT-12-1-A | 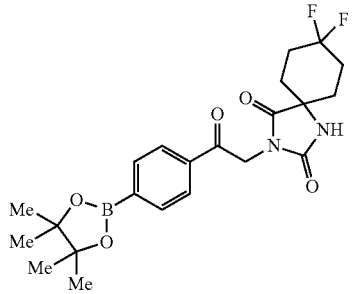 [SMILES: CC1(C)OB(c2ccc(C(=O)CN3C(=O)NC4(CCC(F)(F)CC4)C3=O)cc2)OC1(C)C] | A | 428.3 | 1.28 min. (QC1) |
| Example-6-11 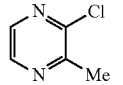 | 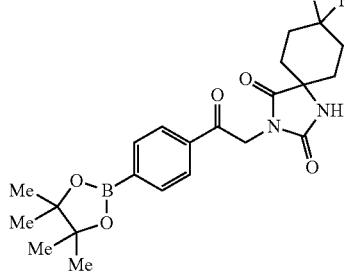  INT-12-1-A | 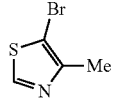 | A | 413.2 | 1.43 min. (QC1) |
| Example-6-12 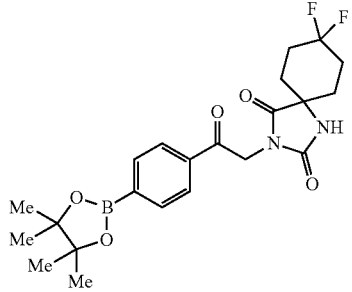 [SMILES: CC1(C)OB(c2ccc(C(=O)CN3C(=O)NC4(CCC(F)(F)CC4)C3=O)cc2)OC1(C)C] |   INT-12-1-A | 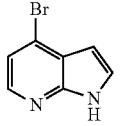 | A | 418.3 | 1.51 min. (QC1) |
| Example-6-13 | 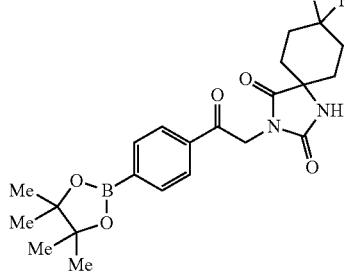  INT-12-1-A |  | A | 437.3 | 1.47 min. (QC1) |

TABLE 20-continued
| Examples | Bronic acid derivative | halides | conditions | observed MS | tR/ method |
|---|---|---|---|---|---|
| Example-6-14 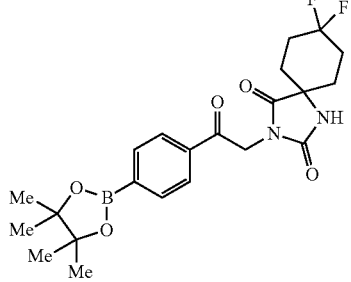 | 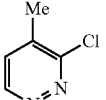 INT-12-1-A | 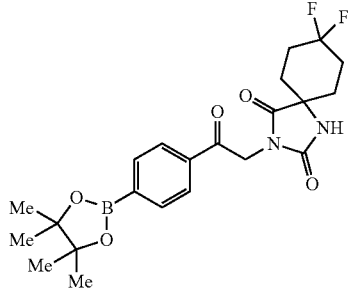 [SMILES: CC1(C)OB(c2ccc(C(=O)CN3C(=O)NC4(CCC(F)(F)CC4)C3=O)cc2)OC1(C)C] | A | 413.2 | 1.71 min. (QC2) |
| Example-6-15 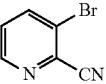 | 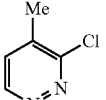 INT-12-1-A | 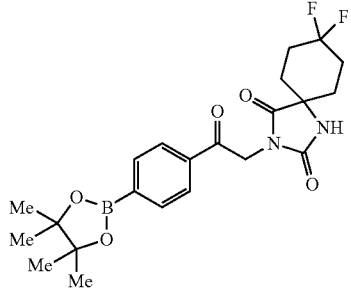 [SMILES: CC1(C)OB(c2ccc(C(=O)CN3C(=O)NC4(CCC(F)(F)CC4)C3=O)cc2)OC1(C)C] | A | 423.3 | 1.50 min. (QC1) |
| Example-6-16 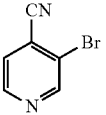 | 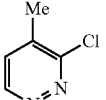 INT-12-1-A | 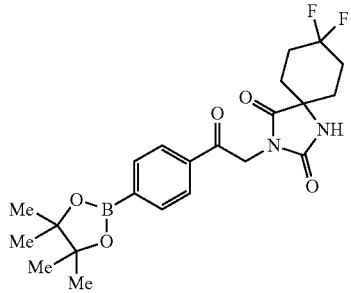 [SMILES: CC1(C)OB(c2ccc(C(=O)CN3C(=O)NC4(CCC(F)(F)CC4)C3=O)cc2)OC1(C)C] | A | 423.3 | 1.47 min. (QC1) |
| Example-6-17 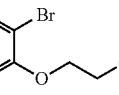 | 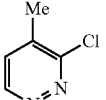 INT-12-1-A |  | A | 458.3 | 1.47 min. (QC1) |

TABLE 20-continued

| Examples | Bronic acid derivative | halides | conditions | observed MS | tR/method |
|---|---|---|---|---|---|
| Example-6-18 | INT-12-1-A | | C | 449.3 | 1.43 min. (QC1) |
| Example-6-19 | INT-12-1-A | | A | 413.4 | 1.59 min. (QC1) |
| Example-6-20 | INT-12-1-A | | A | 438.3 | 1.35 min. (QC1) |
| Example-6-21 | INT-12-1-A | | A | 437.3 | 1.43 min. (QC1) |

TABLE 20-continued

| Examples | Bronic acid derivative | halides | conditions | observed MS | tR/ method |
|---|---|---|---|---|---|
| Example-6-22 | INT-12-1-A | | A | 432.3 | 1.61 min. (QC1) |
| Example-6-23 | INT-12-1-A | | A | 439.4 | 1.33 min. (QC1) |
| Example-6-24 | INT-12-1-A | | A | 437.3 | 1.40 min. (QC1) |
| Example-6-25 | INT-12-1-A | | A | 448.4 | 1.67 min. (QC1) |

TABLE 20-continued

| Examples | Bronic acid derivative | halides | conditions | observed MS | tR/method |
|---|---|---|---|---|---|
| Example-6-26 | INT-12-1-A | CN, Br-pyridine | A | 423.2 | 1.59 min. (QC1) |
| Example-6-27 | INT-12-1-A | F, Br-pyridine | A | 416.3 | 1.58 min. (QC1) |
| Example-6-28 | INT-12-1-A | Me, Cl-pyrazine | A | 413.2 | 1.52 min. (QC1) |
| Example-6-29 | INT-12-1-A | Br, Me-thiophene | A | 417.3 | 1.81 min. (QC1) |

TABLE 20-continued

| Examples | Bronic acid derivative | halides | conditions | observed MS | tR/method |
|---|---|---|---|---|---|
| Example-6-30 | INT-12-1-A | Br-quinoxaline | A | 449.3 | 1.58 min. (QC1) |
| Example-6-31 | INT-12-1-A | 4-chlorofuro[3,2-c]pyridine | A | 438.4 | 1.58 min. (QC1) |
| Example-6-32 | INT-12-1-A | 3-iodo-1H-indazole | A | 437.3 | 1.58 min. (QC1) |
| Example-6-33 | INT-12-1-A | 4-chloro-2-methylquinazoline | A | 463.3 | 1.57 min. (QC1) |

TABLE 20-continued

| Examples | Bronic acid derivative | halides | conditions | observed MS | tR/method |
|---|---|---|---|---|---|
| Example-6-34 | INT-12-1-A | 5-bromo-4-methylpyrimidine | A | 413.4 | 1.37 min. (QC1) |
| Example-6-35 | INT-12-1-A | 3-iodophenol | A | 413.3 | 1.54 min. (QC1) |
| Example-6-36 | INT-12-1-A | (2-chloropyridin-3-yl)methanol | A | 428.3 | 1.29 min. (QC1) |
| Example-6-37 | INT-12-1-A | 1-chloro-2,7-naphthyridine | A | 449.3 | 1.43 min. (QC1) |

TABLE 20-continued
| Examples | Bronic acid derivative | | halides | conditions | observed MS | tR/ method |
|---|---|---|---|---|---|---|
| Example-6-38 | 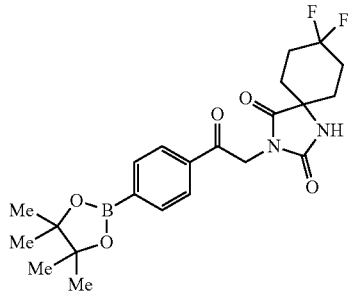 [SMILES: CC1(C)OB(c2ccc(C(=O)CN3C(=O)NC4(CCC(F)(F)CC4)C3=O)cc2)OC1(C)C] | 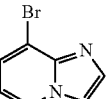 INT-12-1-A | 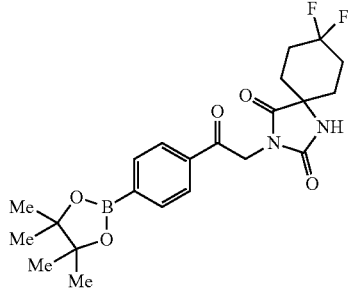 [SMILES: CC1(C)OB(c2ccc(C(=O)CN3C(=O)NC4(CCC(F)(F)CC4)C3=O)cc2)OC1(C)C] | A | 437.3 | 1.47 min. (QC1) |
| Example-6-39 | 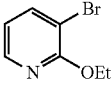 | 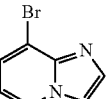 INT-12-1-A | 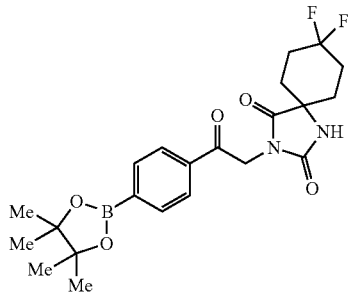 [SMILES: CC1(C)OB(c2ccc(C(=O)CN3C(=O)NC4(CCC(F)(F)CC4)C3=O)cc2)OC1(C)C] | A | 442.3 | 1.75 min. (QC1) |
| Example-6-40 | 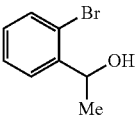 | 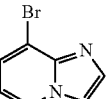 INT-12-1-A | 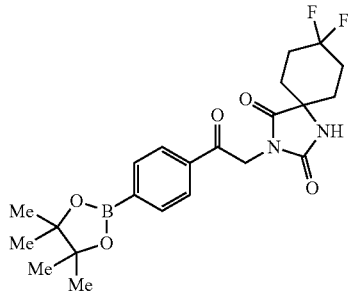 [SMILES: CC1(C)OB(c2ccc(C(=O)CN3C(=O)NC4(CCC(F)(F)CC4)C3=O)cc2)OC1(C)C] | A | 441.4 | 1.58 min. (QC1) |
| Example-6-41 | 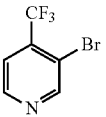 | 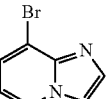 INT-12-1-A |  | A | 466.3 | 1.62 min. (QC1) |

TABLE 20-continued

| Examples | Bronic acid derivative | halides | conditions | observed MS | tR/method |
|---|---|---|---|---|---|
| Example-6-42 | INT-12-1-A | | A | 453.4 | 1.32 min. (QC1) |
| Example-6-43 | INT-12-1-A | | C | 424.5 | 1.38 min. (QC1) |
| Example-6-44 | INT-12-1-A | | A | 449.5 | 1.42 min. (QC1) |
| Example-6-45 | INT-12-1-A | | A | 449.5 | 1.49 min. (QC1) |

TABLE 20-continued

| Examples | Bronic acid derivative | halides | conditions | observed MS | tR/method |
|---|---|---|---|---|---|
| Example-6-46 | INT-12-1-A | | A | 457.3 | 1.43 min. (QC1) |
| Example-6-47 | INT-12-1-A | | A | 457.4 | 1.32 min. (QC1) |
| Example-6-48 | INT-12-1-A | | A | 469.3 | 1.41 min. (QC1) |
| Example-6-49 | INT-12-1-A | | A | 453.3 | 1.58 min. (QC1) |

TABLE 20-continued

| Examples | Bronic acid derivative | halides | conditions | observed MS | tR/method |
|---|---|---|---|---|---|
| Example-6-50 | INT-12-1-A | | A | 453.4 | 1.65 min. (QC1) |
| Example-6-51 | INT-12-1-A | | A | 450.3 | 1.40 min. (QC1) |
| Example-6-52 | INT-12-1-A | | A | 466.3 | 1.46 min. (QC1) |
| Example-6-53 | INT-12-1-A | | A | 475.3 | 1.54 min. (QC1) |

225

Example-6-54: 8,8-difluoro-3-(2-(4-(3-(2-hydroxy-ethoxy)pyrazin-2-yl)phenyl)-2-oxoethyl)-1,3-diaz-aspiro[4.5]decane-2,4-dione {Chem. 127}

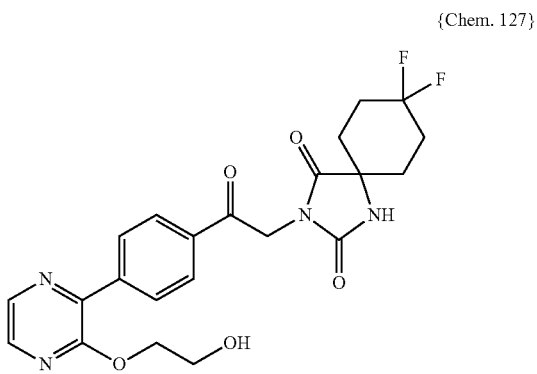 [SMILES: O=C(CN1C(=O)NC2(CCC(F)(F)CC2)C1=O)c1ccc(-c2nccnc2OCCO)cc1]

<Step-1>: Intermediate-6-54-1 (INT 6-54-1): 2-chloro-3-(2-((tetrahydro-2H-pyran-2-yl)oxy)ethoxy)pyrazine {Chem. 128}

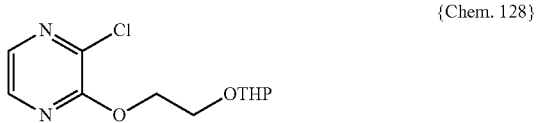

To a solution of 2,3-dichloropyrazine (397 mg, 2.67 mmol) and 2-((tetrahydro-2H-pyran-2-yl)oxy)ethanol (300 mg, 2.05 mmol) in DMSO (2 mL) is added t-BuOK (299 mg, 2.67 mmol) at 0° C. The mixture is stirred at rt for 1 h. The mixture is diluted with water and extracted with EtOAc-hexane (2:1, ×2). The combined organic layers are dried over $Na_2SO_4$, filtered and concentrated. The purification is carried out by column chromatography on silica gel eluting with a gradient of 0-30% EtOAc in hexane to give the titled compound (350 mg, 66% yield) as a pale yellow oil.

$^1$H-NMR (270 MHz, $CDCl_3$): delta 8.01 (d, J=2.7 Hz, 1H), 7.93 (d, J=2.7 Hz, 1H), 4.75 (t, J=3.0 Hz, 1H), 4.65-4.55 (m, 2H), 4.19-4.05 (m, 1H), 4.00-3.80 (m, 2H), 3.60-3.50 (m, 1H), 1.89-1.48 (m, 6H).

<Step-2>: Intermediate-6-54-2 (INT 6-54-2): 8,8-difluoro-3-(2-oxo-2-(4-(3-(2-((tetrahydro-2H-pyran-2-yl)oxy)ethoxy)pyrazin-2-yl)phenyl)ethyl)-1,3-diazaspiro[4.5]decane-2,4-dione {Chem. 129}

226

The titled compound is prepared according to the procedure described in Suzuki-Miyaura cross coupling reaction of condition-C from INT 12-1-A (30 mg, 0.067 mmol), INT 6-54-1 (17 mg, 0.067 mmol), and bis(di-tert-butyl(4-dimethylaminophenyl)phosphine)dichloropalladium(II) (5.5 mg, 0.0067 mmol) instead of $PdCl_2$(dppf) in a microwave irradiation system at 120° C. for 20 min. The crude brown oil (36 mg) is obtained and this compound is used for next step without purification.

MS (ESI) m/z: 545.2 (M+H)$^+$.

<Step-3>: Example-6-54: 8,8-difluoro-3-(2-(4-(3-(2-hydroxyethoxy)pyrazin-2-yl)phenyl)-2-oxoethyl)-1,3-diazaspiro[4.5]decane-2,4-dione To a solution of INT 6-54-2 (crude oil prepared in step-2 of example 6-54) in THF (1 mL) is added 2 M HCl aq. solution (1 mL) and the mixture is stirred at rt for 3 h. The mixture is quenched with saturated sodium carbonate solution and extracted with DCM. The combined organic layers are dried over $Na_2SO_4$, filtered and concentrated. The purification is carried out by column chromatography on silica gel eluting with a gradient of 30-100% EtOAc in hexane to give the titled compound (20 mg, 66% yield in 2 steps) as a pale yellow solid. The further purification is carried out by preparative LC-MS system in the usual manner.

$^1$H-NMR (270 MHz, $CDCl_3$): delta 8.33 (d, J=2.6 Hz, 1H), 8.24 (d, J=8.6 Hz, 2H), 8.11 (d, J=2.6 Hz, 1H), 8.05 (d, J=8.6 Hz, 2H), 6.05 (br.s, 1H), 4.97 (s, 2H), 4.65-4.57 (m, 2H), 4.08-4.00 (m, 2H), 2.58-2.19 (m, 5H), 2.12-1.90 (m, 4H).

Observed MS: 459.3 tR/method: 1.41 min./(QC1)

Example-6-55: 3-(2-(2'-(aminomethyl)-[1,1'-biphenyl]-4-yl)-2-oxoethyl)-8,8-difluoro-1,3-diazaspiro[4.5]decane-2,4-dione hydrochloride {Chem. 130}

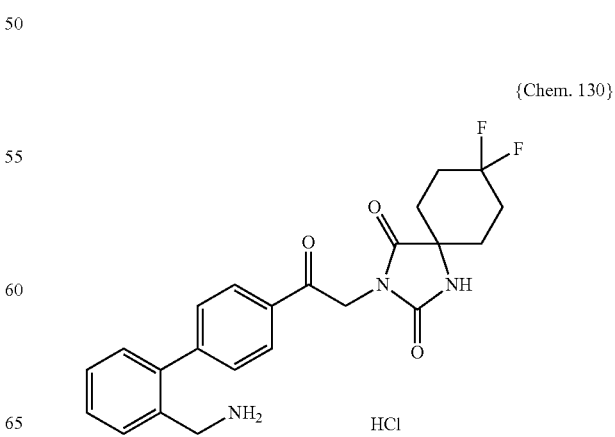

227

<Step-1>: Intermediate-6-55-1 (INT-6-55-1): tert-butyl ((4'-(2-(8,8-difluoro-2,4-dioxo-1,3-diazaspiro[4.5]decan-3-yl)acetyl)-[1,1-biphenyl]-2-yl)methyl)carbamate {Chem. 131}

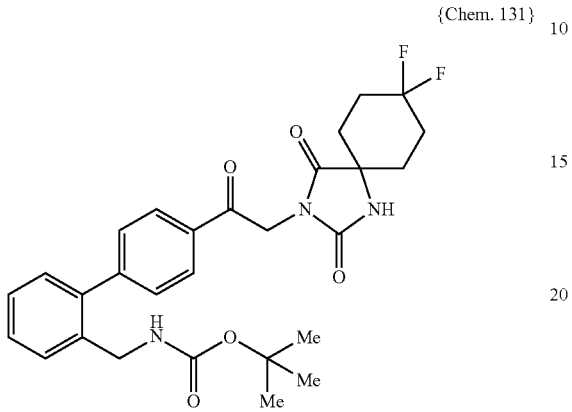

The titled compound is prepared according to the procedure described in Suzuki-Miyaura cross coupling reaction of condition-A from INT-12-1-A (838 mg, 1.87 mmol), tert-butyl 2-bromobenzylcarbamate (642 mg, 2.24 mmol) under microwave irradiation at 120° C. for 20 min. The reaction mixture is filtered through Celite pad and the Celite pad is washed with EtOAc. The filtrate and washings are extracted with EtOAc and the combined organic solution is washed with water and brine, dried over sodium sulfate, filtered and concentrated in vacuo. The residue is purified by column chromatography (Biotage) on silica gel (50 g) eluting with 10-80% ethyl acetate in DCM to give the titled compound (756 mg, 77% yield) as a white solid.

$^1$H-NMR (270 MHz, CDCl$_3$): delta 8.04 (d, J=8.5 Hz, 2H), 7.50-7.35 (m, 4H), 7.28-7.24 (m, 2H), 6.94 (br.s, 1H), 4.98 (s, 2H), 4.68 (br.s, 1H), 4.29 (d, J=5.3 Hz, 2H), 2.38-2.24 (m, 4H), 2.04-1.98 (m, 4H), 1.63 (s, 3H), 1.43 (s, 9H).

MS (ESI) m/z: 526.4 (M–H)$^-$.

<Step-2>: Example-6-55: 3-(2-(2'-(aminomethyl)-[1,1'-biphenyl]-4-yl)-2-oxoethyl)-8,8-difluoro-1,3-diazaspiro[4.5]decane-2,4-dione hydrochloride To a solution of INT-6-55-1 (756 mg, 1.43 mmol) in 1,4-dioxane (3 mL) is added 4 M HCl-dioxane (10 mL). The mixture is stirred at rt for 3 h. The precipitated solid is collected by filtration to give the titled compound (600 mg, 90% yield) as a white solid.

$^1$H-NMR (270 MHz, DMSO-d$_6$): delta 9.05 (s, 1H), 8.33 (s, 2H), 8.16 (d, J=8.5 Hz, 2H), 7.71 (d, J=7.2 Hz, 1H), 7.62-7.48 (m, 4H), 7.37 (d, J=7.2 Hz, 1H), 5.03 (s, 2H), 3.97 (s, 2H), 2.19-1.81 (m, 8H).

MS (ESI) m/z: 428.3 (M+H)$^-$.

228

Example-6-56: 3-(2-(4-(2-(aminomethyl)pyridin-3-yl)phenyl)-2-oxoethyl)-8,8-difluoro-1,3-diazaspiro[4.5]decane-2,4-dione {Chem. 132}

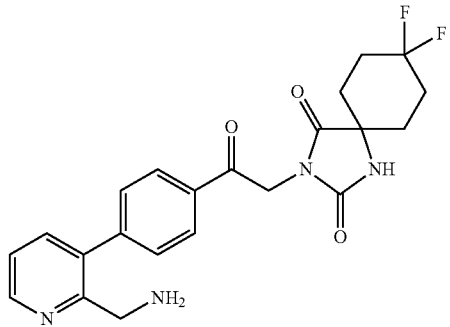

<Step-1>: Intermediate-6-56-1 (INT-6-56-1): 3-(2-(4-(2-(aminomethyl)pyridin-3-yl)phenyl)-2-oxoethyl)-8,8-difluoro-1,3-diazaspiro[4.5]decane-2,4-dione The titled compound is prepared according to the procedure described in Suzuki-Miyaura cross coupling reaction of condition-A from INT-12-1-A and (3-bromopyridin-2-yl)methanamine to give the product (173 mg, 21% yield; chemical purity of 73%) as a dark red solid.

MS (ESI) m/z: 429.29 (M+H)$^+$.

<Step-2>: Intermediate-6-56-2 (INT-6-56-2): tert-butyl ((3-(4-(2-(8,8-difluoro-2,4-dioxo-1,3-diazaspiro[4.5]decan-3-yl)acetyl)phenyl)pyridin-2-yl)methyl)carbamate {Chem. 133}

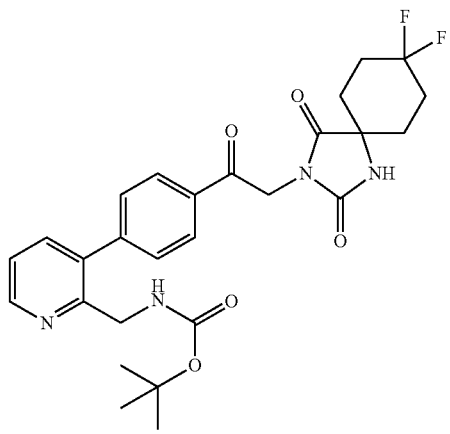

To a stirred solution of the crude INT-6-56-1 (178 mg, 0.415 mmol) and triethylamine (116 microL, 0.831 mmol) in THF (5 mL) is added di-tert-butyl dicarbonate (90 microL, 0.416 mmol) at rt. The mixture is stirred at rt for 3 days. After the removal of solvent, the crude product is purified by column chromatography on silica gel (45 g) eluting with 3-20% methanol in DCM followed by preparative TLC (1 mm×4) with MeOH-DCM (1:20)(eluting with 10% MeOH in DCM) to give the titled compound (103.6 mg, yellow amorphous solid) $^1$H-NMR (270 MHz, CDCl$_3$): delta 8.64-8.58 (m, 1H), 8.10-8.00 (m, 2H), 7.62-7.55 (m, 1H), 7.53-7.45 (m, 2H), 7.36-7.28 (m, 1H), 7.00 (br.s, 1H), 6.00 (br.s, 1H), 4.96 (s, 2H), 4.38 (d, J=3.9 Hz, 2H), 2.50-1.90 (m, 8H), 1.65 (s, 3H), 1.43 (s, 9H).

MS (ESI) m/z: 529.41 (M+H)$^+$.

<Step-3>: Example-6-56: 3-(2-(4-(2-(aminomethyl)pyridin-3-yl)phenyl)-2-oxoethyl)-8,8-difluoro-1,3-diazaspiro[4.5]decane-2,4-dione A mixture of INT-6-56-2 (98 mg, 0.185 mmol) in MeOH (3 mL) is treated with 10% HCl-methanol (8 mL). After 2.5 h at 50° C., the solvent is evaporated in vacuo. The residue is basified to pH>8 with saturated sodium bicarbonate solution and extracted with DCM (×3). The combined solution is washed with brine, dried over sodium sulfate, filtered and concentrated in vacuo to give the titled compound (74.3 mg, 94% yield) as a pale brown ~yellow solid. The further purification is carried out by preparative LC-MS system in the usual manner.

$^1$H-NMR (270 MHz, DMSO-d$_6$): delta 9.03 (br.s, 1H), 8.65-8.60 (m, 1H), 8.18-8.10 (m, 2H), 7.75-7.40 (m, 3H), 7.44-7.35 (m, 1H), 5.02 (s, 2H), 3.73 (s, 2H), 2.30-1.75 (m, 8H). (A signal due to NH is not observed.)

Observed MS: 427.3 tR/method: 1.23 min./(QC1)

Synthesis of Example-6-57: N-((3-(4-(2-(8,8-difluoro-2,4-dioxo-1,3-diazaspiro[4.5]decan-3-yl)acetyl)phenyl)pyridin-2-yl) methyl)acetamide {Chem. 134}

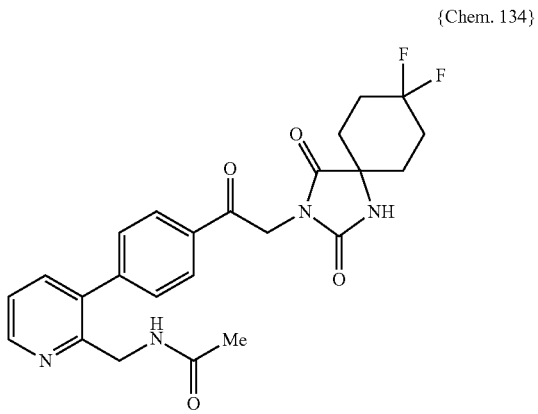 [SMILES: CC(=O)NCc1ncccc1-c1ccc(C(=O)CN2C(=O)NC3(CCC(F)(F)CC3)C2=O)cc1]

To a stirred suspension of Example-6-56 (38.1 mg, 0.089 mmol) in DCM (3 mL)-THF (1 mL) is added triethylamine (25 microL, 0.179 mmol) followed by acetic anhydride (10 microL, 0.107 mmol) at rt. The mixture is stirred at rt for 5 h. After the removal of solvent, the residue is purified by column chromatography (Biotage) on amine silica gel (10 g) with 50-100% EtOAc in hexane to give the titled compound (38.6 mg, 92% yield) as a colorless amorphous solid.

The further purification is carried out by preparative LC-MS system in the usual manner.

$^1$H-NMR (270 MHz, DMSO-d$_6$): delta 9.03 (s, 1H), 8.65-8.60 (m, 1H), 8.24-8.20 (m, 1H), 8.18-8.10 (m, 2H), 7.75-7.60 (m, 3H), 7.48-7.40 (m, 1H), 5.03 (s, 2H), 4.32 (d, J=4.3 Hz, 2H), 2.30-1.75 (m, 8H), 1.80 (s, 3H).

Observed MS: 469.4 tR/method: 1.33 min./(QC1)

Example-6-58: 3-(2-(4-(4-(aminomethyl)pyridin-3-yl)phenyl)-2-oxoethyl)-8,8-difluoro-1,3-diazaspiro[4.5]decane-2,4-dione {Chem. 135}

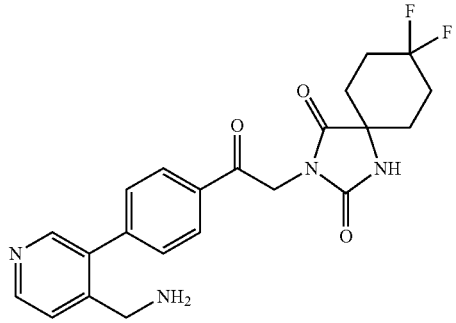

<Step-1>: Intermediate-6-58-1 (INT-6-58-1): tert-butyl ((3-(4-(2-(8,8-difluoro-2,4-dioxo-1,3-diazaspiro[4.5]decan-3-yl)acetyl)phenyl)pyridin-4-yl)methyl)carbamate {Chem. 136}

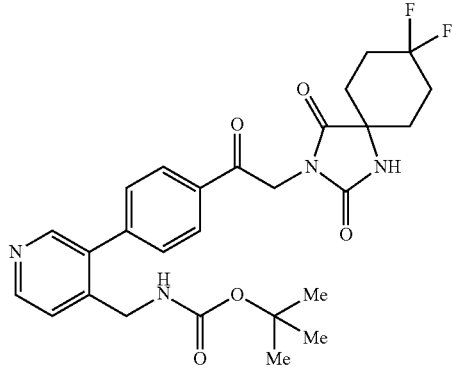

The titled compound is prepared according to the procedure described in Suzuki-Miyaura cross coupling reaction of condition-A from INT-12-1-A (60 mg, 0.134 mmol), tert-butyl ((3-bromopyridin-4-yl)methyl)carbamate (46 mg, 0.161 mmol) in a microwave irradiation system at 120° C. for 20 min. The residue is purified by column chromatography (Biotage) on silica gel (10 g) eluting with 10-80% ethyl acetate in DCM to give the product (63 mg, 89% yield) as a pale yellow solid.

$^1$H-NMR (270 MHz, DMSO-d$_6$): delta 9.02 (s, 1H), 8.59 (d, J=5.3 Hz, 1H), 8.43 (s, 1H), 8.14 (d, J=7.9 Hz, 2H), 7.64 (d, J=7.9 Hz, 2H), 7.51 (t, J=5.3 Hz, 1H), 7.39 (d, J=4.6 Hz, 1H), 5.02 (s, 2H), 4.11 (d, J=5.3 Hz, 2H), 2.17-1.86 (m, 8H), 1.36 (s, 9H).

MS (ESI) m/z: 529.3 (M-H)$^-$.

<Step-2>: Example-6-58: 3-(2-(4-(4-(aminomethyl)pyridin-3-yl)phenyl)-2-oxoethyl)-8,8-difluoro-1,3-diazaspiro[4.5]decane-2,4-dione To a solution of INT-6-58-1 (63 mg, 0.119 mmol) in DCM (1 mL) is added trifluoroacetic acid (0.5 mL). The mixture is stirred at rt for 2 h. The reaction mixture is concentrated by nitrogen flow. The residue is loaded onto an SCX cartridge (Biotage, ISOLUTE-SCX-2, 1 g/6 mL) conditioned with 1 mL of MeOH, rinsed with 5 mL of MeOH and eluted with 5 mL of 1M $NH_3$/MeOH. Volatiles are removed by nitrogen flow to give the titled compound (41 mg, 76% yield) as a pale yellow amorphous solid. The further purification is carried out by preparative LC-MS system in the usual manner.

Observed MS: 427.4 tR/method: 1.19 min./(QC1)

The following examples (6-59 to 6-123) are prepared according to the condition A to F in Table 19 from the synthesized aryl boronic acid derivative (INT-12-1-A) and the known or synthesized halide derivatives in Table 21. The further purification is carried out by preparative LC-MS system in the usual manner. The retention time and observed MS by HPLC-QC method are summarized in Table 21.

TABLE 21

| Examples | Boronic acid derivative | halides | conditions | observed MS | tR/method |
|---|---|---|---|---|---|
| Example-6-59 | INT-12-1-A | | C | 452.2 | 1.30 min. (QC1) |
| Example-6-60 | INT-12-1-A | | A | 454.1 | 1.51 min. (QC1) |

TABLE 21-continued

| Examples | Boronic acid derivative | halides | conditions | observed MS | tR/method |
|---|---|---|---|---|---|
| Example-6-61 | INT-12-1-A | | A | 403.3 | 1.32 min. (QC1) |
| Example-6-62 | INT-12-1-A | | A | 440.1 | 1.41 min. (QC1) |

TABLE 21-continued
| Examples | Boronic acid derivative | halides | conditions | observed MS | tR/method |
|---|---|---|---|---|---|
| Example-6-63 | INT-12-1-A |  | A | 439.2 | 2.09 min. (QC2) |
| Example-6-64 | INT-12-1-A |  | A | 439.1 | 2.05 min. (QC2) |

TABLE 21-continued

| Examples | Boronic acid derivative | halides | conditions | observed MS | tR/method |
|---|---|---|---|---|---|
| Example-6-65 | INT-12-1-A | | A | 453.6 | 1.45 min. (QC1) |
| Example-6-66 | INT-12-1-A | | A | 440.6 | 1.30 min. (QC1) |

TABLE 21-continued

| Examples | Boronic acid derivative | halides | conditions | observed MS | tR/method |
|---|---|---|---|---|---|
| Example-6-67 | INT-12-1-A | (3-bromo-pyrazolo[1,5-a]pyridine) | A | 439.6 | 1.55 min. (QC1) |
| Example-6-68 | INT-12-1-A | (3-bromo-pyrazolo[1,5-a]pyrimidine) | A | 440.6 | 1.47 min. (QC1) |

TABLE 21-continued
| Examples | Boronic acid derivative | halides | conditions | observed MS | tR/method |
|---|---|---|---|---|---|
| Example-6-69 | INT-12-1-A | 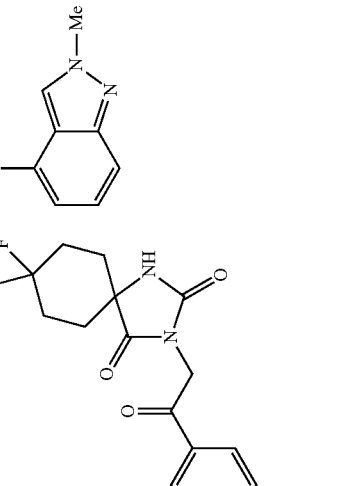 | A | 453.5 | 1.47 min. (QC1) |
| Example-6-70 | INT-12-1-A | 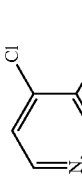 | A | 414.8 | 1.48 min. (QC1) |

TABLE 21-continued

| Examples | Boronic acid derivative | halides | conditions | observed MS | tR/method |
|---|---|---|---|---|---|
| Example-6-71 | INT-12-1-A | 6-chloropyridin-2-amine | A | 415.1 | 1.47 min. (QC1) |
| Example-6-72 | INT-12-1-A | 4-chloro-2,3-dihydro-1H-indole | C | 440.8 | 1.60 min. (QC1) |

TABLE 21-continued

| Examples | Boronic acid derivative | halides | conditions | observed MS | tR/method |
|---|---|---|---|---|---|
| Example-6-73 | INT-12-1-A | Me, Cl-pyridazine | A | 415.3 | 2.82 min. (Metod-E) |
| Example-6-74 | INT-12-1-A | MeO, Cl-pyridazine | B | 431.6 | 1.36 min. (QC1) |

TABLE 21-continued

| Examples | Boronic acid derivative | halides | conditions | observed MS | tR/method |
|---|---|---|---|---|---|
| Example-6-75 | INT-12-1-A | | B | 415.6 | 1.38 min. (QC1) |
| Example-6-76 | INT-12-1-A | | C | 429.5 | 1.33 min. (QC1) |

TABLE 21-continued

| Examples | Boronic acid derivative | halides | conditions | observed MS | tR/method |
|---|---|---|---|---|---|
| Example-6-77 | INT-12-1-A | 3-bromo-1,2-dimethylbenzene (Me, Br, Me) | A | 427.6 | 1.89 min. (QC1) |
| Example-6-78 | INT-12-1-A | 2-bromo-1,4-dimethylbenzene (Br, Me, Me) | A | 427.6 | 1.90 min. (QC1) |

TABLE 21-continued

| Examples | Boronic acid derivative | halides | conditions | observed MS | tR/method |
|---|---|---|---|---|---|
| Example-6-79 | INT-12-1-A | OMe, Cl, pyrazine | C | 431.7 | 1.41 min. (QC1) |
| Example-6-80 | INT-12-1-A | NH₂, Br, pyridine | C | 415.7 | 1.33 min. (QC1) |

TABLE 21-continued

| Examples | Boronic acid derivative | halides | conditions | observed MS | tR/method |
|---|---|---|---|---|---|
| Example-6-81 | INT-12-1-A | | C | 439.7 | 1.41 min. (QC1) |
| Example-6-82 | INT-12-1-A | | A | 414.8 | 1.53 min. (QC1) |

TABLE 21-continued

| Examples | Boronic acid derivative | halides | conditions | observed MS | tR/method |
|---|---|---|---|---|---|
| Example-6-83 | INT-12-1-A | 2-bromo-4-methylpyridine | A | 414.8 | 1.59 min. (QC1) |
| Example-6-84 | INT-12-1-A | 2-bromo-3-methoxypyridine | A | 430.6 | 1.51 min. (QC1) |

TABLE 21-continued

| Examples | Boronic acid derivative | halides | conditions | observed MS | tR/method |
|---|---|---|---|---|---|
| Example-6-85 | INT-12-1-A | | A | 440.7 | 1.39 min. (QC1) |
| Example-6-86 | INT-12-1-A | | A | 425.7 | 1.51 min. (QC1) |

TABLE 21-continued

| Examples | Boronic acid derivative | halides | conditions | observed MS | tR/method |
|---|---|---|---|---|---|
| Example-6-87 | INT-12-1-A | | A | 425.7 | 1.46 min. (QC1) |
| Example-6-88 | INT-12-1-A | | A | 439.7 | 1.38 min. (QC1) |

TABLE 21-continued

| Examples | Boronic acid derivative | halides | conditions | observed MS | tR/method |
|---|---|---|---|---|---|
| Example-6-89 | INT-12-1-A | 4-bromo-3-methoxypyridine (OMe, Br on pyridine) | A | 430.8 | 1.45 min. (QC1) |
| Example-6-90 | INT-12-1-A | 3-bromo-5-methoxypyridine (MeO, Br on pyridine) | A | 430.8 | 1.49 min. (QC1) |

TABLE 21-continued

| Examples | Boronic acid derivative | halides | conditions | observed MS | tR/method |
|---|---|---|---|---|---|
| Example-6-91 | INT-12-1-A | (2-chloro-4-methylpyridine) | A | 430.7 | 1.53 min. (QC1) |
| Example-6-92 | INT-12-1-A | (2-chloro-6-methyl-3-cyanopyridine) | A | 439.8 | 1.56 min. (QC1) |

TABLE 21-continued

| Examples | Boronic acid derivative | halides | conditions | observed MS | tR/method |
|---|---|---|---|---|---|
| Example-6-93 | INT-12-1-A | | C | 426.8 | 1.43 min. (QC1) |
| Example-6-94 | INT-12-1-A | | C | 417.8 | 1.48 min. (QC1) |

TABLE 21-continued
| Examples | Boronic acid derivative | halides | conditions | observed MS | tR/method |
|---|---|---|---|---|---|
| Example-6-95 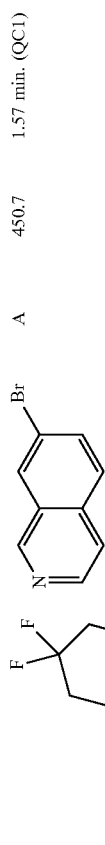 | 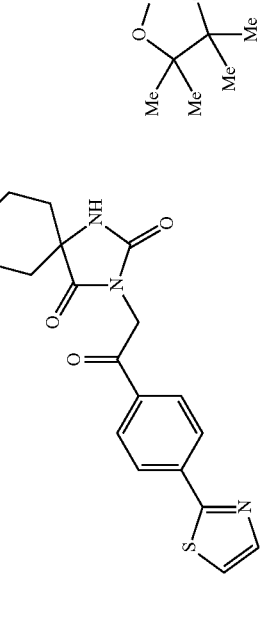 INT-12-1-A | 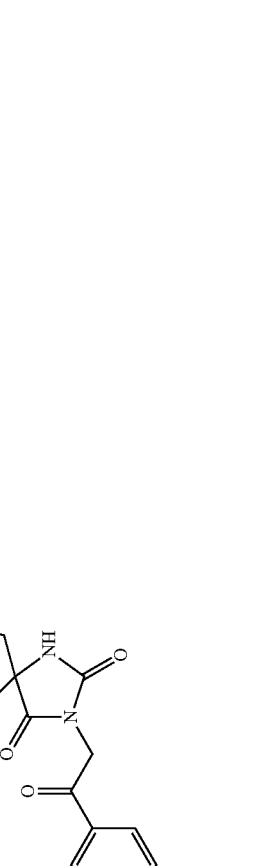 | C | 406.7 | 1.53 min. (QC1) |
| Example-6-96  |  INT-12-1-A | 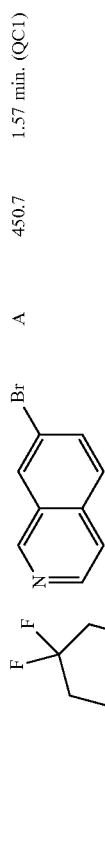 | A | 450.7 | 1.57 min. (QC1) |

TABLE 21-continued

| Examples | Boronic acid derivative | halides | conditions | observed MS | tR/method |
|---|---|---|---|---|---|
| Example-6-97 | INT-12-1-A | 2-chloro-3-methoxypyrazine | A | 431.6 | 1.59 min. (QC1) |
| Example-6-98 | INT-12-1-A | 4-chloro-3-cyanopyridine | B | 425.6 | 1.44 min. (QC1) |

TABLE 21-continued

| Examples | Boronic acid derivative | halides | conditions | observed MS | tR/method |
|---|---|---|---|---|---|
| Example-6-99 | INT-12-1-A | 2-bromobenzamide | A | 442.6 | 1.36 min. (QC1) |
| Example-6-100 | INT-12-1-A | 2-chloropyrazine | C | 401.7 | 1.42 min. (QC1) |

TABLE 21-continued

| Examples | Boronic acid derivative | halides | conditions | observed MS | tR/method |
|---|---|---|---|---|---|
| Example-6-101 | INT-12-1-A | | A | 443.7 | 1.52 min. (QC1) |
| Example-6-102 | INT-12-1-A | | A | 441.8 | 1.63 min. (QC1) |

TABLE 21-continued
| Examples | Boronic acid derivative | halides | conditions | observed MS | tR/method |
|---|---|---|---|---|---|
| Example-6-103 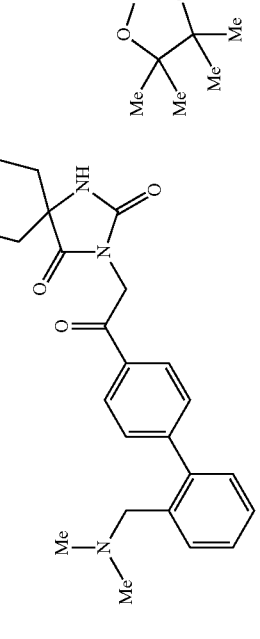 | INT-12-1-A  |  | A | 456.7 | 1.57 min. (QC1) |
| Example-6-104  | INT-12-1-A 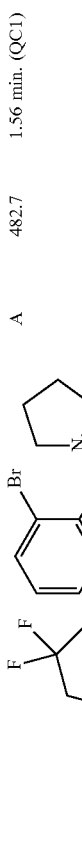 | 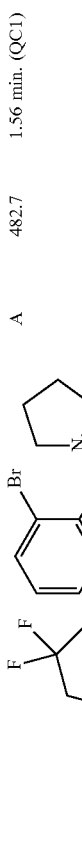 | A | 482.7 | 1.56 min. (QC1) |

TABLE 21-continued

| Examples | Boronic acid derivative | halides | conditions | observed MS | tR/method |
|---|---|---|---|---|---|
| Example-6-105 | INT-12-1-A | | A | 496.7 | 1.83 min. (QC1) |
| Example-6-106 | INT-12-1-A | | A | 443.7 | 1.56 min. (QC1) |

TABLE 21-continued

| Examples | Boronic acid derivative | halides | conditions | observed MS | tR/method |
|---|---|---|---|---|---|
| Example-6-107 | INT-12-1-A | | C | 454.8 | 1.31 min. (QC1) |
| Example-6-108 | INT-12-1-A | | C | 438.7 | 1.64 min. (QC1) |

TABLE 21-continued
| Examples | Boronic acid derivative | halides | conditions | observed MS | tR/method |
|---|---|---|---|---|---|
| Example-6-109 | INT-12-1-A | 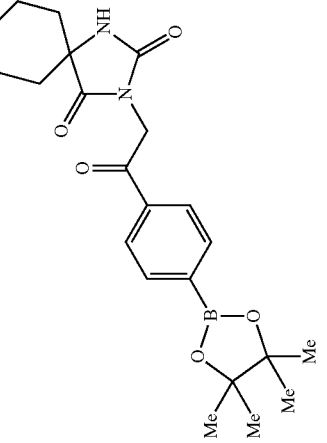 | C | 415.8 | 1.20 min. (QC1) |
| Example-6-110 | INT-12-1-A | 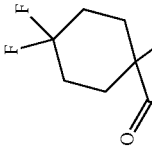 | C | 442.7 | 1.37 min. (QC1) |

TABLE 21-continued

| Examples | Boronic acid derivative | halides | conditions | observed MS | tR/method |
|---|---|---|---|---|---|
| Example-6-111 | INT-12-1-A | 3-bromoacetophenone | C | 441.8 | 1.63 min. (QC1) |
| Example-6-112 | INT-12-1-A | 4-bromo-3,5-dimethylpyridine | C | 428.8 | 1.52 min. (QC1) |

TABLE 21-continued

| Examples | Boronic acid derivative | halides | conditions | observed MS | tR/method |
|---|---|---|---|---|---|
| Example-6-113 | INT-12-1-A | 3-bromo-2-aminopyridine | A | 415.7 | 1.40 min. (QC1) |
| Example-6-114 | INT-12-1-A | 2-bromo-(methoxymethyl)benzene | C | 443.7 | 1.74 min. (QC1) |

TABLE 21-continued

| Examples | Boronic acid derivative | halides | conditions | observed MS | tR/method |
|---|---|---|---|---|---|
| Example-6-115 | INT-12-1-A | | A | 440.3 | 1.33 min. (QC1) |
| Example-6-116 | INT-12-1-A | | A | 440.2 | 1.91 min. (QC2) |

TABLE 21-continued
| Examples | Boronic acid derivative | halides | conditions | observed MS | tR/method |
|---|---|---|---|---|---|
| Example-6-117 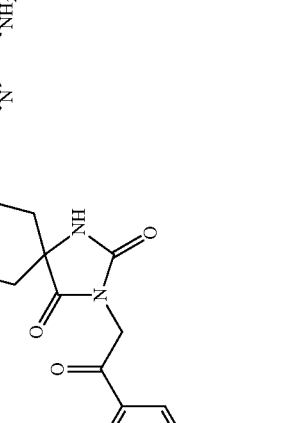 | 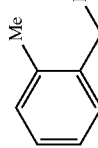 INT-12-1-A | 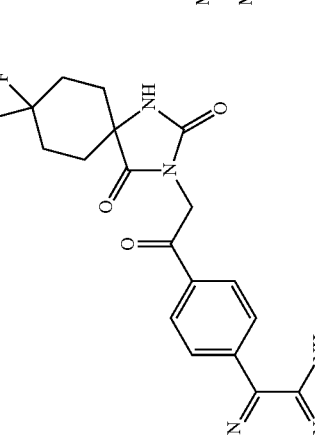 | A | 416.6 | 1.30 min. (QC1) |
| Example-6-118  | 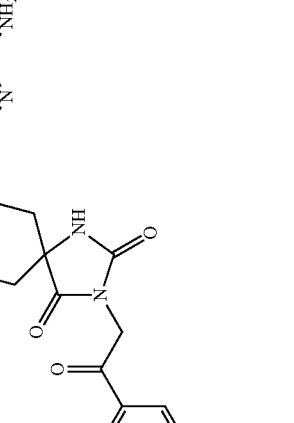 INT-12-1-A | 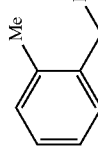 | A | 427.7 | 1.84 min. (QC1) |

TABLE 21-continued

| Examples | Boronic acid derivative | halides | conditions | observed MS | tR/method |
|---|---|---|---|---|---|
| Example-6-119 | INT-12-1-A | | A | 414.7 | 1.47 min. (QC1) |
| Example-6-120 | INT-12-1-A | | A | 438.7 | 1.66 min. (QC1) |

TABLE 21-continued

| Examples | Boronic acid derivative | halides | conditions | observed MS | tR/method |
|---|---|---|---|---|---|
| Example-6-121 | INT-12-1-A | | A | 468.6 | 1.59 min. (QC1) |
| Example-6-122 | INT-12-1-A | | A | 434.8 | 1.55 min. (QC1) |

TABLE 21-continued
| Examples | Boronic acid derivative | halides | conditions | observed MS | tR/method |
|---|---|---|---|---|---|
| Example-6-123 | 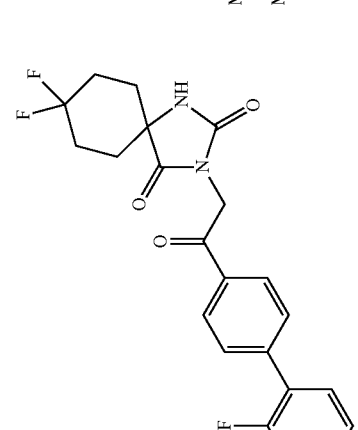<br>INT-12-1-A | 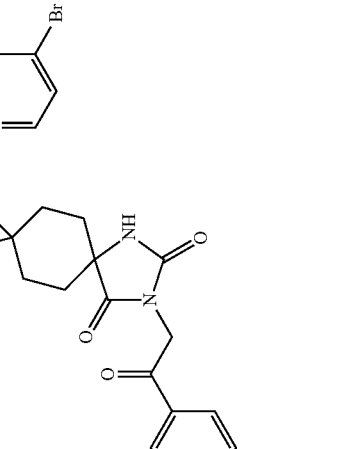 | A | 418.7 | 1.48 min. (QC1) |
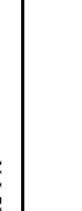

The following examples (7-1 to 7-28) are prepared according to the condition A to F in Table 19 from the synthesized aryl boronic acid derivatives and the known or synthesized halide derivatives in Table 22. The further purification is carried out by preparative LC-MS system in the usual manner. The retention time and observed MS by HPLC-QC method are summarized in Table 22.

TABLE 22

| Examples | Boronic acid derivatives | halides | conditions | observed MS | tR/method |
|---|---|---|---|---|---|
| Example-7-1 | INT-12-3-A | | A | 376.4 | 1.48 min. (QC1) |
| Example-7-2 | INT-12-3-A | | A | 376.4 | 1.49 min. (QC1) |

TABLE 22-continued
| Examples | Boronic acid derivatives | halides | conditions | observed MS | tR/method |
|---|---|---|---|---|---|
| Example-7-3 | INT-12-3-A | 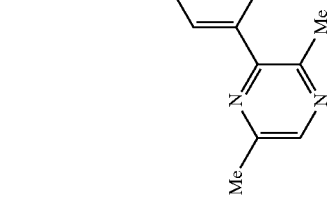 | A | 381.3 | 1.81 min. (QC1) |
| Example-7-4 | INT-12-3-A | | A | 391.4 | 1.49 min. (QC1) |

TABLE 22-continued

| Examples | Boronic acid derivatives | halides | conditions | observed MS | tR/method |
|---|---|---|---|---|---|
| Example-7-5 | INT-12-3-A | | A | 387.4 | 1.59 min. (QC1) |
| Example-7-6 | INT-12-3-A | | A | 365.5 | 1.43 min. (QC1) |

TABLE 22-continued

| Examples | Boronic acid derivatives | halides | conditions | observed MS | tR/method |
|---|---|---|---|---|---|
| Example-7-7 | INT-12-3-A | 2-chloro-3-(hydroxymethyl)pyridine | A | 392.1 | 1.28 min. (QC1) |
| Example-7-8 | INT-12-4-A | 3-bromo-2-cyanopyridine | A | 387.3 | 1.49 min. (QC1) |

TABLE 22-continued

| Examples | Boronic acid derivatives | halides | conditions | observed MS | tR/method |
|---|---|---|---|---|---|
| Example-7-9 | INT-12-4-A | 3-bromo-4-(hydroxymethyl)pyridine | A | 392.2 | 1.27 min. (QC1) |
| Example-7-10 | INT-12-4-A | 3-chloro-2-(hydroxymethyl)pyrazine | A | 393.3 | 1.25 min. (QC1) |

TABLE 22-continued

| Examples | Boronic acid derivatives | halides | conditions | observed MS | tR/method |
|---|---|---|---|---|---|
| Example-7-11 | INT-12-4-A | 3-bromo-2-(hydroxymethyl)pyridine | A | 392.3 | 1.35 min. (QC1) |
| Example-7-12 | INT-12-4-A | 2-chloro-3-cyanopyridine | A | 387.2 | 1.48 min. (QC1) |

TABLE 22-continued

| Examples | Boronic acid derivatives | halides | conditions | observed MS | tR/method |
|---|---|---|---|---|---|
| Example-7-13 | INT-12-4-A | 3-bromo-2-aminopyridine | A | 377.2 | 1.41 min. (QC1) |
| Example-7-14 | INT-12-3-A | 3-chloro-2-methylpyrazine | A | 377.5 | 1.41 min. (QC1) |

TABLE 22-continued
Boronic acid derivatives

| Examples | Boronic acid derivatives | halides | conditions | observed MS | tR/method |
|---|---|---|---|---|---|
| Example-7-15 | INT-12-2-A | | A | 411.3 | 1.56 min. (QC1) |
| Example-7-16 | INT-12-2-A | | A | 415.3 | 1.35 min. (QC1) |

TABLE 22-continued

Boronic acid derivatives

| Examples | Boronic acid derivatives | halides | conditions | observed MS | tR/method |
|---|---|---|---|---|---|
| Example-7-17 | INT-12-2-A | | A | 414.3 | 1.55 min. (QC1) |
| Example-7-18 | INT-12-2-A | | A | 415.3 | 1.43 min. (QC1) |

TABLE 22-continued

| Examples | Boronic acid derivatives | halides | conditions | observed MS | tR/method |
|---|---|---|---|---|---|
| Example-7-19 | INT-12-2-A | 3-bromo-2-methylpyrazine | A | 400.3 | 1.49 min. (QC1) |
| Example-7-20 | INT-12-2-A | 3-bromo-2-cyanopyridine | A | 410.4 | 1.56 min. (QC1) |

TABLE 22-continued

| Examples | Boronic acid derivatives | halides | conditions | observed MS | tR/method |
|---|---|---|---|---|---|
| Example-7-21 | INT-12-7-A | | C | 416.1 | 1.51 min. (QC1) |
| Example-7-22 | INT-12-7-A | | C | 452.4 | 1.59 min. (QC1) |

TABLE 22-continued

| Examples | Boronic acid derivatives | halides | conditions | observed MS | tR/method |
|---|---|---|---|---|---|
| Example-7-23 | INT-12-4-A | 3-chloro-4-methylpyridazine | A | 379.7 | 1.31 min. (QC1) |
| Example-7-24 | INT-12-7-A | 2-bromopyridine | A | 401.1 | 1.72 min. (QC1) |

TABLE 22-continued

| Examples | Boronic acid derivatives | halides | conditions | observed MS | tR/method |
|---|---|---|---|---|---|
| Example-7-25 | INT-12-7-A | | A | 426.0 | 1.75 min. (QC1) |
| Example-7-26 | INT-12-7-A | | A | 402.1 | 1.67 min. (QC1) |

TABLE 22-continued

| Examples | Boronic acid derivatives | halides | conditions | observed MS | tR/method |
|---|---|---|---|---|---|
| Example-7-27 | INT-12-2-A | | A | 402.2 | 1.40 min. (QC1) |
| Example-7-28 | INT-12-2-A | | A | 418.2 | 1.33 min. (QC1) |

The following examples (8-1 to 8-9) are prepared according to the condition A to F in Table 19 from the aryl boronic acid derivative prepared in situ and the known or synthesized halide derivatives in Table 23. The further purification is carried out by preparative LC-MS system in the usual manner. The retention time and observed MS by HPLC-QC method are summarized in Table 23.

TABLE 23

| Examples | Boronic acid derivatives | halides | conditions | observed MS | tR/method |
|---|---|---|---|---|---|
| Example-8-1 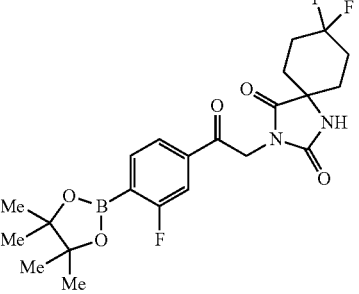 | 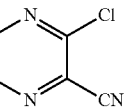 INT-12-5-A | 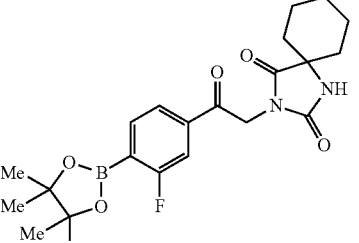 | A | 442.3 | 1.52 min. (QC1) |
| Example-8-2 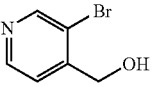 | 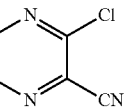 INT-12-5-A | 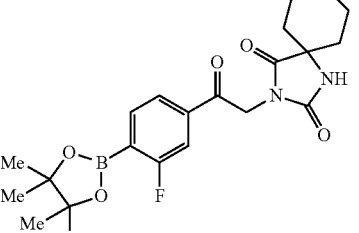 | A | 446.3 | 1.32 min. (QC1) |
| Example-8-3 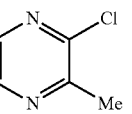 | 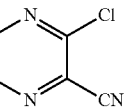 INT-12-5-A | 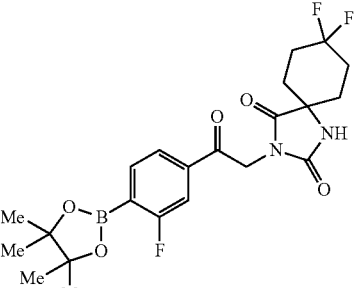 | A | 431.3 | 1.47 min. (QC1) |
| Example-8-4 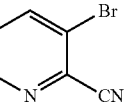 | 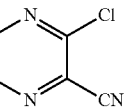 INT-12-5-A | 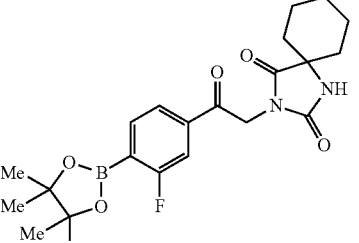 | A | 441.3 | 1.54 min. (QC1) |

TABLE 23-continued

| Examples | Boronic acid derivatives | halides | conditions | observed MS | tR/method |
|---|---|---|---|---|---|
| Example-8-5 | INT-12-5-A | 3-bromo-2-(hydroxymethyl)pyridine | A | 446.3 | 1.39 min. (QC1) |
| Example-8-6 | INT-12-5-A | 3-chloro-4-methylpyridazine | C | 433.8 | 1.37 min. (QC1) |
| Example-8-7 | INT-12-6-A | 3-chloro-4-methylpyridazine | C | 433.8 | 1.37 min. (QC1) |
| Example-8-8 | INT-12-6-A | 3-chloropyrazine-2-carbonitrile | C | 444.5 | 1.52 min. (QC1) |

TABLE 23-continued

| Examples | Boronic acid derivatives | halides | conditions | observed MS | tR/ method |
|---|---|---|---|---|---|
| Example-8-9 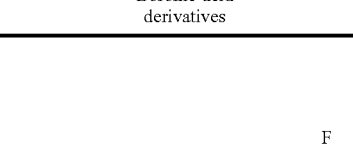 | 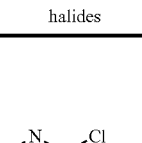 INT-12-6-A | 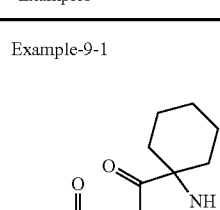 | C | 449.5 | 1.31 min. (QC1) |

The following examples (9-1 to 13-72) are prepared according to the condition A to F in Table 19 from the synthesized halide derivatives and the known or synthesized boronic acid derivatives in Table 24-28. (The boronic acid derivatives of example 9-22 to 9-27 are prepared in situ from the corresponding bromo derivatives.) The further purification is carried out by preparative LC-MS system in the usual manner. The retention time and observed MS by HPLC-QC method are summarized in Table 24-28.

TABLE 24

| Examples | halides | Bronic acid derivatives | conditions | observed MS | tR/ method |
|---|---|---|---|---|---|
| Example-9-1 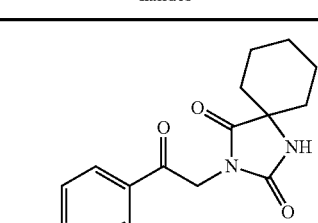 | 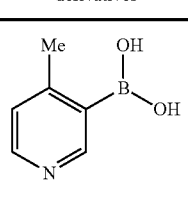 INT-8-3-A | 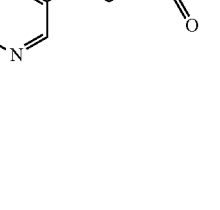 | A | 377.1 | 1.35 min. (QC1) |
| Example-9-2 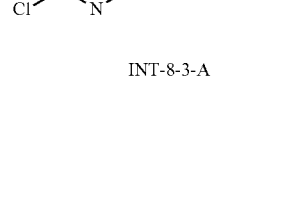 | INT-8-3-A |  | A | 376.2 | 1.65 min. (QC1) |

TABLE 24-continued
| Examples | halides | Bronic acid derivatives | conditions | observed MS | tR/method |
|---|---|---|---|---|---|
| Example-9-3 | 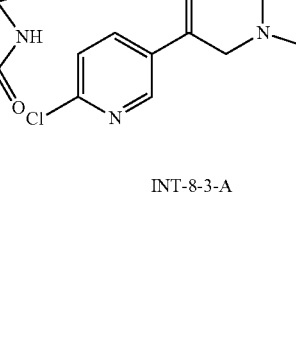<br>INT-8-3-A |  | A | 392.1 | 1.61 min. (QC1) |
| Example-9-4 | 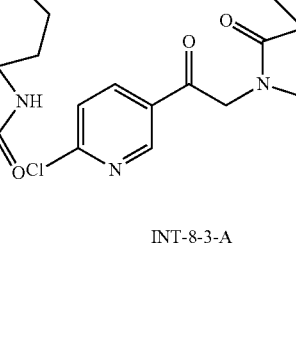<br>INT-8-3-A | 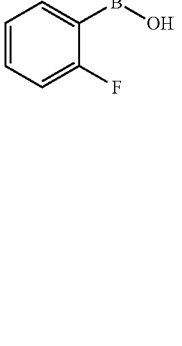 | A | 380.3 | 1.63 min. (QC1) |
| Example-9-5 | 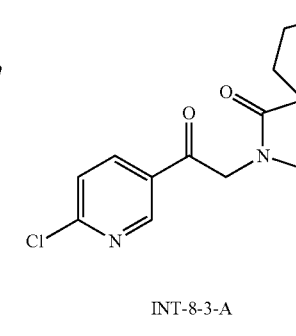<br>INT-8-3-A | 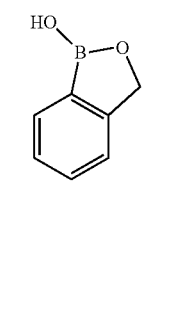 | A | 392.1 | 1.43 min. (QC1) |
|  | 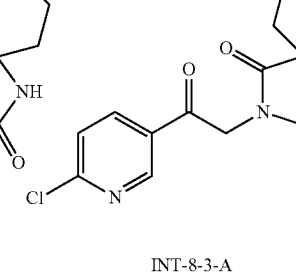<br>INT-8-3-A | 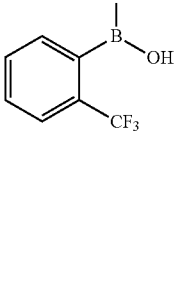 | A | 430.2 | 1.68 min. (QC1) |

TABLE 24-continued
| Examples | halides | | Bronic acid derivatives | conditions | observed MS | tR/method |
|---|---|---|---|---|---|---|
| | 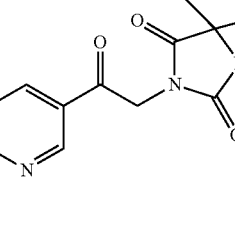 | 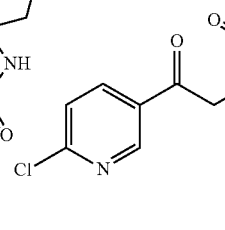 INT-8-3-A |  | A | 377.1 | 1.32 min. (QC1) |
| Example-9-8 |  | 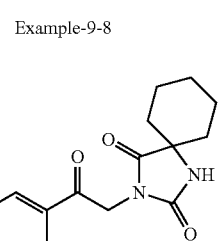 INT-8-3-A | 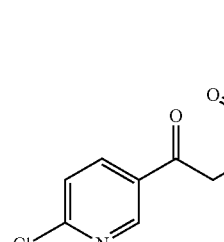 | A | 387.3 | 1.51 min. (QC1) |
| Example-9-9 | 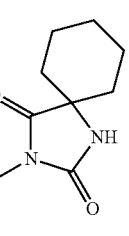 | 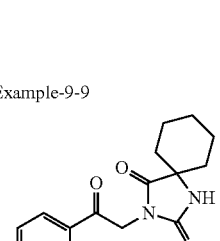 INT-8-3-A | 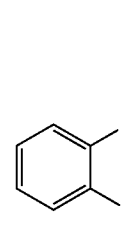 | A | 387.1 | 1.57 min. (QC1) |
| Example-9-10 | 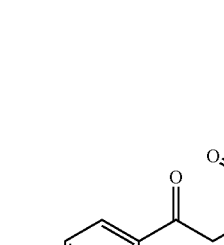 | 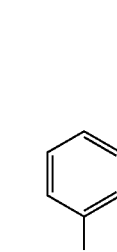 INT-8-1-A |  | A | 437.3 | 1.51 min. (QC1) |

TABLE 24-continued
| Examples | halides | Bronic acid derivatives | conditions | observed MS | tR/method |
|---|---|---|---|---|---|
| Example-9-11 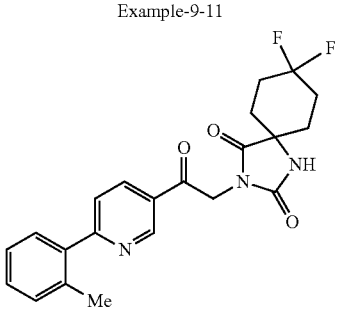 [SMILES: Cc1ccccc1-c1ccc(C(=O)CN2C(=O)NC3(CCC(F)(F)CC3)C2=O)cn1] | 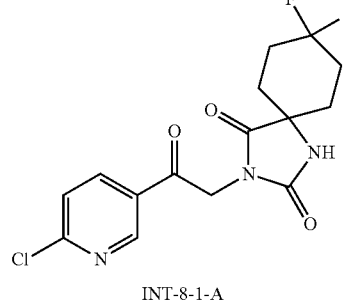 INT-8-1-A | 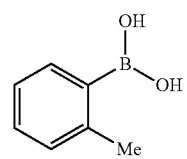 | A | 412.3 | 2.16 min. (QC2) |
| Example-9-12 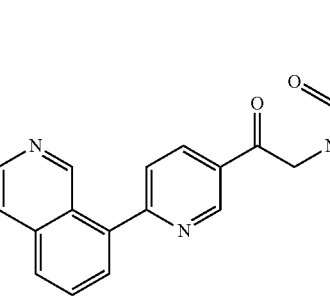 | 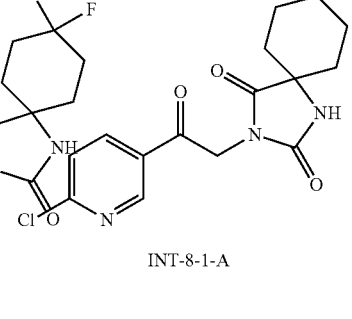 INT-8-1-A | 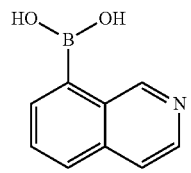 | A | 449.3 | 1.48 min. (QC1) |
| Example-9-13 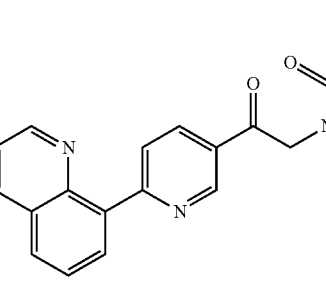 | 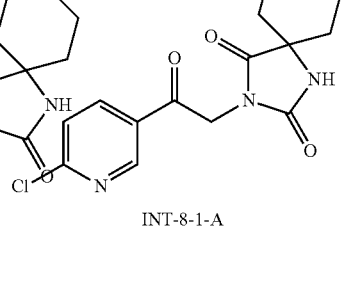 INT-8-1-A | 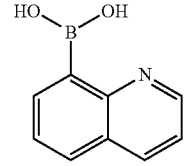 | A | 449.3 | 1.55 min. (QC1) |
| Example-9-14 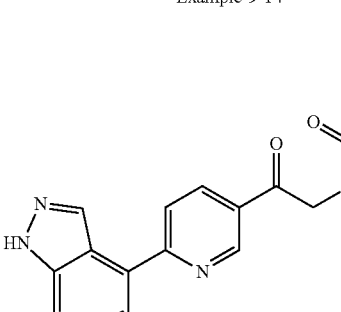 | 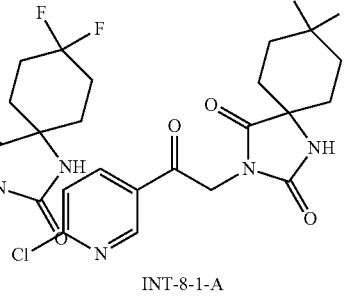 INT-8-1-A | 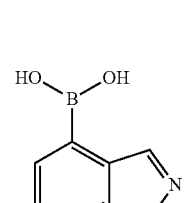 | A | 438.3 | 1.40 min. (QC1) |

TABLE 24-continued

| Examples | halides | Bronic acid derivatives | conditions | observed MS | tR/method |
|---|---|---|---|---|---|
| Example-9-15 | INT-8-1-A | | A | 413.3 | 1.34 min. (QC1) |
| Example-9-16 | INT-8-1-A | | A | 449.3 | 1.48 min. (QC1) |
| Example-9-17 | INT-8-1-A | | A | 428.3 | 1.44 min. (QC1) |
| Example-9-18 | INT-8-1-A | | A | 449.3 | 1.47 min. (QC1) |

TABLE 24-continued

| Examples | halides | Bronic acid derivatives | conditions | observed MS | tR/method |
|---|---|---|---|---|---|
| Example-9-19 | INT-8-1-A | | A | 453.3 | 1.37 min. (QC1) |
| Example-9-20 | INT-8-1-A | | A | 426.3 | 2.33 min. (QC2) |
| Example-9-21 | INT-8-1-A | | A | 449.3 | 1.44 min. (QC1) |
| Example-9-22 | INT-8-1-A | | A | 438.4 | 1.37 min. (QC1) |

TABLE 24-continued

| Examples | halides | Bronic acid derivatives | conditions | observed MS | tR/method |
|---|---|---|---|---|---|
| Example-9-23 | INT-8-1-A | | A | 438.4 | 1.30 min. (QC1) |
| Example-9-24 | INT-8-1-A | | A | 429.2 | 1.21 min. (QC1) |
| Example-9-25 | INT-8-1-A | | A | 429.3 | 1.26 min. (QC1) |
| Example-9-26 | INT-8-1-A | | A | 439.4 | 1.41 min. (QC1) |

TABLE 24-continued
| Examples | halides | Bronic acid derivatives | conditions | observed MS | tR/method |
|---|---|---|---|---|---|
| Example-9-27 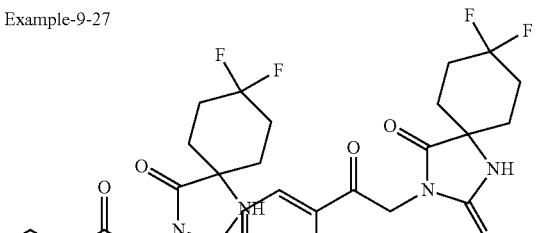 | 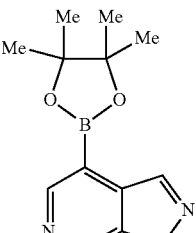 INT-8-1-A | 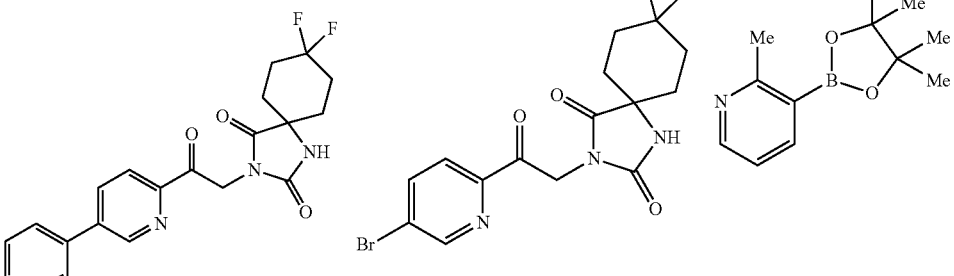 | A | 439.3 | 1.27 min. (QC1) |
TABLE 25
| Examples | halides | Bronic acid derivatives | conditions | observed MS | tR/method |
|---|---|---|---|---|---|
| Example-10-1 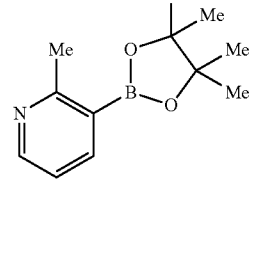 | 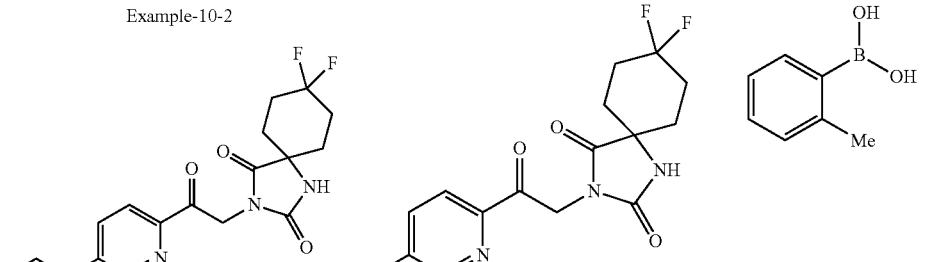 INT-8-2-A | 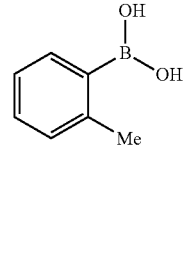 | A | 413.4 | 1.44 min. (QC1) |
| Example-10-2  |  INT-8-2-A |  | A | 412.3 | 1.80 min. (QC1) |

TABLE 26

| Examples | halides | Bronic acid derivatives | Conditions | Observed MS | tR/method |
|---|---|---|---|---|---|
| Example-11-1 | INT-8-4-A | | B | 401.3 | 1.53 min. (QC1) |
| Example-11-2 | INT-8-4-A | | A | 376.3 | 1.63 min. (QC1) |

TABLE 27

| Examples | halides | Bronic acid derivatives | condition | Observed MS | tR/method |
|---|---|---|---|---|---|
| Example-12-1 | INT-9-1-A | | C | 414.2 | 1.39 min. (QC1) |
| Example-12-2 | INT-9-1-A | | C | 413.2 | 1.73 min. (QC1) |

TABLE 27-continued

| Examples | halides | Bronic acid derivatives | condition | Observed MS | tR/method |
|---|---|---|---|---|---|
| Example-12-3 | INT-9-1-A | | A | 429.5 | 1.45 min. (QC1) |
| Example-12-4 | INT-9-1-A | | A | 430.5 | 1.62 min. (QC1) |
| | INT-9-1-A | | A | 430.5 | 1.37 min. (QC1) |
| | INT-9-1-A | | A | 450.5 | 1.65 min. (QC1) |

TABLE 27-continued
| Examples | halides | Bronic acid derivatives | condition | Observed MS | tR/method |
|---|---|---|---|---|---|
| 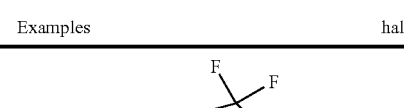 | 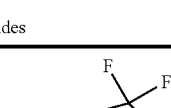\nINT-8-5-A | 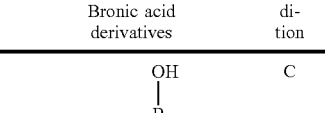 | C | 413.3 | 1.64 min. (QC1) |

TABLE 28
| Examples | halides | Bronic acid derivatives | Condition | Observed MS | tR/method |
|---|---|---|---|---|---|
| Example-13-1 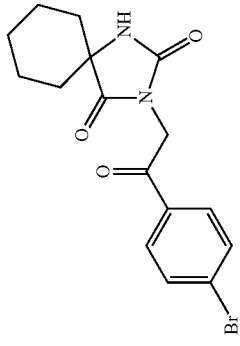 | INT-7-4-A 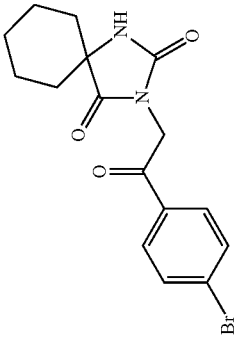 | 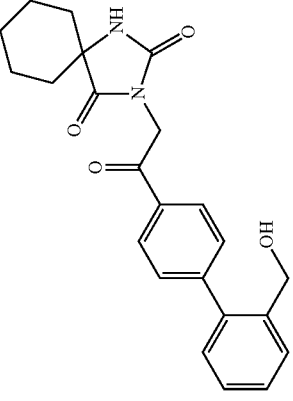 | A | 391.5 | 1.53 min. (QC1) |
| Example-13-2 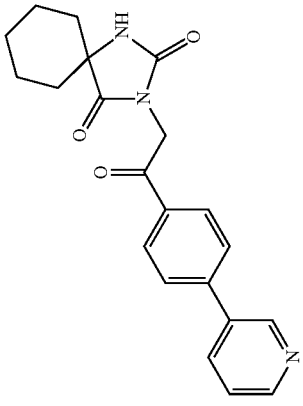 | INT-7-4-A | 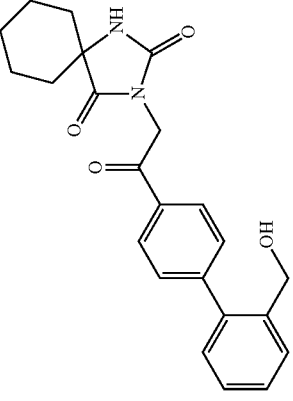 | D | 364.3 | 1.44 min. (QC1) |

TABLE 28-continued

| Examples | halides | Bronic acid derivatives | Condition | Observed MS | tR/method |
|---|---|---|---|---|---|
| Example-13-3 | INT-7-4-A | 2-methoxyphenylboronic acid | A | 391.5 | 1.77 min. (QC1) |
| Example-13-4 | INT-7-4-A | 2-methylphenylboronic acid | A | 375.5 | 1.85 min. (QC1) |

TABLE 28-continued
| Examples | halides | Bronic acid derivatives | Condition | Observed MS | tR/method |
|---|---|---|---|---|---|
| Example-13-5 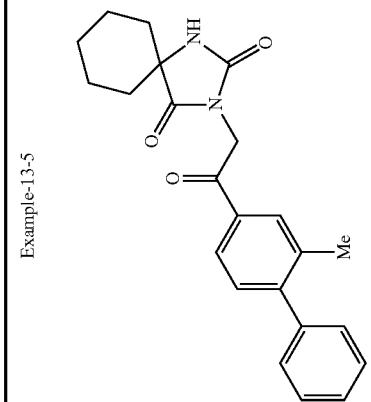 | 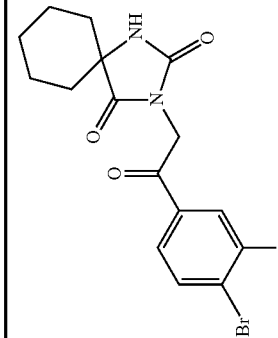 INT-7-2-A | 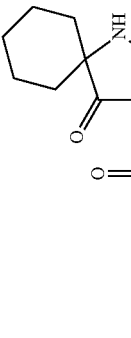 | D | 375.3 | 1.85 min. (QC1) |
| Example-13-6 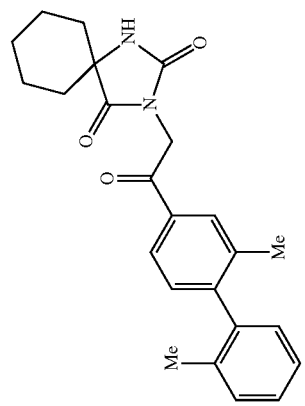 | 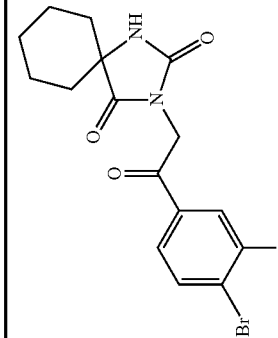 INT-7-2-A | 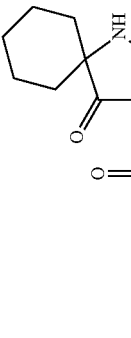 | A | 389.3 | 1.92 min. (QC1) |

TABLE 28-continued
| Examples | halides | Bronic acid derivatives | Condition | Observed MS | tR/method |
|---|---|---|---|---|---|
| Example-13-7 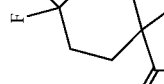 | INT-7-2-B 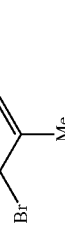 | 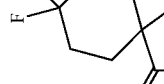 | B | 412.4 | 1.50 min. (QC1) |
| Example-13-8 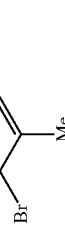 | INT-7-2-B  |  | B | 430.4 | 1.59 min. (QC1) |

TABLE 28-continued

| Examples | halides | Bronic acid derivatives | Condition | Observed MS | tR/method |
|---|---|---|---|---|---|
| Example-13-9 | INT-7-2-B | | B | 436.4 | 1.69 min. (QC1) |
| Example-13-10 | INT-7-2-B | | B | 466.4 | 1.44 min. (QC1) |

TABLE 28-continued

| Examples | halides | Bronic acid derivatives | Condition | Observed MS | tR/method |
|---|---|---|---|---|---|
| Example-13-11 | INT-7-2-B | | B | 436.4 | 1.71 min. (QC1) |
| Example-13-12 | INT-7-2-B | | B | 441.4 | 1.59 min. (QC1) |

TABLE 28-continued
| Examples | halides | Bronic acid derivatives | Condition | Observed MS | tR/method |
|---|---|---|---|---|---|
| Example-13-13 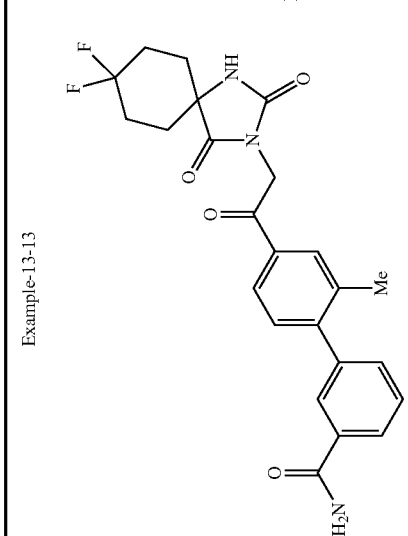 | INT-7-2-B 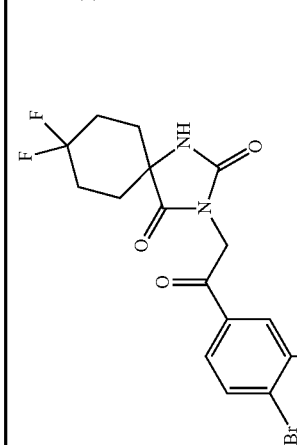 | 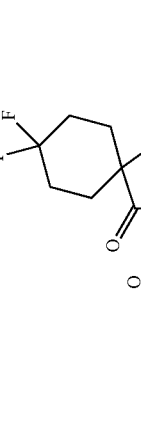 | B | 454.4 | 1.44 min. (QC1) |
| Example-13-14 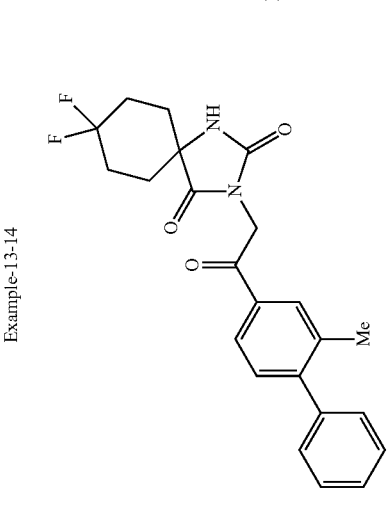 | INT-7-2-B | | B | 411.4 | 1.83 min. (QC1) |

TABLE 28-continued

| Examples | halides | Bronic acid derivatives | Condition | Observed MS | tR/method |
|---|---|---|---|---|---|
| Example-13-15 | INT-7-2-B | | B | 462.4 | 1.68 min. (QC1) |
| Example-13-16 | INT-7-2-B | | B | 447.4 | 1.86 min. (QC1) |

TABLE 28-continued

| Examples | halides | Bronic acid derivatives | Condition | Observed MS | tR/method |
|---|---|---|---|---|---|
| Example-13-17 | INT-7-2-B | | B | 429.4 | 1.83 min. (QC1) |
| Example-13-18 | INT-7-5-A | | D | 382.2 | 1.48 min. (QC1) |

TABLE 28-continued
| Examples | halides | Bronic acid derivatives | Condition | Observed MS | tR/method |
|---|---|---|---|---|---|
| Example-13-19 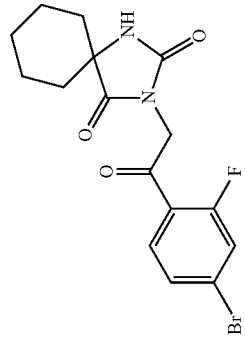 | 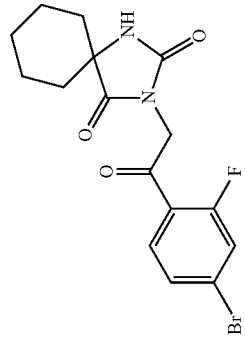 INT-7-5-A | 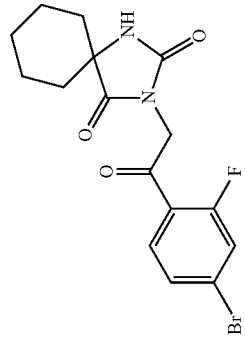 | D | 406.2 | 1.70 min. (QC1) |
| Example-13-20 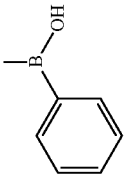 | 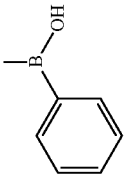 INT-7-5-A | 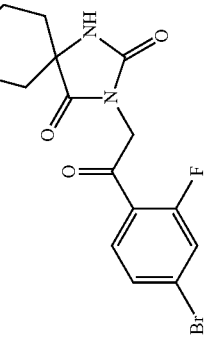 | D | 381.3 | 1.82 min. (QC1) |

TABLE 28-continued

| Examples | halides | Bronic acid derivatives | Condition | Observed MS | tR/method |
|---|---|---|---|---|---|
| Example-13-21 | INT-7-6-A | | A | 466.3 | 1.70 min. (QC1) |
| Example-13-22 | INT-7-6-A | | A | 466.3 | 1.61 min. (QC1) |

TABLE 28-continued

| Examples | halides | Bronic acid derivatives | Condition | Observed MS | tR/method |
|---|---|---|---|---|---|
| Example-13-23 | INT-7-3-A | | B | 446.2 | 1.58 min. (QC1) |
| Example-13-24 | INT-7-3-A | | B | 432.2 | 1.53 min. (QC1) |

TABLE 28-continued

| Examples | halides | Bronic acid derivatives | Condition | Observed MS | tR/method |
|---|---|---|---|---|---|
| Example-13-25 | INT-7-3-A | | B | 456.2 | 1.70 min. (QC1) |
| Example-13-26 | INT-7-3-A | | B | 450.1 | 1.63 min. (QC1) |

TABLE 28-continued
| Examples | halides | Boronic acid derivatives | Condition | Observed MS | tR/method |
|---|---|---|---|---|---|
| Example-13-27 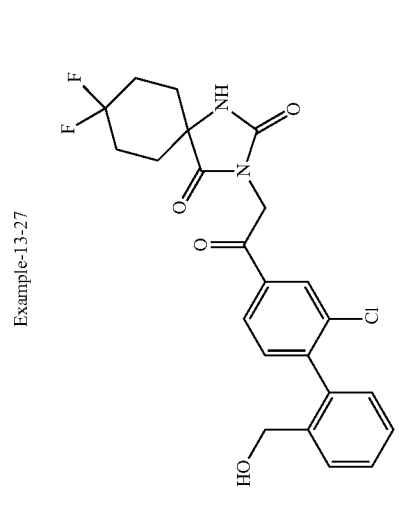 | INT-7-3-A 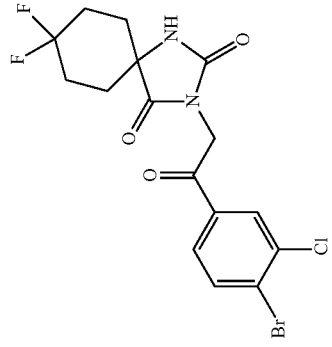 | 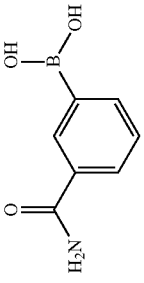 | B | 461.2 | 1.60 min. (QC1) |
| Example-13-28 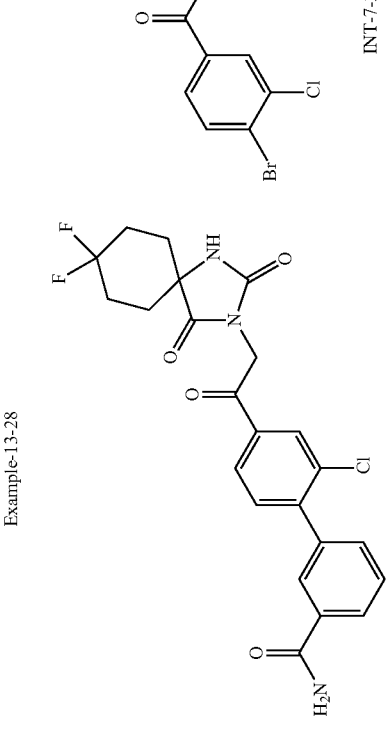 | INT-7-3-A | | B | 474.2 | 1.46 min. (QC1) |

TABLE 28-continued

| Examples | halides | Bronic acid derivatives | Condition | Observed MS | tR/method |
|---|---|---|---|---|---|
| Example-13-29 | INT-7-3-A | | B | 482.2 | 1.68 min. (QC1) |
| Example-13-30 | INT-7-7-A | | B | 448.4 | 1.56 min. (QC1) |

TABLE 28-continued

| Examples | halides | Bronic acid derivatives | Condition | Observed MS | tR/method |
|---|---|---|---|---|---|
| Example-13-31 | INT-7-7-A | | B | 458.5 | 1.68 min. (QC1) |
| Example-13-32 | INT-7-7-A | | B | 463.1 | 1.58 min. (QC1) |

TABLE 28-continued

| Examples | halides | Bronic acid derivatives | Condition | Observed MS | tR/method |
|---|---|---|---|---|---|
| Example-13-33 | INT-7-7-A | 3-cyanophenylboronic acid | B | 458 | 1.69 min. (QC1) |
| Example-13-34 | INT-7-1-A | benzo[c][1,2]oxaborol-1(3H)-ol | A | 427.2 | 1.54 min. (QC1) |

TABLE 28-continued

| Examples | halides | Boronic acid derivatives | Condition | Observed MS | tR/method |
|---|---|---|---|---|---|
| Example-13-35 | INT-7-1-A | | A | 412.3 | 1.50 min. (QC1) |
| Example-13-36 | INT-7-1-A | | A | 448.4 | 1.62 min. (QC1) |

TABLE 28-continued

| Examples | halides | Bronic acid derivatives | Condition | Observed MS | tR/method |
|---|---|---|---|---|---|
| Example-13-37 | INT-7-1-A | | A | 448.3 | 1.62 min. (QC1) |
| Example-13-38 | INT-7-1-A | | A | 412.3 | 1.48 min. (QC1) |

TABLE 28-continued
| Examples | halides | Bronic acid derivatives | Condition | Observed MS | tR/method |
|---|---|---|---|---|---|
| Example-13-39 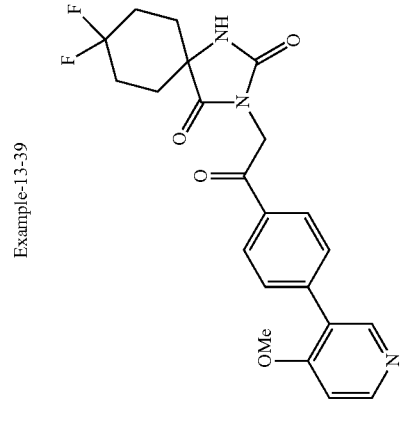 | INT-7-1-A 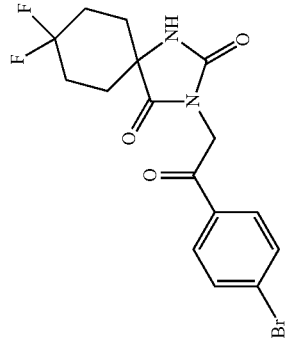 | 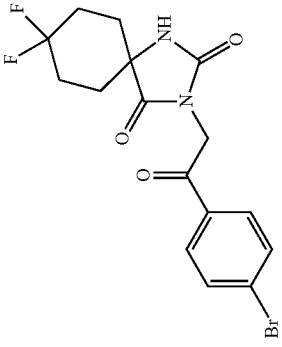 | A | 428.3 | 1.44 min. (QC1) |
| Example-13-40 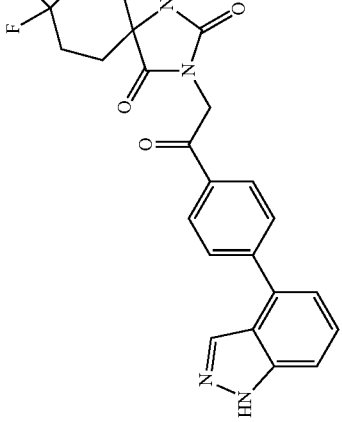 | INT-7-1-A 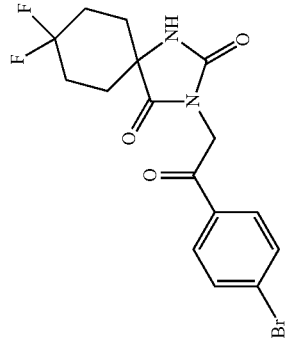 | 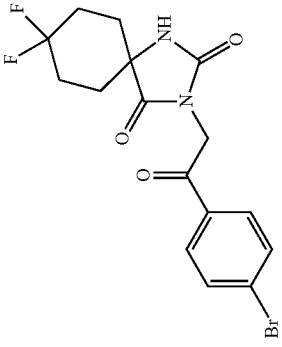 | A | 437.3 | 1.51 min. (QC1) |

TABLE 28-continued

| Examples | halides | Boronic acid derivatives | Condition | Observed MS | tR/method |
|---|---|---|---|---|---|
| Example-13-41 | INT-7-1-A | | A | 448.3 | 1.60 min. (QC1) |
| Example-13-42 | INT-7-1-A | | A | 436.3 | 1.63 min. (QC1) |

TABLE 28-continued

| Examples | halides | Bronic acid derivatives | Condition | Observed MS | tR/method |
|---|---|---|---|---|---|
| Example-13-43 | INT-7-1-A | quinolin-4-yl boronic acid | A | 448.3 | 1.61 min. (QC1) |
| Example-13-44 | INT-7-1-A | 4-(4,4,5,5-tetramethyl-1,3,2-dioxaborolan-2-yl)indolin-2-one | A | 452.3 | 1.45 min. (QC1) |

TABLE 28-continued

| Examples | halides | Bronic acid derivatives | Condition | Observed MS | tR/method |
|---|---|---|---|---|---|
| Example-13-45 | INT-7-1-A | 2-methoxypyridin-3-yl boronic acid | A | 428.3 | 1.66 min. (QC1) |
| Example-13-46 | INT-7-1-A | quinolin-8-yl boronic acid | A | 448.3 | 1.71 min. (QC1) |

TABLE 28-continued

| Examples | halides | Bronic acid derivatives | Condition | Observed MS | tR/method |
|---|---|---|---|---|---|
| Example-13-47 | INT-7-1-A | | A | 448.3 | 1.71 min. (QC1) |
| Example 13-48 | INT-7-1-A | | A | 398.4 | 1.44 min. (QC1) |

TABLE 28-continued

| Examples | halides | Bronic acid derivatives | Condition | Observed MS | tR/method |
|---|---|---|---|---|---|
| Example 13-49 | INT-7-1-A | | F | 398.4 | 1.54 min. (QC1) |
| Example 13-50 | INT-7-1-A | | A | 456.3 | 1.46 min. (QC1) |

TABLE 28-continued

| Examples | halides | Bronic acid derivatives | Condition | Observed MS | tR/method |
|---|---|---|---|---|---|
| Example 13-51 | INT-13-1-A | | A | 363.2 | 1.62 min. (QC1) |
| Example 13-52 | INT-13-1-A | | A | 378.3 | 1.66 min. (QC1) |

TABLE 28-continued

| Examples | halides | Boronic acid derivatives | Condition | Observed MS | tR/method |
|---|---|---|---|---|---|
| Example 13-53 | INT-12-2-2 | | A | 399.3 | 1.55 min. (QC1) |
| Example 13-54 | INT-12-2-2 | | A | 423.4 | 1.70 min. (QC1) |

TABLE 28-continued

| Examples | halides | Bronic acid derivatives | Condition | Observed MS | tR/method |
|---|---|---|---|---|---|
| Example 13-55 | INT-12-2-2 | | A | 414.2 | 1.59 min. (QC1) |
| Example 13-56 | INT-12-2-2 | | A | 399.3 | 1.54 min. (QC1) |

TABLE 28-continued

| Examples | halides | Bronic acid derivatives | Condition | Observed MS | tR/method |
|---|---|---|---|---|---|
| Example 13-57 | INT-12-2-2 | | A | 435.4 | 1.76 min. (QC1) |
| Example 13-58 | INT-13-2-A | | A | 430.4 | 1.64 min. (QC1) |

TABLE 28-continued

| Examples | halides | Boronic acid derivatives | Condition | Observed MS | tR/method |
|---|---|---|---|---|---|
| Example 13-59 | INT-13-2-A | | A | 415.4 | 1.60 min. (QC1) |
| Example 13-60 | INT-13-2-A | | A | 415.3 | 1.61 min. (QC1) |

TABLE 28-continued

| Examples | halides | Bronic acid derivatives | Condition | Observed MS | tR/method |
|---|---|---|---|---|---|
| Example 13-61 | INT-13-3-A | | A | 444.2 | 1.67 min. (QC1) |
| Example 13-62 | INT-13-3-A | | A | 429.1 | 1.63 min. (QC1) |

TABLE 28-continued

| Examples | halides | Boronic acid derivatives | Condition | Observed MS | tR/method |
|---|---|---|---|---|---|
| Example 13-63 | INT-13-3-A | | A | 429.1 | 1.63 min. (QC1) |
| Example 13-64 | INT-13-4-A | | A | 458.1 | 1.77 min. (QC1) |

TABLE 28-continued
| Examples | halides | Bronic acid derivatives | Condition | Observed MS | tR/method |
|---|---|---|---|---|---|
| Example 13-65 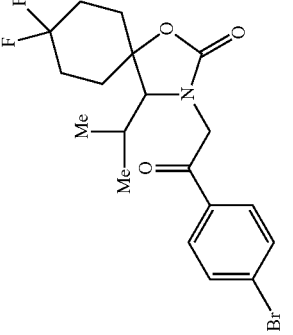 | 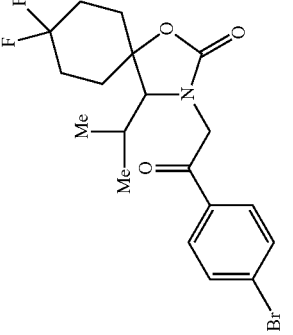 INT-13-4-A | 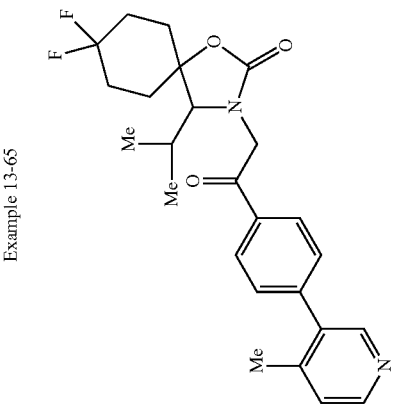 | A | 443.2 | 1.74 min. (QC1) |
| Example 13-66 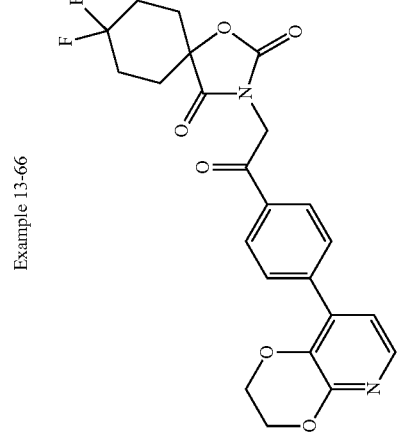 | 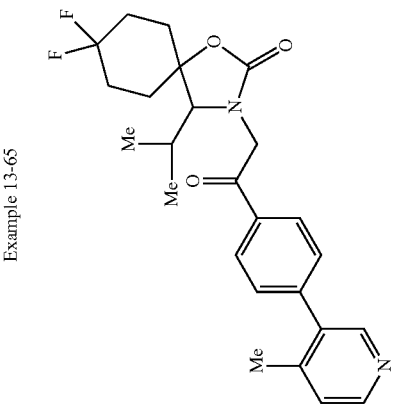 INT-7-16-A | 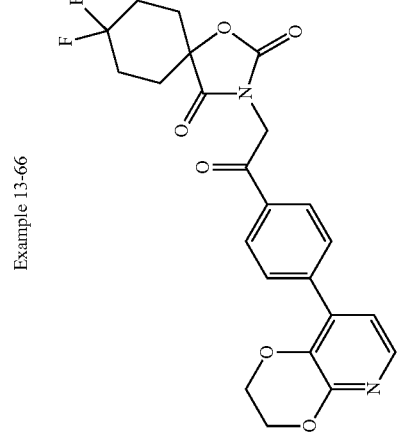 | E | 459.3 | 1.63 min. (QC1) |

TABLE 28-continued
| Examples | halides | Bronic acid derivatives | Condition | Observed MS | tR/method |
|---|---|---|---|---|---|
| Example 13-67 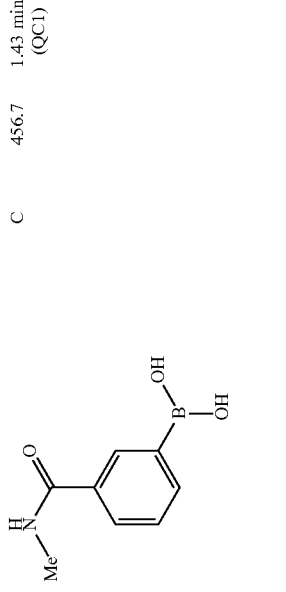 | 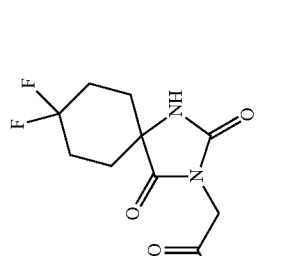 INT-7-1-A | 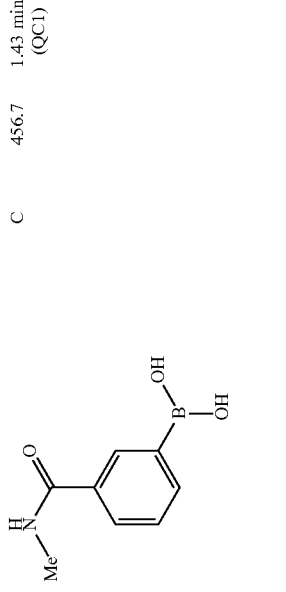 | C | 456.7 | 1.43 min. (QC1) |
| Example 13-68 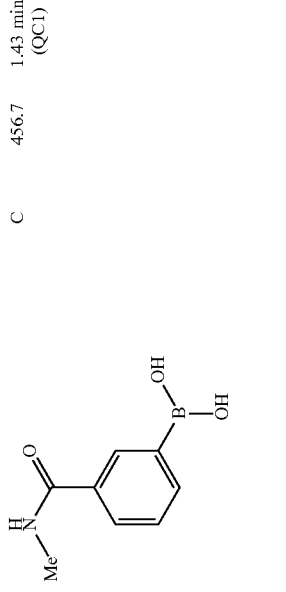 | 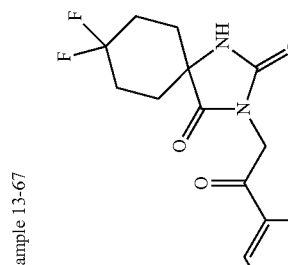 INT-7-3-A | 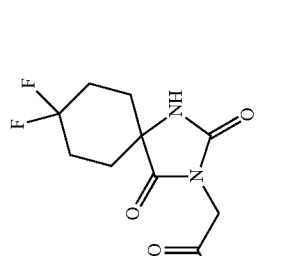 | B | 458.1 | 1.73 min. (QC1) |

TABLE 28-continued
| Examples | halides | Bronic acid derivatives | Condition | Observed MS | tR/method |
|---|---|---|---|---|---|
| Example 13-69 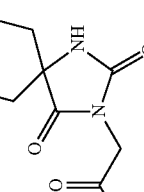 | 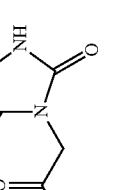 INT-7-19-A | 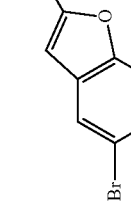 | A | 440.2 | 1.50 min. (QC1) |
| Example 13-70 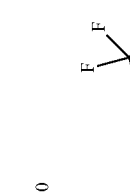 | 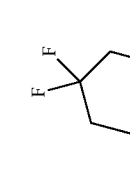 INT-7-1-A |  | B | 430.7 | 1.74 min. (QC1) |

TABLE 28-continued

| Examples | halides | Bronic acid derivatives | Condition | Observed MS | tR/method |
|---|---|---|---|---|---|
| Example 13-71 | INT-7-16-A | | A | 430.2 | 1.70 min. (QC1) |
| Example 13-72 | INT-7-16-A | | A | 415.1 | 1.66 min. (QC1) |

The following examples (14-1 to 18-13) are prepared according to the condition A to F in Table 19 from the synthesized halide derivatives and the known or synthesized boronic acid derivatives in Table 29-33 (The boronic acid derivative of example-14-6 is prepared in situ from the corresponding bromo derivatives). The further purification is carried out by preparative LC-MS system in the usual manner. The retention time and observed MS by HPLC-QC method are summarized in Table 29-33.

TABLE 29

| Examples | halides | Bronic acid derivatives | conditions | observed MS | tR/method |
|---|---|---|---|---|---|
| Example-14-1 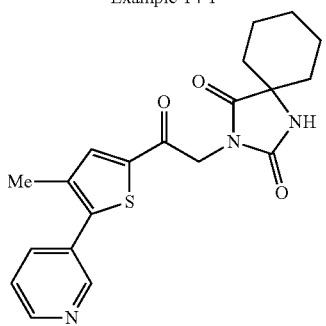 | 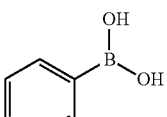 INT-7-8-B | 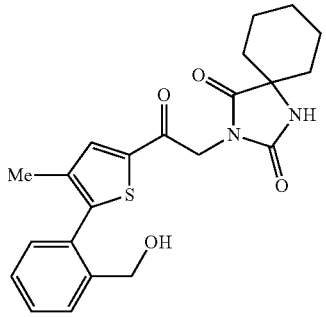 [SMILES: Cc1cc(C(=O)CN2C(=O)NC3(CCCCC3)C2=O)sc1-c1ccccc1CO] | D | 382.3 | 1.50 min. (QC1) |
| Example-14-2 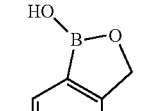 | 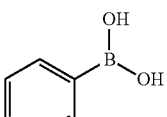 INT-7-8-B | 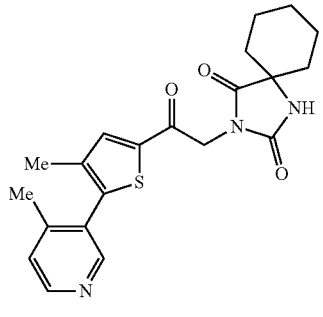 [SMILES: Cc1ccncc1-c1sc(C(=O)CN2C(=O)NC3(CCCCC3)C2=O)cc1C] | B | 411.3 | 1.58 min. (QC1) |
| Example-14-3 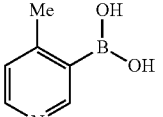 | 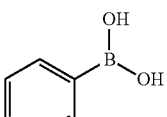 INT-7-8-B | 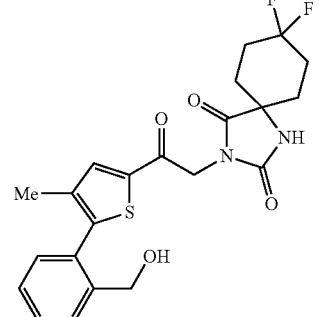 | B | 396.2 | 1.54 min. (QC1) |
| Example-14-4 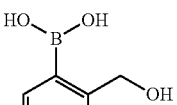 | 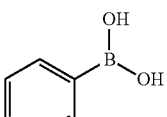 INT-7-8-A | 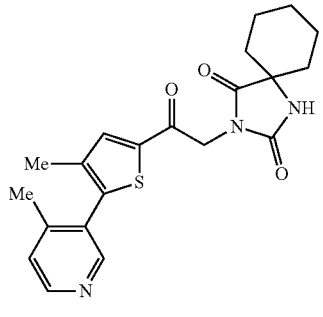 [SMILES: Cc1ccncc1-c1sc(C(=O)CN2C(=O)NC3(CCCCC3)C2=O)cc1C] | B | 447.2 | 1.58 min. (QC1) |

TABLE 29-continued
| Examples | halides | Bronic acid derivatives | conditions | observed MS | tR/method |
|---|---|---|---|---|---|
| Example-14-5 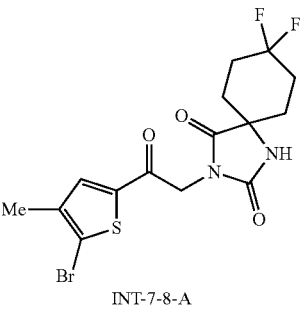 | 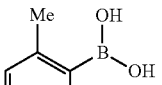 INT-7-8-A | | A | 432.3 | 1.55 min. (QC1) |
| Example-14-6 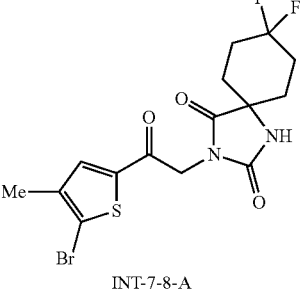 | 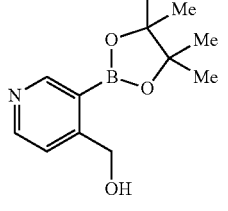 INT-7-8-A | | A | 448.3 | 1.33 min. (QC1) |
| Example-14-7 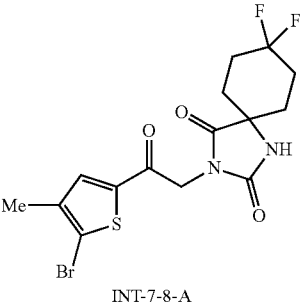 | 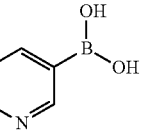 INT-7-8-A | | A | 418.2 | 1.50 min. (QC1) |
| Example-14-8 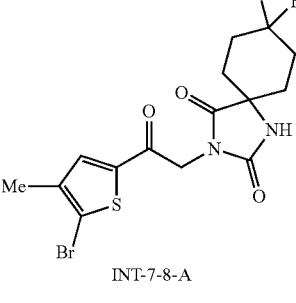 | 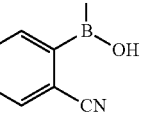 INT-7-8-A | | A | 442.3 | 1.70 min. (QC1) |

TABLE 29-continued

| Examples | halides | Bronic acid derivatives | conditions | observed MS | tR/method |
|---|---|---|---|---|---|
| Example-14-9 | INT-7-8-A | 2-methylpyridine-3-boronic acid pinacol ester | A | 432.3 | 1.54 min. (QC1) |
| Example-14-10 | INT-7-8-A | 3-cyanophenylboronic acid | B | 442.3 | 1.70 min. (QC1) |
| Example-14-11 | INT-7-8-A | 2-methylphenylboronic acid | B | 431.2 | 1.89 min. (QC1) |
| Example-14-12 | INT-7-8-A | 2-methoxyphenylboronic acid | A | 447.2 | 1.79 min. (QC1) |

TABLE 29-continued

| Examples | halides | Bronic acid derivatives | conditions | observed MS | tR/method |
|---|---|---|---|---|---|
| Example-14-13 | INT-7-8-A | 5-cyanopyridin-3-yl boronic acid | B | 443.3 | 1.55 min. (QC1) |
| Example-14-14 | INT-7-8-A | 2-chlorophenyl boronic acid | A | 451.3 | 1.87 min. (QC1) |
| Example-14-15 | INT-7-8-A | 4-(trifluoromethyl)pyridin-3-yl boronic acid | A | 486.3 | 1.66 min. (QC1) |
| Example-14-16 | INT-7-8-A | 4-methoxypyridin-3-yl boronic acid | A | 448.3 | 1.47 min. (QC1) |

TABLE 29-continued

| Examples | halides | Bronic acid derivatives | conditions | observed MS | tR/method |
| --- | --- | --- | --- | --- | --- |
| Example-14-17 | INT-7-8-A | | B | 436.4 | 1.59 min. (QC1) |
| Example-14-18 | INT-7-8-A | | B | 460.4 | 1.42 min. (QC1) |
| Example-14-19 | INT-7-8-A | | A | 450.1 | 1.41 min. (QC1) |
| Example-14-20 | INT-7-8-A | | A | 470.1 | 1.73 min. (QC1) |

TABLE 29-continued

| Examples | halides | Bronic acid derivatives | conditions | observed MS | tR/method |
|---|---|---|---|---|---|
| Example-14-21 | INT-7-8-A | | B | 449.0 | 1.55 min. (QC1) |

TABLE 30

| Examples | halides | Bronic acid derivatives | conditions | observed MS | tR/method |
|---|---|---|---|---|---|
| Example-15-1 | INT-7-9-A | | B | 456.2 | 1.74 min. (QC1) |
| Example-15-2 | INT-7-9-A | | A | 432.3 | 1.54 min. (QC1) |
| Example-15-3 | INT-7-9-A | | B | 456.3 | 1.75 min. (QC1) |

TABLE 30-continued
| Examples | halides | Bronic acid derivatives | conditions | observed MS | tR/method |
|---|---|---|---|---|---|
| Example-15-4 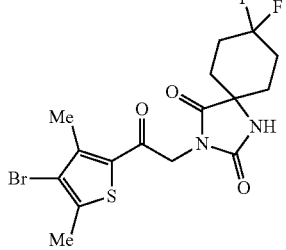 | 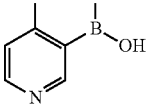 INT-7-9-A | 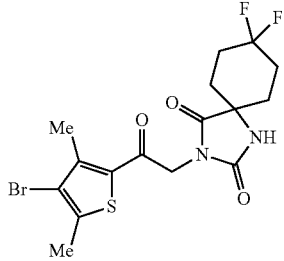 [SMILES: Cc1sc(C(=O)CN2C(=O)NC3(CCC(F)(F)CC3)C2=O)c(C)c1Br] | B | 446.3 | 1.58 min. (QC1) |
| Example-15-5 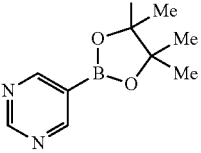 | 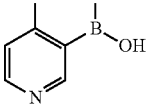 INT-7-9-A | 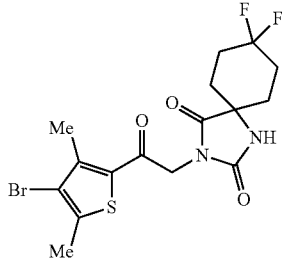 [SMILES: Cc1sc(C(=O)CN2C(=O)NC3(CCC(F)(F)CC3)C2=O)c(C)c1Br] | B | 433.3 | 1.44 min. (QC1) |
| Example-15-6 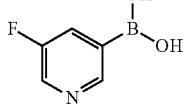 | 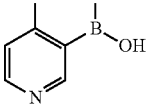 INT-7-9-A | 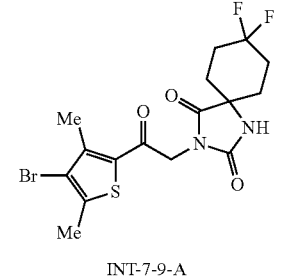 | B | 450.4 | 1.62 min. (QC1) |
| Example-15-7 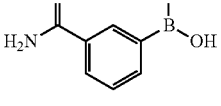 | 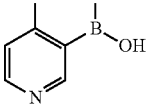 INT-7-9-A | 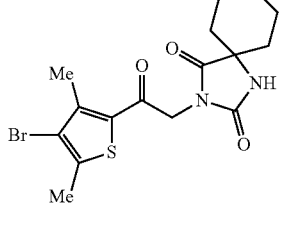 | B | 474.5 | 1.48 min. (QC1) |
| Example-15-8 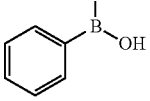 | 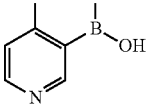 |  | A | 433.1 | 1.88 min. (QC1) |

TABLE 30-continued

| Examples | halides | Bronic acid derivatives | conditions | observed MS | tR/method |
|---|---|---|---|---|---|
| Example-15-9 | INT-7-9-A | 2-methylphenylboronic acid | B | 447.2 | 1.94 min. (QC1) |
| Example-15-10 | INT-7-9-A | 5-(pinacolboronate)nicotinamide | B | 477.2 | 1.32 min. (QC1) |
| Example-15-11 | INT-7-9-A | 3-methylphenylboronic acid | A | 447.1 | 1.96 min. (QC1) |
| Example-15-12 | INT-7-9-A | 3-(hydroxymethyl)phenylboronic acid | B | 463.1 | 1.60 min. (QC1) |

TABLE 31

| Examples | halides | Bronic acid derivatives | conditions | observed MS | tR/ method |
|---|---|---|---|---|---|
| Example-16-1 | INT-7-10-A | | A | 425.3 | 1.63 min. (QC1) |
| Example-16-2 | INT-7-10-A | | A | 415.4 | 1.47 min. (QC1) |
| Example-16-3 | INT-7-10-A | | A | 401.4 | 1.41 min. (QC1) |
| Example-16-4 | INT-7-11-A | | B | 439.4 | 1.69 min. (QC1) |
| Example-16-5 | INT-7-11-A | | B | 432.3 | 1.81 min. (QC1) |

TABLE 31-continued

| Examples | halides | Bronic acid derivatives | conditions | observed MS | tR/method |
|---|---|---|---|---|---|
| Example-16-6 | INT-7-11-A | | B | 457.3 | 1.42 min. (QC1) |
| Example-16-7 | INT-7-11-A | | B | 439.3 | 1.69 min. (QC1) |
| Example-16-8 | INT-7-11-A | | B | 444.3 | 1.60 min. (QC1) |
| Example-16-9 | INT-7-11-A | | B | 450.3 | 1.84 min. (QC1) |
| Example-16-10 | INT-7-11-A | | B | 429.4 | 1.53 min. (QC1) |

TABLE 31-continued

| Examples | halides | Bronic acid derivatives | conditions | observed MS | tR/ method |
|---|---|---|---|---|---|
| Example-16-11 | INT-7-11-A | pyridin-3-yl boronic acid | B | 415.4 | 1.48 min. (QC1) |
| Example-16-12 | INT-7-11-A | 3-chlorophenyl boronic acid | B | 448.3 | 1.90 min. (QC1) |
| Example-16-13 | INT-7-11-A | 2-fluorophenyl boronic acid | B | 432.3 | 1.80 min. (QC1) |
| Example-16-14 | INT-7-11-A | 3-methoxyphenyl boronic acid | B | 444.4 | 1.80 min. (QC1) |
| Example-16-15 | INT-7-11-A | isoquinolin-8-yl boronic acid | B | 465.3 | 1.64 min. (QC1) |

TABLE 31-continued
| Examples | halides | Bronic acid derivatives | conditions | observed MS | tR/ method |
|---|---|---|---|---|---|
| Example-16-16 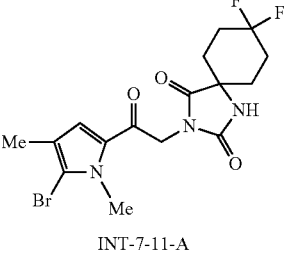 | 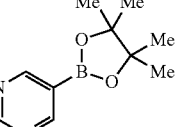 INT-7-11-A | 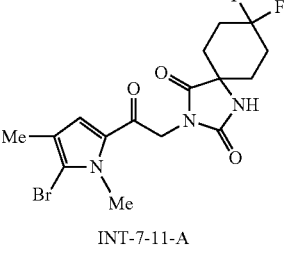 | B | 416.3 | 1.40 min. (QC1) |
| Example-16-17 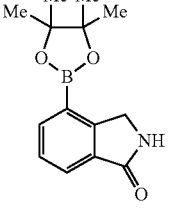 | 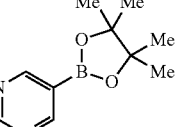 INT-7-11-A | 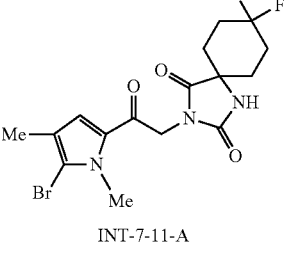 | B | 469.4 | 1.43 min. (QC1) |
| Example-16-18 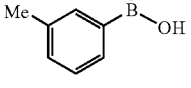 | 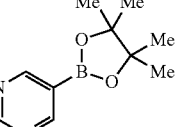 INT-7-11-A | 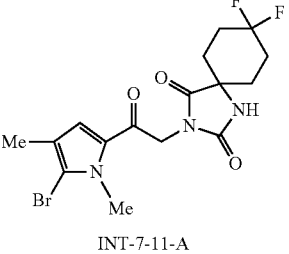 | B | 428.4 | 1.89 min. (QC1) |
| Example-16-19 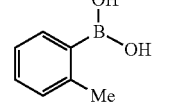 | 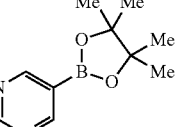 INT-7-11-A | 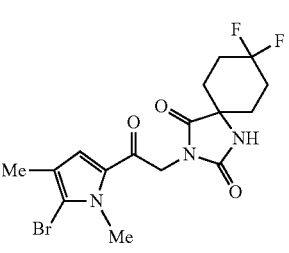 | B | 428.3 | 1.89 min. (QC1) |
| Example-16-20 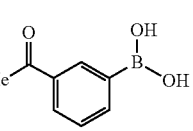 | 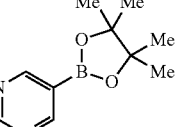 INT-7-11-A |  | B | 456.4 | 1.69 min. (QC1) |

TABLE 31-continued
| Examples | halides | Bronic acid derivatives | conditions | observed MS | tR/ method |
|---|---|---|---|---|---|
| Example-16-21 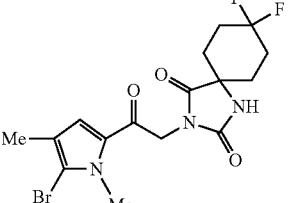 | 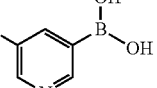 INT-7-11-A | 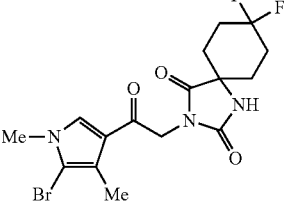 | B | 433.4 | 1.57 min. (QC1) |
| Example-16-22 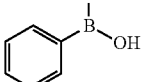 | 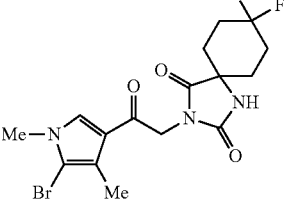 INT-7-12-A | 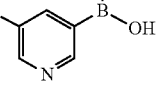 | B | 439.5 | 1.60 min. (QC1) |
| Example-16-23 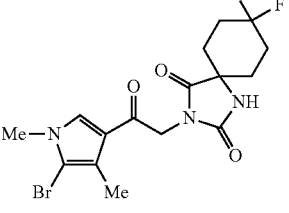 | 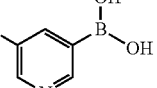 INT-7-12-A | 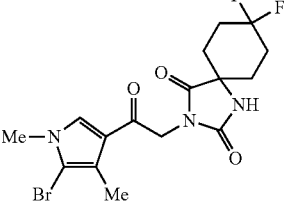 | B | 433.6 | 1.48 min. (QC1) |
| Example-16-24 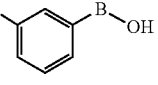 | 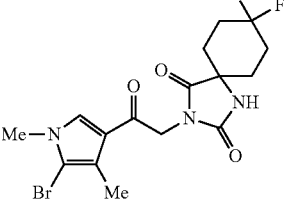 INT-7-12-A | 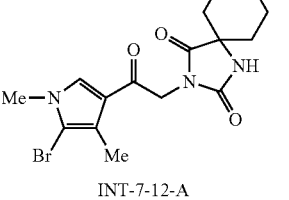 | B | 432.7 | 1.70 min. (QC1) |
| Example-16-25 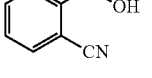 | 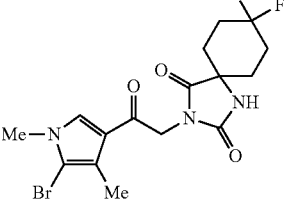 INT-7-12-A | 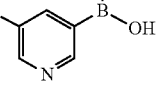 | B | 439.6 | 1.58 min. (QC1) |

TABLE 31-continued

| Examples | halides | Bronic acid derivatives | conditions | observed MS | tR/method |
|---|---|---|---|---|---|
| Example-16-26 | INT-7-12-A | | B | 415.6 | 1.39 min. (QC1) |
| Example-16-27 | INT-7-12-A | | B | 465.3 | 1.55 min. (QC1) |
| Example-16-28 | INT-7-12-A | | B | 429.3 | 1.41 min. (QC1) |
| Example-16-29 | INT-7-10-A | | B | 427.1 | 1.63 min. (QC1) |
| Example-16-30 | INT-7-10-A | | A | 432.2 | 1.50 min. (QC1) |

TABLE 31-continued
| Examples | halides | Bronic acid derivatives | conditions | observed MS | tR/method |
|---|---|---|---|---|---|
| Example-16-31 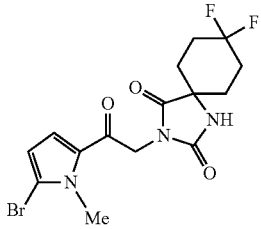 | 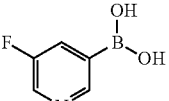 INT-7-10-A | 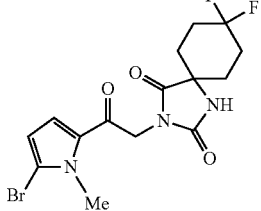 | B | 421.1 | 1.50 min. (QC1) |
| Example-16-32 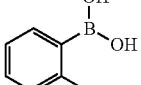 | 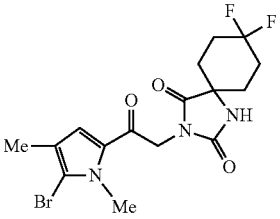 INT-7-10-A | 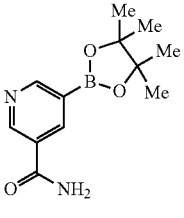 [SMILES: CC1(C)OB(c2cncc(C(N)=O)c2)OC1(C)C] | A | 416.2 | 1.80 min. (QC1) |
| Example-16-33 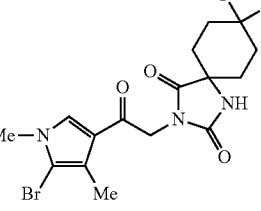 | 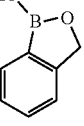 INT-7-11-A | 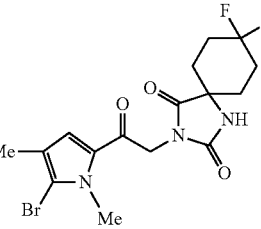 | B | 460.3 | 1.28 min. (QC1) |
| Example-16-34 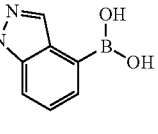 | INT-7-12-A | | B | 446.4 | 1.48 min. (QC1) |
| Example-16-35 | INT-7-11-A | | B | 456.0 | 1.54 min. (QC1) |

457 458
TABLE 31-continued
| Examples | halides | Bronic acid derivatives | conditions | observed MS | tR/ method |
|---|---|---|---|---|---|
| Example-16-36 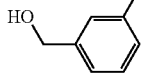 | 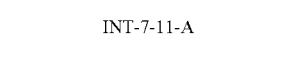 INT-7-11-A | 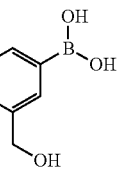 | B | 446.1 | 1.53 min. (QC1) |
TABLE 32
| Examples | halides | Bronic acid derivatives | conditions | observed MS | tR/ method |
|---|---|---|---|---|---|
| Example-17-1 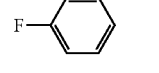 | 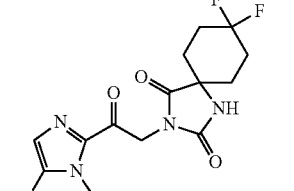 INT-7-15-A | 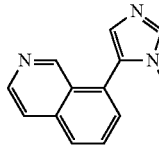 | C | 419.3 | 1.64 min. (QC1) |
| Example-17-2 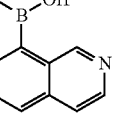 | 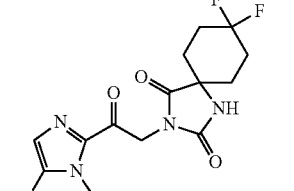 INT-7-15-A | 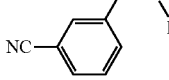 | A | 452.4 | 1.48 min. (QC1) |
| Example-17-3 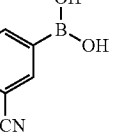 | 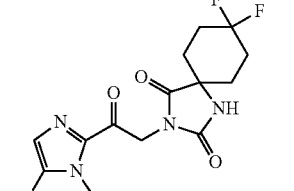 INT-7-15-A | 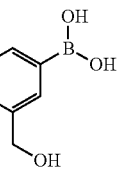 | C | 426.4 | 1.53 min. (QC1) |

TABLE 32-continued
| Examples | halides | Bronic acid derivatives | conditions | observed MS | tR/method |
|---|---|---|---|---|---|
| Example-17-4 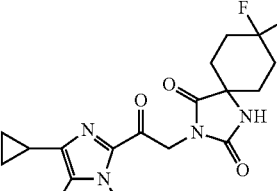 | 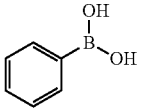<br>INT-7-14-A | 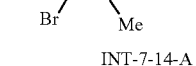 | C | 441.4 | 1.84 min. (QC1) |
| Example-17-5 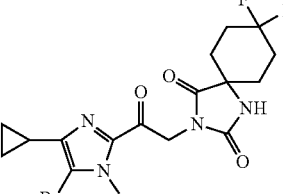 | 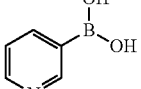<br>INT-7-14-A | 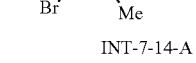 | C | 442.4 | 1.53 min. (QC1) |
| Example-17-6 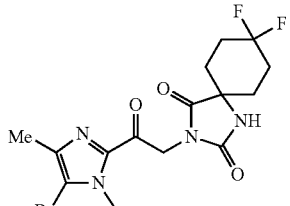 | 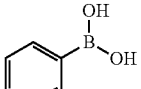<br>INT-7-13-A |  | C | 433.4 | 1.67 min. (QC1) |
| Example-17-7 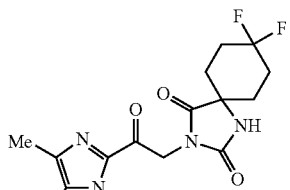 | 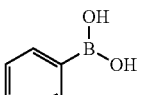<br>INT-7-13-A | 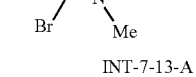 | C | 415.4 | 1.65 min. (QC1) |
| Example-17-8 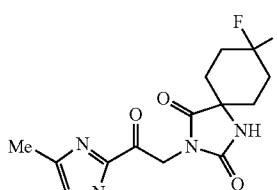 | 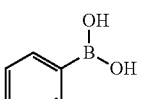<br>INT-7-13-A | 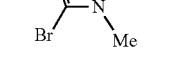 | C | 440.4 | 1.56 min. (QC1) |

TABLE 32-continued

| Examples | halides | Bronic acid derivatives | conditions | observed MS | tR/method |
|---|---|---|---|---|---|
| Example-17-9 | INT-7-13-A | isoquinolin-8-yl boronic acid | C | 466.4 | 1.50 min. (QC1) |
| Example-17-10 | INT-7-13-A | (2-(hydroxymethyl)phenyl)boronic acid | C | 445.4 | 1.44 min. (QC1) |
| Example-17-11 | INT-7-13-A | (3,5-difluorophenyl)boronic acid | C | 451.4 | 1.70 min. (QC1) |
| Example-17-12 | INT-7-13-A | pyridin-3-ylboronic acid | C | 418.1 | 1.35 min. (QC1) |
| Example-17-13 | INT-7-13-A | (2-methylpyridin-3-yl)boronic acid | C | 432.2 | 1.38 min. (QC1) |

TABLE 32-continued
| Examples | halides | Bronic acid derivatives | conditions | observed MS | tR/ method |
|---|---|---|---|---|---|
| Example-17-14 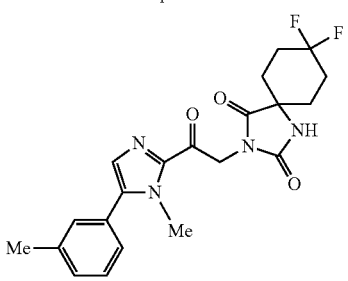 | INT-7-15-A 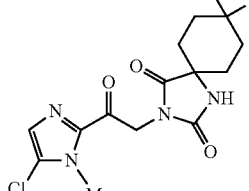 | 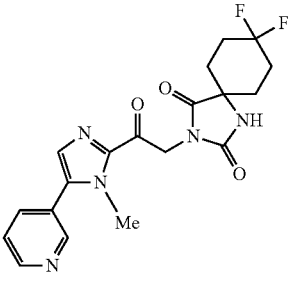 | C | 417.1 | 1.71 min. (QC1) |
| Example-17-15 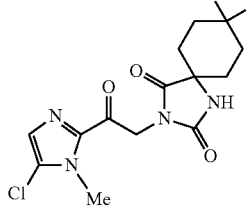 | INT-7-15-A 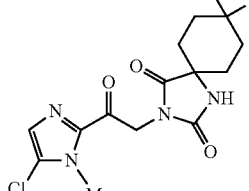 | 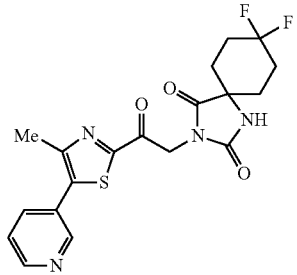 | C | 404.1 | 1.32 min. (QC1) |
TABLE 33
| Examples | halides | Bronic acid derivatives | conditions | observed MS | tR/ method |
|---|---|---|---|---|---|
| Example-18-1 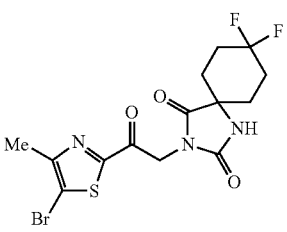 | INT-9-2-A 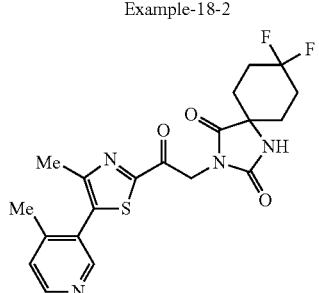 | 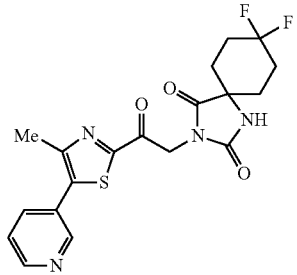 | B | 419.3 | 1.49 min. (QC1) |
| Example-18-2 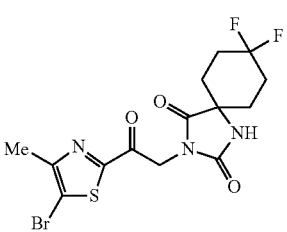 | INT-9-2-A 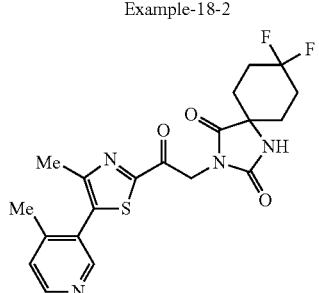 | 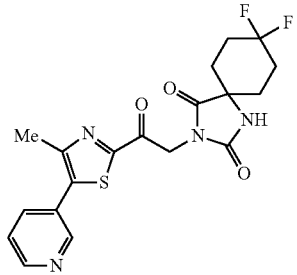 | B | 433.3 | 1.52 min. (QC1) |

TABLE 33-continued

| Examples | halides | Bronic acid derivatives | conditions | observed MS | tR/method |
|---|---|---|---|---|---|
| Example-18-3 | INT-9-2-A | | B | 443.2 | 1.68 min. (QC1) |
| Example-18-4 | INT-9-2-A | | B | 448.3 | 1.56 min. (QC1) |
| Example-18-5 | INT-9-2-A | | B | 436.3 | 1.81 min. (QC1) |
| Example-18-6 | INT-9-2-A | | B | 443.2 | 1.66 min. (QC1) |
| Example-18-7 | INT-9-2-A | | B | 461.3 | 1.41 min. (QC1) |

TABLE 33-continued

| Examples | halides | Bronic acid derivatives | conditions | observed MS | tR/ method |
|---|---|---|---|---|---|
| Example-18-8 | INT-9-2-A | | B | 433.3 | 1.51 min. (QC1) |
| Example-18-9 | INT-9-2-A | | B | 437.3 | 1.57 min. (QC1) |
| Example-18-10 | INT-9-2-A | | B | 469.2 | 1.64 min. (QC1) |
| Example-18-11 | INT-9-2-A | | B | 454.2 | 1.84 min. (QC1) |
| Example-18-12 | INT-9-2-A | | B | 473.2 | 1.41 min. (QC1) |

TABLE 33-continued

| Examples | halides | Bronic acid derivatives | conditions | observed MS | tR/ method |
|---|---|---|---|---|---|
| Example-18-13 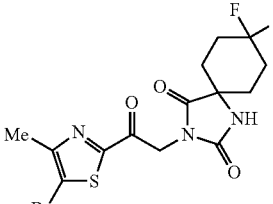 | INT-9-2-A 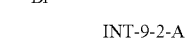 | 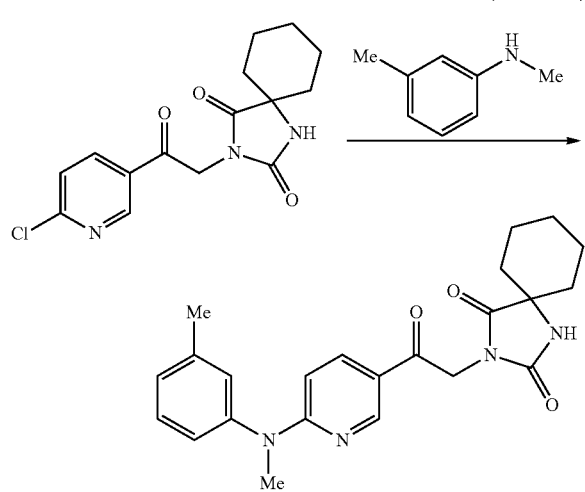 | B | 446.1 | 1.52 min. (QC1) |

Example 19-1: 3-(2-(6-(methyl(m-tolyl)amino)pyridin-3-yl)-2-oxoethyl)-1,3-diazaspiro[4.5]decane-2,4-dione {Chem. 137}

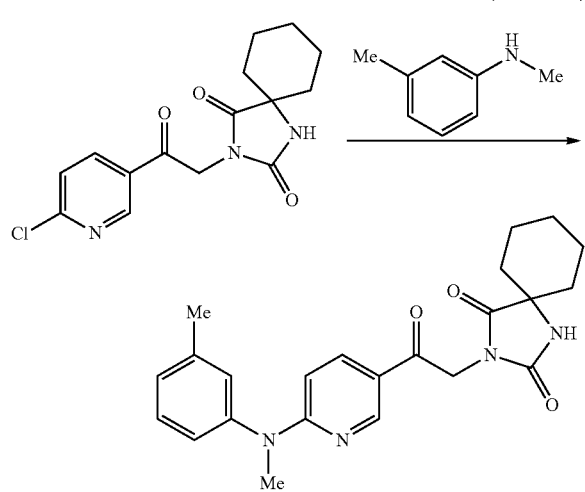

Condition-A

To a solution of INT-8-3-A (30 mg, 0.093 mmol) in DME (1 mL) is added N-Methyl-m-toluidine (12 mg, 0.103 mmol), potassium tert-butoxide (16 mg, 0.140 mmol) and Pd-PEPPSI(trademark)-IPr (1.3 mg, 1.86 mmol). The mixture is irradiated in a microwave reactor (Biotage Initiator) for 30 min. at 140° C. (or heated at 100-150° C. for 3-15 h in oil bath). The mixture is quenched with water and filtered through a pad of celite. The filter cake is washed with EtOAc and the filtrate and washings are washed with brine, dried over sodium sulfate, filtered, and concentrated in vacuo. The residue is purified by column chromatography on silica gel with 10-100% EtOAc in hexane to give the titled compound (13 mg, 34% yield). The further purification is carried out by preparative LC-MS system in the usual manner.

Observed MS: 405.4 tR/method: 1.76 min./(QC1)

Other than the above condition A, the following conditions (B-I) are also summarized in Table 34.

TABLE 34

| Conditions | Catalyst | Ligand | Base | Solvent | Times/ Temperature |
|---|---|---|---|---|---|
| A | Pd-PEPPSI (trademark)-IPr | | KO t-Bu | DME | 30 min/140° C. |
| B | Pd(OAc)$_2$ | racemic-BINAP | Cs$_2$CO$_3$ | 1,4-dioxane | 20 min/120° C. |
| C | Pd$_2$(dba)$_3$ | DavePhos | K$_3$PO$_4$ | 1,4-dioxane | 30 min/140° C. |
| D | Pd$_2$(dba)$_3$ | Xantphos | K$_3$PO$_4$ | 1,4-dioxane | 20 min/140° C. |
| E | Pd$_2$(dba)$_3$ | DavePhos | NaO t-Bu | 1,4-dioxane | 30 min/140° C. |
| F | Pd(OAc)$_2$ | XPhos | NaO t-Bu | 1,4-dioxane-tert-BuOH | 30 min/120° C. |
| G | | | Cs$_2$CO$_3$ | DMSO | 60 min/rt |
| H | | | K$_2$CO$_3$ | DMF | 24 h/100-120° C. |
| I | | | Cs$_2$CO$_3$ | NMP | 50 min/160° C. |

The following examples (19-2 to 19-40) are prepared according to the condition A to I in Table 34 from the synthesized halide derivatives and the known or synthesized amine derivatives in Table 35. The further purification is carried out by preparative LC-MS system in the usual manner. The retention time and observed MS by HPLC-QC method are summarized in Table 35.

TABLE 35

| Examples | halides | Amines | conditions | observed MS | tR/method |
|---|---|---|---|---|---|
| Example-19-2 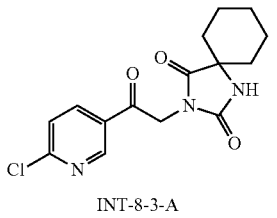 [SMILES: O=C(CN1C(=O)NC2(CCCCC2)C1=O)c1ccc(Cl)nc1] | INT-8-3-A 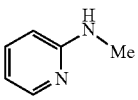 | 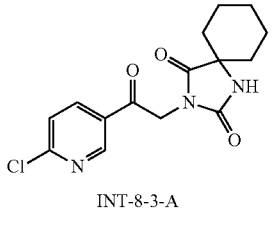 [SMILES: O=C(CN1C(=O)NC2(CCCCC2)C1=O)c1ccc(Cl)nc1] | A | 392.3 | 1.79 min. (QC2) |
| Example-19-3 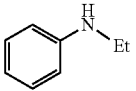 | INT-8-3-A | 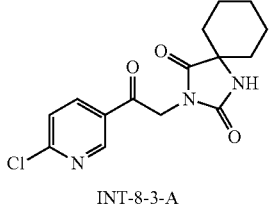 [SMILES: O=C(CN1C(=O)NC2(CCCCC2)C1=O)c1ccc(Cl)nc1] | A | 405.4 | 1.76 min. (QC1) |
| Example-19-4 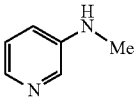 | INT-8-3-A | 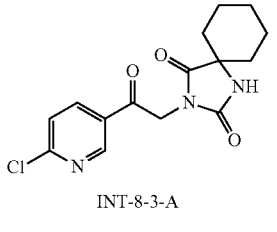 [SMILES: O=C(CN1C(=O)NC2(CCCCC2)C1=O)c1ccc(Cl)nc1] | A | 392.3 | 1.71 min. (QC2) |
| Example-19-5 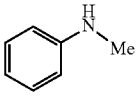 | INT-8-3-A | 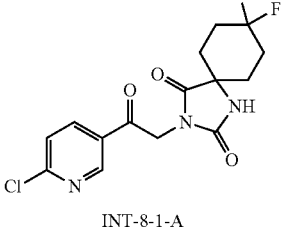 | B | 391.3 | 1.66 min. (QC1) |
| Example-19-6 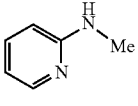 | INT-8-1-A | | A | 428.3 | 1.45 min. (QC1) |

TABLE 35-continued
| Examples | halides | Amines | conditions | observed MS | tR/ method |
|---|---|---|---|---|---|
| Example-19-7 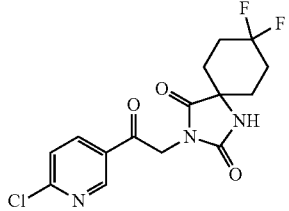 | 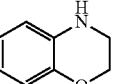 INT-8-1-A | 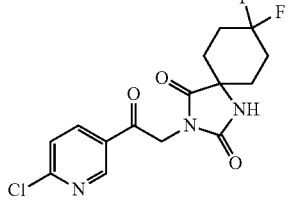 | A | 455.3 | 1.68 min. (QC1) |
| Example-19-8 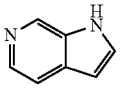 | 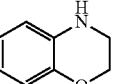 INT-8-1-A | 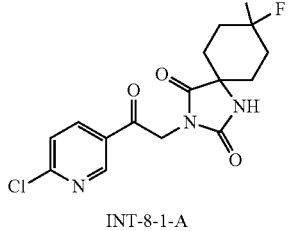 | C | 438.4 | 1.44 min. (QC1) |
| Example-19-9 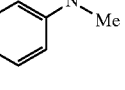 | 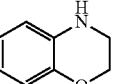 INT-8-1-A | 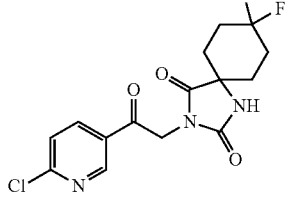 | A | 427.3 | 1.67 min. (QC1) |
| Example-19-10 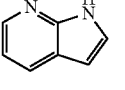 | 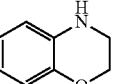 INT-8-1-A | 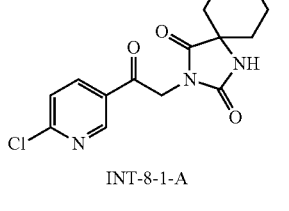 | C | 438.4 | 1.75 min. (QC1) |
| Example-19-11 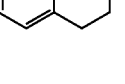 | 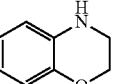 INT-8-1-A | 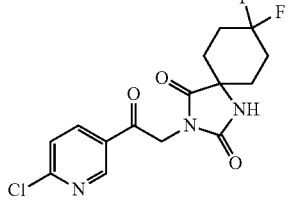 | A | 453.3 | 2.38 min. (QC2) |

TABLE 35-continued
| Examples | halides | Amines | conditions | observed MS | tR/ method |
|---|---|---|---|---|---|
| Example-19-12 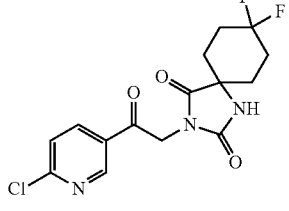 | 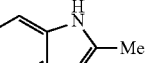 INT-8-1-A | 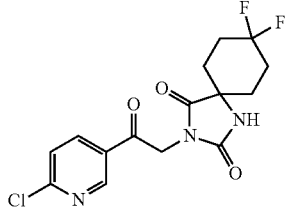 | C | 451.4 | 1.79 min. (QC1) |
| Example-19-13 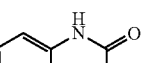 | 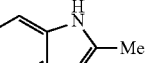 INT-8-1-A | 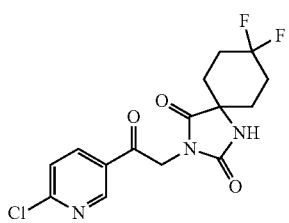 | D | 469.4 | 1.51 min. (QC1) |
| Example-19-14 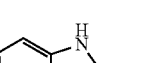 | 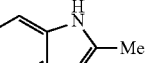 INT-8-1-A | 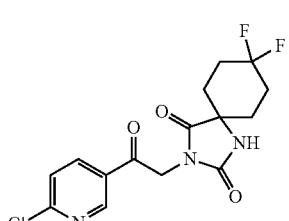 | A | 455.2 | 1.67 min. (QC1) |
| Example-19-15 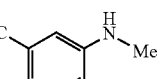 | 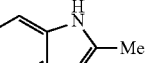 INT-8-1-A | 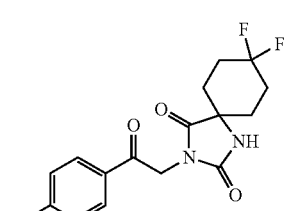 | A | 495.2 | 2.43 min. (QC2) |
| Example-19-16 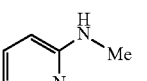 | 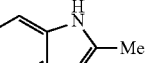 INT-7-1-A | 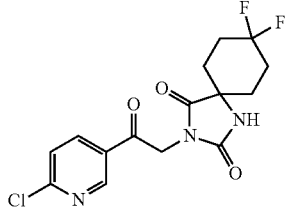 | F | 427.3 | 1.59 min. (QC1) |

TABLE 35-continued

| Examples | halides | Amines | conditions | observed MS | tR/ method |
|---|---|---|---|---|---|
| Example-19-17 | INT-7-1-A | | E | 437.3 | 1.71 min. (QC1) |
| Example-19-18 | INT-7-1-A | | E | 436.3 | 1.84 min. (QC1) |
| Example-19-19 | INT-7-1-A | | E | 450.4 | 1.88 min. (QC1) |
| Example-19-20 | INT-7-1-A | | A | 454.4 | 1.75 min. (QC1) |
| Example-19-21 | INT-7-1-A | | D | 468.4 | 1.60 min. (QC1) |

TABLE 35-continued

| Examples | halides | Amines | conditions | observed MS | tR/ method |
|---|---|---|---|---|---|
| Example-19-22 | INT-7-1-A | | D | 453.5 | 1.47 min. (QC1) |
| Example-19-23 | INT-7-1-A | | D | 467.5 | 1.58 min. (QC1) |
| Example-19-24 | INT-9-1-A | | G | 439.4 | 1.52 min. (QC1) |
| Example-19-25 | INT-9-1-A | | D | 470.4 | 1.58 min. (QC1) |
| Example-19-26 | INT-7-1-A | | D | 454.4 | 1.58 min. (QC1) |

TABLE 35-continued
| Examples | halides | Amines | conditions | observed MS | tR/method |
|---|---|---|---|---|---|
| Example-19-27 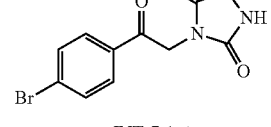 | INT-7-1-A |  | D | 468.4 | 1.60 min. (QC1) |
| Example-19-28 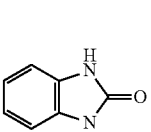 | INT-7-1-A | 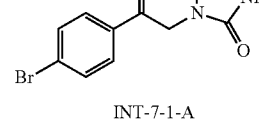 | D | 497.4 | 1.73 min. (QC1) |
| Example-19-29  | INT-7-1-A |  | D | 482.1 | 1.65 min. (QC1) |
| Example-19-30 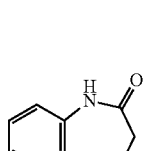 | INT-7-1-A | | D | 456.4 | 1.62 min. (QC1) |
| Example-19-31  | INT-7-1-A | | D | 456.2 | 2.09 min. (QC2) |

TABLE 35-continued
| Examples | halides | Amines | conditions | observed MS | tR/ method |
|---|---|---|---|---|---|
| Example-19-32 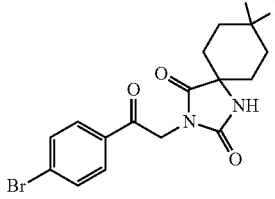 | 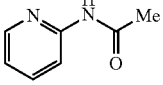 INT-7-1-A | 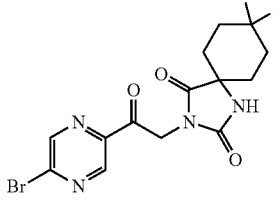 | D | 457.2 | 1.79 min. (QC2) |
| Example-19-33 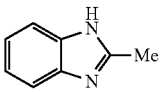 | 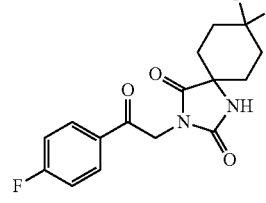 INT-9-1-A | 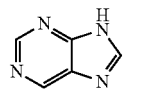 | D | 455.4 | 1.49 min. (QC1) |
| Example-19-34 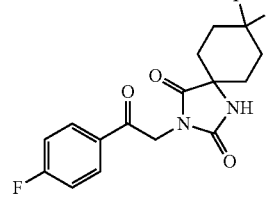 | 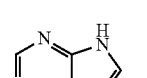 INT-7-17-A | 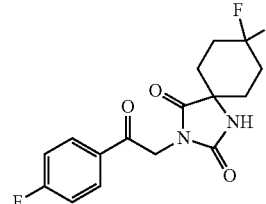 | H | 441.0 | 1.29 min. (QC1) |
| Example-19-35 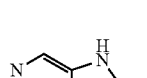 | INT-7-17-A | | H | 441.0 | 1.21 min. (QC1) |
| Example-19-36 | INT-7-17-A | | H | 441.2 | 1.53 min. (QC2) |

TABLE 35-continued

| Examples | halides | Amines | conditions | observed MS | tR/ method |
|---|---|---|---|---|---|
| Example-19-37 | INT-7-17-A | | H | 441.2 | 1.74 min. (QC2) |
| Example-19-38 | INT-7-17-A | | I | 454.6 | 1.33 min. (QC1) |
| Example-19-39 | INT-7-17-A | | H | 455.7 | 1.29 min. (QC1) |
| Example-19-40 | INT-7-1-A | | D | 466.2 | 2.50 min. (QC2) |

Example-19-41: 3-(2-(4-(3,5-dimethyl-1H-pyrazol-1-yl)phenyl)-2-oxoethyl)-8,8-difluoro-1,3-diazaspiro[4.5]decane-2,4-dione

Example-20-1: 3-(2-(6-(3-chlorophenoxy)pyridin-3-yl)-2-oxoethyl)-1,3-diazaspiro[4.5]decane-2,4-dione

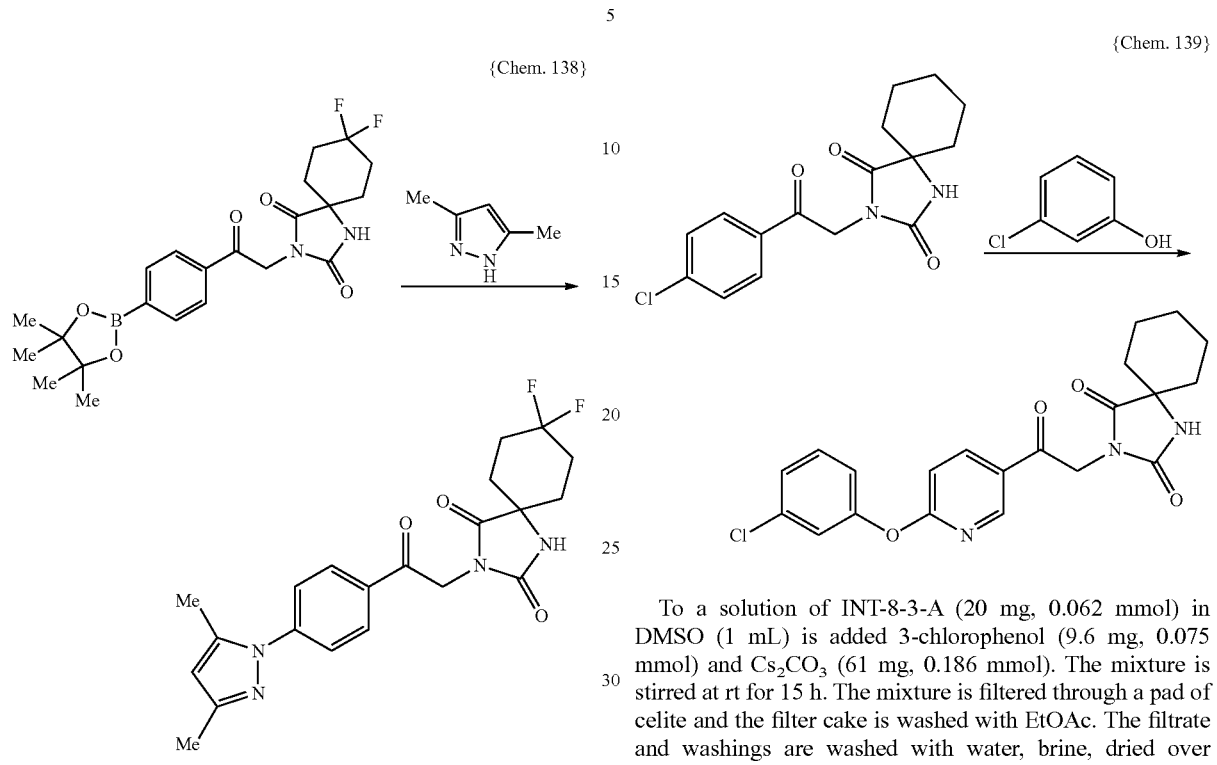

{Chem. 138}

{Chem. 139}

A mixture of INT-12-1-A (30 mg, 0.067 mmol), 3,5-dimethyl-1H-pyrazole (12.9 mg, 0.134 mmol) and copper (II) acetate (12.2 mg, 0.067 mmol) in pyridine (1 mL) is stirred at 60° C. for 20 h. The mixture is diluted with EtOAc and washed with 2 M HCl aq. solution, water, and brine. The organic layer is dried over Na$_2$SO$_4$, filtered and concentrated in vacuo. The residue is purified by column chromatography on amino bounded silica-gel eluting with EtOAc to give the crude titled compound. The further purification is carried out by preparative LC-MS system in the usual manner.

Observed MS: 417.7
tR/method: 1.56 min./(QC1)

To a solution of INT-8-3-A (20 mg, 0.062 mmol) in DMSO (1 mL) is added 3-chlorophenol (9.6 mg, 0.075 mmol) and Cs$_2$CO$_3$ (61 mg, 0.186 mmol). The mixture is stirred at rt for 15 h. The mixture is filtered through a pad of celite and the filter cake is washed with EtOAc. The filtrate and washings are washed with water, brine, dried over Na$_2$SO$_4$, filtered and concentrated in vacuo. The residue is purified by column chromatography eluting with 10-100% EtOAc in hexane to give the titled compound (18 mg, 70% yield) as a white solid. The further purification is carried out by preparative LC-MS system in the usual manner.

The following examples (20-1 to 20-9) are prepared according to the procedure of example-20-1 from the synthesized halide derivatives and the known or synthesized phenol, thiol or alcohol derivatives in Table 36. The further purification is carried out by preparative LC-MS system in the usual manner. The retention time and observed MS by HPLC-QC method are summarized in Table 36.

TABLE 36

| Examples | halides | phenols alcohol thiol | observed MS | tR/method |
|---|---|---|---|---|
| Example-20-1 | INT-8-3-A | 3-chlorophenol | 412.1 | 1.77 min. (QC1) |

TABLE 36-continued
| Examples | halides | phenols alcohol thiol | observed MS | tR/method |
|---|---|---|---|---|
| Example-20-2 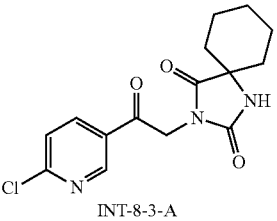 | 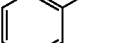 INT-8-3-A | 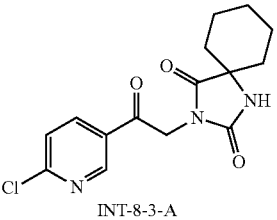 | 379.2 | 1.37 min. (QC1) |
| Example-20-3 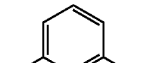 | 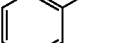 INT-8-3-A | 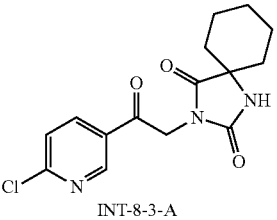 | 392.2 | 1.73 min. (QC1) |
| Example-20-4 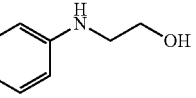 | 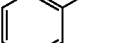 INT-8-3-A |  | 421.3 | 2.23 min (QC2) |
| Example-20-5 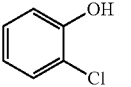 | 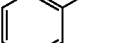 INT-8-3-A | 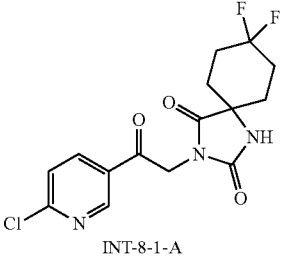 | 412.1 | 1.72 min. (QC1) |
| Example-20-6 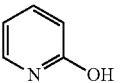 | 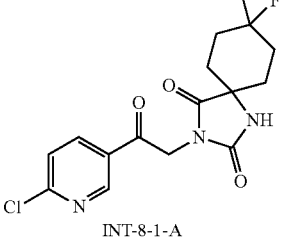 INT-8-1-A | 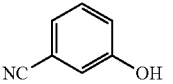 | 415.2 | 1.28 min. (QC1) |
| Example-20-7 | 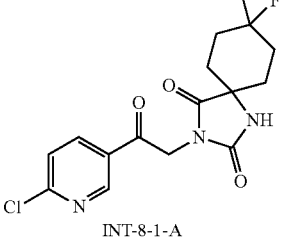 INT-8-1-A | | 439.2 | 1.59 min. (QC1) |

TABLE 36-continued

| Examples | halides | phenols alcohol thiol | observed MS | tR/method |
|---|---|---|---|---|
| Example-20-8 | INT-8-1-A | Cl–C6H4–OH (3-chlorophenol) | 448.2 | 1.77 min. (QC1) |
| Example-20-9 | INT-8-1-A | C6H5–SH (thiophenol) | 430.2 | 1.71 min. (QC1) |

Example-21-1: 2-(4-(2-(8,8-difluoro-2,4-dioxo-1,3-diazaspiro[4.5]decan-3-yl)acetyl)phenoxy)nicotinonitrile Example-21-2: 3-(2-(4-((3-chloropyridin-2-yl)oxy)phenyl)-2-oxoethyl)-8,8-difluoro-1,3-diazaspiro[4.5]decane-2,4-dione {Chem. 140}

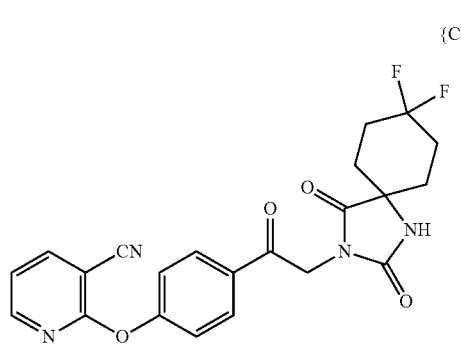

{Chem. 141}

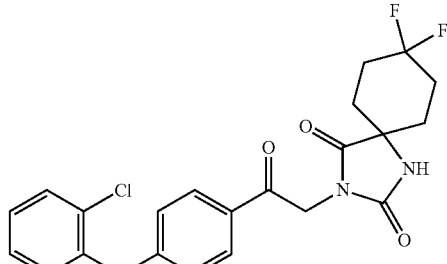

A mixture of INT-14-1-A (35 mg, 0.10 mmol), 2-chloronicotinonitrile (20 mg, 0.145 mmol) and $K_2CO_3$ (29 mg, 0.207 mmol) in DMF (1.5 mL) is irradiated in a microwave reactor (Biotage Initiator) for 30 min at 140° C. The reaction mixture is filtered through a pad of celite and the filter cake is washed with EtOAc. The filtrate and washings are washed with water and brine, dried over $Na_2SO_4$, filtered and concentrated in vacuo. The residue is purified by column chromatography on silica gel eluting with 5-50% EtOAc in DCM to give the titled compound (43 mg, 94% yield) as a pale yellow amorphous solid. The further purification is carried out by preparative LC-MS system in the usual manner.

Observed MS: 439.3 tR/method: 1.53 min./(QC1)

A mixture of INT-14-1-A (34 mg, 0.101 mmol), 2-bromo-3-chloropyridine (15 mg, 0.078 mmol), 2-(dimethylamino)acetic acid (2.4 mg, 0.023 mmol), copper(I) iodide (4.45 mg, 0.023 mmol) and $Cs_2CO_3$ (76 mg, 0.234 mmol) in 1,4-dioxane (1.5 mL) is irradiated with microwave at 170° C. for 1 h. After the usual workup (quenching with water, dilution with EtOAc, filtration through celite, and washing with EtOAc), the residue is purified by column chromatography on silica gel eluting with 5-50% EtOAc in DCM to give the titled compound (10 mg, 29% yield). The further purification is carried out by preparative LC-MS system in the usual manner.

Observed MS: 448.2 tR/method: 1.68 min./(QC1)

The following examples (21-3 to 21-10) are prepared according to the procedure of example-21-2 from the synthesized phenol derivative (INT-14-1-A) and the known or synthesized halide derivatives in Table 37. The further purification is carried out by preparative LC-MS system in the usual manner. The retention time and observed MS by HPLC-QC method are summarized in Table 37.

TABLE 37

| Examples | phenols | halides | Observed MS | tR/method |
|---|---|---|---|---|
| Example-21-3 | INT-14-1-A | 3-Me, 2-Br pyridine | 428.3 | 1.66 min. (QC1) |
| Example-21-4 | INT-14-1-A | 4-Me, 2-Br pyridine | 428.3 | 1.64 min (QC1) |
| Example-21-5 | INT-14-1-A | 2-CN, 6-Br pyridine | 441.3 | 1.58 min. (QC1) |
| Example-21-6 | INT-14-1-A | 2-Me, 6-Br pyridine | 430.3 | 1.64 min. (QC1) |
| Example-21-7 | INT-14-1-A | 4-Me, 2-Cl pyrimidine | 431.2 | 1.45 min. (QC1) |

TABLE 37-continued

| Examples | phenols | halides | Observed MS | tR/method |
|---|---|---|---|---|
| Example-21-8 | (structure) | (structure) INT-14-1-A | (structure) | 442.1 | 1.54 min. (QC1) |
| Example-21-9 | (structure) | (structure) INT-14-1-A | (structure) | 467.1 | 1.53 min. (QC1) |
| Example-21-10 | (structure) | (structure) INT-14-1-A | (structure) | 431.6 | 1.41 min. (QC1) |

Example-21-11: 8,8-difluoro-3-(2-(4-((4-methyl-pyridazin-3-yl)oxy)phenyl)-2-oxoethyl)-1,3-diazaspiro[4.5]decane-2,4-dione {Chem. 142}

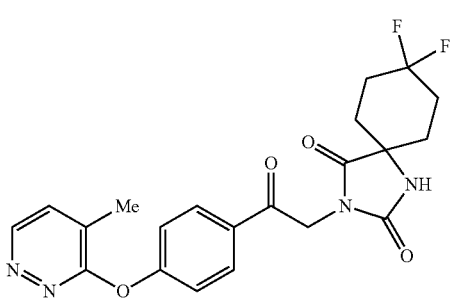

A mixture of INT-14-1-A (30 mg, 0.089 mmol), 3-chloro-4-methylpyridazine (13.7 mg, 0.106 mmol), Pd$_2$(dba)$_3$ (8.1 mg, 0.0089 mmol), tBuXPhos (18.8 mg, 0.044 mmol) and K$_3$PO$_4$ (56.5 mg, 0.266 mmol) in 1,4-dioxane (1.5 mL) is irradiated with microwave at 160° C. for 45 min. After the usual workup (quenching with water, dilution with EtOAc, filtration through celite, and washing with EtOAc), the residue is purified by column chromatography on silica gel eluting with 5-80% EtOAc in DCM to give the titled compound (10 mg, 26% yield). The further purification is carried out by preparative LC-MS system in the usual manner.

Observed MS: 431.2
tR/method: 1.43 min./(QC1)

Example-21-12: 3-(4-(2-(8,8-difluoro-2,4-dioxo-1,3-diazaspiro[4.5]decan-3-yl)acetyl)phenoxy)pyridazine-4-carbonitrile {Chem. 143}

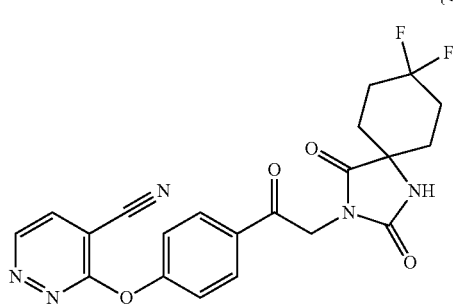

The titled compound is prepared according to the procedure of example-21-11 from the INT-14-1-A (30 mg, 0.089 mmol) and 3-chloropyridazine-4-carbonitrile (30.9 mg, 0.222 mmol) to give the product (31 mg, 79% yield) as a brown amorphous solid. The further purification is carried out by preparative LC-MS system in the usual manner.

Observed MS: 442.2 tR/method: 1.43 min./(QC1)

Example-21-13: 8,8-difluoro-3-(2-oxo-2-(4-(thiazol-2-yloxy)phenyl)ethyl)-1,3-diazaspiro[4.5]decane-2,4-dione {Chem. 144}

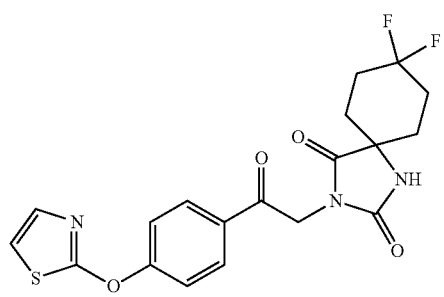

A mixture of INT-14-1-A (30 mg, 0.089 mmol), 2-chlorothiazole (26.5 mg, 0.222 mmol), and $Cs_2CO_3$ (87 mg, 0.266 mmol) in DMF (1.5 mL) is irradiated with microwave at 140° C. for 0.5 h. After the usual workup (quenching with water, dilution with EtOAc, filtration through celite, and washing with EtOAc), the residue is purified by column chromatography on silica gel eluting with 10-100% EtOAc in DCM to give the titled compound (18 mg, 48% yield) as a yellow amorphous solid. The further purification is carried out by preparative LC-MS system in the usual manner.

Observed MS: 422.1 tR/method: 1.56 min./(QC1)

Example-21-14: 8,8-difluoro-3-(2-oxo-2-(4-(pyridin-3-yloxy)phenyl)ethyl)-1,3-diazaspiro[4.5]decane-2,4-dione {Chem. 145}

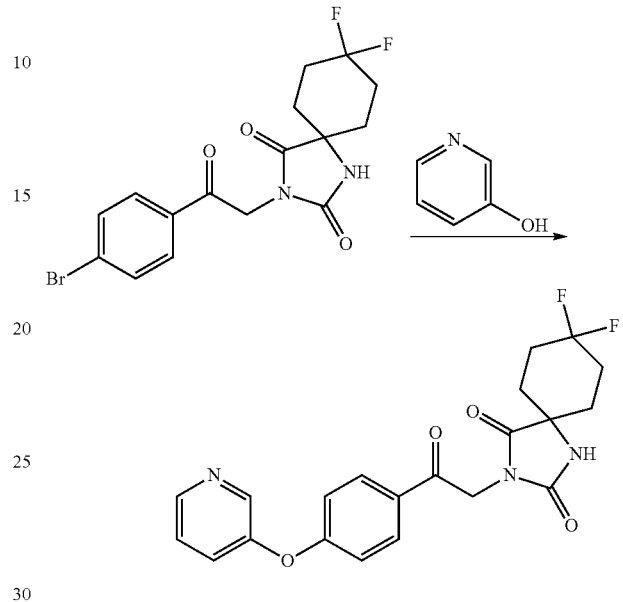

The titled compound is prepared according to the procedure of example-21-11 from the INT-7-1-A (60 mg, 0.15 mmol), pyridin-3-ol (17.1 mg, 0.179 mmol), t-BuXPhos (31.8 mg, 0.075 mmol), $Pd_2(dba)_3$ (13.7 mg, 0.015 mmol) and potassium phosphate (95 mg, 0.45 mmol) in 1,4-dioxane (3 mL) to give the product (19 mg, 30% yield) as a slightly yellow solid. The further purification is carried out by preparative LC-MS system in the usual manner.

Observed MS: 416.4 tR/method: 1.47 min./(QC1)

The following examples (21-15 to 21-17) are prepared according to the procedure of example-21-11 from the halide derivatives (INT-7-1-A, INT-7-18-A and INT-7-20-A) and the known phenol derivatives in Table 38. The further purification is carried out by preparative LC-MS system in the usual manner. The retention time and observed MS by HPLC-QC method are summarized in Table 38.

TABLE 38

| Examples | Halides | Phenols | Observed MS | tR/method |
|---|---|---|---|---|
| Example-21-15 | | | 417.4 | 1.40 min. (QC1) |

TABLE 38-continued

| Examples | Halides | Phenols | Observed MS | tR/method |
|---|---|---|---|---|
| Example-21-16 | INT-7-18-A | (pyridin-3-ol) | 434.5 | 1.50 min. (QC1) |
| Example-21-17 | INT-7-20-A | (pyridin-3-ol) | 434.5 | 1.49 min. (QC1) |

Example-21-18: 8,8-difluoro-3-(2-oxo-2-(4-(pyridin-3-ylmethoxy)phenyl)ethyl)-1,3-diazaspiro[4.5]decane-2,4-dione {Chem. 146}

To a solution of INT-14-1-A (30 mg, 0.089 mmol) and potassium carbonate (37 mg, 0.266 mmol) in DMF (2 mL) is added 3-(chloromethyl)pyridine (14 mg, 0.089 mmol) at rt. The mixture is stirred at 80° C. for 15 h. To this is added water and the mixture is extracted with EtOAc. The organic layer is washed with brine, dried over sodium sulfate, filtered and concentrated in vacuo. The residue is purified by column chromatography on silica gel eluting with 10-80% ethyl acetate in DCM to give the titled compound (33 mg, 87% yield) as a white solid. The further purification is carried out by preparative LC-MS system in the usual manner.

Observed MS: 430.1
tR/method: 1.45 min./(QC1)

Example-21-19: 8,8-difluoro-3-(2-oxo-2-(4-(pyridin-4-ylmethoxy)phenyl)ethyl)-1,3-diazaspiro[4.5]decane-2,4-dione {Chem. 147}

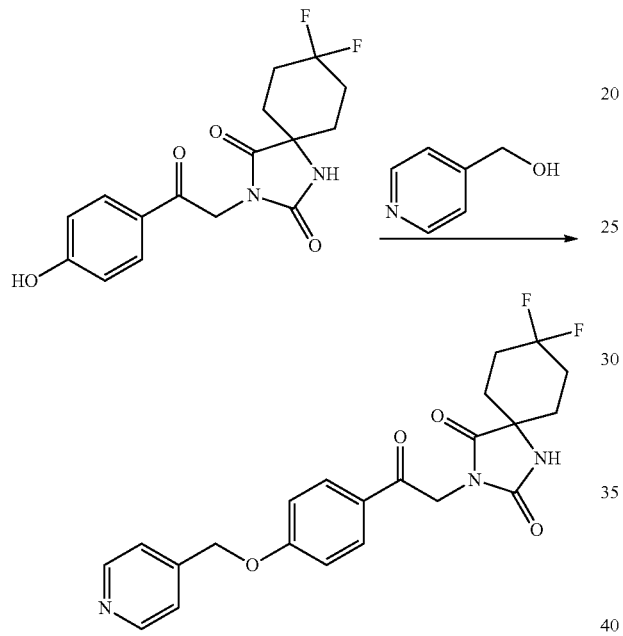

To a solution of INT-14-1-A (30 mg, 0.089 mmol) in THF (2 mL) is added pyridin-4-ylmethanol (10 mg, 0.089 mmol), DEAD (2.2 M in toluene solution, 0.060 mL, 0.133 mmol) and triphenylphosphine (35 mg, 0.133 mmol) at 0° C. After stirring at rt for 1 h, the reaction mixture is concentrated in vacuo. The residue is purified by column chromatography on silica gel eluting with 10-100% ethyl acetate in DCM to give the titled compound (44 mg, quant.) as a colorless amorphous solid. The further purification is carried out by preparative LC-MS system in the usual manner.

Observed MS: 430.2
tR/method: 1.44 min./(QC1)

Example-21-20: 8,8-difluoro-3-(2-oxo-2-(4-(pyrimidin-2-ylmethoxy)phenyl)ethyl)-1,3-diazaspiro[4.5]decane-2,4-dione {Chem. 148}

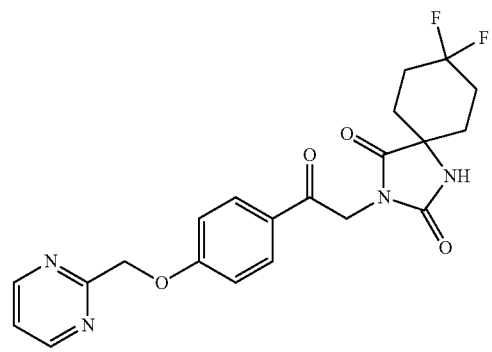

The titled compound is prepared according to the procedure of example-21-17 from the INT-14-1-A (50 mg, 0.148 mmol), 2-(chloromethyl)pyrimidine (24 mg, 0.148 mmol) and cesium carbonate (144 mg, 0.443 mmol) in DMF (2 mL) to give the product (28 mg, 44% yield) as a colorless amorphous solid. The further purification is carried out by preparative LC-MS system in the usual manner.

Observed MS: 431.2
tR/method: 1.34 min./(QC1)

The following examples (22-1 to 22-6) are prepared according to the procedure of step-3 in intermediate-9-2-A from the synthesized alcohol derivatives (INT-11-1-A to INT-11-6-A) in Table 39. The further purification is carried out by preparative LC-MS system in the usual manner. The retention time and observed MS by HPLC-QC method are summarized in Table 39.

TABLE 39

| Examples | Alcohols | Observed MS | tR/method |
|---|---|---|---|
| Example-22-1 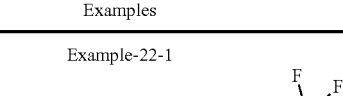 | 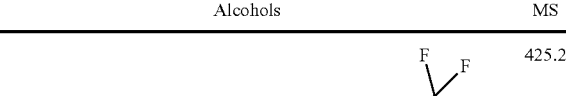 INT-11-1-A | 425.2 | 1.47 min. (QC1) |

TABLE 39-continued
| Examples | Alcohols | Observed MS | tR/ method |
|---|---|---|---|
| Example-22-2 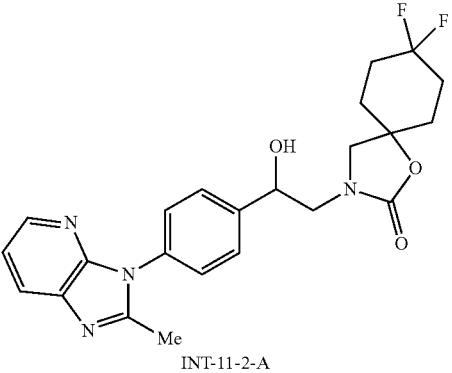 | INT-11-2-A | 439.2 | 1.42 min. (QC1) |
| Example-22-3 | INT-11-3-A | 438.4 | 1.56 min. (QC1) |
| Example-22-4 | INT-11-4-A | 424.4 | 1.56 min. (QC1) |
| Example-22-5 | INT-11-5-A | 404.1 | 1.41 min. (QC1) |

TABLE 39-continued

| Examples | Alcohols | Observed MS | tR/method |
|---|---|---|---|
| Example-22-6 | INT-11-6-A | 455.2 | 1.50 min. (QC1) |

Example-23-1: 8,8-difluoro-3-(2-oxo-2-(4-(2-oxo-1H-imidazo[4,5-b]pyridin-3(2H)-yl)phenyl)ethyl)-1,3-diazaspiro[4.5]decane-2,4-dione {Chem. 149}

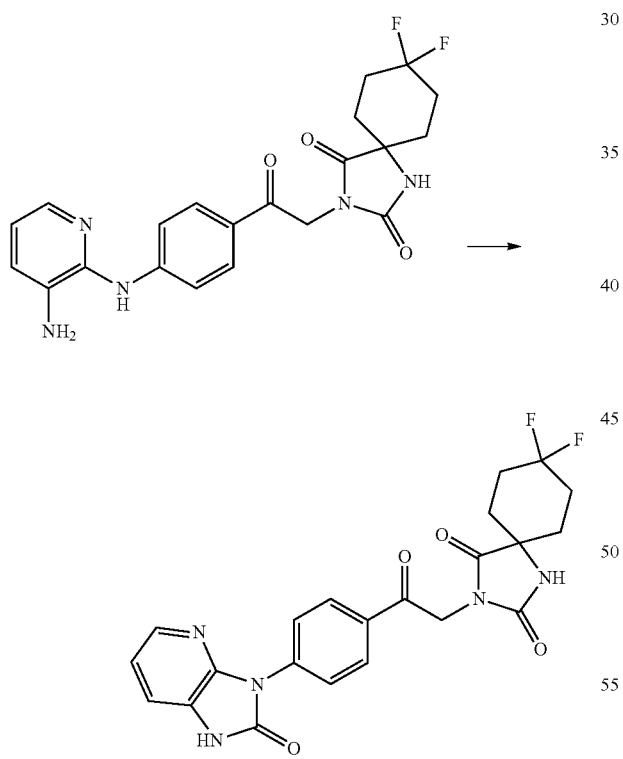

To a stirred solution of INT-15-1-A (40 mg, 0.093 mmol) in THF (1.5 mL) is added CDI (38 mg, 0.233 mmol) and pyridine (18 mg, 0.233 mmol). The mixture is stirred at 65° C. for 4 h. After cooling, the reaction mixture is quenched with water and extracted with EtOAc. The combined organic layer is washed with brine, dried over sodium sulfate, filtered and concentrated in vacuo. The residue is purified by column chromatography (Biotage) on silica gel (10 g) eluting with 10-100% ethyl acetate in DCM to give the titled compound (27 mg, 64% yield) as a white amorphous solid. The further purification is carried out by preparative LC-MS system in the usual manner to give the title compound (6.1 mg).

Observed MS: 454.4 tR/method: 1.34 min./(QC1)

Example-23-2: 8,8-difluoro-3-(2-(4-(5-methyl-2-oxo-1H-imidazo[4,5-b]pyridin-3(2H)-yl)phenyl)-2-oxoethyl)-1,3-diazaspiro[4.5]decane-2,4-dione {Chem. 150}

The titled compound is prepared according to the procedure of example-23-1 from the INT-15-2-A (80 mg, 0.18 mmol), CDI (73.1 mg, 0.451 mmol) and pyridine (36 microL, 0.451 mmol) in THF (3 mL) to give the product (75 mg, 89% yield) as a dark yellow solid. The further purification is carried out by preparative LC-MS system in the usual manner.

Observed MS: 470.4 tR/method: 1.42 min./(QC1)

Example-24-1: 3-(2-(4-(2-(difluoromethyl)-1H-benzo[d]imidazol-1-phenyl)-2-oxoethyl)-8,8-difluoro-1,3-diazaspiro[4.5]decane-2,4-dione {Chem. 151}

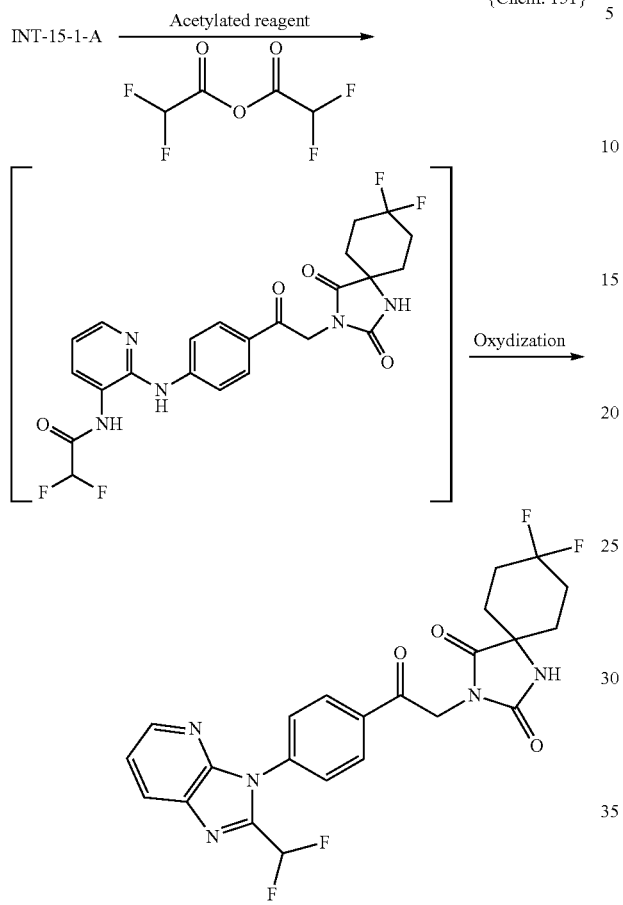

To a stirred solution of INT-15-1-A (50.0 mg, 0.116 mmol) and triethylamine (40 microL, 0.282 mmol) in THF (3 mL) is added 2,2-difluoroacetic anhydride (24, 5 mg, 0.141 mmol) at the ambient temperature. After 5 h at rt, the solvent is evaporated in vacuo to give the crude product (~0.116 mmol) as an orange oil, which is dissolved in acetic acid (3 mL). The mixture is heated at 100° C. for 16 h. After the removal of solvent, the residue is basified to pH>10 with sat. sodium bicarbonate solution and extracted with ethyl acetate (×2). The combined solution is washed with brine, dried over sodium sulfate, filtered and concentrated in vacuo to give the crude product (orange oil, 146.4 mg), which is purified by column chromatography on silica gel (10 g) eluting with 5-60% ethyl acetate in DCM to give the titled compound (36.8 mg, 65% yield) as an orange solid. The further purification is carried out by preparative LC-MS system in the usual manner.

Observed MS: 490.1
tR/method: 2.05 min./(QC2)

The following examples (24-2 to 24-5) are prepared according to the procedure of Example-24-1 from INT-15-1-A and INT-15-2-A in Table 40. The further purification is carried out by preparative LC-MS system in the usual manner. The retention time and observed MS by HPLC-QC method are summarized in Table 40.

TABLE 40

| Examples | Starting Material | Acetylated reagents | Observed MS | tR/method |
|---|---|---|---|---|
| Example-24-2 | | | 468.2 | 1.44 min. (QC1) |

TABLE 40-continued

| Examples | Starting Material | Acetylated reagents | Observed MS | tR/method |
|---|---|---|---|---|
| Example-24-3 | INT-15-1-A | cyclopropanecarbonyl chloride | 480.2 | 1.49 min. (QC1) |
| Example-24-4 | INT-15-1-A | methoxyacetyl chloride | 484.5 | 1.40 min. (QC1) |
| Example-24-5 | INT-15-2-A | difluoroacetic anhydride | 504.4 | 1.57 min. (QC1) |

Example-24-6: 8,8-difluoro-3-(2-oxo-2-(4-(2-(trifluoromethyl)-3H-imidazo[4,5-b]pyridin-3-yl)phenyl)ethyl)-1, 3-diazaspiro[4.5]decane-2,4-dione {Chem. 152}

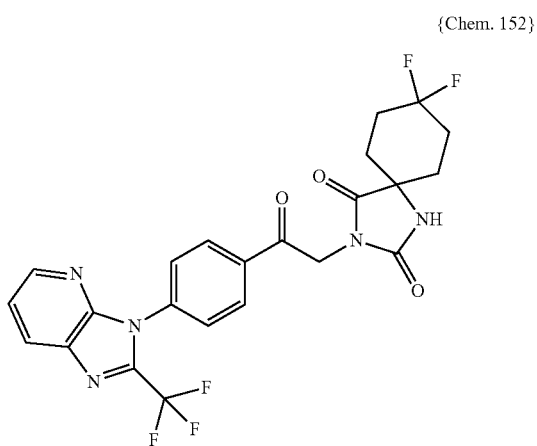 [SMILES: O=C(CN1C(=O)NC2(CCC(F)(F)CC2)C1=O)c1ccc(-n2c(C(F)(F)F)nc3cccnc32)cc1]

A mixture of INT-15-1-A (50 mg, 0.116 mmol) is dissolved in trifluoroacetic acid (1 mL) and the reaction is stirred at 70° C. for 18 h. After the removal of solvent, to this is added triethylamine and the mixture is stirred at 70° C. for 2 h. After the removal of solvent, the residual product is purified by column chromatography on silica gel (10 g) eluting with 10-90% ethyl acetate in DCM to give the titled compound (53 mg, 90% yield; chemical purity of 40%) as an orange solid. The further purification is carried out by preparative LC-MS system in the usual manner.

Observed MS: 508.6
tR/method: 1.58 min./(QC1)

Example-24-7: 8,8-difluoro-3-(2-(4-(5-methyl-2-(trifluoromethyl)-3H-imidazo[4,5-b]pyridin-3-yl)phenyl)-2-oxoethyl)-1,3-diazaspiro[4.5]decane-2,4-dione {Chem. 153}

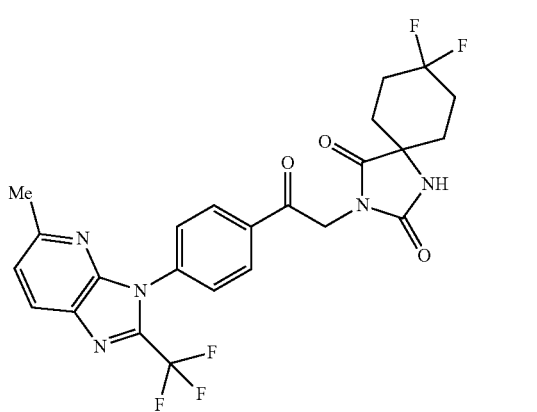

A mixture (suspension) of INT-15-2-A (50 mg, 0.113 mmol) in trifluoroacetic acid (1 mL) is irradiated with microwave at 100° C. for 30 min. The treatment of reaction is carried out according to the procedure of example-24-6 to give the titled compound (58 mg, 99% yield) as an orange solid. The further purification is carried out by preparative LC-MS system in the usual manner.

Observed MS: 522.7
tR/method: 1.67 min./(QC1)

Example-25-1: 3-(2-(4-(2-((dimethylamino)methyl)-5-methyl-3H-imidazo[4,5-b]pyridin-3-yl)phenyl)-2-oxoethyl)-8,8-difluoro-1,3-diazaspiro[4.5]decane-2, 4-dione {Chem. 154}

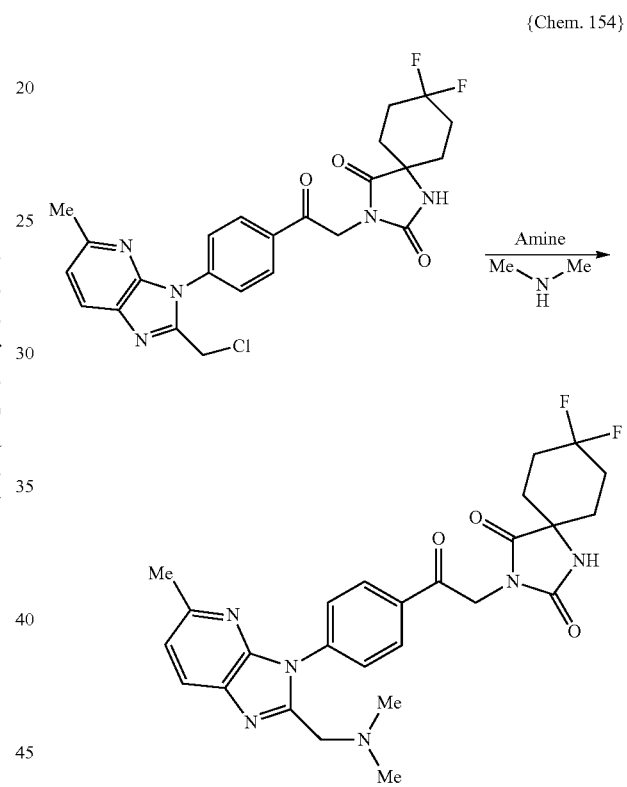

A mixture of INT-17-1-A (30 mg, 0.06 mmol), 2 M dimethylamine in THF solution (90 microL, 0.18 mmol) and potassium carbonate (41.3 mg, 0.299 mmol) in THF (1.5 mL) is heated at 45° C. for 10 h. After the filtration through Celite pad, the filter cake is washed with THF. The filtrate and washings are concentrated in nitrogen flow to give the titled compound (35.1 mg) as an orange oil. The further purification is carried out by preparative LC-MS system in the usual manner.

Observed MS: 511.7
tR/method: 1.48 min./(QC1)

The following examples (25-2 to 25-6) are prepared according to the procedure of Example-25-1 from INT-17-1-A and the corresponding amines in Table 41. The further purification is carried out by preparative LC-MS system in the usual manner. The retention time and observed MS by HPLC-QC method are summarized in Table 41.

TABLE 41

| Examples | Starting Material | Amines | Observed MS | tR/method |
|---|---|---|---|---|
| Example-25-2 | INT-17-1-A | pyrrolidine | 537.8 | 1.56 min. (QC1) |
| Example-25-3 | INT-17-1-A | piperidine | 551.8 | 1.69 min. (QC1) |
| Example-25-4 | INT-17-1-A | azetidine | 523.8 | 1.43 min. (QC1) |

TABLE 41-continued

| Examples | Starting Material | Amines | Observed MS | tR/method |
|---|---|---|---|---|
| Example-25-5 (structure) | (structure) INT-17-1-A | morpholine (structure) | 553.8 | 1.46 min. (QC1) |
| Example-25-6 (structure) | (structure) INT-17-1-A | (structure) HN-pyrrolidine-OMe | 567.8 | 1.51 min. (QC1) |

Example-26-1: 8,8-difluoro-3-(2-(4-(2-methoxy-3H-imidazo[4,5-b]pyridin-3-yl)phenyl)-2-oxoethyl)-1,3-diazaspiro[4.5]decane-2,4-dione {Chem. 155}

A mixture of INT-15-1-A (50 mg, 0.116 mmol), tetramethoxymethane (0.16 mL, 1.199 mmol) and acetic acid (15 microL) in THF (1.5 mL) is heated at 85° C. for 18 h. After the removal of solvent, the residue (brown oil) is purified by column chromatography on silica gel (10 g) eluting with 5-70% ethyl acetate in DCM to give the titled compound (43 mg, 78% yield) as a slightly purple solid.

The further purification is carried out by preparative LC-MS system in the usual manner.

Observed MS: 470.2 tR/method: 2.02 min./(QC2)

The following examples (26-2 to 26-4) are prepared according to the procedure of Example-26-1 from INT-15-2-A in Table 42. Example-26-2 is carried out in the condition of p-TsOH (0.3 eq.) instead of AcOH. The further purification is carried out by preparative LC-MS system in the usual manner. The retention time and observed MS by HPLC-QC method are summarized in Table 42.

TABLE 42

| Examples | Starting Material | Reagents | Observed MS | tR/method |
|---|---|---|---|---|
| Example-26-2 | INT-15-2-A | MeEtO-CH(OEt)-OEtMe (triethyl orthoacetate-like) | 454.3 | 1.51 min. (QC1) |
| Example-26-3 | INT-15-2-A | MeO-C(OMe)(OMe)-OMe | 484.4 | 1.57 min. (QC1) |
| Example-26-4 | INT-15-2-A | tetraethyl orthocarbonate-like | 498.6 | 1.63 min. (QC1) |

Example-27-1: 3-(4-(2-(8,8-difluoro-2,4-dioxo-1,3-diazaspiro[4.5]decan-3-yl)acetyl)phenyl)-2-methyl-3H-imidazo[4,5-b]pyridine-5-carbonitrile {Chem. 156}

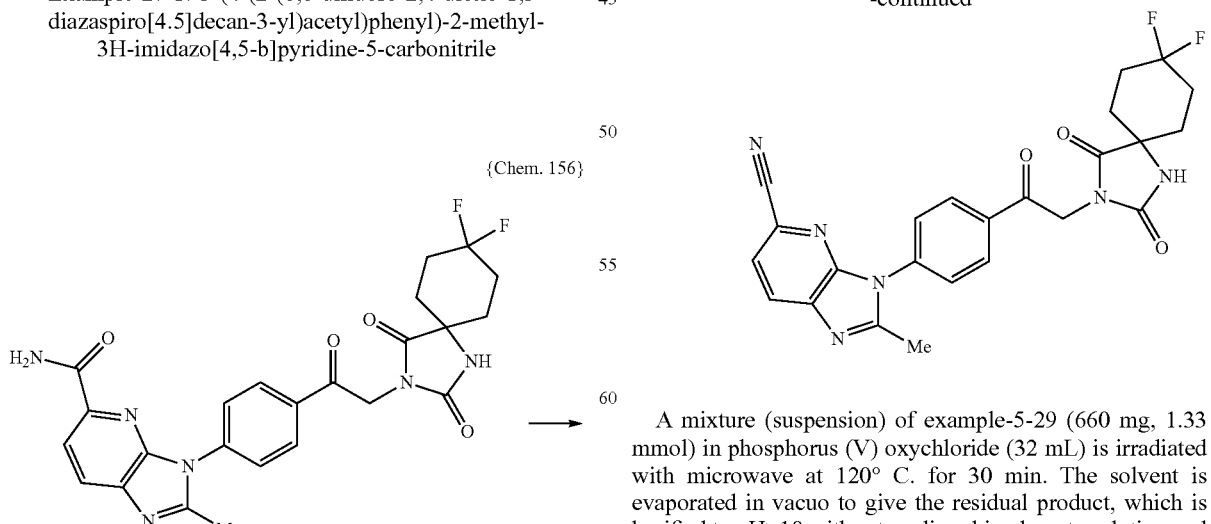

A mixture (suspension) of example-5-29 (660 mg, 1.33 mmol) in phosphorus (V) oxychloride (32 mL) is irradiated with microwave at 120° C. for 30 min. The solvent is evaporated in vacuo to give the residual product, which is basified to pH>10 with sat. sodium bicarbonate solution and extracted with ethyl acetate (×2). The combined solution is washed with water, brine, dried over sodium sulfate, filtered and concentrated in vacuo to give the crude product, which is purified by column chromatography on silica gel (100 g) eluting with EtOAc only to give the crude product (solid). The product is triturated with minimum AcOEt and excess hexane to give the titled product (324 mg, 51% yield) as a white solid.

MS (ESI) m/z: 479.3 (M+H)+.

The further purification for the assay sample is carried out by preparative LC-MS system in the usual manner.

Observed MS: 479.2 tR/method: 1.96 min./(QC2)

Example-28-1: 3-(2-(4-(2-(dimethylamino)-5-methyl-3H-imidazo[4,5-b]pyridin-3-yl)phenyl)-2-oxoethyl)-8,8-difluoro-1,3-diazaspiro[4.5]decane-2,4-dione {Chem. 157}

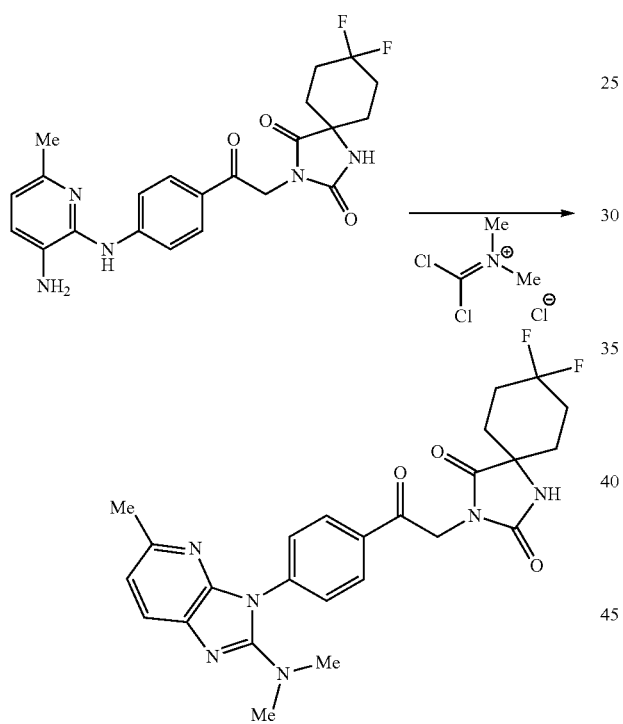

A mixture of INT-15-2-A (50 mg, 0.113 mmol), (dichloromethane)dimethyliminium chloride (43 mg, 0.338 mmol) and triethylamine (22 microL, 0.451 mmol) in 1,2-dichloroethane (3 mL) is heated at 80° C. for 2 h. The mixture is quenched with methanol and the solvent is evaporated in vacuo. The residue is dissolved in DCM (50 mL) and the organic solution is washed with water, brine, dried over sodium sulfate, filtered and concentrated in vacuo to give the crude product (dark brown oil), which is purified by column chromatography on silica gel (10 g) eluting with 20-100% ethyl acetate in DCM to give the titled compound (14.2 mg, 20% yield, chemical purity of 80%) as a pale yellow film. The further purification is carried out by preparative LC-MS system in the usual manner.

Observed MS: 497.8 tR/method: 1.51 min./(QC1)

Example-28-2: N-(2-(4-(2-(8,8-difluoro-2,4-dioxo-1,3-diazaspiro[4.5]decan-3-yl)acetyl)phenyl)amino)pyridin-3-yl)acetamide {Chem. 158}

To a stirred mixture of INT-15-1-A (50 mg, 0.116 mmol) and triethylamine (40.6 microL, 0,291 mmol) in THF (3 mL) is added acetyl chloride (13.2 mg, 0.169 mmol) via a syringe at rt. After 45 min at rt, the mixture is quenched with water and extracted with ethyl acetate. The combined organic solution is washed with brine, dried over sodium sulfate, filtered and concentrated in vacuo to give the crude product, which is purified by column chromatography on silica gel (10 g) eluting with ethyl acetate only to give the titled compound (34.4 mg, 62% yield) as a slightly tan solid.

$^1$H-NMR (270 MHz, DMSO-$d_6$): delta 9.56 (s, 1H), 8.98 (s, 1H), 8.71 (s, 1H), 8.14-8.08 (m, 1H), 7.97 (d, J=8.6 Hz, 2H), 7.82-7.72 (m, 3H), 7.02-6.95 (m, 1H), 4.87 (s, 2H), 2.25-1.75 (m, 11H, including delta 2.12 (s, 3H)).

MS (ESI) m/z: 472.2 (M+H)+.

The further purification for the assay sample is carried out by preparative LC-MS system in the usual manner.

Observed MS: 472.7 tR/method: 1.35 min./(QC1)

521

Example-28-3: 3-(2-(4-(2-acetylisoindolin-4-yl)phenyl)-2-oxoethyl)-8,8-difluoro-1,3-diazaspiro[4.5]decane-2,4-dione {Chem. 159}

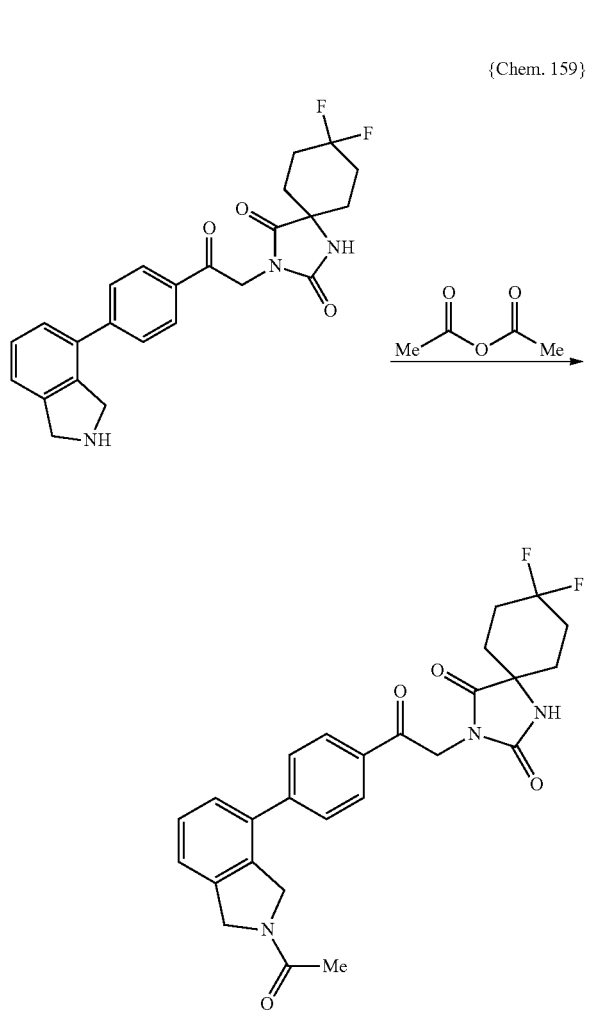

To a solution of example-6-115 (32 mg, 0.073 mmol) in DCM (2 mL) are added acetic anhydride (0.021 mL, 0.218 mmol) and TEA (0.030 mL, 0.218 mmol) at rt. The mixture is stirred at rt for 5 h. The mixture is quenched with sat. NaHCO$_3$ solution and extracted with DCM. The organic solution is dried over Na$_2$SO$_4$, filtered and concentrated in vacuo. The purification is carried out by column chromatography on silica gel eluting with a gradient of 50-100% EtOAc then 0-5% MeOH in EtOAc to give the titled compound (27 mg, 77% yield) as a pale purple solid.

$^1$H-NMR (270 MHz, CDCl$_3$): delta 8.10-8.06 (m, 2H), 7.61-7.53 (m, 2H), 7.49-7.27 (m, 3H), 6.67 (br s, 1H), 5.00-4.93 (m, 2H), 4.93-4.80 (m, 4H), 2.50-1.90 (m, 11H).

MS (ESI) m/z: 482.0 (M+H)$^+$.

The further purification is carried out by preparative LC-MS system in the usual manner.

Observed MS: 482.3 tR/method: 1.51 min./(QC1)

522

Example-28-4: 8,8-difluoro-3-(2-(4-(2-(hydroxymethyl)-3H-imidazo[4,5-b]pyridin-3-yl)phenyl)-2-oxoethyl)-1, 3-diazaspiro[4.5]decane-2,4-dione {Chem. 160}

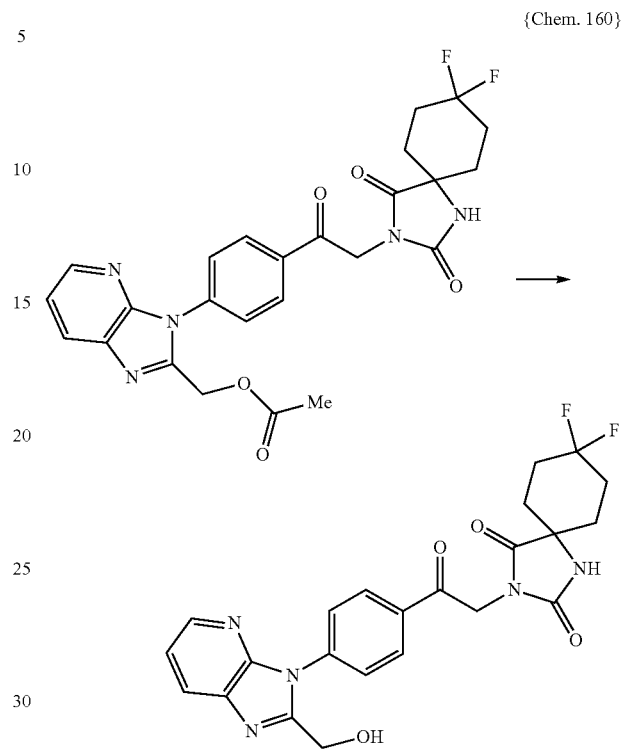

A mixture of INT-17-2-A (52 mg, 0.102 mmol) and potassium carbonate (42 mg, 0.305 mmol) in methanol (3 mL) is stirred at rt for 16 h. After the filtration through Celite pad, the filtrate and washings are concentrated in vacuo. The residue is loaded onto an SCX cartridge (Varian Bond Elute, 1 g/6 mL) conditioned with 1 mL of MeOH, rinsed with 5 mL of MeOH and eluted with 5 mL of 1M NH$_3$/MeOH. Volatiles are removed by nitrogen flow to give the titled compound (21 mg, 44% yield). The further purification is carried out by preparative LC-MS system in the usual manner.

Observed MS: 470.3 tR/method: 1.27 min./(QC1)

Example-28-5: 8,8-difluoro-3-(2-(4-(2-(hydroxymethyl)-5-methyl-3H-imidazo[4,5-b]pyridin-3-yl)phenyl)-2-oxoethyl)-1,3-diazaspiro[4.5]decane-2,4-dione {Chem. 161}

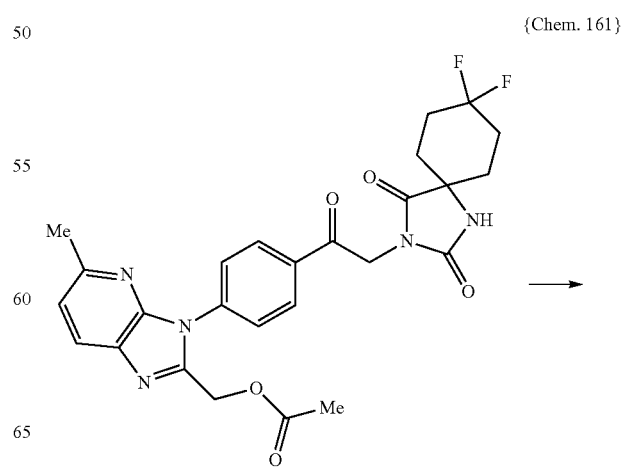

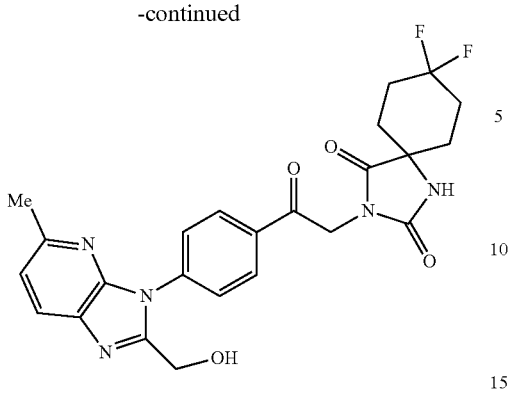

The titled compound is prepared according to the procedure of example-28-4 from the INT-17-3-A (75.9 mg, 0.144 mmol) and potassium carbonate (60 mg, 0.433 mmol) in methanol (4 mL) to give the product (29 mg, 41% yield) as a white solid. The further purification is carried out by preparative LC-MS system in the usual manner.

Observed MS: 484.6
tR/method: 1.33 min./(QC1)

Example-29-1: 4'-(2-(8,8-difluoro-2,4-dioxo-1,3-diazaspiro[4.5]decan-3-yl)acetyl)-N,N-dimethyl-[1,1'-biphenyl]-2-carboxamide {Chem. 162}

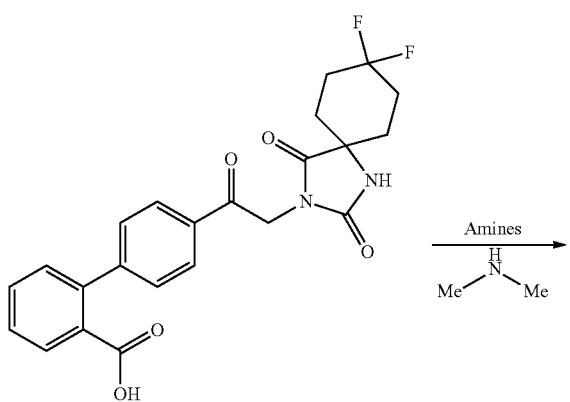

To a stirred solution of INT-16-1-A (20 mg, 0.045 mmol), N,N,N',N'-tetramethyl-O-(benzotriazol-1-yl)uronium hexafluorophosphate (HBTU) (34 mg, 0.090 mmol) and TEA (0.025 mL, 0.181 mmmol) in DMF (1 mL) is added 10% dimethylamine in THF (0.2 mL) at rt. After stirring at 50° C. for 1 h, the mixture is diluted with EtOAc (4 mL) and washed with water (4 mL×2). The organic fraction is dried over sodium sulfate, filtered and concentrated in vacuo. The residue is purified by column chromatography on amino bounded silica-gel (1 g) eluting with ethyl acetate to give the titled compound (20 mg, 94% yield) as a pale yellow gum. The further purification is carried out by preparative LC-MS system in the usual manner to give the title compound (12.7 mg).

Observed MS: 470.7
tR/method: 1.49 min./(QC1)

The following examples (29-2 to 29-7) are prepared according to the procedure of Example-29-1 from INT-16-1-A/INT-16-2-A and the corresponding amines in Table 43. The further purification is carried out by preparative LC-MS system in the usual manner. The retention time and observed MS by HPLC-QC method are summarized in Table 43.

TABLE 43

| Examples | Starting Material | Amines | Observed MS | tR/method |
|---|---|---|---|---|
| Example-29-2 | | H₂N-CH₂CH₂-OH | 486.8 | 1.32 min. (QC1) |

TABLE 43-continued
| Examples | Starting Material | Amines | Observed MS | tR/ method |
|---|---|---|---|---|
| Example-29-3 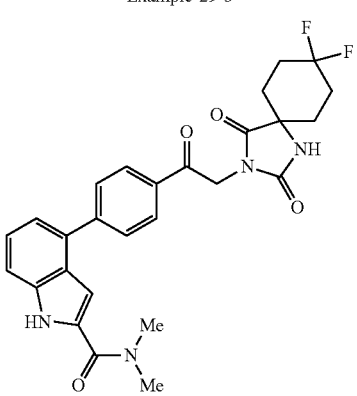 | 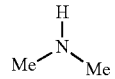 INT-16-2-A | Me−NH−Me | 509.8 | 1.55 min. (QC1) |
| Example-29-4 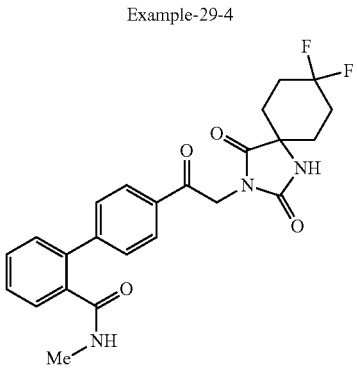 [SMILES: CNC(=O)c1ccccc1-c1ccc(C(=O)CN2C(=O)NC3(CCC(F)(F)CC3)C2=O)cc1] | 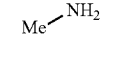 INT-16-1-A | Me−NH$_2$ | 456.7 | 1.40 min. (QC1) |
| Example-29-5 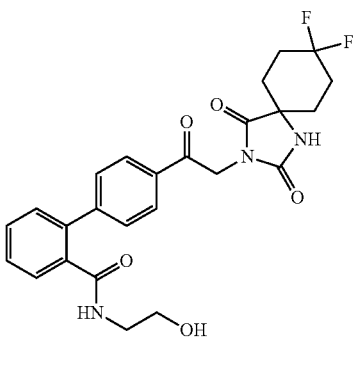 |  INT-16-1-A | H$_2$N−CH$_2$CH$_2$−OMe | 500.8 | 1.44 min. (QC1) |

TABLE 43-continued
| Examples | Starting Material | Amines | Observed MS | tR/ method |
|---|---|---|---|---|
| Example-29-6 | INT-16-2-A | H₂N-H | 481.8 | 1.47 min. (QC1) |
| Example-29-7 | INT-16-2-A | Me-NH₂ | 495.8 | 1.52 min. (QC1) |
TABLE 44
| Examples | Structure | ¹H-NMR Data |
|---|---|---|
| Ex. 1-2 | 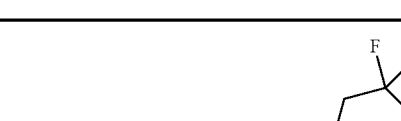 | ¹H-NMR (270 MHz, DMSO-d₆): delta 6.70 (s, 1H), 6.68 (s, 1H), 4.74 (s, 2H), 2.52 (s, 3H), 2.37 (s, 3H), 2.12 (s, 3H), 2.30-1.95 (m, 8H). |

TABLE 44-continued

| Examples | Structure | ¹H-NMR Data |
|---|---|---|
| Ex. 2-2 | 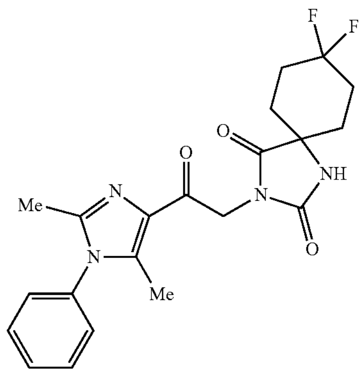 [SMILES: Cc1nc(C(=O)CN2C(=O)NC3(CCC(F)(F)CC3)C2=O)c(C)n1-c1ccccc1] | ¹H-NMR (270 MHz, DMSO-d₆): delta 8.94 (s, 1H), 7.62-7.58 (m, 3H), 7.47-7.44 (m, 2H), 4.74 (s, 2H), 2.22 (s, 3H), 2.16 (s, 3H), 2.11-1.80 (m, 8H). |
| Ex. 2-3 | 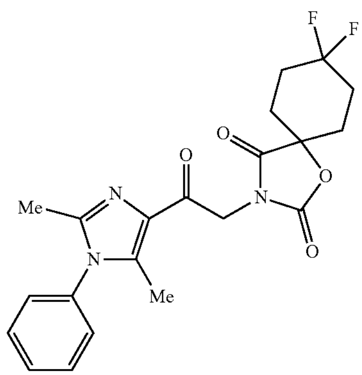 [SMILES: Cc1nc(C(=O)CN2C(=O)OC3(CCC(F)(F)CC3)C2=O)c(C)n1-c1ccccc1] | ¹H-NMR (270 MHz, DMSO-d₆): delta 7.68-7.57 (m, 3H), 7.50-7.42 (m, 2H), 4.84 (s, 2H), 2.30-2.00 (m, 8H), 2.23 (s, 3H), 2.16 (m, 3H). |
| Ex. 4-10 | 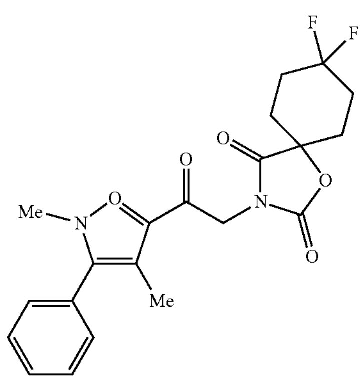 | ¹H-NMR (270 MHz, DMSO-d₆): delta 7.62-7.42 (m, 5H), 4.91 (s, 2H), 3.84 (s, 3H), 2.30-2.00 (m, 11H). |
| Ex. 5-6 | 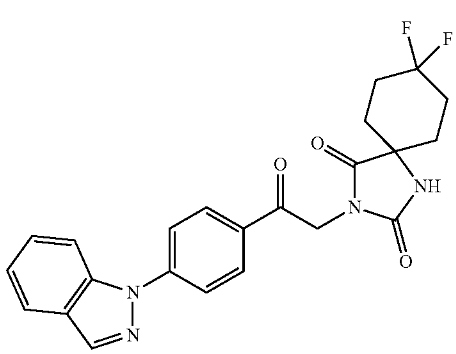 [SMILES: O=C(CN1C(=O)NC2(CCC(F)(F)CC2)C1=O)c1ccc(-n2ncc3ccccc32)cc1] | ¹H-NMR (270 MHz, DMSO-d₆): delta 9.03 (s, 1H), 8.51 (s, 1H), 8.26 (d, J = 8.6 Hz, 2H), 8.05 (d, J = 7.9 Hz, 3H), 7.95 (d, J = 7.9 Hz, 1H), 7.63-7.53 (m, 1H), 7.40-7.30 (m, 1H), 5.03 (s, 2H), 2.27-1.75 (m, 8H). |

TABLE 44-continued

| Examples | Structure | ¹H-NMR Data |
|---|---|---|
| Ex. 5-8 | 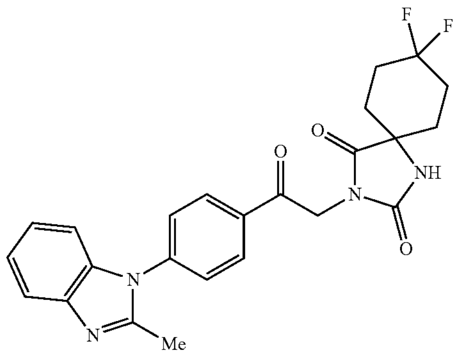 [SMILES: Cc1nc2ccccc2n1-c1ccc(C(=O)CN2C(=O)NC3(CCC(F)(F)CC3)C2=O)cc1] | ¹H-NMR (270 MHz, DMSO-d₆): delta 9.06 (s, 1H), 8.30 (d, J = 7.9 Hz, 2H), 7.80 (d, J = 7.9 Hz, 2H), 7.65 (d, J = 5.9 Hz, 1H), 7.23 (s, 3H), 5.08 (s, 2H), 2.50 (s, 3H), 2.18-1.87 (m, 8H). |
| Ex. 5-9 | 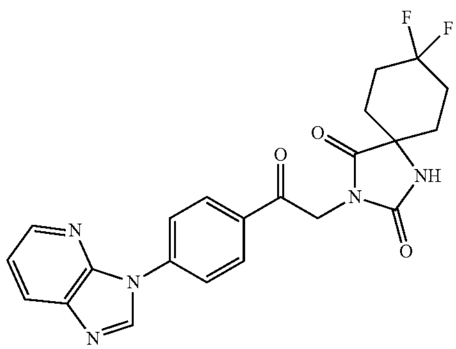 [SMILES: O=C(CN1C(=O)NC2(CCC(F)(F)CC2)C1=O)c1ccc(-n2cnc3cccnc32)cc1] | ¹H-NMR (270 MHz, DMSO-d₆): delta 9.12 (s, 1H), 9.06 (s, 1H), 8.50 (d, J = 4.0 Hz, 1H), 8.35-8.25 (m, 5H), 7.46 (dd, J = 7.9, 4.6 Hz, 1H), 5.06 (s, 2H), 2.19-1.83 (m, 8H). |
| Ex. 5-10 | 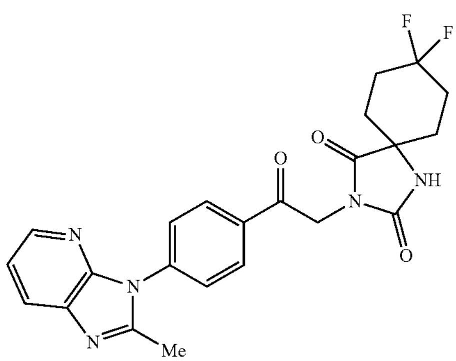 [SMILES: Cc1nc2cccnc2n1-c1ccc(C(=O)CN2C(=O)NC3(CCC(F)(F)CC3)C2=O)cc1] | ¹H-NMR (270 MHz, DMSO-d₆): delta 9.06 (s, 1H), 8.36-8.25 (m, 3H), 8.07 (d, J = 7.9 Hz, 1H), 7.84 (d, J = 8.5 Hz, 2H), 7.33 (dd, J = 7.9, 5.3 Hz, 1H), 5.08 (s, 2H), 2.55 (s, 3H), 2.19-1.83 (m, 8H). |
| Ex. 5-15 | 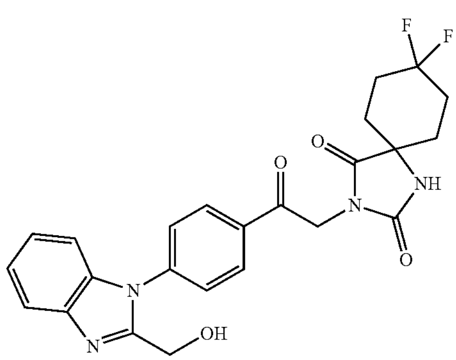 [SMILES: O=C(CN1C(=O)NC2(CCC(F)(F)CC2)C1=O)c1ccc(-n2c(CO)nc3ccccc32)cc1] | ¹H-NMR (270 MHz, DMSO-d₆): delta 9.06 (s, 1H), 8.30 (d, J = 8.5 Hz, 2H), 7.84 (d, J = 8.5 Hz, 2H), 7.34-7.28 (m, 4H), 5.61 (t, J = 5.9 Hz, 1H), 5.07 (s, 2H), 4.65 (d, J = 5.9 Hz, 2H), 2.19-1.76 (m, 8H). |

TABLE 44-continued

| Examples | Structure | ¹H-NMR Data |
|---|---|---|
| Ex. 5-17 | 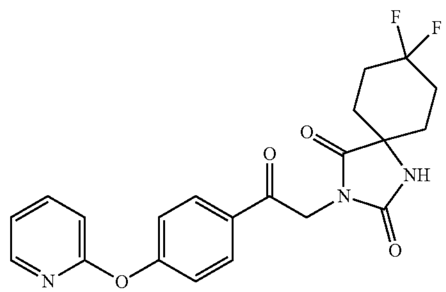 | ¹H-NMR (270 MHz, DMSO-d₆): delta 9.01 (s, 1H), 8.26-8.19 (m, 1H), 8.15-8.06 (m, 2H), 7.98-7.87 (m, 1H), 7.35-7.12 (m, 4H), 4.96 (s, 2H), 2.26-1.75 (m, 8H). |
| Ex. 5-20 | 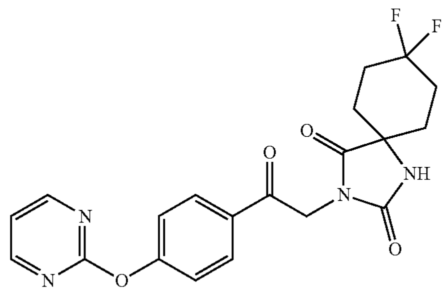 [SMILES: O=C(CN1C(=O)NC2(CCC(F)(F)CC2)C1=O)c1ccc(Oc2ncccn2)cc1] | ¹H-NMR (270 MHz, DMSO-d₆): delta 9.03 (s, 1H), 8.70 (dd, J = 4.6, 1.3 Hz, 2H), 8.15-8.12 (m, 2H), 7.44-7.41 (m, 2H), 7.37-7.33 (m, 1H), 4.99 (s, 2H), 2.18-1.82 (m, 8H). |
| Ex. 5-22 | 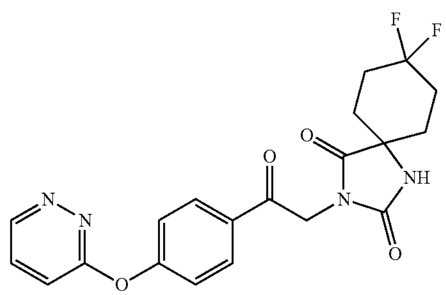 [SMILES: O=C(CN1C(=O)NC2(CCC(F)(F)CC2)C1=O)c1ccc(Oc2cccnn2)cc1] | ¹H-NMR (270 MHz, DMSO-d₆): delta 9.08 (d, J = 4.6 Hz, 1H), 9.03 (s, 1H), 8.15 (d, J = 8.5 Hz, 2H), 7.85 (dd, J = 8.5, 4.6 Hz, 1H), 7.60 (d, J = 7.9 Hz, 1H), 7.42 (d, J = 8.5 Hz, 2H), 4.99 (s, 2H), 2.17-1.86 (m, 8H). |
| Ex. 5-27 | 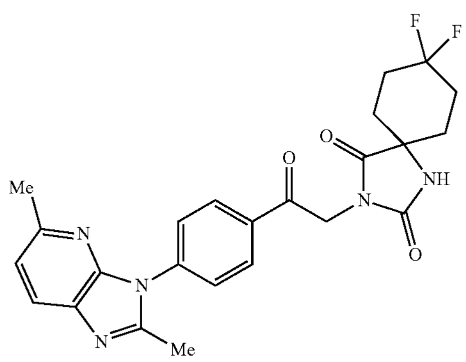 [SMILES: Cc1ccc2nc(C)n(-c3ccc(C(=O)CN4C(=O)NC5(CCC(F)(F)CC5)C4=O)cc3)c2n1] | ¹H-NMR (270 MHz, DMSO-d₆): delta 9.05 (br.s, 1H), 8.33-8.24 (m, 2H), 7.98-7.90 (m, 1H), 7.85-7.75 (m, 2H), 7.22-7.14 (m, 1H), 5.08 (s, 2H), 2.54-2.46 (m, 6H, overlapped with DMSO peak), 2.30-1.75 (m, 8H). |
| Ex. 6-3 | 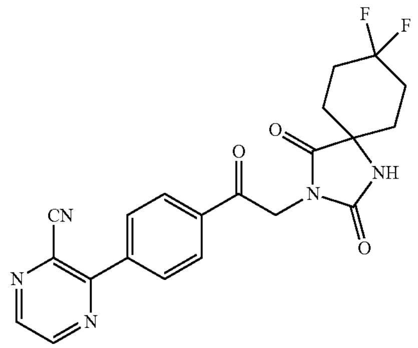 [SMILES: N#Cc1nccnc1-c1ccc(C(=O)CN2C(=O)NC3(CCC(F)(F)CC3)C2=O)cc1] | ¹H-NMR (270 MHz, CDCl₃): delta 8.90 (d, J = 2.6 Hz, 1H), 8.74 (d, J = 2.6 Hz, 1H), 8.17 (s, 4H), 7.00 (br s, 1H), 4.99 (s, 2H), 2.48-2.18 (m, 4H), 2.11-1.88 (m, 4H). |

TABLE 44-continued

| Examples | Structure | ¹H-NMR Data |
|---|---|---|
| Ex. 6-6 | 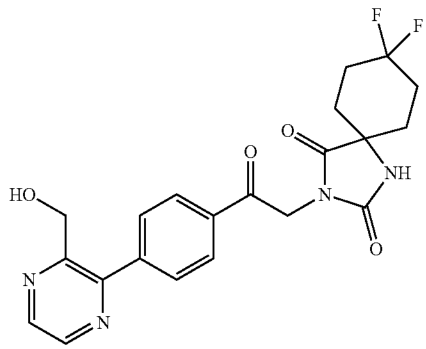 [SMILES: O=C(CN1C(=O)NC2(CCC(F)(F)CC2)C1=O)c1ccc(-c2nccnc2CO)cc1] | ¹H-NMR (270 MHz, DMSO-d$_6$): delta 9.03 (s, 1H), 8.73 (d, J = 2.6 Hz, 1H), 8.71 (d, J = 2.6 Hz, 1H), 8.19 (d, J = 8.6 Hz, 2H), 7.96 (d, J = 8.6 Hz, 2H), 5.58 (t, J = 5.9 Hz, 1H), 5.04 (s, 2H), 4.59 (d, J = 5.9 Hz, 2H), 2.26-1.79 (m, 8H). |
| Ex. 6-9 | 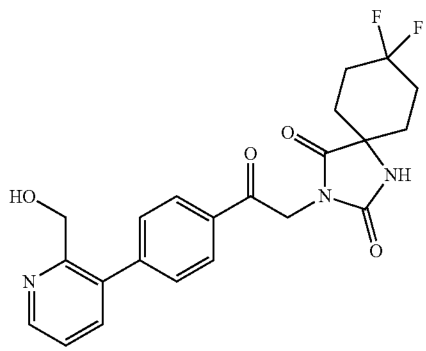 | ¹H-NMR (270 MHz, DMSO-d$_6$): delta 9.03 (s, 1H), 8.64 (d, J = 4.6 Hz, 1H), 8.14 (d, J = 7.9 Hz, 2H), 7.79 (d, J = 7.9 Hz, 1H), 7.71 (d, J = 7.9 Hz, 2H), 7.47 (dd, J = 7.9, 4.6 Hz, 1H), 5.25 (t, J = 5.9 Hz, 1H), 5.03 (s, 2H), 4.48 (d, J = 5.9 Hz, 2H), 2.29-1.78 (m, 8H). |
| Ex. 6-10 | 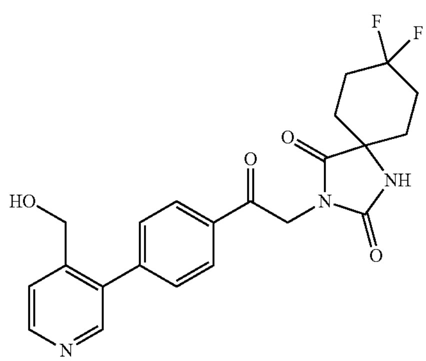 [SMILES: O=C(CN1C(=O)NC2(CCC(F)(F)CC2)C1=O)c1ccc(-c2cnccc2CO)cc1] | ¹H-NMR (270 MHz, DMSO-d$_6$): delta 9.03 (s, 1H), 8.62 (d, J = 4.0 Hz, 1H), 8.45 (s, 1H), 8.14 (d, J = 7.9 Hz, 2H), 7.69-7.60 (m, 3H), 5.84 (t, J = 5.3 Hz, 1H), 5.03 (s, 2H), 4.48 (d, J = 5.3 Hz, 2H), 2.26-1.78 (m, 8H). |
| Ex. 6-11 | 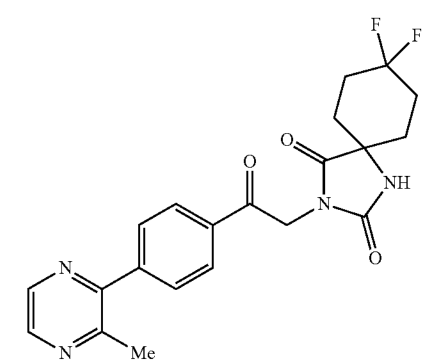 [SMILES: Cc1nccnc1-c1ccc(C(=O)CN2C(=O)NC3(CCC(F)(F)CC3)C2=O)cc1] | ¹H-NMR (270 MHz, CDCl$_3$): delta 8.55-8.51 (m, 2H), 8.09 (d, J = 7.9 Hz, 2H), 7.76 (d, J = 7.9 Hz, 2H), 6.99 (br s, 1H), 4.98 (s, 2H), 2.65 (s, 3H), 2.48-2.19 (m, 4H), 2.12-1.89 (m, 4H). |

TABLE 44-continued
| Examples | Structure | 1H-NMR Data |
|---|---|---|
| Ex. 6-14 | 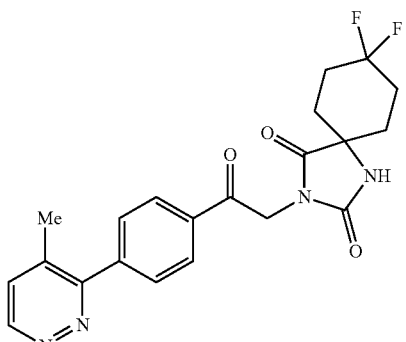 | 1H-NMR (270 MHz, DMSO-d6): delta 9.14 (d, J = 5.3 Hz, 1H), 9.05 (s, 1H), 8.20 (d, J = 8.6 Hz, 2H), 7.84 (d, J = 8.6 Hz, 2H), 7.70 (d, J = 5.3 Hz, 1H), 5.06 (s, 2H), 2.35 (s, 3H), 2.26-1.78 (m, 8H). |
| Ex. 6-15 | 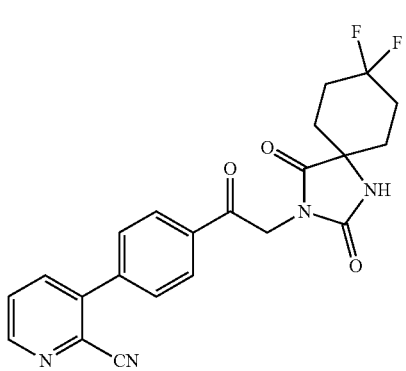 [SMILES: N#Cc1ncccc1-c1ccc(C(=O)CN2C(=O)NC3(CCC(F)(F)CC3)C2=O)cc1] | 1H-NMR (270 MHz, CDCl3): delta 8.78 (dd, J = 4.6, 1.3 Hz, 1H), 8.13 (d, J = 8.6 Hz, 2H), 6.90 (dd, J = 7.9, 1.3 Hz, 1H), 7.74 (d, J = 8.6 Hz, 2H), 7.65 (dd, J = 7.9, 1.3 Hz, 1H), 6.68 (s, 1H) 4.97 (s, 2H), 2.5-2.2 (m, 4H), 2.1-1.19 (m, 4H). |
| Ex. 6-16 | 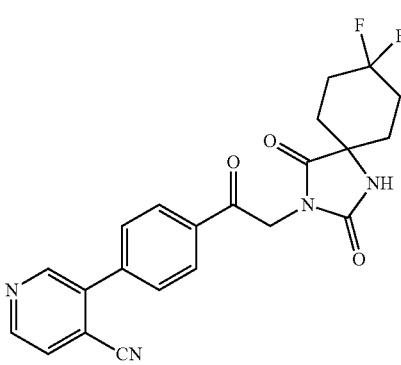 [SMILES: N#Cc1ccncc1-c1ccc(C(=O)CN2C(=O)NC3(CCC(F)(F)CC3)C2=O)cc1] | 1H-NMR (270 MHz, DMSO-d6): delta 9.03 (s, 1H), 8.99 (s, 1H), 8.90 (d, J = 5.3 Hz, 1H), 8.23 (d, J = 7.9 Hz, 2H), 8.05 (d, J = 5.3 Hz, 1H), 7.90 (d, J = 7.9 Hz, 2H), 5.05 (s, 2H), 2.29-1.78 (m, 8H). |
| Ex. 6-17 | 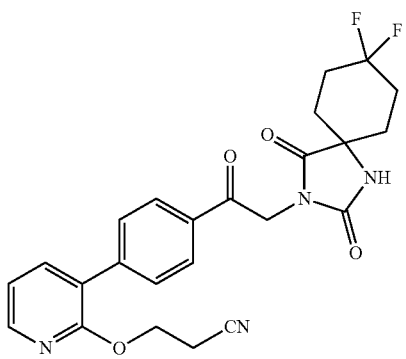 [SMILES: N#CCCOc1ncccc1-c1ccc(C(=O)CN2C(=O)NC3(CCC(F)(F)CC3)C2=O)cc1] | 1H-NMR (270 MHz, CDCl3): delta 8.17 (dd, J = 5.3, 2.0 Hz, 1H), 8.03 (d, J = 8.6 Hz, 2H), 7.73-7.66 (m, 3H), 7.06 (dd, J = 7.3, 5.3 Hz, 1H), 6.55 (br s, 1H), 4.96 (s, 2H), 4.57-4.52 (m, 2H), 3.99-3.92 (m, 2H), 3.75-3.65 (m, 1H), 2.51-2.18 (m, 4H), 2.10-1.90 (m, 4H). |

TABLE 44-continued

| Examples | Structure | ¹H-NMR Data |
| --- | --- | --- |
| Ex. 6-22 | 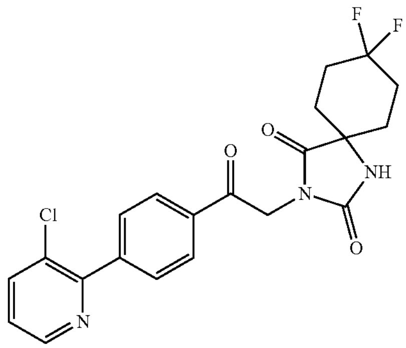 [SMILES: O=C(CN1C(=O)NC2(CCC(F)(F)CC2)C1=O)c1ccc(-c2ncccc2Cl)cc1] | ¹H-NMR (270 MHz, CDCl₃): delta 8.64 (d, J = 4.6 Hz, 1H), 8.07 (d, J = 7.9 Hz, 2H), 7.90 (d, J = 7.9 Hz, 2H), 7.84 (d, J = 8.6 Hz, 1H), 7.30 (dd, J = 8.8, 4.6 Hz, 1H), 6.23 (br s, 1H), 4.97 (s, 2H), 2.52-2.19 (m, 4H), 2.11-1.90 (m, 4H). |
| Ex. 6-26 | 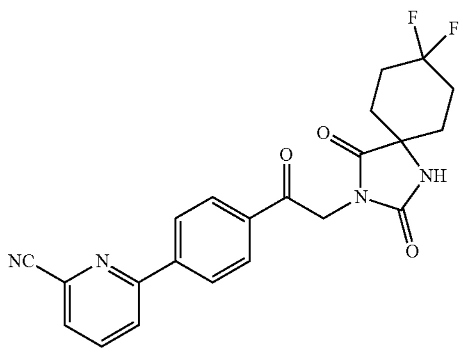 [SMILES: N#Cc1cccc(-c2ccc(C(=O)CN3C(=O)NC4(CCC(F)(F)CC4)C3=O)cc2)n1] | ¹H-NMR (270 MHz, CDCl₃): delta 8.20 (d, J = 8.6 Hz, 2H), 8.09 (d, J = 8.6 Hz, 2H), 8.06-7.92 (m, 2H), 7.71 (d, J = 7.3 Hz, 1H), 6.32 (br s, 1H), 4.97 (s, 2H), 2.51-2.19 (m, 4H), 2.10-1.90 (m, 4H). |
| Ex. 6-27 | 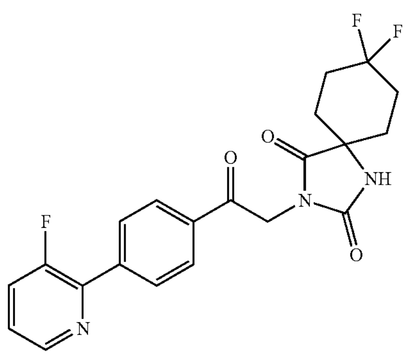 [SMILES: O=C(CN1C(=O)NC2(CCC(F)(F)CC2)C1=O)c1ccc(-c2ncccc2F)cc1] | ¹H-NMR (270 MHz, CDCl₃): delta 8.58 (dd, J = 4.6, 1.3 Hz, 1H), 8.16 (d, J = 8.6 Hz, 2H), 8.07 (d, J = 8.6 Hz, 2H), 7.55 (dd, J = 11.2, 7.9 Hz, 1H), 7.40-7.31 (m, 1H), 4.98 (s, 2H), 2.51-2.19 (m, 4H), 2.12-1.89 (m, 4H), —NH is not observed. |
| Ex. 6-28 | 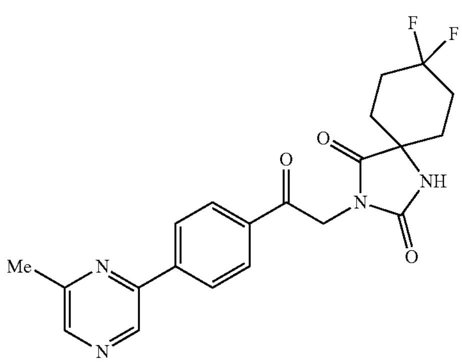 [SMILES: Cc1cncc(-c2ccc(C(=O)CN3C(=O)NC4(CCC(F)(F)CC4)C3=O)cc2)n1] | ¹H-NMR (270 MHz, CDCl₃): delta 8.90 (s, 1H), 8.47 (s, 1H), 8.19 (d, J = 8.6 Hz, 2H), 8.09 (d, J = 8.6 Hz, 2H), 6.52 (br s, 1H), 4.97 (s, 2H), 2.67 (s, 3H), 2.52-2.19 (m, 4H), 2.11-1.90 (m, 4H). |

TABLE 44-continued

| Examples | Structure | ¹H-NMR Data |
|---|---|---|
| Ex. 6-43 | 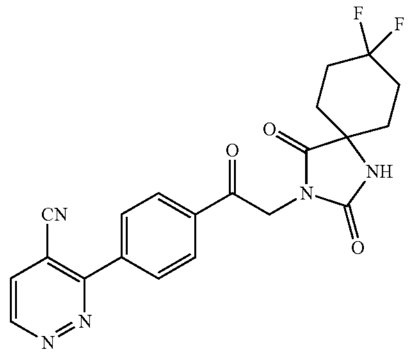 [SMILES: N#Cc1ccnnc1-c1ccc(C(=O)CN2C(=O)NC3(CCC(F)(F)CC3)C2=O)cc1] | ¹H-NMR (270 MHz, DMSO-d₆): delta 9.62 (d, J = 5.3 Hz, 1H), 9.03 (br.s, 1H), 8.45 (d, J = 5.3 Hz, 1H), 8.29 (d, J = 8.6 Hz, 2H), 8.13 (d, J = 8.6 Hz, 2H), 5.08 (s, 2H), 2.30-1.75 (m, 8H). |
| Ex. 6-44 | 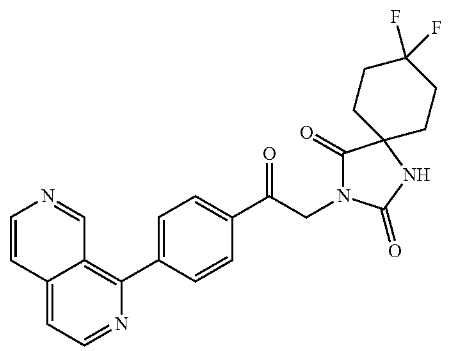 [SMILES: O=C(CN1C(=O)NC2(CCC(F)(F)CC2)C1=O)c1ccc(-c2nccc3ccncc23)cc1] | ¹H-NMR (270 MHz, DMSO-d₆): delta 9.38 (s, 1H), 9.07 (s, 1H), 8.87 (d, J = 5.3 Hz, 1H), 8.80 (d, J = 5.3 Hz, 1H), 8.28 (d, J = 8.6 Hz, 2H), 8.05-7.95 (m, 4H), 5.09 (s 2H), 2.28-1.80 (m, 8H). |
| Ex. 6-87 | 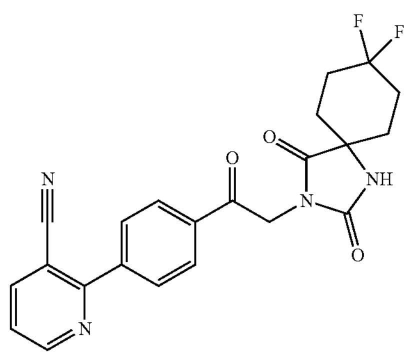 [SMILES: N#Cc1cccnc1-c1ccc(C(=O)CN2C(=O)NC3(CCC(F)(F)CC3)C2=O)cc1] | ¹H-NMR (270 MHz, DMSO-d₆): delta 9.03 (br.s, 1H), 9.01-8.96 (m, 1H), 8.53-8.47 (m, 1H), 8.23 (d, J = 8.6 Hz, 2H), 8.05 (d, J = 8.6 Hz, 2H), 7.74-7.65 (m, 1H), 5.06 (s, 2H), 2.25-1.75 (m, 8H). |
| Ex. 6-97 | 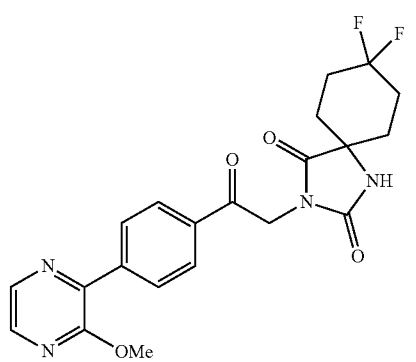 [SMILES: COc1nccnc1-c1ccc(C(=O)CN2C(=O)NC3(CCC(F)(F)CC3)C2=O)cc1] | ¹H-NMR (270 MHz, DMSO-d₆): delta 9.03 (br.s, 1H), 8.40 (d, J = 2.6 Hz, 1H), 8.31 (d, J = 2.6 Hz, 1H), 8.24-8.12 (m, 4H), 5.02 (s, 2H), 4.02 (s, 3H), 2.25-1.75 (m, 8H). |

TABLE 44-continued

| Examples | Structure | ¹H-NMR Data |
|---|---|---|
| Ex. 6-98 | 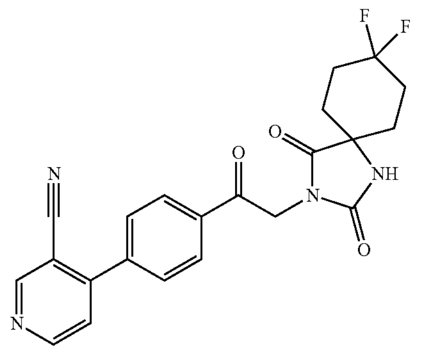 [SMILES: N#Cc1cnccc1-c1ccc(C(=O)CN2C(=O)NC3(CCC(F)(F)CC3)C2=O)cc1] | ¹H-NMR (270 MHz, DMSO-d₆): delta 9.18 (br.s, 1H), 9.06 (s, 1H), 9.00-8.90 (m, 1H), 8.24 (d, J = 8.6 Hz, 2H), 7.90 (d, J = 8.6 Hz, 2H), 7.80 (d, J = 5.3 Hz, 1H), 5.06 (s, 2H), 2.30-1.75 (m, 8H) |
| Ex. 7-10 | 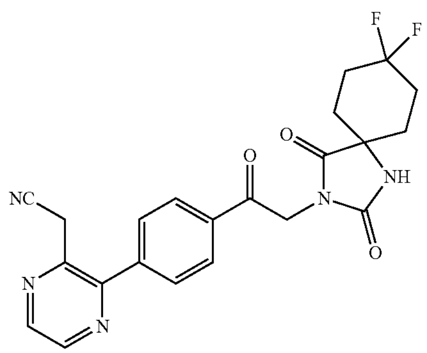 [SMILES: N#CCc1nccnc1-c1ccc(C(=O)CN2C(=O)NC3(CCC(F)(F)CC3)C2=O)cc1] | ¹H-NMR (270 MHz, CDCl₃): delta 8.67 (d, J = 2.6 Hz, 1H), 8.61 (d, J = 2.6 Hz, 1H), 8.10 (d, J = 7.9 Hz, 2H), 7.74 (d, J = 7.9 Hz, 2H), 5.96 (br s, 1H), 4.96 (s, 2H), 4.83 (d, J = 5.3 Hz, 2H), 3.93 (t, J = 5.3 Hz, 1H), 2.04-1.37 (m, 10 H). |
| Ex. 8-7 | 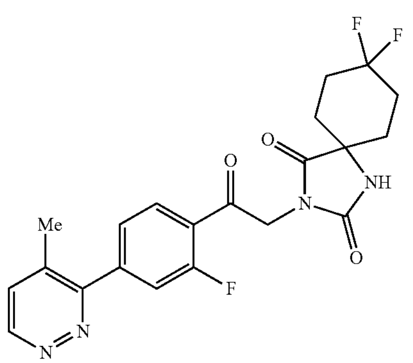 [SMILES: Cc1ccnnc1-c1ccc(C(=O)CN2C(=O)NC3(CCC(F)(F)CC3)C2=O)c(F)c1] | ¹H-NMR (270 MHz, DMSO-d₆): delta 9.15 (d, J = 5.3 Hz, 1H), 9.04 (br.s, 1H), 8.10-8.00 (m, 1H), 7.80-7.60 (m, 4.89 (s, 2H), 2.37 (s, 3H), 2.25-1.70 (m, 8H). |
| Ex. 9-13 | 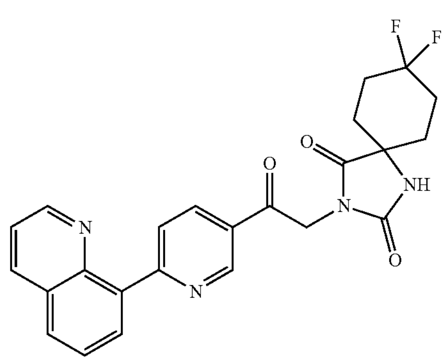 [SMILES: O=C(CN1C(=O)NC2(CCC(F)(F)CC2)C1=O)c1ccc(-c2cccc3cccnc23)nc1] | ¹H-NMR (270 MHz, DMSO-d₆): delta 9.36 (s, 1H), 9.05 (s, 1H), 8.98 (dd, J = 4.0, 1.9 Hz, 1H), 853-8.46 (m, 2H), 8.40 (d, J = 8.5 Hz, 1H), 8.25 (d, J = 7.2 Hz, 1H), 8.16 (d, J = 8.5 Hz, 1H), 7.82-7.76 (m, 1H), 7.67-7.62 (m, 1H), 5.11 (s, 2H), 2.19-1.88 (m, 8H). |

TABLE 44-continued

| Examples | Structure | ¹H-NMR Data |
|---|---|---|
| Ex. 10-1 | 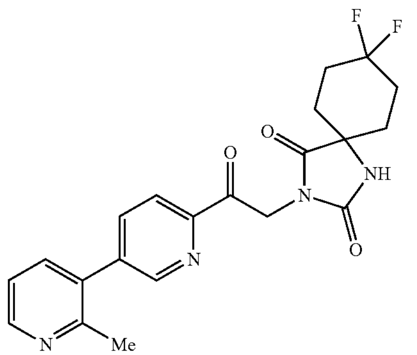 [SMILES: Cc1ncccc1-c1ccc(C(=O)CN2C(=O)NC3(CCC(F)(F)CC3)C2=O)nc1] | ¹H-NMR (270 MHz, DMSO-d₆): delta 9.04 (s, 1H), 8.86 (d, J = 2.6 Hz, 1H), 8.57 (d, J = 4.6 Hz, 1H), 8.17 (dd, J = 7.9, 2.6 Hz, 1H), 8.08 (d, J = 7.9 Hz, 1H), 7.77 (d, J = 7.3 Hz, 1H), 7.40 (dd, J = 7.3, 4.6 Hz, 1H), 5.08 (s, 2H), 2.48 (s, 3H), 2.29-1.79 (m, 8H). |
| Ex. 12-1 | 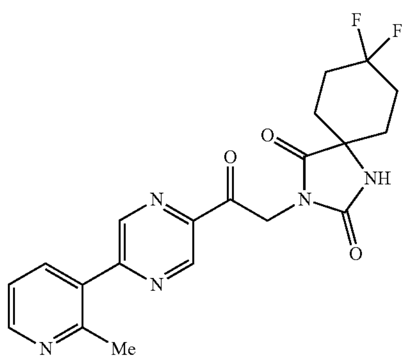 [SMILES: Cc1ncccc1-c1cnc(C(=O)CN2C(=O)NC3(CCC(F)(F)CC3)C2=O)cn1] | ¹H-NMR (270 MHz, CDCl₃): delta 9.32 (s, 1H), 8.85 (s, 1H), 8.67 (d, J = 4.6 Hz, 1H), 7.85 (d, J = 7.9 Hz, 1H), 7.40-7.20 (m, 1H), 6.47 (br.s, 1H), 5.20 (s, 2H), 2.55-1.90 (m, 8H), 1.59 (s, 3H). |
| Ex. 12-3 | 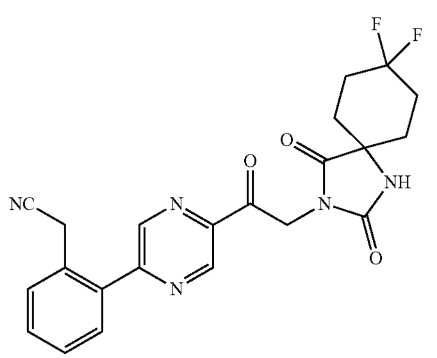 [SMILES: N#CCc1ccccc1-c1cnc(C(=O)CN2C(=O)NC3(CCC(F)(F)CC3)C2=O)cn1] | ¹H-NMR (270 MHz, CDCl₃): delta 9.24 (s, 1H), 9.03 (s, 1H), 7.68 (d, J = 7.3 Hz, 1H), 7.63-7.50 (m, 3H), 7.08 (br s, 1H), 5.21 (s, 2H), 4.74 (t, J = 7.3 Hz, 1H), 4.53 (d, J = 7.3 Hz, 2H), 2.50-2.18 (m, 4H), 2.13-1.91 (m, 4H). |
| Ex. 12-5 | 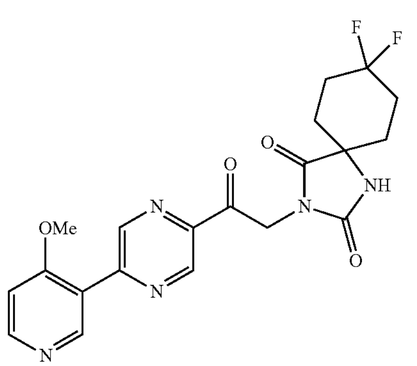 [SMILES: COc1ccncc1-c1cnc(C(=O)CN2C(=O)NC3(CCC(F)(F)CC3)C2=O)cn1] | ¹H-NMR (270 MHz, CDCl₃): delta 9.30 (s, 1H), 9.25 (s, 1H), 9.07 (s, 1H), 8.63 (d, J = 5.9 Hz, 1H), 7.00 (d, J = 5.9 Hz, 1H), 6.27 (br s, 1H), 5.19 (s, 2H), 4.03 (s, 3H), 2.55-2.19 (m, 4H), 2.12-1.89 (m, 4H). |

TABLE 44-continued
| Examples | Structure | ¹H-NMR Data |
|---|---|---|
| Ex. 13-34 | 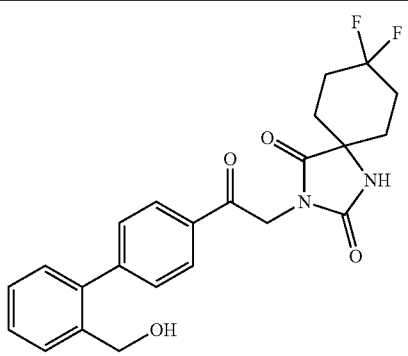 | ¹H-NMR (270 MHz, DMSO-d₆): delta 9.02 (s, 1H), 8.11 (d, J = 8.6 Hz, 2H), 7.60 (d, J = 7.9 Hz, 3H), 7.47-7.35 (m, 2H), 7.28 (d, J = 7.2 Hz, 1H), 5.22 (t, J = 5.3 Hz, 1H), 5.01 (s, 2H), 4.41 (d, J = 5.3 Hz, 2H), 2.18-1.82 (m, 8H). |
| Ex. 13-39 | 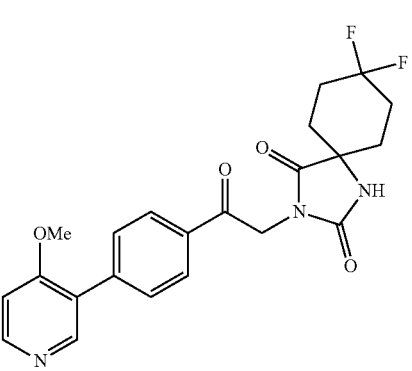 [SMILES: COc1ccncc1-c1ccc(C(=O)CN2C(=O)NC3(CCC(F)(F)CC3)C2=O)cc1] | ¹H-NMR (270 MHz, CDCl₃): delta 8.53 (d, J = 5.9 Hz, 1H), 8.47 (s, 1H), 8.03 (d, J = 8.6 Hz, 2H), 7.73 (br s, 1H), 7.67 (d, J = 8.6 Hz, 2H), 6.94 (d, J = 5.9 Hz, 1H), 4.95 (s, 2H), 3.91 (s, 3H), 2.42-1.86 (m, 8H). |
| Ex. 13-45 | 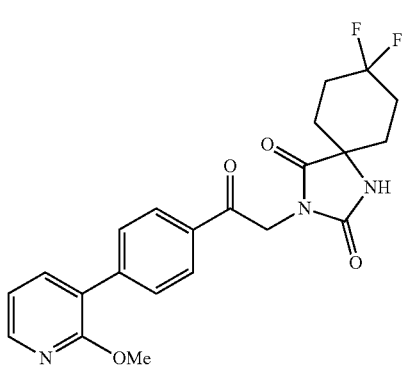 [SMILES: COc1ncccc1-c1ccc(C(=O)CN2C(=O)NC3(CCC(F)(F)CC3)C2=O)cc1] | ¹H-NMR (270 MHz, CDCl₃): delta 7.53-7.46 (m, 1H), 7.23-8.02 (d, J = 7.9 Hz, 2H), 7.71 (d, J = 7.9 Hz, 2H), 7.65 (d, J = 7.3 Hz, 1H), 7.02 (dd, J = 7.3, 4.6 Hz, 1H), 4.96 (s, 2H), 3.99 (s, 3H), 2.50-2.18 (m, 4H), 2.11-1.88 (m, 4H), -NH is not observed. |
| Ex. 14-4 | 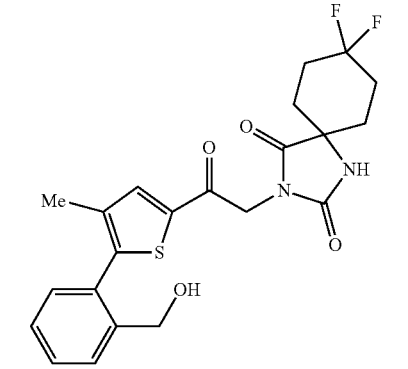 [SMILES: Cc1cc(C(=O)CN2C(=O)NC3(CCC(F)(F)CC3)C2=O)sc1-c1ccccc1CO] | ¹H-NMR (270 MHz, CDCl₃): delta 7.65 (s, 1H), 7.62 (d, J = 7.3 Hz, 1H), 7.48 (dd, J = 7.3, 7.3 Hz, 1H), 7.37 (dd, J = 7.3, 7.3 Hz, 1H), 7.26-7.23 (m, 1H), 6.22 (br. s, 1H), 4.85 (s, 2H), 4.57 (d, J = 5.9 Hz, 2H), 2.09 (s, 3H), 2.51-1.88 (m, 8H), 1.67 (t, J = 5.9 Hz, 1H). |

TABLE 44-continued

| Examples | Structure | ¹H-NMR Data |
|---|---|---|
| Ex. 17-6 | 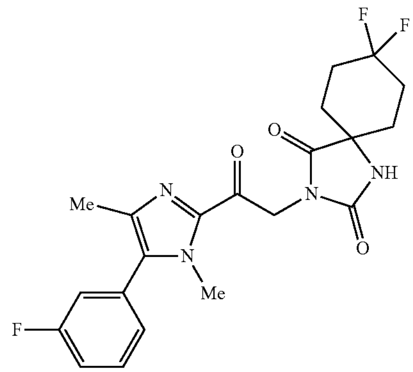 [SMILES: Cc1nc(C(=O)CN2C(=O)NC3(CCC(F)(F)CC3)C2=O)n(C)c1-c1cccc(F)c1] | ¹H-NMR (270 MHz, CDCl₃): delta 7.53-7.43 (m, 1H), 7.23-7.14 (m, 1H), 7.08 (d, J = 7.3 Hz, 1H), 7.06-6.98 (m, 1H), 6.35 (br s, 1H), 5.11 (s, 2H), 3.81 (s, 3H), 2.51-2.18 (m, 4H), 2.25 (s, 3H), 2.10-1.88 (m, 4H). |
| Ex. 17-7 | 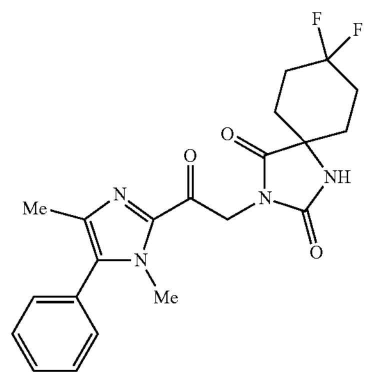 | ¹H-NMR (270 MHz, CDCl₃): delta 7.55-7.45 (m, 3H), 7.32-7.27 (m, 2H), 5.11 (s, 2H), 3.80 (s, 3H), 2.53-2.18 (m, 4H), 2.25 (s, 3H), 2.10-1.88 (m, 4H), —NH is not observed. |
| Ex. 17-8 | 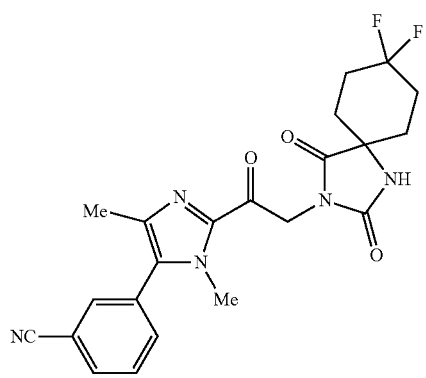 [SMILES: Cc1nc(C(=O)CN2C(=O)NC3(CCC(F)(F)CC3)C2=O)n(C)c1-c1cccc(C#N)c1] | ¹H-NMR (270 MHz, CDCl₃): delta 7.76 (dt, J = 7.9, 1.3 Hz, 1H), 7.67 (d, J = 7.9 Hz, 1H), 7.61 (br s, 1H), 7.55 (dt, J = 7.9, 1.3 Hz, 1H), 6.62 (br s, 1H), 5.10 (s, 2H), 3.81 (s, 3H), 2.50-2.16 (m, 4H), 2.24 (s, 3H), 2.11-1.88 (m, 4H). |
| Ex. 17-9 | 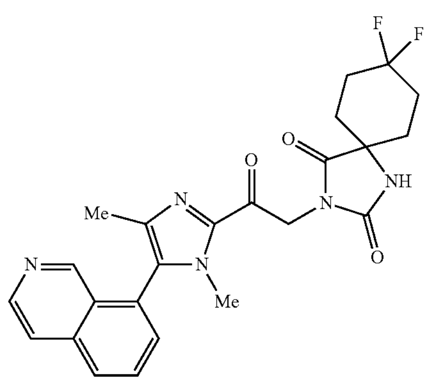 [SMILES: Cc1nc(C(=O)CN2C(=O)NC3(CCC(F)(F)CC3)C2=O)n(C)c1-c1cccc2ccncc12] | ¹H-NMR (270 MHz, CDCl₃): delta 8.89 (s, 1H), 8.65 (d, J = 5.9 Hz, 1H), 7.98 (d, J = 7.9 Hz, 1H), 7.84 td, J = 7.9 Hz, 1H), 7.77 (d, J = 7.9 Hz, 1H), 7.51 (d, J = 5.9 Hz, 1H), 5.18 (s, 2H), 3.68 (s, 3H), 2.52 2.20 (m, 4H), 2.15 (s, 3H), 2.10 1.92 (m, 4H), —NH is not observed. |

TABLE 44-continued
| Examples | Structure | ¹H-NMR Data |
|---|---|---|
| Ex. 17-10 | 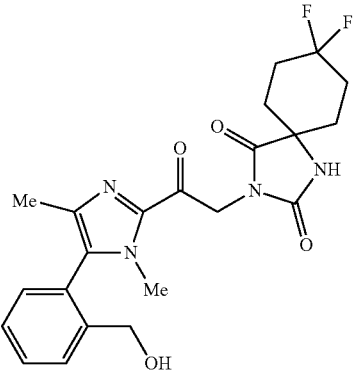 [SMILES: Cc1nc(C(=O)CN2C(=O)NC3(CCC(F)(F)CC3)C2=O)n(C)c1-c1ccccc1CO] | ¹H-NMR (270 MHz, CDCl₃): delta 7.65 (d, J = 7.3 Hz, 1H), 7.55 (dd, J = 7.9, 7.3 Hz, 1 H), 7.43 (dd, J = 7.9, 7.3 Hz, 1H), 7.17 (d, J = 7.3 Hz, 1H), 6.85 (br s, 1H), 5.11 (s, 2H), 4.44 (d, J = 3.3 Hz, 2H), 3.63 (s, 3H), 2.50-2.15 (m, 4H), 2.10 (s, 3H), 2.08-1.80 (m, 4H), —OH is not observed. |
| Ex. 17-11 | 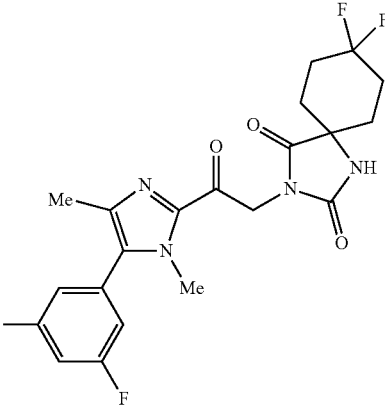 | ¹H-NMR (270 MHz, CDCl₃): delta 6.99-6.89 (m, 1H), 6.89-6.79 (m, 2H), 6.40 (br s, 1H), 5.10 (s, 2H), 3.82 (s, 3H), 2.50-2.17 (m, 4H), 2.25 (s, 3H), 2.11-1.88 (m, 4H). |
| Ex. 19-21 | 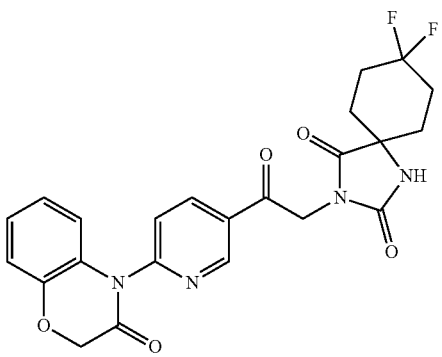 [SMILES: O=C(CN1C(=O)NC2(CCC(F)(F)CC2)C1=O)c1ccc(N2C(=O)COc3ccccc32)nc1] | ¹H-NMR (270 MHz, DMSO-d₆): delta 9.04 (s, 1H), 8.24 (d, J = 8.5 Hz, 2H), 7.58 (d, J = 8.5 Hz, 2H), 7.13-7.00 (m, 2H), 6.90 (td, J = 7.9.1.3 Hz, 1H), 6.36 (dd, J = 7.9, 1.3 Hz, 1H), 5.04 (s, 2H), 4.84 (s, 2H), 2.18-1.87 (m, 8H). |
| Ex. 19-24 | 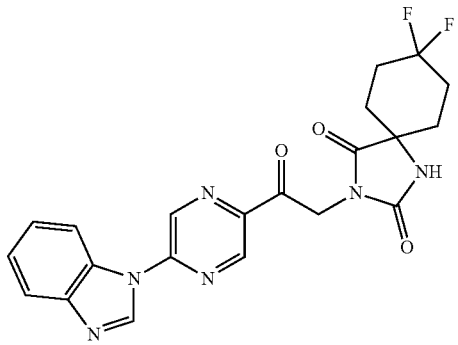 [SMILES: O=C(CN1C(=O)NC2(CCC(F)(F)CC2)C1=O)c1cnc(-n2cnc3ccccc32)cn1] | ¹H-NMR (270 MHz, CDCl₃): delta 9.21 (d, J = 1.3 Hz, 1H), 9.08 (d, J = 1.3 Hz, 1H), 8.74 (s, 1H), 8.24 (dd, J = 7.3, 2.0 Hz, 1H), 7.93 (dd, J = 9.2, 2.0 Hz, 1H), 7.54-7.41 (m, 2H), 5.18 (s, 2H), 2.55-2.21 (m, 4H), 2.09-1.91 (m, 4H), —NH is not observed. |

TABLE 44-continued

| Examples | Structure | ¹H-NMR Data |
|---|---|---|
| Ex. 19-30 | 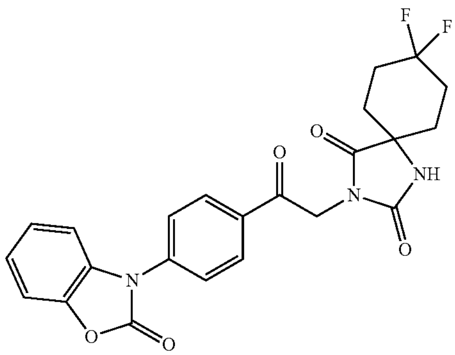 [SMILES: O=C(CN1C(=O)NC2(CCC(F)(F)CC2)C1=O)c1ccc(-n2c(=O)oc3ccccc32)cc1] | ¹H-NMR (270 MHz, DMSO-d₆): delta 9.05 (br. s, 1H), 8.27 (d, J = 7.9 Hz, 2H), 7.87 (d, J = 7.9 Hz, 2H), 7.53-7.44 (m, 1H), 7.30-7.22 (m, 3H), 5.04 (s, 2H), 2.25-1.80 (m, 8H). |
| Ex. 21-1 | 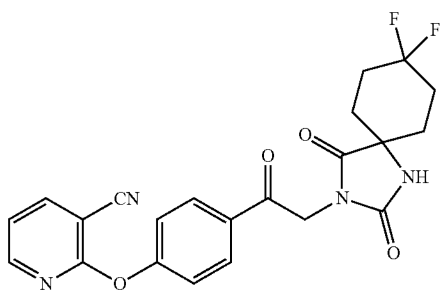 [SMILES: N#Cc1cccnc1Oc1ccc(C(=O)CN2C(=O)NC3(CCC(F)(F)CC3)C2=O)cc1] | ¹H-NMR (270 MHz, DMSO-d₆): delta 9.03 (s, 1H), 8.48 (dd, J = 7.9, 2.0 Hz, 1H), 8.42-8.41 (m, 1H), 8.15 (d, J = 8.5 Hz, 2H), 7.47 (d, J = 8.5 Hz, 2H), 7.41-7.36 (m, 1H), 4.99 (s, 2H), 2.18-1.86 (m, 8H). |
| Ex. 21-12 | 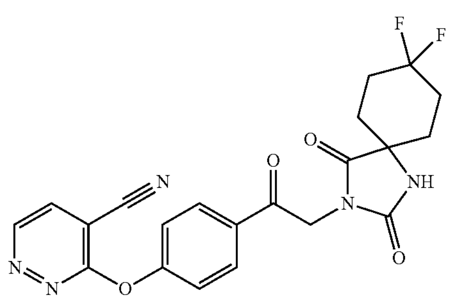 [SMILES: N#Cc1ccnnc1Oc1ccc(C(=O)CN2C(=O)NC3(CCC(F)(F)CC3)C2=O)cc1] | ¹H-NMR (270 MHz, DMSO-d₆): delta 9.31 (d, J = 4.6 Hz 1H), 9.01 (br.s, 1H), 8.41 (d, J = 4.6 Hz, 1H), 8.18 (d, J = 8.6 Hz, 2H), 7.55 (d, J = 8.6 Hz, 2H), 5.00 (s, 2H), 2.25-1.75 (m, 8H). |
| Ex. 22-1 | 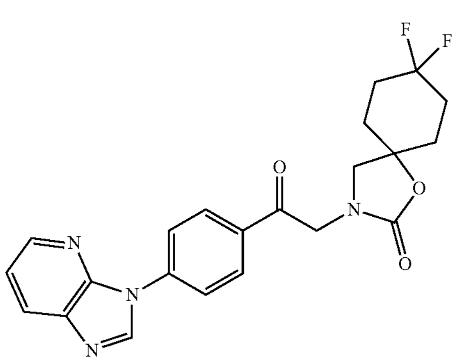 [SMILES: O=C(CN1CC2(CCC(F)(F)CC2)OC1=O)c1ccc(-n2cnc3cccnc32)cc1] | ¹H-NMR (270 MHz, DMSO-d₆): delta 9.11 (s, 1H), 8.51-8.49 (m, 1H), 8.33-8.21 (m, 5H), 7.48-7.43 (m, 1H), 4.87 (s, 2H), 3.47 (s, 2H), 2.10-1.91 (m, 8H). |

TABLE 44-continued

| Examples | Structure | $^1$H-NMR Data |
|---|---|---|
| Ex. 23-1 | 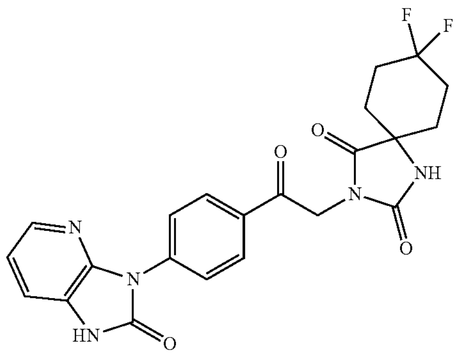 [SMILES: O=C(CN1C(=O)NC2(CCC(F)(F)CC2)C1=O)c1ccc(-n2c(=O)[nH]c3cccnc32)cc1] | $^1$H-NMR (270 MHz, DMSO-$d_6$): delta 11.6 (br. s, 1H), 9.05 (s, 1H), 8.22 (d, J = 8.6 Hz, 2H), 8.10-7.96 (m, 3H), 7.45 (d, J = 7.9 Hz, 1H), 7.16 (dd, J = 7.9, 5.3 Hz, 1H), 5.03 (s, 2H), 2.30-1.78 (m, 8H). |
| Ex. 24-5 | 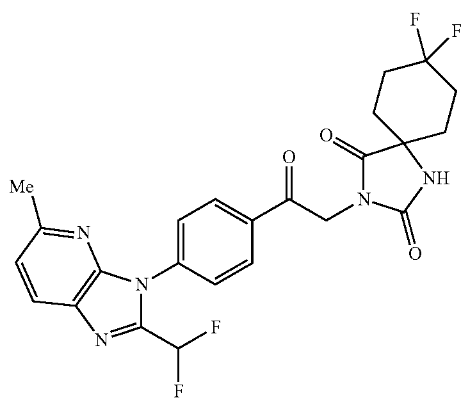 [SMILES: Cc1ccc2nc(C(F)F)n(-c3ccc(C(=O)CN4C(=O)NC5(CCC(F)(F)CC5)C4=O)cc3)c2n1] | $^1$H-NMR (270 MHz, DMSO-$d_6$): delta 9.06 (br.s, 1H), 8.29 (d, J = 8.6 Hz, 2H), 8.23 (d, J = 7.9 Hz, 1H), 7.82 (d, J = 8.6 Hz, 2H), 7.37 (d, J = 7.9 Hz, 1H), 7.32 (t, J = 52.1 Hz, 1H), 5.09 (s, 2H), 2.54 (s, 3H), 2.30-1.75 (m, 8H). |
| Ex. 24-7 | 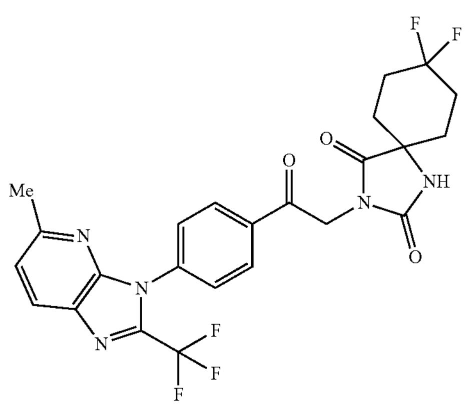 [SMILES: Cc1ccc2nc(C(F)(F)F)n(-c3ccc(C(=O)CN4C(=O)NC5(CCC(F)(F)CC5)C4=O)cc3)c2n1] | $^1$H-NMR (270 MHz, DMSO-$d_6$): delta 9.05 (br.s, 1H), 8.35-8.25 (m, 3H), 7.85 (d, J = 8.6 Hz, 2H), 7.43 (d, J = 7.9 Hz, 1H), 5.10 (s, 2H), 2.55 (s, 3H), 2.30-1.75 (m, 8H). |
| Ex. 26-3 | 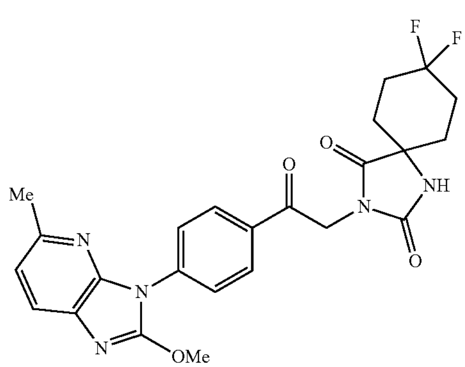 [SMILES: COc1nc2ccc(C)nc2n1-c1ccc(C(=O)CN2C(=O)NC3(CCC(F)(F)CC3)C2=O)cc1] | $^1$H-NMR (270 MHz, DMSO-$d_6$): delta 9.03 (br.s, 1H), 8.24 (d, J = 8.6 Hz, 2H), 7.89 (d, J = 8.6 Hz, 2H), 7.79 (d, J = 7.9 Hz, 1H), 7.14 (d, J = 7.9 Hz, 1H), 5.04 (s, 2H), 4.16 (s, 3H), 2.48 (s, 3H), 2.30-1.75 (m, 8H). |

TABLE 44-continued

| Examples | Structure | ¹H-NMR Data |
| --- | --- | --- |
| Ex. 27-1 | 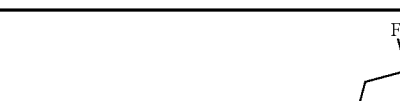 | ¹H-NMR (270 MHz, DMSO-d₆): delta 9.04 (br.s, 1H), 8.35-8.26 (m, 3H), 7.96 (d, J = 7.9 Hz, 1H), 7.86 (d, J = 8.6 Hz, 2H), 5.09 (s, 2H), 2.59 (s, 3H), 2.30-1.75 (m, 8H). |

Measurement of the Menthol-Induced $Ca^{2+}$ Influx in HEK293 Cells Stably Expressing Human TRPM8

A cell-based $Ca^{2+}$ influx assay using HEK293 cells stably expressing human TRPM8 is used to identify the activity of compounds.

HEK293 cells stably expressing human TRPM8 are grown in T175 flasks at 37° C. in a 5% $CO_2$ humidified incubator to about 80% confluence. Media composition consists of Dulbecco's Modified Eagle Medium (high glucose), 10% fetal calf serum (FCS), 100 units/mLPenicillin, 100 microg/mL Streptomycin and 600 microg/mL Geneticine. At 24 hours prior to assay, cells are seeded in poly-D-lysine coated 384-well plates (BD FALCON) at a density of 30,000 cells per well in culture medium and grown overnight in 5% $CO_2$ at 37° C. On the assay day, growth media is removed and cells are loaded with 0.5 microM Fluo4-AM (Molecular Probes) and 0.005% Pluronic F-127 dissolved in assay buffer (Hank's balanced salt solution (HBSS), 19.4 mM HEPES pH7.4, 2.5 mM Probenecid) for 1 hour at room temperature. After washing with assay buffer, the cells are preincubated with various concentrations of the compounds for 5 min. The changes in intracellular calcium concentration by addition of 30 microM menthol are monitored by the cell imaging technology by Hamamatsu Photonics Functional Drug Screening System (FDSS).

The $IC_{50}$ values for compounds of the present invention are determined from 11-point dose-response studies. Curves are generated using the average of duplicate wells for each data point. Finally, the $IC_{50}$ values are calculated with the best-fit dose curve determined by XLfit (ID Business Solutions Ltd.).

All tested compounds show less than about 3 microM of $IC_{50}$ against TRPM8 in the above assays. Preferable compounds show less than about 500 nM of $IC_{50}$ against TRPM8 in the above assays. More preferable compounds show less than about 100 nM of $IC_{50}$ against TRPM8 in the above assays. Most preferable compounds show less than about 10 nM of $IC_{50}$ against TRPM8 in the above assays.

Compounds with $IC_{50}$ against TRPM8<500 nM are: 1-1, 1-2, 1-3, 1-4, 1-5, 1-6, 1-13, 1-14, 2-1, 2-2, 2-3, 2-4, 2-5, 2-6, 2-7, 2-8, 2-11, 2-12, 2-13, 2-14, 2-15, 2-16, 2-17, 2-18, 3-1, 3-2, 3-3, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 3-26, 3-27, 3-28, 3-29, 4-1, 4-2, 4-3, 4-4, 4-5, 4-6, 4-7, 4-8, 4-9, 4-10, 4-11, 4-12, 5-1, 5-2, 5-3, 5-4, 5-5, 5-6, 5-7, 5-8, 5-9, 5-10, 5-11, 5-12, 5-13, 5-14, 5-15, 5-16, 5-17, 5-18, 5-19, 5-20, 5-21, 5-22, 5-23, 5-24, 5-25, 5-26, 5-27, 5-28, 5-30, 5-31, 5-32, 5-33, 5-39, 5-40, 5-41, 6-1, 6-2, 6-3, 6-4, 6-5, 6-6, 6-7, 6-8, 6-9, 6-10, 6-11, 6-12, 6-13, 6-14, 6-15, 6-16, 6-17, 6-18, 6-19, 6-20, 6-21, 6-22, 6-23, 6-24, 6-25, 6-26, 6-27, 6-28, 6-29, 6-30, 6-31, 6-32, 6-33, 6-34, 6-35, 6-36, 6-37, 6-38, 6-39, 6-40, 6-41, 6-42, 6-43, 6-44, 6-45, 6-46, 6-47, 6-48, 6-49, 6-50, 6-51, 6-52, 6-53, 6-54, 6-55, 6-56, 6-57, 6-58, 6-59, 6-62, 6-63, 6-64, 6-65, 6-67, 6-68, 6-69, 6-71, 6-72, 6-76, 6-78, 6-80, 6-81, 6-82, 6-84, 6-85, 6-87, 6-90, 6-92, 6-93, 6-95, 6-96, 6-97, 6-98, 6-99, 6-100, 6-102, 6-104, 6-106, 6-108, 6-110, 6-113, 6-114, 6-116, 6-117, 6-119, 6-120, 6-122, 7-1, 7-2, 7-3, 7-4, 7-5, 7-6, 7-7, 7-8, 7-9, 7-10, 7-11, 7-12, 7-13, 7-14, 7-15, 7-16, 7-17, 7-18, 7-19, 7-20, 7-21, 7-22, 7-23, 7-24, 7-25, 7-26, 8-1, 8-2, 8-3, 8-4, 8-5, 8-6, 8-7, 8-8, 8-9, 9-1, 9-2, 9-3, 9-4, 9-5, 9-6, 9-7, 9-8, 9-9, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 10-1, 10-2, 11-1, 11-2, 12-1, 12-2, 12-3, 12-4, 12-5, 12-6, 12-7, 13-1, 13-2, 13-3, 13-4, 13-5, 13-6, 13-7, 13-8, 13-9, 13-10, 13-11, 13-12, 13-13, 13-14, 13-15, 13-16, 13-17, 13-18, 13-19, 13-20, 13-21, 13-22, 13-23, 13-24, 13-25, 13-26, 13-27, 13-28, 13-29, 13-30, 13-31, 13-32, 13-33, 13-34, 13-35, 13-36, 13-37, 13-38, 13-39, 13-40, 13-41, 13-42, 13-43, 13-44, 13-45, 13-46, 13-47, 13-48, 13-49, 13-50, 13-51, 13-52, 13-53, 13-54, 13-55, 13-56, 13-57, 13-68, 13-69, 13-71, 13-72, 14-1, 14-2, 14-3, 14-4, 14-5, 14-6, 14-7, 14-8, 14-9, 14-10, 14-11, 14-12, 14-13, 14-14, 14-15, 14-16, 14-17, 14-18, 14-19, 14-20, 14-21, 15-1, 15-2, 15-3, 15-4, 15-5, 15-6, 15-7, 15-8, 15-9, 15-10, 15-11, 15-12, 16-1, 16-2, 16-3, 16-4, 16-5, 16-6, 16-7, 16-8, 16-9, 16-10, 16-11, 16-12, 16-13, 16-14, 16-15, 16-16, 16-17, 16-18, 16-19, 16-20, 16-21, 16-22, 16-23, 16-24, 16-25, 16-26, 16-27, 16-28, 16-29, 16-30, 16-31, 16-32, 16-33, 16-34, 16-35, 16-36, 17-1, 17-2, 17-3, 17-4, 17-5, 17-6, 17-7, 17-8, 17-9, 17-10, 17-11, 17-12, 17-13, 17-14, 17-15, 18-1, 18-2, 18-3, 18-4, 18-5, 18-6, 18-7, 18-8, 18-9, 18-10, 18-11, 18-12, 18-13, 19-1, 19-2, 19-3, 19-4, 19-5, 19-6, 19-7, 19-8, 19-9, 19-10, 19-11, 19-12, 19-13, 19-14, 19-15, 19-16, 19-17, 19-18, 19-19, 19-20, 19-21, 19-22, 19-23, 19-24, 19-25, 19-26, 19-27, 19-30, 19-33, 19-34, 19-35, 19-37, 19-39, 20-1, 20-2, 20-3, 20-4, 20-5, 20-6, 20-7, 20-8, 20-9, 21-1, 21-2, 21-3, 21-4, 21-5, 21-6, 21-7, 21-8, 21-11, 21-12, 21-13, 21-14, 21-15, 21-16, 21-17, 22-1, 22-2, 22-3, 22-4, 22-6, 23-1, 23-2, 24-1, 24-2, 24-3, 24-4, 24-5, 24-6, 24-7, 25-3, 25-4, 26-1, 26-2, 26-3, 26-4, 27-1, 28-4, 28-5.

Compounds with $IC_{50}$ against TRPM8<100 nM are: 1-1, 1-2, 1-3, 2-1, 2-2, 2-3, 2-4, 2-5, 2-11, 2-12, 2-13, 2-14, 2-15, 3-1, 3-2, 3-3, 3-4, 3-5, 3-6, 3-7, 3-8, 3-9, 3-10, 3-11, 3-12, 3-13, 3-14, 3-15, 3-16, 3-17, 3-18, 3-19, 4-1, 4-2, 4-3, 4-4, 4-5, 4-6, 4-10, 5-1, 5-2, 5-3, 5-5, 5-6, 5-7, 5-8, 5-9, 5-10, 5-11, 5-12, 5-13, 5-14, 5-15, 5-17, 5-18, 5-19, 5-20, 5-22, 5-25, 5-26, 5-27, 5-28, 5-30, 5-31, 5-32, 5-33, 5-39, 5-41, 6-1, 6-2, 6-3, 6-4, 6-5, 6-6, 6-7, 6-8, 6-9, 6-10, 6-11, 6-12, 6-13, 6-14, 6-15, 6-16, 6-17, 6-18, 6-19, 6-20, 6-21, 6-22, 6-23, 6-24, 6-25, 6-26, 6-27, 6-28, 6-29, 6-30, 6-31, 6-32, 6-33, 6-34, 6-35, 6-36, 6-37, 6-38, 6-39, 6-40, 6-41, 6-43, 6-44, 6-45, 6-54, 6-55, 6-57, 6-58, 6-63, 6-67, 6-68, 6-76, 6-81, 6-84, 6-87, 6-92, 6-97, 6-98, 6-106, 6-108, 6-114, 6-116, 6-122, 7-1, 7-2, 7-3, 7-4, 7-5, 7-6, 7-7, 7-8, 7-9, 7-10, 7-11, 7-12, 7-13, 7-14, 7-21, 7-22, 7-24, 7-25, 7-26, 8-1, 8-2, 8-3, 8-4, 8-5, 8-7, 8-8, 8-9, 9-1, 9-2, 9-3, 9-4, 9-5, 9-6, 9-7, 9-8, 9-9, 9-10, 9-11, 9-12, 9-13, 9-14, 9-15, 9-16, 9-17, 9-18, 9-19, 9-20, 9-21, 9-22, 9-23, 9-24, 9-25, 10-1, 10-2, 11-1, 11-2, 12-1, 12-2, 12-3, 12-4, 12-5, 12-6, 13-1, 13-2, 13-3, 13-4, 13-5, 13-6, 13-7, 13-8, 13-9, 13-10, 13-11, 13-12, 13-13, 13-14, 13-15, 13-16, 13-17, 13-18, 13-19, 13-20, 13-21, 13-22, 13-23, 13-24, 13-25, 13-26, 13-27, 13-28, 13-29, 13-30, 13-31, 13-32, 13-34, 13-35, 13-36, 13-37, 13-38, 13-39, 13-40, 13-41, 13-42, 13-43, 13-44, 13-45, 13-46, 13-47, 13-48, 13-49, 13-51, 13-53, 13-54, 13-55, 13-71, 13-72, 14-1, 14-2, 14-3, 14-4, 14-5, 14-6, 14-7, 14-8, 14-9, 14-10, 14-11, 14-12, 14-13, 14-14, 14-15, 14-16, 14-17, 15-1, 15-2, 15-3, 15-4, 15-5, 15-6, 15-7, 16-1, 16-2, 16-3, 16-4, 16-5, 16-6, 16-7, 16-8, 16-9, 16-10, 16-11, 16-12, 16-13, 16-14, 16-15, 16-16, 16-17, 16-18, 16-19, 16-20, 16-21, 16-22, 16-23, 16-24, 16-25, 16-27, 17-1, 17-2, 17-3, 17-4, 17-5, 17-6, 17-7, 17-8, 17-9, 17-10, 17-11, 18-1, 18-2, 18-3, 18-4, 18-5, 18-6, 18-9, 18-10, 18-11, 19-1, 19-2, 19-3, 19-4, 19-5, 19-6, 19-7, 19-8, 19-9, 19-10, 19-11, 19-12, 19-13, 19-14, 19-16, 19-17, 19-18, 19-20, 19-21, 19-22, 19-23, 19-24, 19-25, 19-26, 19-30, 19-33, 19-37, 20-1, 20-6, 20-7, 20-8, 21-1, 21-2, 21-5, 21-8, 21-12, 21-13, 21-14, 21-17, 22-1, 22-3, 22-4, 23-1, 23-2, 24-1, 24-5, 24-6, 24-7, 26-1, 26-2, 26-3, 26-4, 27-1, 28-5.

Compounds with $IC_{50}$ against TRPM8<10 nM are: 5-7, 5-9, 5-10, 5-14, 5-27, 5-28, 6-1, 6-2, 6-3, 6-4, 6-5, 6-6, 6-7, 6-8, 7-1, 7-22, 9-1, 9-2, 9-3, 9-10, 9-11, 9-12, 12-1, 13-34, 13-35, 13-36, 13-37, 13-38, 13-71, 14-5, 15-6, 16-4, 17-6, 18-2, 19-14, 19-30, 19-33, 24-5, 24-7, 26-1, 26-3, 27-1.

Measurement of the Menthol-Induced $Ca^{2+}$ Influx in a Human Malignant Melanoma Cell Lines Since TRPM8 is expressed in a human malignant melanoma cell lines, G-361 (Health Science Research Resources Bank, Osaka, Japan), the G-361 cells are used for in vitro functional assay.

G-361 cells are grown in T175 flasks at 37° C. in a 5% $CO_2$ humidified incubator to about 80% confluence. Media composition consists of McCoy's 5A medium and 10% FCS. At 48 hours prior to assay, cells are seeded in poly-D-lysine coated 96-well plates (Corning) at a density of 12,000 cells per well in culture medium and grown in 5% $CO_2$ at 37° C. On the assay day, growth media is removed and cells are loaded with 5 microM Fluo-4 AM (Molecular Probes) and 0.005% Pluronic F-127 dissolved in assay buffer (HBSS, 19.4 mM HEPES pH7.4, 2.5 mM Probenecid) for 1 hour at room temperature. After washing with assay buffer, the cells are preincubated with various concentrations of the compounds for 5 min. The changes in intracellular calcium concentration by addition of 300 microM menthol are monitored by FDSS.

The $IC_{50}$ values for compounds of the present invention are determined from dose-response studies. Curves are generated using the average of duplicate wells for each data point. Finally, the $IC_{50}$ values are calculated with the best-fit dose curve determined by XLfit (ID Business Solutions Ltd.).

Compounds of this invention show good $IC_{50}$ values, which show the above-mentioned practical use.

Chronic Constriction Injury (CCI)-Induced Model of Neuropathic Pain; Cold Allodynia Male Sprague Dawley rats (7 weeks old at the start of experiment, n=7-10/treatment) purchased from Charles River Japan, Inc. are used. The CCI is made according to the method of Bennett G J and Xie Y K (Pain 1988, 33: 87-107). Rats are anesthetized with intraperitoneal injection of sodium pentobarbital. The left common sciatic nerve is exposed at the level of the middle of the thigh and four ligatures are loosely tided around it by using 4-0 silk thread (Ethicon Inc.) with about 1 mm space. Sham operation is performed in the same manner except of sciatic nerve ligation. One to two weeks following CCI surgery, cold allodynia is assessed using a cold plate (LHP-1700CP, TECA) with a temperature controller (Model 3300-0, CAL Controls Inc.) as described by Tanimoto-Mori S et al. (Behav Pharmacol., 19: 85-90, 2008). The animals are habituated to the apparatus which consists of a transparent acrylic box (10×12×12 cm) on a stainless-steel plate (15×33 cm). The surface of the cold plate held on 10° C. and the temperature of the plate is monitored continuously with a precision of 0.1° C. For testing, the rat is placed on the cold plate and the paw withdrawal latency (PWL) is measured before and after the compound administration, with a cut-off value of 120 seconds. The compounds of the invention or their vehicles are administered perorally, subcutaneously or intraperitoneally. The percentages of inhibition are calculated as follows;

$$\text{Inhibition (\%)} = \frac{PWL_{drug} - PWL_{vehicle}}{PWL_{sham} - PWL_{vehicle}} \times 100. \qquad [\text{Math. 1}]$$

Compounds of this invention show potent activities in this model, which show the above-mentioned practical use.

Chronic Constriction Injury (CCI)-Induced Model of Neuropathic Pain; Static Allodynia Male Sprague Dawley rats (7 weeks old at the start of experiment, n=7-10/treatment) purchased from Charles River Japan, Inc. are used. The CCI is made according to the method of Bennett G J and Xie Y K (Pain 1988, 33: 87-107). Rats are anesthetized with intraperitoneal injection of sodium pentobarbital. The left common sciatic nerve is exposed at the level of the middle of the thigh and four ligatures are loosely tided around it by using 4-0 silk thread (Ethicon Inc.) with about 1 mm space. Sham operation is performed in the same manner except of sciatic nerve ligation. Static allodynia is assessed using von Frey hairs (VFHs) at two to three weeks following CCI surgery as described by Field M J et al. (Pain 1999, 83: 303-311). The animals are habituated to grid bottom cages prior to the start of experiment. VFHs in ascending order of force (0.16, 0.4, 0.6, 1, 1.4, 2, 4, 6, 8, 10, 15 and 26 gram) are applied to the plantar surface of the hind paw. Each VFH is applied to the ipsilateral paw for 6 seconds or until a withdrawal response is occurred. Once a withdrawal response is happened, the paw is re-tested, starting with the next descending VFH until no response is occurred. The lowest amount of force required to elicit a response is recorded as paw withdrawal threshold (PWT). Static allodynia is defined as present if animals responded to or below the innocuous 1.4 gram VFH. The compounds of the invention or their vehicles are administered perorally, subcutaneously or intraperitoneally. The percentages of inhibition are calculated as follows;

$$\text{Inhibition (\%)} = \frac{\log_{10}(PWT_{drug}) \cdot \log_{10}(PWT_{vehicle})}{\log_{10}(PWT_{sham}) \cdot \log_{10}(PWT_{vehicle})} \times 100. \quad \text{[Math. 2]}$$

Compounds of this invention show potent activities in this model, which show the above-mentioned practical use.

Oxaliplatin-Induced Model of Neuropathic Pain; Cold and Static Allodynia

Male Sprague Dawley rats (7 weeks old at the start of experiment, n=7-10/treatment) purchased from Charles River Japan, Inc. are used. The study is conducted according to the method of Gauchan P et al. (NeuroSci Lett, 2009, 458, 93-95). Oxaliplatin (Yakult Co., Ltd.) is dissolved in 5% glucose. Oxaliplatin (4 mg/kg) is injected intraperitoneally twice a week for two-week. Cold allodynia is assessed using a cold plate (LHP-1700CP, TECA) with a temperature controller (Mode13300-0, CAL Controls Inc.) as described by Tanimoto-Mori S et al. (Behav Pharmacol., 19: 85-90, 2008). The animals are habituated to the apparatus which consists of a transparent acrylic box (10×12×12 cm) on a stainless-steel plate (15×33 cm). The surface of the cold plate held on 10° C. and the temperature of the plate is monitored continuously with a precision of 0.1° C. For testing, the animal is placed on the cold plate and PWL is measured before and after the compound administration, with a cut-off value of 120 seconds. Static allodynia is assessed using VFHs. The animals are habituated to grid or mesh bottom cages prior to the start of experiment. VFHs in ascending order of force (0.16, 0.4, 0.6, 1, 1.4, 2, 4, 6, 8, 10, 15 and 26 gram) are applied to the plantar surface of the hind paw. Once a withdrawal response is happened, the paw is re-tested, starting with the next descending VFH until no response is occurred. The lowest amount of force required to elicit a response is recorded as paw withdrawal threshold (PWT). For testing, PWT is measured before and after the compound administration. The compounds of the invention or their vehicles are administered perorally, subcutaneously or intraperitoneally.

Compounds of this invention show potent activities in this model, which show the above-mentioned practical use.

Oxaliplatin-Induced Model of Neuropathic Pain; Cold Hyperalgesia/Allodynia

Male Sprague Dawley rats (7 weeks old, n=8-10/treatment) purchased from Charles River Japan, Inc. were used. Oxaliplatin (Wako Pure Chemical Industries, Ltd.) was dissolved in 5% glucose for injection to make 4 mg/mL solution. Oxaliplatin (4 mg/kg) was injected intraperitoneally twice a week for two-week (on Days 1, 2, 8, 9) in a volume of 1 mL/kg. First day of treatment was defined as Day 1. Cold hyperalgesia/allodynia was assessed by acetone test. The animals were habituated to grid or mesh bottom cages prior to the start of experiment. Acetone (50 mL) was applied to the plantar surface of the hind paw. After the application, nociceptive responses were scored as follows: 0; no response, 1; stamping and/or lifting of the paw, 2; licking/biting or flinching of the paw once, 3; repeated licking/biting and/or flinching of the paw. Acetone was repeatedly applied to the left and right hind paws (twice for each, total 4 applications), thus total score were maximum 12 and minimum 0. For testing, total score was measured before and after the compound administration. The compounds of the invention or their vehicles were administered perorally, subcutaneously or intraperitoneally.

Compounds of this invention showed potent activities in this model, which show the above-mentioned practical use Icilin-Induced Wet-Dog Shakes in Rats Male Sprague Dawley rats (6-7 weeks old, Charles River Japan, Inc., n=5-8/treatment) are used to evaluate the ability of the compounds of the invention to block the spontaneous wet-dog shakes (WDS) behavior induced by icilin. Rats are acclimated in observation boxes (21.5×26.5×25.0 cm) for at least 20 minutes before icilin injection. Icilin (Sigma) dissolved in PEG400 is administered intraperitoneally at 0.5, 1.0 or 2.5 mg/kg and spontaneous WDS are counted over 30 min post-icilin. The compounds of the invention or their vehicles are administered perorally, subcutaneously or intraperitoneally before icilin injection. The percentages of inhibition are calculated as follows;

$$\% \text{ inhibition} = [1-(\text{compound WDS count/vehicle WDS count})] \times 100. \quad \{\text{Math. 3}\}$$

Compounds of this invention show potent activities in this model, which show the above-mentioned practical use.

Measurement of the Micturition Frequency in Guinea Pigs In Vivo

Female Guinea Pigs (300-450 g) are anaesthetized with urethane. A midline abdominal incision is performed, both ureters are exposed and ligated, a catheter is implanted in the bladder pole and the abdomen is closed. For administration of the compounds the vena jugularis is exposed and cannulated with a catheter. After this surgery the bladder catheter is connected via a t-shaped tube to an infusion pump and to a pressure transducer. Saline is infused and intrabladder pressure is registered. After 1 h of equilibration period and the establishment of constant voiding cycles, menthol (0.2-0.6 mM) is added to the infused saline. At this point also vehicle (control group) or TRPM8 antagonists are administered i.v. as bolus injection. The effect of treatment on the micturition interval (corresponding to bladder capacity) and micturition pressure is calculated and compared between vehicle-treated and compound-treated groups.

Compounds of this invention show potent activities in this model, which show the above-mentioned practical use.

Measurement of Over Active Bladder in Anesthetized Cystitis Rats

Female Sprague-Dawley rats (7-8 weeks/Japan SLC) are used. Cyclophosphamide (Wako) dissolved in saline (Otsuka) is administered intraperitoneally at 200 mg/kg. On the next day, rats are anesthetized by administration of urethane at 0.9 mg/kg, s.c. The abdomen is opened through a midline incision, and a polyethylene catheter is implanted into the bladder through the dome. The bladder catheter is connected via T-tube to a pressure transducer and a microinjection pump. Saline is infused at room temperature into the bladder at a rate of 3 mL/hour. Intravesical pressure is recorded continuously on a chart pen recorder for about 1 hour before a test compound administration.

A testing compound dissolved in PBS containing Well-Solve (Celeste) is administered intravenously at 1 mg/kg, 3 mg/kg, 5 mg/kg or 10 mg/kg.

The micturition frequency calculated from micturition interval during 60 min after administration of testing compound was analyzed from the cystometry data. The testing compounds mediated inhibition of the frequency was evaluated using Dunnett' method vs vehicle. A probability levels less than 5% is accepted as significant difference. Data are anslyzsd as this mean+/−SEM from 8-12 rats.

All tested compounds show significant effect on over active bladder in anesthetized cystitis rats.

Human Dofetilide Binding Assay

Human HERG transfected HEK293S cells are prepared and grown in-house. The collected cells are suspended in 50 mM Tris-HCl (pH 7.4 at 4° C.) and homogenized using a hand held Polytron PT 1200 disruptor set at full power for 20 sec on ice. The homogenates are centrifuged at 48,000×g at 4° C. for 20 min. The pellets are then resuspended, homogenized, and centrifuged once more in the same manner. The final pellets are resuspended in an appropriate volume of 50 mM Tris-HCl, 10 mM KCl, 1 mM MgCl$_2$ (pH 7.4 at 4° C.), homogenized, aliquoted and stored at −80° C. until use. An aliquot of membrane fractions is used for protein concentration determination using BCA protein assay kit (PIERCE) and ARVOsx plate reader (Wallac). Binding assays are conducted in a total volume of 30 microL in 384-well plates. The activity is measured by PHERAstar (BMG LABTECH) using fluorescence polarization technology. Ten microL of test compounds are incubated with 10 microL of fluorescence ligand (6 nM Cy3B tagged dofetilide derivative) and 10 microL of membrane homogenate (6 microgram protein) for 120 minutes at room temperature. Nonspecific binding is determined by 10 microM E4031 at the final concentration.

All tested compounds of the invention show higher IC$_{50}$ values in human dofetilide binding than IC$_{50}$ values in TRPM8 functional assay described above.

The closest compound described as an example 2-121 in WO2014/130582 to the present invention is the following compound.

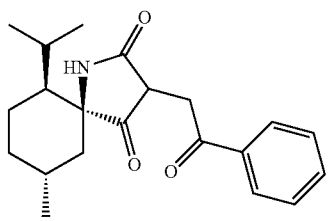

{Chem. 163}

The closest compound has 19 microM of IC$_{50}$ and 6.5 microM of Ki values in human dofetilide binding assay, whereas the compounds of the present invention have the higher IC$_{50}$ values in human dofetilide binding assay, which leads to reducing the risk of cardiovascular adverse events.
Metabolic Stability Assay:
Half-Life in Human Liver Microsomes (HLM)

Test compounds (1 microM) are incubated with 1 mM MgCl$_2$ and 0.78 mg/mL HLM (HL101) or 0.74 mg/mL HLM (Gentest UltraPool 150) or 0.61 mg/mL HLM (XenoTech XTreme 200) in 100 mM potassium phosphate buffer (pH 7.4) at 37° C. on the 96-deep well plate. The reaction mixture is split into two groups, a non-P450 and a P450 groupon necessary. NADPH is only added to the reaction mixture of the P450 group. (NADPH generation system is also used instead of NADPH.) An aliquot of samples of P450 group is collected at 0, 10, 30, and 60 min time point, where 0 min time point indicated the time when NADPH is added into the reaction mixture of P450 group. An aliquot of samples of non-P450 group is collected at −10 and 65 min time point. Collected aliquots are extracted with acetonitrile solution containing an internal standard. The precipitated protein is spun down in centrifuge (2000 rpm, 15 min). The compound concentration in supernatant is measured by LC/MS/MS system.

The half-life value is obtained by plotting the natural logarithm of the peak area ratio of compounds/internal standard versus time. The slope of the line of best fit through the points yield the rate of metabolism (k). This is converted to a half-life value using following equations:

Half-life=ln 2/k {Math. 4}

The compounds of this invention show preferable stability, which show the above-mentioned practical use.

The closest compound described as an example 2-121 in WO2014/130582 has less than 5 minutes of the half-live in HLM and has the large intrinsic clearance (CL$_{int}$) of more than 215 mL/min/kg, whereas the present invention has more than 5 minutes in the half-live in HLM and CL$_{int}$ of <100 mL/min/kg in metabolism stability assay, which leads to good pharmacokinetic properties.
Drug-Drug Interaction Assay This method essentially involves determining the percent inhibition of metabolites formation from probes (Tacrine 2 microM or phenacetin 50 microM for CYP1A2, bupropion 3 microM for CYP2B6, amodiaquine 2 microM for CYP2C8, diclofenac 5 or 10 microM for CYP2C9, S-mephenytoin 40 microM for CYP2C19, dextromethorphan 5 microM or bufuralol 5 microM for CYP2D6, and midazolam 2 microM or 2.5 microM for CYP3A4) at 3 microM or 0.4-50 microM of the each compound.

More specifically, the assay is carried out as follows. The compounds (60 microM, 10 microL) are pre-incubated in 170 microL of mixture including 0.1 mg protein/mL or 0.05 mg protein/mL human liver microsomes, 100 mM potassium phosphate buffer (pH 7.4), 1 mM MgCl$_2$ or 3.3 mM MgCl$_2$ and probes as substrate for appropriate time (5 min or 30 min). Reaction is started by adding a 20 microL of 10 mM NADPH or 10 microL of 13 microM NADPH. The assay plate is incubated at 37° C. Acetonitrile or methanol is added to the incubate solution at appropriate time (8 min or 10 min).

The metabolites' concentration in the supernatant is measured by LC/MS/MS system. The degree of drug-drug interaction is interpreted based on generation % of metabolites in the presence or absence of test compound or IC$_{50}$ values calculated from generation % of metabolites vs. compound concentration.

The compounds of this invention show preferable results, which show the above-mentioned practical use.
Plasma Protein Binding Assay Plasma protein binding of the test compound (1 microM) is measured by the method of equilibrium dialysis using 96-well plate type equipment. HTD96a(registeredtrademark), regenerated cellulose membranes (molecular weight cut-off 12,000-14,000, 22 mm×120 mm) are soaked for over night in distilled water, then for 15 minutes in 30% ethanol; and finally for 20 minutes in dialysis buffer (Dulbecco's phosphate buffered saline, minus CaCl$_2$ and MgCl$_2$). Frozen plasma of human, Sprague-Dawley rats, and Beagle dogs are used. The dialysis equipment is assembled and added 150 microL of compound-fortified plasma to one side of each well and 150 microL of dialysis buffer to the other side of each well. After 4 hours incubation at 37° C. for 150 r.p.m, aliquots of plasma and buffer are sampled. The compound in plasma and buffer are extracted with 300 microL of acetonitrile or acetonitrile/methanol (1/1) containing internal standard compounds for analysis. The concentration of the compound is determined with LC/MS/MS analysis.

The fraction of the compound unbound is calculated by the following equation (A) or (B):

$(A) fu=1-\{([plasma]_{eq}-[buffer]_{eq})/([plasma]_{eq})\}$ {Math. 5} wherein [plasma]$_{eq}$ and [buffer]$_{eq}$ are the concentrations of the compound in plasma and buffer, respectively.

[Math. 6]

$$fu(\%) = \frac{Cb/Cis, b \times 4}{Cp/Cis, p \times 4/3} \times 100 \quad (B)$$

wherein Cp is the peak area of the compound in plasma sample;
Cis,p is the peak area of the internal standard in plasma sample;
Cb is the peak area of the compound in buffer sample;
Cis,b is the peak area of the internal standard in buffer sample;
4 and 4/3 is the reciprocal of the dilution rate in plasma and buffer, respectively.

The compounds of this invention show preferable plasma protein binding, which show the above-mentioned practical use.

Equilibrium Aqueous Solubility Study

The DMSO solution (2 microL, 30 mM) of each compound is dispensed into each well of a 96-well glass bottom plate. Potassium phosphate buffer solution (50 mM, 198 microL, pH 6.5) is added to each well, and the mixture is incubated at 37° C. with rotate shaking for 24 hours. After centrifugation at 2000 g for 5 minutes, the supernatant is filtered through the polycarbonate Isopore membrane. The concentration of samples is determined by a general gradient HPLC method (J. Pharm. Sci., 95, 2115-2122, 2006).

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. A compound of the following formula (I):

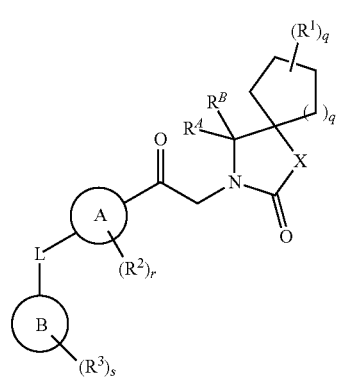

(I)

wherein
A is phenyl or 5 to 6 membered heteroaryl;
B is phenyl, 5 to 6 membered heteroaryl, or 9 to 10 membered bicyclic heteroaryl;
L is independently selected from the group consisting of: a chemical bond, oxygen, and —$NR^4$—;
X is independently selected from the group consisting of: —$CH_2$—, oxygen, and NH;

$R^A$ and $R^B$ are independently selected from the group consisting of: (1) hydrogen and (3) ($C_1$-$C_6$)alkyl; or $R^A$ and $R^B$ form an oxo group (=O);
$R^1$ is independently selected from the group consisting of: (2) halogen, (8) ($C_1$-$C_6$)haloalkyl, (9) ($C_1$-$C_6$)alkoxy, and (10) ($C_1$-$C_6$)haloalkoxy; or alternatively, when q is 2, 3 or 4, then one $R^1$ or two $R^1$s is or are halogen or two halogens, and the other $R^1$ or $R^1$s is or are independently (6) ($C_1$-$C_6$) alkyl;
$R^2$ is independently selected from the group consisting of: (1) hydrogen, (2) fluorine, (3) chlorine, (4) iodine, (7) hydroxyl, (10) ($C_1$-$C_6$)alkyl, (12) ($C_1$-$C_6$)alkoxy, (13) ($C_1$-$C_6$)haloalkyl and (14) ($C_1$-$C_6$)haloalkoxy;
$R^3$ is independently selected from the group consisting of: (1) hydrogen, (2) halogen, (3) cyano, (5) hydroxyl, (8) ($C_1$-$C_6$)alkylsulfonyl, (9) —$NR^5R^6$, (10) —C(=O)$NR^5R^6$, (12) ($C_1$-$C_6$)alkyl, (14) ($C_1$-$C_6$)alkoxy($C_0$-$C_6$)alkyl, and (16) —C(=O)($C_1$-$C_6$)alkyl; wherein the ($C_1$-$C_6$)alkyl and ($C_1$-$C_6$)alkoxy($C_0$-$C_6$)alkyl are optionally substituted with 1 to 3 substituents independently selected from the group consisting of: (1) hydrogen, (2) halogen, (3) hydroxyl, (4) cyano, and (9) —$NR^6R^5$; wherein $R^5$ and $R^6$ together with nitrogen atom to which they are attached, may form a 3 to 7 membered ring which may contain an atom selected from oxygen and nitrogen; and the 3 to 7 membered ring is optionally substituted with a substituent selected from the group consisting of: (1) hydrogen, (3) hydroxyl, and (7) ($C_1$-$C_6$)alkoxy;
$R^4$ is independently selected from the group consisting of: (1) hydrogen and (2) ($C_1$-$C_6$)alkyl;
$R^5$ and $R^6$ are independently selected from the group consisting of: (1) hydrogen, (2) ($C_1$-$C_6$)alkyl, (5) hydroxyl($C_1$-$C_6$)alkyl, (6) ($C_1$-$C_6$)alkoxy($C_1$-$C_6$)alkyl, and (7) $H_2N$—($C_1$-$C_6$)alkyl;
p is 1, 2 or 3;
q is 1, 2, 3 or 4;
r is 1 or 2, and when r is 2, then $R^2$ is the same or different;
s is 1 or 2, and when s is 2, then $R^3$ is the same or different;
or a pharmaceutically acceptable salt thereof.

2. The compound according to claim 1, wherein
$R^1$ is independently selected from the group consisting of: (2) halogen and (8) ($C_1$-$C_6$)haloalkyl;
or a pharmaceutically acceptable salt thereof.

3. The compound according to claim 1, wherein
$R^1$ is (2) halogen;
or a pharmaceutically acceptable salt thereof.

4. The compound according to claim 1, wherein
A is phenyl or 5 to 6 membered heteroaryl, wherein the heteroaryl contains one to two heteroatoms selected from the group consisting of nitrogen, oxygen, and sulfur; and
B is phenyl, 5 to 6 membered heteroaryl, or 9 to 10 membered bicyclic heteroaryl, wherein the heteroaryl contains one to four heteroatoms selected from the group consisting of nitrogen, oxygen, and sulfur;
or a pharmaceutically acceptable salt thereof.

5. The compound according to claim 1, wherein
A is selected from the group consisting of: phenyl, pyridine, pyridazine, pyrazine, thiophene, pyrrole, imidazole, pyrazole, thiazole, and triazole; and
B is selected from the group consisting of: phenyl, pyridine, pyridazine, pyrazine, pyrimidine, imidazole, pyrazole, tetrazole, isoxazole, thiophene, thiazole, 1H-indole, 1H-pyrrolo[2,3-b]pyridine, 1H-pyrrolo[2,3-c]pyridine, 1H-pyrrolo[3,2-c]pyridine, 1H-pyrrolo[3,2-b]pyridine, 7H-pyrrolo[2,3-d]pyrimidine, 7H-pyrrolo

[2,3-c]pyridazine, 1H-indazole, 2H-indazole, 1H-pyrazolo[3,4-b]pyridine, 1H-pyrazolo[3,4-c]pyridine, 1H-pyrazolo[4,3-c]pyridine, 1H-pyrazolo[4,3-b]pyridine, 1H-pyrazolo[3,4-d]pyrimidine, 1H-benzo[d]imidazole, 3H-imidazo[4,5-b]pyridine, 1H-imidazo[4,5-b]pyridine, 9H-purine, 1H-imidazo[4,5-d]pyridazine, 1H-imidazo[4,5-b]pyrazine, imidazo[1,2-a]pyridine, imidazo[1,5-a]pyridine, imidazo[1,2-a]pyrazine, imidazo[1,2-b]pyridazine, pyrazolo[1,5-a]pyridine, pyrazolo[1,5-a]pyrimidine, furo[3,2-c]pyridine, benzo[d]isoxazole, 2,3-dihydro-1H-indene, indoline, isoindoline, indolin-2-one, isoindolin-1-one, 1H-benzo[d]imidazol-2(3H)-one, benzo[d]oxazol-2(3H)-one, 1H-pyrrolo[2,3-b]pyridin-2(3H)-one, 1H-imidazo[4,5-b]pyridin-2(3H)-one, quinoline, isoquinoline, quinazoline, phthalazine, 2,6-naphthyridine, 2,7-naphthyridine, quinoxaline, pyrido[3,4-d]pyrimidine, pyrido[2,3-d]pyrimidine, 1,2,3,4-tetrahydroquinoline, 1,2,3,4-tetrahydroisoquinoline, 3,4-dihydro-2H-benzo[b][1,4]oxazine, 2,3-dihydro-[1,4]dioxino[2,3-b]pyridine, 3,4-dihydroquinolin-2(1H)-one, 2H-benzo[b][1,4]oxazin-3(4H)-one, quinolin-2(1H)-one, and 4,5-dihydro-1H-benzo[b]azepin-2(3H)-one;

or a pharmaceutically acceptable salt thereof.

6. The compound according to claim 1, which is selected from the group consisting of:

3-(2-(2,5-dimethyl-1-(5-methylisoxazol-3-yl)-1H-pyrrol-3-yl)-2-oxoethyl)-8,8-difluoro-1,3-diazaspiro[4.5]decane-2,4-dione;

3-(2-(2,5-dimethyl-1-phenyl-1H-imidazol-4-yl)-2-oxoethyl)-8,8-difluoro-1,3-diazaspiro[4.5]decane-2,4-dione;

3-(2-(1-(3-chlorophenyl)-2,5-dimethyl-1H-imidazol-4-yl)-2-oxoethyl)-8,8-difluoro-1,3-diazaspiro[4.5]decane-2,4-dione;

8,8-difluoro-3-(2-(1-(3-fluorophenyl)-2,5-dimethyl-1H-imidazol-4-yl)-2-oxoethyl)-1,3-diazaspiro[4.5]decane-2,4-dione;

3-(2-(1,4-dimethyl-5-phenyl-1H-pyrazol-3-yl)-2-oxoethyl)-8,8-difluoro-1,3-diazaspiro[4.5]decane-2,4-dione;

8,8-difluoro-3-(2-(4-(6-methylpyrazin-2-yl)phenyl)-2-oxoethyl)-1,3-diazaspiro[4.5]decane-2,4-dione;

6-(4-(2-(8,8-difluoro-2,4-dioxo-1,3-diazaspiro[4.5]decan-3-yl)acetyl)phenyl)picolinonitrile;

8,8-difluoro-3-(2-(2'-(hydroxymethyl)-[1,1'-biphenyl]-4-yl)-2-oxoethyl)-1,3-diazaspiro[4.5]decane-2,4-dione;

8,8-difluoro-3-(2-(4-(3-methylpyrazin-2-yl)phenyl)-2-oxoethyl)-1,3-diazaspiro[4.5]decane-2,4-dione;

3-(2-(2,5-dimethyl-1-phenyl-1H-imidazol-4-yl)-2-oxoethyl)-8,8-difluoro-1-oxa-3-azaspiro[4.5]decane-2,4-dione;

8,8-difluoro-3-(2-(4-(2-(hydroxymethyl)pyridin-3-yl)phenyl)-2-oxoethyl)-1,3-diazaspiro[4.5]decane-2,4-dione;

8,8-difluoro-3-(2-(4-(4-(hydroxymethyl)pyridin-3-yl)phenyl)-2-oxoethyl)-1,3-diazaspiro[4.5]decane-2,4-dione;

3-(2-(2,5-dimethyl-1-(5-methylisoxazol-3-yl)-1H-pyrrol-3-yl)-2-oxoethyl)-8,8-difluoro-1-oxa-3-azaspiro[4.5]decane-2,4-dione;

8,8-difluoro-3-(2-(5-(2-(hydroxymethyl)phenyl)-4-methylthiophen-2-yl)-2-oxoethyl)-1,3-diazaspiro[4.5]decane-2,4-dione;

3-(2-(1,4-dimethyl-5-phenyl-1H-pyrazol-3-yl)-2-oxoethyl)-8,8-difluoro-1-oxa-3-azaspiro[4.5]decane-2,4-dione;

8,8-difluoro-3-(2-(4-(4-methylpyridazin-3-yl)phenyl)-2-oxoethyl)-1,3-diazaspiro[4.5]decane-2,4-dione;

3-(4-(2-(8,8-difluoro-2,4-dioxo-1,3-diazaspiro[4.5]decan-3-yl)acetyl)phenyl)pyrazine-2-carbonitrile;

3-(2-(1,4-dimethyl-5-phenyl-1H-pyrrol-2-yl)-2-oxoethyl)-8,8-difluoro-1,3-diazaspiro[4.5]decane-2,4-dione;

8,8-difluoro-3-(2-(4-(3-(hydroxymethyl)pyrazin-2-yl)phenyl)-2-oxoethyl)-1,3-diazaspiro[4.5]decane-2,4-dione;

3-(4-(2-(8,8-difluoro-2,4-dioxo-1,3-diazaspiro[4.5]decan-3-yl)acetyl)phenyl)picolinonitrile;

8,8-difluoro-3-(2-oxo-2-(4-(quinolin-8-yl)phenyl)ethyl)-1,3-diazaspiro[4.5]decane-2,4-dione;

3-(2-(4-(1H-indol-4-yl)phenyl)-2-oxoethyl)-8,8-difluoro-1,3-diazaspiro[4.5]decane-2,4-dione;

8,8-difluoro-3-(2-oxo-2-(4-(quinolin-2-yl)phenyl)ethyl)-1,3-diazaspiro[4.5]decane-2,4-dione;

8,8-difluoro-3-(2-(4-(isoquinolin-8-yl)phenyl)-2-oxoethyl)-1,3-diazaspiro[4.5]decane-2,4-dione;

8,8-difluoro-3-(2-(4-(isoquinolin-1-yl)phenyl)-2-oxoethyl)-1,3-diazaspiro[4.5]decane-2,4-dione;

8,8-difluoro-3-(2-(4-(furo[3,2-c]pyridin-4-yl)phenyl)-2-oxoethyl)-1,3-diazaspiro[4.5]decane-2,4-dione;

8,8-difluoro-3-(2-(6-(methyl(pyridin-2-yl)amino)pyridin-3-yl)-2-oxoethyl)-1,3-diazaspiro[4.5]decane-2,4-dione;

8,8-difluoro-3-(2-(6-(methyl(phenyl)amino)pyridin-3-yl)-2-oxoethyl)-1,3-diazaspiro[4.5]decane-2,4-dione;

8,8-difluoro-3-(2-(4-(3-fluoropyridin-2-yl)phenyl)-2-oxoethyl)-1,3-diazaspiro[4.5]decane-2,4-dione;

3-(4-(2-(8,8-difluoro-2,4-dioxo-1,3-diazaspiro[4.5]decan-3-yl)acetyl)phenyl)isonicotinonitrile;

8,8-difluoro-3-(2-(4-(2-methoxypyridin-3-yl)phenyl)-2-oxoethyl)-1,3-diazaspiro[4.5]decane-2,4-dione;

8,8-difluoro-3-(2-(4-(4-methoxypyridin-3-yl)phenyl)-2-oxoethyl)-1,3-diazaspiro[4.5]decane-2,4-dione;

8,8-difluoro-3-(2-oxo-2-(4-(2-oxoindolin-4-yl)phenyl)ethyl)-1,3-diazaspiro[4.5]decane-2,4-dione;

3-(2-(4-(7H-pyrrolo[2,3-d]pyrimidin-4-yl)phenyl)-2-oxoethyl)-8,8-difluoro-1,3-diazaspiro[4.5]decane-2,4-dione;

3-(2-(4-(1H-pyrrolo[3,2-c]pyridin-4-yl)phenyl)-2-oxoethyl)-8,8-difluoro-1,3-diazaspiro[4.5]decane-2,4-dione;

3-(2-(4-(1H-pyrrolo[2,3-b]pyridin-4-yl)phenyl)-2-oxoethyl)-8,8-difluoro-1,3-diazaspiro[4.5]decane-2,4-dione;

3-(2-(4-(3-chloropyridin-2-yl)phenyl)-2-oxoethyl)-8,8-difluoro-1,3-diazaspiro[4.5]decane-2,4-dione;

8,8-difluoro-3-(2-(4-(2-methyl-1H-benzo[d]imidazol-1-yl)phenyl)-2-oxoethyl)-1,3-diazaspiro[4.5]decane-2,4-dione;

3-(2-(4-(1H-indazol-4-yl)phenyl)-2-oxoethyl)-8,8-difluoro-1,3-diazaspiro[4.5]decane-2,4-dione;

3-(2-(6-(1H-indazol-4-yl)pyridin-3-yl)-2-oxoethyl)-8,8-difluoro-1,3-diazaspiro[4.5]decane-2,4-dione;

3-(2-(4-(1H-benzo[d]imidazol-1-yl)phenyl)-2-oxoethyl)-8,8-difluoro-1,3-diazaspiro[4.5]decane-2,4-dione;

3-(5-(2-(8,8-difluoro-2,4-dioxo-1,3-diazaspiro[4.5]decan-3-yl)acetyl)-1,3-dimethyl-1H-pyrrol-2-yl)benzonitrile;

3-(2-(4-(1H-pyrrolo[2,3-c]pyridin-4-yl)phenyl)-2-oxoethyl)-8,8-difluoro-1,3-diazaspiro[4.5]decane-2,4-dione;

8,8-difluoro-3-(2-(3-fluoro-4-(quinolin-8-yl)phenyl)-2-oxoethyl)-1,3-diazaspiro[4.5]decane-2,4-dione;

3-(5-(2-(8,8-difluoro-2,4-dioxo-1,3-diazaspiro[4.5]decan-3-yl)acetyl)-1-methyl-1H-pyrrol-2-yl)benzonitrile;

3-(5-(2-(8,8-difluoro-2,4-dioxo-1,3-diazaspiro[4.5]decan-3-yl)acetyl)-3-methylthiophen-2-yl)benzonitrile;

8,8-difluoro-3-(2-(4-(2-(2-hydroxyethoxy)pyridin-3-yl)phenyl)-2-oxoethyl)-1,3-diazaspiro[4.5]decane-2,4-dione;

8,8-difluoro-3-(2-(5-(3-fluorophenyl)-1,4-dimethyl-1H-pyrrol-2-yl)-2-oxoethyl)-1,3-diazaspiro[4.5]decane-2,4-dione;

3-(2-(5-(3-chlorophenyl)-1,4-dimethyl-1H-pyrrol-2-yl)-2-oxoethyl)-8,8-difluoro-1,3-diazaspiro[4.5]decane-2,4-dione;

3-(5-(2-(8,8-difluoro-2,4-dioxo-1,3-diazaspiro[4.5]decan-3-yl)acetyl)-1,3-dimethyl-1H-pyrrol-2-yl)benzamide;

8,8-difluoro-3-(2-(5-(2-fluorophenyl)-1,4-dimethyl-1H-pyrrol-2-yl)-2-oxoethyl)-1,3-diazaspiro[4.5]decane-2,4-dione;

3-(2-(4-(1H-pyrazolo[3,4-b]pyridin-4-yl)phenyl)-2-oxoethyl)-8,8-difluoro-1,3-diazaspiro[4.5]decane-2,4-dione;

3-(2-(4-(1H-pyrazolo[4,3-c]pyridin-4-yl)phenyl)-2-oxoethyl)-8,8-difluoro-1,3-diazaspiro[4.5]decane-2,4-dione;

3-(2-(4-(1H-indazol-1-yl)phenyl)-2-oxoethyl)-8,8-difluoro-1,3-diazaspiro[4.5]decane-2,4-dione;

8,8-difluoro-3-(2-(5-(3-fluorophenyl)-1-methyl-1H-imidazol-2-yl)-2-oxoethyl)-1,3-diazaspiro[4.5]decane-2,4-dione;

8,8-difluoro-3-(2-(4-(2-methyl-3H-imidazo[4,5-b]pyridin-3-yl)phenyl)-2-oxoethyl)-1,3-diazaspiro[4.5]decane-2,4-dione;

8,8-difluoro-3-(2-oxo-2-(4-(pyridin-2-yloxy)phenyl)ethyl)-1,3-diazaspiro[4.5]decane-2,4-dione;

3-(2-(5-(3,5-difluorophenyl)-1,4-dimethyl-1H-pyrrol-2-yl)-2-oxoethyl)-8,8-difluoro-1,3-diazaspiro[4.5]decane-2,4-dione;

8,8-difluoro-3-(2-(2'-methyl-[3,3'-bipyridin]-6-yl)-2-oxoethyl)-1,3-diazaspiro[4.5]decane-2,4-dione;

3-(2-(4-(1H-pyrazolo[3,4-d]pyrimidin-4-yl)phenyl)-2-oxoethyl)-8,8-difluoro-1,3-diazaspiro[4.5]decane-2,4-dione;

3-(2-(6-(1H-pyrrolo[2,3-c]pyridin-4-yl)pyridin-3-yl)-2-oxoethyl)-8,8-difluoro-1,3-diazaspiro[4.5]decane-2,4-dione;

8,8-difluoro-3-(2-(4-(3-(2-hydroxyethoxy)pyrazin-2-yl)phenyl)-2-oxoethyl)-1,3-diazaspiro[4.5]decane-2,4-dione;

8,8-difluoro-3-(2-oxo-2-(4-(phthalazin-1-yl)phenyl)ethyl)-1,3-diazaspiro[4.5]decane-2,4-dione;

3-(2-(4-(3H-imidazo[4,5-b]pyridin-3-yl)phenyl)-2-oxoethyl)-8,8-difluoro-1,3-diazaspiro[4.5]decane-2,4-dione;

3-(2-(2-(8,8-difluoro-2,4-dioxo-1,3-diazaspiro[4.5]decan-3-yl)acetyl)-4-methylthiazol-5-yl)benzonitrile;

3-(2-(1,4-dimethyl-5-phenyl-1H-imidazol-2-yl)-2-oxoethyl)-8,8-difluoro-1,3-diazaspiro[4.5]decane-2,4-dione;

8,8-difluoro-3-(2-(5-(3-fluorophenyl)-1,4-dimethyl-1H-imidazol-2-yl)-2-oxoethyl)-1,3-diazaspiro[4.5]decane-2,4-dione;

3-(2-(2-(8,8-difluoro-2,4-dioxo-1,3-diazaspiro[4.5]decan-3-yl)acetyl)-1,4-dimethyl-1H-imidazol-5-yl)benzonitrile;

8,8-difluoro-3-(2-(5-(isoquinolin-8-yl)-1,4-dimethyl-1H-imidazol-2-yl)-2-oxoethyl)-1,3-diazaspiro[4.5]decane-2,4-dione;

8,8-difluoro-3-(2-(5-(2-(hydroxymethyl)phenyl)-1,4-dimethyl-1H-imidazol-2-yl)-2-oxoethyl)-1,3-diazaspiro[4.5]decane-2,4-dione;

8,8-difluoro-3-(2-(4-(2-(hydroxymethyl)-1H-benzo[d]imidazol-1-yl)phenyl)-2-oxoethyl)-1,3-diazaspiro[4.5]decane-2,4-dione;

8,8-difluoro-3-(2-(5-(3-fluorophenyl)-1,4-dimethyl-1H-pyrrol-3-yl)-2-oxoethyl)-1,3-diazaspiro[4.5]decane-2,4-dione;

3-(4-(2-(8,8-difluoro-2,4-dioxo-1,3-diazaspiro[4.5]decan-3-yl)acetyl)-1,3-dimethyl-1H-pyrrol-2-yl)benzonitrile;

3-(2-(5-(1H-benzo[d]imidazol-1-yl)pyrazin-2-yl)-2-oxoethyl)-8,8-difluoro-1,3-diazaspiro[4.5]decane-2,4-dione;

3-(2-(4-(2,7-naphthyridin-1-yl)phenyl)-2-oxoethyl)-8,8-difluoro-1,3-diazaspiro[4.5]decane-2,4-dione;

8,8-difluoro-3-(2-oxo-2-(4-(2-oxo-2,3-dihydro-1H-benzo[d]imidazol-1-yl)phenyl)ethyl)-1,3-diazaspiro[4.5]decane-2,4-dione;

8,8-difluoro-3-(2-(5-(2-(hydroxymethyl)phenyl)pyrazin-2-yl)-2-oxoethyl)-1,3-diazaspiro[4.5]decane-2,4-dione;

8,8-difluoro-3-(2-(5-(4-methoxypyridin-3-yl)pyrazin-2-yl)-2-oxoethyl)-1,3-diazaspiro[4.5]decane-2,4-dione;

3-(5-(2-(8,8-difluoro-2,4-dioxo-1,3-diazaspiro[4.5]decan-3-yl)acetyl)-2,4-dimethylthiophen-3-yl)benzamide;

3-(2-(5-(3,5-difluorophenyl)-1,4-dimethyl-1H-imidazol-2-yl)-2-oxoethyl)-8,8-difluoro-1,3-diazaspiro[4.5]decane-2,4-dione;

8,8-difluoro-3-(2-oxo-2-(4-(pyridazin-3-yloxy)phenyl)ethyl)-1,3-diazaspiro[4.5]decane-2,4-dione;

8,8-difluoro-3-(2-oxo-2-(4-(2-oxo-1H-imidazo[4,5-b]pyridin-3(2H)-yl)phenyl)ethyl)-1,3-diazaspiro[4.5]decane-2,4-dione;

3-(2-(5-(3,5-difluorophenyl)-4-methylthiazol-2-yl)-2-oxoethyl)-8,8-difluoro-1,3-diazaspiro[4.5]decane-2,4-dione;

4'-(2-(8,8-difluoro-2,4-dioxo-1,3-diazaspiro[4.5]decan-3-yl)acetyl)-2'-methoxy-[1,1'-biphenyl]-2-carbonitrile;

2-(4-(2-(8,8-difluoro-2,4-dioxo-1,3-diazaspiro[4.5]decan-3-yl)acetyl)phenoxy)nicotinonitrile;

3-(2-(4-((3-chloropyridin-2-yl)oxy)phenyl)-2-oxoethyl)-8,8-difluoro-1,3-diazaspiro[4.5]decane-2,4-dione;

8,8-difluoro-3-(2-(4-(3-(hydroxymethyl)pyridin-2-yl)phenyl)-2-oxoethyl)-1,3-diazaspiro[4.5]decane-2,4-dione;

3-(2-(2'-(aminomethyl)-[1,1'-biphenyl]-4-yl)-2-oxoethyl)-8,8-difluoro-1,3-diazaspiro[4.5]decane-2,4-dione;

8,8-difluoro-3-(2-oxo-2-(6-(quinolin-8-yl)pyridin-3-yl)ethyl)-1,3-diazaspiro[4.5]decane-2,4-dione;

8,8-difluoro-3-(2-(5-(2-methylpyridin-3-yl)pyrazin-2-yl)-2-oxoethyl)-1,3-diazaspiro[4.5]decane-2,4-dione;

3-(2-(4-(2,7-naphthyridin-1-yl)phenyl)-2-oxoethyl)-8,8-difluoro-1-oxa-3-azaspiro[4.5]decane-2,4-dione;

3-(4-(2-(8,8-difluoro-2,4-dioxo-1,3-diazaspiro[4.5]decan-3-yl)acetyl)phenyl)-2-methyl-3H-imidazo[4,5-b]pyridine-5-carbonitrile;

8,8-difluoro-3-(2-oxo-2-(4-(2-oxobenzo[d]oxazol-3(2H)-yl)phenyl)ethyl)-1,3-diazaspiro[4.5]decane-2,4-dione;

3-(2-(4-(2,5-dimethyl-3H-imidazo[4,5-b]pyridin-3-yl)phenyl)-2-oxoethyl)-8,8-difluoro-1,3-diazaspiro[4.5]decane-2,4-dione;

8,8-difluoro-3-(2-(5-(2-methyl-1H-benzo[d]imidazol-1-yl)pyrazin-2-yl)-2-oxoethyl)-1,3-diazaspiro[4.5]decane-2,4-dione;

8,8-difluoro-3-(2-(4-(2-methoxy-5-methyl-3H-imidazo[4,5-b]pyridin-3-yl)phenyl)-2-oxoethyl)-1,3-diazaspiro[4.5]decane-2,4-dione;

8,8-difluoro-3-(2-(4-(5-methyl-2-(trifluoromethyl)-3H-imidazo[4,5-b]pyridin-3-yl)phenyl)-2-oxoethyl)-1,3-diazaspiro[4.5]decane-2,4-dione;

3-(2-(4-(2-(difluoromethyl)-5-methyl-3H-imidazo[4,5-b]pyridin-3-yl)phenyl)-2-oxoethyl)-8,8-difluoro-1,3-diazaspiro[4.5]decane-2,4-dione;

8,8-difluoro-3-(2-(4-(5-methyl-2-oxo-1H-imidazo[4,5-b]pyridin-3(2H)-yl)phenyl)-2-oxoethyl)-1,3-diazaspiro[4.5]decane-2,4-dione;

6-(4-(2-(8,8-difluoro-2,4-dioxo-1,3-diazaspiro[4.5]decan-3-yl)acetyl)phenoxy)picolinonitrile;

8,8-difluoro-3-(2-(4-(5-methyl-3H-imidazo[4,5-b]pyridin-3-yl)phenyl)-2-oxoethyl)-1,3-diazaspiro[4.5]decane-2,4-dione;

8,8-difluoro-3-(2-(4-(3-methoxypyrazin-2-yl)phenyl)-2-oxoethyl)-1,3-diazaspiro[4.5]decane-2,4-dione;

3-(4-(2-(8,8-difluoro-2,4-dioxo-1,3-diazaspiro[4.5]decan-3-yl)acetyl)-3-fluorophenyl)pyrazin-2-carbonitrile;

8,8-difluoro-3-(2-(4-(imidazo[1,2-b]pyridazin-3-yl)phenyl)-2-oxoethyl)-1,3-diazaspiro[4.5]decane-2,4-dione;

8,8-difluoro-3-(2-(2'-(2-hydroxyethyl)-[1,1'-biphenyl]-4-yl)-2-oxoethyl)-1,3-diazaspiro[4.5]decane-2,4-dione;

2-(4'-(2-(8,8-difluoro-2,4-dioxo-1,3-diazaspiro[4.5]decan-3-yl)acetyl)-[1,1'-biphenyl]-2-yl)acetonitrile;

3-(2-(4-(1H-imidazo[4,5-b]pyrazin-1-yl)phenyl)-2-oxoethyl)-8,8-difluoro-1,3-diazaspiro[4.5]decane-2,4-dione;

8,8-difluoro-3-(2-(4-(4-methylpyridazin-3-yl)phenyl)-2-oxoethyl)-1-oxa-3-azaspiro[4.5]decane-2,4-dione;

3-(4-(2-(8,8-difluoro-2,4-dioxo-1,3-diazaspiro[4.5]decan-3-yl)acetyl)phenoxy)pyridazine-4-carbonitrile;

8,8-difluoro-3-(2-(4-(2-(hydroxymethyl)-5-methyl-3H-imidazo[4,5-b]pyridin-3-yl)phenyl)-2-oxoethyl)-1,3-diazaspiro[4.5]decane-2,4-dione;

8,8-difluoro-3-(2-oxo-2-(4-(pyrazolo[1,5-a]pyrimidin-3-yl)phenyl)ethyl)-1,3-diazaspiro[4.5]decane-2,4-dione;

4-(4-(2-(8,8-difluoro-2,4-dioxo-1,3-diazaspiro[4.5]decan-3-yl)acetyl)phenyl)nicotinonitrile;

8,8-difluoro-3-(2-(2-fluoro-4-(4-methylpyridazin-3-yl)phenyl)-2-oxoethyl)-1,3-diazaspiro[4.5]decane-2,4-dione;

8,8-difluoro-3-(2-(2-fluoro-4-(3-(hydroxymethyl)pyrazin-2-yl)phenyl)-2-oxoethyl)-1,3-diazaspiro[4.5]decane-2,4-dione; and 2-(4-(2-(8,8-difluoro-2,4-dioxo-1,3-diazaspiro[4.5]decan-3-yl)acetyl)phenyl)nicotinonitrile;

or a pharmaceutically acceptable salt thereof.

7. A method of antagonizing a TRPM8 receptor in a mammal, which comprises administering to the mammal a therapeutically effective amount of a compound according to claim 1 or a pharmaceutically acceptable salt thereof.

8. A method for treating a condition or disorder, comprising administering to a mammal in need thereof a therapeutically effective amount of a compound according to claim 1 or a pharmaceutically acceptable salt thereof, wherein the condition or disorder is at least one selected from the group consisting of a pain disease or disorder, ischemia, irritable bowel syndrome, Raynaud's syndrome, neurodegeneration, fibromyalgia, stroke, itch, a psychiatric disorder, an inflammatory disorder, anxiety, and a urological disease or disorder.

9. A pharmaceutical composition comprising a compound or a pharmaceutically acceptable salt thereof according to claim 1, and a pharmaceutically acceptable carrier or excipient.

10. The pharmaceutical composition according to claim 9, which further comprises another pharmacologically active agent.

11. A process for preparing a pharmaceutical composition comprising mixing a compound according to claim 1 or a pharmaceutically acceptable salt thereof and a pharmaceutically acceptable carrier or excipient.

12. The method according to claim 7, wherein the mammal is a human.

13. The method according to claim 8, wherein the pain disease or disorder is at least one selected from the group consisting of chronic pain, neuropathic pain, postoperative pain, osteoarthritis, rheumatoid arthritic pain, cancer pain, neuralgia, neuropathies, algesia, dentin hypersensitivity, nerve injury, migraine, cluster, and a tension headache.

14. The method according to claim 13, wherein the neuropathic pain is at least one selected from the group consisting of cold allodynia and diabetic neuropathy.

15. The method according to claim 8, wherein the psychiatric disorder is at least one selected from the group consisting of anxiety and depression.

16. The method according to claim 8, wherein the inflammatory disorder is at least one selected from the group consisting of asthma, chronic obstructive pulmonary, airways disease, COPD, and pulmonary hypertension.

17. The method according to claim 8, wherein the urological disease or disorder is at least one selected from the group consisting of detrusor overactivity, overactive bladder, urinary incontinence, neurogenic detrusor overactivity, detrusor hyperflexia, idiopathic detrusor overactivity, detrusor instability, benign prostatic hyperplasia, and a lower urinary tract symptom.

* * * * *